(12) United States Patent
Cheshire et al.

(10) Patent No.: US 8,410,123 B2
(45) Date of Patent: Apr. 2, 2013

(54) PYRIMIDINE SULPHONAMIDE DERIVATIVES AS CHEMOKINE RECEPTOR MODULATORS

(75) Inventors: David Ranulf Cheshire, Leicestershire (GB); Rhona Jane Cox, Leicestershire (GB); Premji Meghani, Leicestershire (GB); Neal Michael Smith, Leicestershire (GB); Jeffrey Paul Stonehouse, Leicestershire (GB); Cherylin Francis Preston, Torquay (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 13/336,269

(22) Filed: Dec. 23, 2011

(65) Prior Publication Data

US 2012/0157431 A1    Jun. 21, 2012

Related U.S. Application Data

(63) Continuation of application No. 12/947,916, filed on Nov. 17, 2010, which is a continuation of application No. 11/574,340, filed as application No. PCT/GB2005/003257 on Aug. 23, 2005, now Pat. No. 7,838,675.

(30) Foreign Application Priority Data

Aug. 28, 2004 (GB) .................................. 0419235.7
Feb. 8, 2005 (GB) .................................. 0502544.0

(51) Int. Cl.
  *A61K 31/506* (2006.01)
  *A61P 11/06* (2006.01)
  *C07D 403/12* (2006.01)

(52) U.S. Cl. ......... 514/269; 544/310; 544/311; 544/317

(58) Field of Classification Search .................. 544/310, 544/311, 317; 514/269
See application file for complete search history.

(56) References Cited

U.S. PATENT DOCUMENTS

| | | | |
|---|---|---|---|
| 2,540,356 A | 2/1951 | Sprague | |
| 3,082,206 A | 3/1963 | Langley | |
| 3,132,139 A | 5/1964 | Bretschneider et al. | |
| 3,328,395 A | 6/1967 | Nitta et al. | |
| 3,452,018 A | 6/1969 | Santilli et al. | |
| 3,457,278 A | 7/1969 | Zimmermann | |
| 3,673,184 A | 6/1972 | Minami et al. | |
| 7,482,355 B2 | 1/2009 | Ebden et al. | |
| 7,582,644 B2 | 9/2009 | Ebden et al. | |
| 7,838,675 B2 * | 11/2010 | Cheshire et al. | 544/310 |
| 8,106,063 B2 | 1/2012 | Ebden et al. | |
| 8,269,002 B2 | 9/2012 | Cheshire et al. | |
| 2006/0025432 A1 | 2/2006 | Ebden et al. | |
| 2008/0096860 A1 | 4/2008 | Cheshire et al. | |
| 2010/0016275 A1 | 1/2010 | Robbins et al. | |
| 2010/0063079 A1 | 3/2010 | Ebden et al. | |
| 2011/0124619 A1 | 5/2011 | Cheshire et al. | |
| 2012/0157431 A1 | 6/2012 | Cheshire et al. | |

FOREIGN PATENT DOCUMENTS

| | | |
|---|---|---|
| JP | 1042295 | 9/1966 |
| JP | 61-118372 | 5/1986 |
| JP | 03-197467 | 8/1991 |
| WO | WO 91/15209 | 10/1991 |
| WO | WO 97/22596 | 6/1997 |
| WO | WO 97/30035 | 8/1997 |
| WO | WO 97/32856 | 9/1997 |
| WO | WO 98/13354 | 4/1998 |
| WO | WO 99/02166 | 1/1999 |
| WO | WO 99/41253 | 8/1999 |
| WO | WO 00/09511 | 2/2000 |
| WO | WO 00/40529 | 7/2000 |
| WO | WO 00/41669 | 7/2000 |
| WO | WO 00/76980 | 12/2000 |
| WO | WO 01/25242 | 4/2001 |
| WO | WO 01/58902 | 8/2001 |
| WO | WO 01/58906 | 8/2001 |
| WO | WO 01/92224 | 12/2001 |
| WO | WO 02/04434 | 1/2002 |
| WO | WO 02/08213 | 1/2002 |
| WO | WO 02/24665 | 3/2002 |
| WO | WO 02/064096 | 8/2002 |
| WO | WO 03/059893 | 7/2003 |
| WO | WO 2004/011443 | 2/2004 |
| WO | WO 2004/018435 | 3/2004 |
| WO | WO 2006/024823 | 3/2006 |

OTHER PUBLICATIONS

Dermer et al., Bio/Technology, 1994, 12:320.*
Freshney et al.,Culture of Animal Cells, A Manual of Basic Technique, Alan R. Liss, Inc., 1983, New York, p. 4.*
Golub et al., Science, 286, 531-537, 1999.*
P. Nair et al., "Safety and efficacy of a CXCR2antagonist in patients with severe asthma and sputum neutrophils: a randomized, placebo-controlled clinical trial," Clinical & Experimental Allergy 42:1097-1103.

(Continued)

*Primary Examiner* — Venkataraman Balasubramanian
(74) *Attorney, Agent, or Firm* — Fish & Richardson P.C.

(57) ABSTRACT

A compound of formula (I), or a pharmaceutically acceptable salt, solvate or in vivo hydrolysable ester thereof and pharmaceutical compositions comprising these, all for use in the treatment of chemokine mediated diseases and disorders.

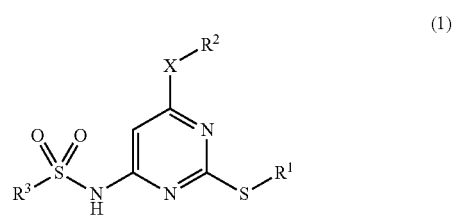

(1)

2 Claims, No Drawings

OTHER PUBLICATIONS

P.M. O'Byrne et al., "Severe asthma: future treatments," Clinical & Experimental Allergy, 42, 706-711.

Backer; Grevenstuk, Red. Tray. Chim. Pays-Bas, Coden: RTCPA3, 64, <1945>, 115, 120.

Banker et al., "Prodrugs", Modern Pharmaceutics, 3$^{rd}$ ed., Marcel Dekker, New York, pp. 451 & 596 (1996).

Bremner et al., "Therapy of Crohn's Disease in childhood", *Expert Opin. Pharmacother.* 3(7):809- 825 (2002).

Budesinsky et al., "Sulfonamides with protracted antibacterial activity. II. Alkoxy- and Alkylthio-4-sulfanilamidopyrimidines", Cesko-Slovenska Farmacie (1961) 10:241-7; CA 55:137544, 1961. CAPLUS abstract.

Budesinsky et al., "4-Sulfanilamidopyrimidines", CS 159015; CA 84:105637, 1976. CAPLUS abstract.

Bundgaard, Design of prodrugs, p. 1 (1985).

Caira, "Crystalline Polymorphism of Organic Compounds", *Topics in Current Chemistry* 198:163-208 (1998).

Cobo et al., "Reactivity of 6-Aminopyrimidin-4-(3H)-ones Towards Dimethyl Acetylenedicarboxylate (DMAD). Tandem Diels-Alder/ Retro Diels-Alder (DA/RDA) Reaction in the Synthesis of 2-Aminopyridines", *Tetrahedron* 50(34):10345-10358 (1994).

Domori et al., "Synthesis and antibacterial activity of fluorine-containing pyrimidinylsulfanilamide derivatives", Yakugaku Zasshi (1967), 87(4):419-29; CA 67:90760, 1967. CAPLUS abstract.

Grigoryan et al., "Arylsulfonic acid derivatives. XV. Synthesis and antibacterial activity of some 4-amino-4-sulfonamidopyrimidines", Armyanskii Khimicheskii Zhurnal (1987), 40(7):443-7; CA 108:131739, 1988. CAPLUS abstract.

Havlioglu et al., "Slit proteins, potential endogenous modulators of inflammation", *J Neuro Virology* 8:486-495 (2002).

Hilbsch and Pfleiderer, "Synthesis and Properties of 8-Substituted 2-Thiolumazines", *Helvetica Chimica Acta* 71:1379-1391 (1988).

Inoue et al., "Preparation of 2-(alkylthio)-6-amino-5-(trifluoromethyl)-4(3H)-pyrimidinone derivatives as insecticides, acaricides, or agrochemical fungicides", CAPLUS Abstract 115:280054 (1991).

Inoue et al., "2-(Alkylthio)-6-amino-3(2H)-pyrimidinones", Caplus Abstract 106:18604 (1987).

Lee et al., "Characterization of Two High Affinity Human Interleukin-8 Receptors", *J Biol. Chem.* 267(23):16283-16287(1992).

Merritt et al., "Use of fluo-3 to measure cytosolic $Ca^{2+}$ in platelets and neutrophils. Loading cells with the dye, calibration of traces, measurements in the presence of plasma, and buffering of cytosolic $Ca^{2+}$", *Biochem. J.* 269:513-519 (1990).

Nakazawa and Watatani, *Takamine Kenkyusho Nempo*, CODEN: TKNEAI 12, 25-31 (1960), Chem. Abstr., 55 (6483), 1961.

Nitta et al., "Pyrimidine Derivatives. I. Synthesis of a New Series of Sulfanilamides having Dialkylamino Groups in the Pyrimidine Nucleus", *Chem. Pharm. Bull.* 13(5):557-567 (1965).

Noell and Robins, "Aromaticity in Heterocyclic Systems. II. The Application of N.M.R. in a Study of the Synthesis and Structure of Certain Imidazo[1,2-c]Pyrimidines and Related Pyrrolo[2,3-d]Pyrimidines", Department of Chemistry, Arizona State University vol. 1: 34-41 (1964).

Nogimori et al., "Synthesis of 6-Anilino-2-thiouracils and Their Inhibition of Human Placenta Iodothyronine Deiodinase", *J. Med. Chem.* 28:1692-1694 (1985).

Patent: Daiichi Seiyaku Co., Ltd., Japan 69 05,229 1966, Chem. Abstr. 70 (115173w), 1969.

Raman et al., "Role of chemokines in tumor growth", *Cancer Letters* 256:137-165 (2007).

Robinson, "Medical Therapy of Inflammatory Bowel Disease for the 21st Century", *Eur J Surg Suppl* 582:90-98 (1998).

Rodriguez et al., "Aminopyrimidines and Derivatives.20. On the Acetylations of 5-Amino-4-Glycosylamino Pyrimidines", *Nucleosides & Nucleotides* 6(5):887-899 (1987).

Rostène et al., "Chemokines: a new class of neuromodulator?", *Nature Reviews Neuroscience* 8:895- 904 (2007).

Simone, Oncology: Introduction, Cecil Textbook of Medicine, edited by Bennet, J.C., and Plum F., 20$^{th}$ ed., vol. 1, pp. 1004-1010 (1996).

Singh et al., "Immune therapy in inflammatory bowel disease and models of colitis", *British Journal of Surgery* 88:1558-1569 (2001).

Spiteller et al., "Preparation of 2,6-disubstituted 4-sulfanilamidopyrimidines", Monatshefte fuer Chemie (1961) 92:183-92, CA 55:131336, 1961. CAPLUS abstract.

Sprague et al., "Sulfonamido Derivatives of Pyrimidines", J. Amer. Chem. Soc., CODEN: JACSAT 63:3028-3030 (1941).

Ueda et al., "Sulfanilamide pyrimidine derivatives", JP 37004894, CA 59:85806, 1963. CAPLUS abstract.

Ulrich, Crystallization: 4. Crystal Characteristics, Kirk-Othmer Encyclopedia of Chemical Technology, Aug. 2002.

Vinkers et al., "Synopsis: SYNthesize and OPtimize System in Silico", *J. Med. Chem.* 46:2765- 2773 (2003).

Vippagunta et al., "Crystalline solids", *Advanced Drug Delivery Reviews* 48:3-26 (2001).

West, "Solid State Chemistry and its Applications", Wiley, New York, pp. 358 & 365 (1988).

Wolff, "Some considerations for prodrug design", Burger's Medicinal Chemistry and Drug Discovery, 5$^{th}$ ed., vol. I: Principles and Practice, John Wiley & Sons, pp. 975-977 (1995).

Zambeli and Kolbah, "Acetylation of some 2-(alkyl)thio-4-amino-6-hydroxy-pyrimidines", *Acta Pharm. Jug.* 21:91-96 (1971).

USPTO Office Action in U.S. Appl. No. 12/508,934, mailed Jun. 25, 2010, 24 pages.

Fish & Richardson P.C., Amendment in Reply to Action of Jun. 25, 2010 in U.S. Appl. No. 12/508,934, filed Oct. 25, 2010, 12 pages.

USPTO Final Office Action in U.S. Appl. No. 12/508,934, mailed Jan. 10, 2011, 16 pages.

Fish & Richardson P.C., Terminal Disclaimer and Amdendment in Reply to Action of Jan. 10, 2011 in U.S. Appl. No. 12/508,934, filed Apr. 11, 2011, 8 pages.

USPTO Notice of Allowance in U.S. Appl. No. 12/508,934, mailed Apr. 25, 2011, 7 pages.

Fish & Richardson P.C., Response to Notice of Allowance of Apr. 25, 2011 in U.S. Appl. No. 12/508,934, filed Jul. 25, 2011, 2 pages.

Fish & Richardson P.C., RCE/Petition to Withdraw/IDS in U.S. Appl. No. 12/508,934, mailed Aug. 9, 2011, 33 pages.

USPTO Notice of Allowance in U.S. Appl. No. 12/508,934, mailed Sep. 28, 2011, 6 pages.

Fish & Richardson P.C., Response to Notice of Allowance of Sep. 28, 2011 in U.S. Appl. No. 12/508,934, filed Dec. 23, 2011, 2 pages.

USPTO Office Action in U.S. Appl. No. 11/574,340, mailed Jan. 4, 2010, 30 pages.

Fish & Richardson P.C., Amendment in Reply to Action of Jan. 4, 2010 in U.S. Appl. No. 11/574,340, filed Mar. 31, 2010, 11 pages.

USPTO Office Action in U.S. Appl. No. 11/574,340, mailed Apr. 29, 2010, 5 pages.

Fish & Richardson P.C., Amendment in Reply to Action of Apr. 29, 2010 in U.S. Appl. No. 11/574,340, filed Jun. 29, 2010, 6 pages.

USPTO Notice of Allowance in U.S. Appl. No. 11/574,340, mailed Jul. 13, 2010, 4 pages.

USPTO Office Action in U.S. App. U.S. Appl. No. 12/947,916, mailed Apr. 11, 2011, 34 pages.

Fish & Richardson P.C., Terminal Disclaimer and Amendment in Reply to Action of Apr. 11, 2011 in U.S. Appl. No. 12/947,916, filed Jul. 11, 2011, 29 pages.

USPTO Notice of Allowance in U.S. Appl. No. 12/947,916, mailed Sep. 26, 2011, 7 pages.

Fish & Richardson P.C., RCE and Preliminary Amendment in Reply to Action of Sep. 26, 2011 in U.S. Appl. No. 12/947,916, filed Dec. 22, 2011, 22 pages.

USPTO Notice of Allowance in U.S. Appl. No. 12/947,916, mailed Feb. 3, 2012, 9 pages.

Fish & Richardson P.C., RCE and IDS in Reply to Notice of Allowance of Feb. 3, 2012 in U.S. Appl. No. 12/947,916, filed May 2, 2012, 4 pages.

USPTO Notice of Allowance in U.S. Appl. No. 12/947,916, mailed May 14, 2012, 8 pages.

Fish & Richardson P.C., Response to Notice of Allowance of May 14, 2012 in U.S. Appl. No. 12/947,916, filed Aug. 14, 2012, 2 pages.

USPTO Restriction Requirement in U.S. Appl. No. 12/503,433, mailed Aug. 18, 2011, 6 pages.
Fish & Richardson P.C., Response to Restriction Requirement of Aug. 18, 2011 in U.S. Appl. No. 12/503,433, filed Sep. 23, 2011, 2 pages.
USPTO Non-Final Office Action in U.S. Appl. No. 12/503,433, mailed Oct. 19, 2011, 18 pages.
P. Nair et al., "Safety and efficacy of a CXCR2 antagonist in patients with severe asthma and sputum neutrophils: a randomized, placebo-controlled clinical trial," Clinical & Experimental Allergy 42:1097-1103, 2012.
R.W. Chapman et al., "CXCR2 antagonists for the treatment of pulmonary disease," Pharmacology & Therapeutics 121 (2009) 55-68.
P.M. O'Byrne et al., "Severe asthma: future treatments," Clinical & Experimental Allergy, 42, 706-711, 2012.

* cited by examiner

PYRIMIDINE SULPHONAMIDE DERIVATIVES AS CHEMOKINE RECEPTOR MODULATORS

CROSS-REFERENCE TO RELATED APPLICATIONS

This application is a continuation of U.S. application Ser. No. 12/947,916, filed Nov. 17, 2010, which is a continuation of U.S. application Ser. No. 11/574,340, filed Feb. 27, 2007 (Now U.S. Pat. No. 7,838,675), which is a national phase application under 35 U.S.C. §371 of PCT International Application No. PCT/GB2005/003257, filed Aug. 23, 2005, which claims the benefit of United Kingdom Application Serial No. 0419235.7, filed Aug. 28, 2004, and United Kingdom Application Serial No. 0502544.0, filed Feb. 8, 2005; each of these prior applications is incorporated herein by reference in its entirety.

The present invention relates to certain heterocyclic compounds, processes and intermediates used in their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved cysteine motif. At the present time, the chemokine superfamily comprises three groups exhibiting characteristic structural motifs, the C—X—C, C—C and C—$X_3$—C families. The C—X—C and C—C families have sequence similarity and are distinguished from one another on the basis of a single amino acid insertion between the NH-proximal pair of cysteine residues. The C—$X_3$—C family is distinguished from the other two families on the basis of having a triple amino acid insertion between the NH-proximal pair of cysteine residues.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils. Examples include human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

The C—$X_3$—C chemokine (also known as fractalkine) is a potent chemoattractant and activator of microglia in the central nervous system (CNS) as well as of monocytes, T cells, NK cells and mast cells.

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR5 and CXCR5 (for the C—X—C family) and $CX_3CR1$ for the C—$X_3$—C family. These receptors represent good targets for drug development since agents which modulate these receptors would be useful in the treatment of disorders and diseases such as those mentioned above.

In our PCT patent application WO 2004/011443 we disclosed amino-substituted pyrimidine sulfonamides for use as modulators of chemokine receptors.

The present invention now provides a compound of formula (1), or a pharmaceutically acceptable salt, solvate or in vivo hydrolysable ester thereof:

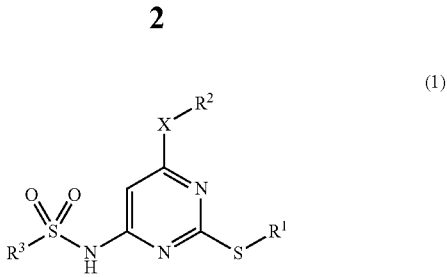

(1)

wherein $R^1$ is a group selected from $C_{3-7}$carbocyclyl, $C_{1-8}$alkyl, $C_{2-6}$alkenyl and $C_{2-6}$alkynyl;
wherein the group is optionally substituted by 1, 2 or 3 substituents independently selected from fluoro, nitrile, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, phenyl or heteroaryl; wherein phenyl and heteroaryl are optionally substituted by 1, 2 or 3 substituents independently selected from halo, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_{1-6}$alkyl and trifluoromethyl;
X is —$CH_2$—, a bond, oxygen, sulphur, sulphoxide, or sulphone;
$R^2$ is $C_{3-7}$carbocyclyl, optionally substituted by 1, 2 or 3 substituents independently selected from: fluoro, —$OR^4$, —$NR^5R^6$—$CONR^5R^6$, —$COOR^7$, —$NR^8COR^9$, —$SR^{10}$, —$SO_2R^{10}$, —$SO_2NR^5R^6$, —$NR^8SO_2R^9$;
or $R^2$ is a 3-8 membered ring optionally containing 1, 2 or 3 atoms selected from O, S, —$NR^8$ and whereby the ring is optionally substituted by 1, 2 or 3 substituents independently selected from $C_{1-3}$alkyl, fluoro, —$OR^4$, —$NR^5R^6$—$CONR^5R^6$, —$COOR^7$, —$NR^8COR^9$, —$SR^{10}$, —$SO_2R^{10}$, —$SO_2NR^5R^6$, —$NR^8SO_2R^9$;
or $R^2$ is phenyl or heteroaryl, each of which is optionally substituted by 1, 2 or 3 substituents independently selected from halo, cyano, nitro, —$OR^4$, —$NR^5R^6$, —$CONR^5R^6$, —$NR^8COR^9$, —$SO_2NR^5R^6$, —$NR^8SO_2R^9$, $C_{1-6}$alkyl and trifluoromethyl;
or $R^2$ is a group selected from $C_{1-8}$alkyl, $C_{2-6}$alkenyl or $C_{2-6}$alkynyl wherein the group is substituted by 1, 2 or 3 substituents independently selected from hydroxy, amino, $C_{1-6}$alkoxy, $C_{1-6}$alkylamino, di($C_{1-6}$alkyl)amino, N—($C_{1-6}$alkyl)-N-(phenyl)amino, N—$C_{1-6}$alkylcarbamoyl, N,N-di ($C_{1-6}$alkyl)carbamoyl, N—($C_{1-6}$alkyl)-N-(phenyl)carbamoyl, carboxy, phenoxycarbonyl, —$NR^8COR^9$, —$SO_2R^{10}$, —$SO_2NR^5R^6$, —$NR^8SO_2R^9$ and —$CONR^5R^6$;
$R^3$ is trifluoromethyl or a group-$NR^5R^6$,
or $R^3$ is phenyl, napthyl, monocyclic or bicyclic heteroaryl wherein a heteroring may be partially or fully saturated and one or more ring carbon atoms may form a carbonyl group, and wherein each phenyl or heteroaryl group is optionally substituted by 1, 2 or 3 substituents independently selected from halo, cyano, nitro, phenyl, heteroaryl, —$OR^4$, —$NR^5R^6$, —$CONR^5R^6$, —$COR^{7-}$, —$COR^{20}$, —$COOR^7$, —$NR^8COR^9$, —$SR^{10}$, —$SO_2R^{10}$, —$SO_2NR^5R^6$, —$NR^8SO_2R^9$, trifluoromethyl or $C_{1-6}$alkyl [optionally further substituted by 1, 2 or 3 substituents independently selected from halo, cyano, nitro, —$OR^{20}$, —$COOR^{20}$, —$COR^{20}$, —$NR^{18}R^{19}$, —$CONR^{18}R^{19}$, —$NR^{18}COR^{19}$, —$SO_2R^{20}$, —$SO_2NR^{18}R^{19}$, $NR^{18}SO_2R^{19}$, phenyl or monocyclic or bicyclic heteroaryl, wherein a heteroring may be partially or fully saturated; and wherein each phenyl or heteroaryl group is optionally substituted by 1, 2 or 3 substituents independently selected from halo, cyano, nitro, —$OR^{20}$, —$NR^5R^6$, —$CONR^5R^6$, —$COR^7$, —$COOR^7$, —$NR^8COR^9$, —$SR^{10}$, —$SO_2R^{10}$, —$SO_2NR^5R^6$, —$NR^8SO_2R^9$, heteroaryl, $C_{1-6}$allyl (optionally further substituted by 1, 2 or 3 substituents independently selected from halo, cyano, nitro, —OR$^{20}$, —COOR$^{20}$, —COR$^{20}$, —NR$^{18}$R$^{19}$, —CONR$^{18}$R$^{19}$, —NR$^{18}$COR$^{19}$, —SO$_2$R$^{20}$, —SO$_2$NR$^{18}$R$^{19}$, NR$^{18}$SO$_2$R$^{19}$.

or R$^3$ is a group selected from $C_{3-7}$carbocyclyl, $C_{1-8}$alkyl, $C_{2-6}$alkenyl and $C_{2-6}$alkynyl whereby the group is optionally substituted by 1, 2 or 3 substituents independently selected from halo, —OR$^4$, —NR$^5$R$^6$, —CONR$^5$R$^6$, —COR$^7$, —COOR$^7$, —NR$^8$COR$^9$, —SR$^{10}$, —SO$_2$R$^{10}$, —SO$_2$NR$^5$R$^6$, —NR$^8$SO$_2$R$^9$, phenyl or monocyclic or bicyclic heteroaryl, wherein a heterering may be partially or fully saturated; and wherein each phenyl or monocyclic or bicyclic heteroaryl group is optionally substituted by 1, 2 or 3 substituents independently selected from halo, cyano, nitro, —OR$^4$, —NR$^5$R$^6$, —CONR$^5$R$^6$, —COR$^7$, —COOR$^7$, —NR$^8$COR$^9$, —SR$^{10}$, —SO$_2$R$^{10}$, —SO$_2$NR$^5$R$^6$, —NR$^8$SO$_2$R$^9$, $C_{1-6}$alkyl, or trifluoromethyl;

R$^4$ is hydrogen or a group selected from $C_{1-6}$alkyl and phenyl, wherein the group is optionally substituted by 1 or 2 substituents independently selected from halo, phenyl, —OR$^{11}$ and —NR$^{12}$R$^{13}$;

R$^5$ and R$^6$ are independently hydrogen or a group selected from $C_{1-6}$alkyl and phenyl and monocyclic or bicyclic heteroaryl, wherein a heterering may be partially or fully saturated; wherein the group is optionally substituted by 1, 2 or 3 substituents independently selected from halo, phenyl, —OR$^{14}$, —NR$^{15}$R$^{16}$, —COOR$^{14}$, —CONR$^{15}$R$^{16}$, —NR$^{15}$COR$^{16}$, —SO$_2$R$^{10}$, —SO$_2$NR$^{15}$R$^{16}$ and NR$^{15}$SO$_2$R$^{16}$;

or

R$^5$ and R$^6$ together with the nitrogen atom to which they are attached form a 4- to 7-membered saturated heterocyclic ring system optionally containing a further heteroatom selected from oxygen, —SO$_{(n)}$— (where n=0, 1 or 2) and nitrogen atoms, in which the ring is optionally substituted by 1, 2 or 3 substituents independently selected from phenyl, heteroaryl, —OR$^{14}$, —COR$^{20}$, —COOR$^{14}$, —NR$^{15}$R$^{16}$, —CONR$^{15}$R$^{16}$, —NR$^{15}$COR$^{16}$, —SO$_2$R$^{10}$, —SO$_2$NR$^{15}$R$^{16}$, NR$^{15}$SO$_2$R$^{16}$ or $C_{1-6}$alkyl (optionally further substituted by 1 or 2 or 3 substituents independently selected from halo, —NR$^{15}$R$^{16}$ and —OR$^{17}$ or cyano, nitro, —OR$^{20}$, —COOR$^{20}$, —COR$^{20}$, —NR$^{18}$R$^{19}$, —CONR$^{18}$R$^{19}$, —SO$_2$R$^{20}$, —SO$_2$NR$^{18}$R$^{19}$, and NR$^{18}$SO$_2$R$^{19}$ groups).

R$^{10}$ is hydrogen or a group selected from $C_{1-6}$alkyl or phenyl, wherein the group is optionally substituted by 1, 2 or 3 substituents independently selected from halo, phenyl, —OR$^{17}$ and —NR$^{15}$R$^{16}$; and each of R$^7$, R$^8$, R$^9$, R$^{11}$, R$^{12}$, R$^{13}$, R$^{14}$, R$^{15}$, R$^{16}$, R$^{17}$ is independently hydrogen, $C_{1-6}$alkyl or phenyl. R$^{18}$, R$^{19}$, and R$^{20}$ are hydrogen or a group selected from $C_{1-6}$alkyl or heteroaryl (wherein a heterering may be partially or fully saturated) or phenyl, wherein the group is optionally substituted by 1, 2 or 3 substituents independently selected from halo, nitro, —CN, —OR$^4$, —NR$^8$R$^9$, —CONR$^8$R$^9$, —COR$^7$—COOR$^7$, —NR$^8$COR$^9$, —SR$^{10}$, —SO$_2$R$^{10}$, —SO$_2$NR$^8$R$^9$, —NR$^8$SO$_2$R$^9$, $C_{1-6}$alkyl or heteroaryl.

Certain compounds of formula (1) are capable of existing in stereoisomeric forms. It will be understood that the invention encompasses all geometric and optical isomers of the compounds of formula (1) and mixtures thereof including racemates.

The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Within the present invention it is to be understood that a compound of formula (1) or a salt, solvate or in vivo hydrolysable ester thereof may exhibit the phenomenon of tautomerism and that the formulae drawings within this specification can represent only one of the possible tautomeric forms. It is to be understood that the invention encompasses any tautomeric form and mixtures thereof and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It is also to be understood that certain compounds of formula (1) and salts thereof can exist in solvated as well as unsolvated forms such as, for example, hydrated forms. It is to be understood that the invention encompasses all such solvated forms.

The present invention relates to the compounds of formula (1) as hereinbefore defined as well as to the salts thereof. Salts for use in pharmaceutical compositions will be pharmaceutically acceptable salts, but other salts may be useful in the production of the compounds of formula (1) and their pharmaceutically acceptable salts. Pharmaceutically acceptable salts of the invention may, for example, include acid addition salts of the compounds of formula (1) as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. Suitable salts include hydrochlorides, hydrobromides, phosphates, sulphates, hydrogen sulphates, alkylsulphonates, arylsulphonates, acetates, benzoates, citrates, maleates, fumarates, succinates, lactates, tartrates, oxalates, methanesulphonates or p-toluenesulphonates. Pharmaceutically acceptable salts of the invention may also include basic addition salts of the compounds of formula (1) as hereinbefore defined which are sufficiently acidic to form such salts. Such salts may be formed with an inorganic or organic base which affords a pharmaceutically acceptable cation. Such salts with inorganic or organic bases include for example an alkali metal salt, such as a lithium, sodium or potassium salt, an alkaline earth metal salt such as a calcium or magnesium salt, an ammonium salt or an organic amine salt, for example a salt with methylamine, dimethylamine, trimethylamine, triethylamine, piperidine, morpholine or tris-(2-hydroxyethyl) amine. Other basic addition salts include aluminium, zinc, benzathine, chloroprocaine, choline, diethanolamine, ethanolamine, ethyldiamine, meglumine, tromethamine or procaine.

The present invention further relates to an in vivo hydrolysable ester of a compound of formula (1). An in vivo hydrolysable ester of a compound of formula (1) which contains carboxy or hydroxy group is, for example a pharmaceutically acceptable ester which is cleaved in the human or animal body to produce the parent acid or alcohol. Such esters can be identified by administering, for example, intravenously to a test animal, the compound under test and subsequently examining the test animal's body fluid.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexycarbonyloxyethyl; 1,3-dioxolen-2-onylmethyl esters for example 5-methyl-1,3-dioxolen-2-onylmethyl; and $C_{1-6}$alkoxycarbonyloxyethyl esters, for example 1-methoxycarbonyloxyethyl and may be formed at any carboxy group in the compounds of this invention.

Suitable pharmaceutically-acceptable esters for hydroxy include inorganic esters such as phosphate esters (including phosphoramidic cyclic esters) and α-acyloxyalkyl ethers and related compounds which as a result of the in vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include $C_{1-10}$alkanoyl, for example acetyl; benzoyl; phenylacetyl; substituted benzoyl and phenylacetyl, $C_{1-10}$alkoxycarbonyl (to give alkyl carbonate esters), for example ethoxycarbonyl; di-($C_{1-4}$)alkylcarbamoyl and N-(di-($C_{1-4}$)alkylaminoethyl)-N—($C_{1-4}$)alkylcarbamoyl (to give carbamates); di-($C_{1-4}$) alkylaminoacetyl and carboxyacetyl. Examples of ring substituents on phenylacetyl and benzoyl include aminomethyl, ($C_{1-4}$)alkylaminomethyl and di-(($C_{1-4}$)alkyl)aminomethyl, and morpholino or piperazino linked from a ring nitrogen atom via a methylene linking group to the 3- or 4-position of the benzoyl ring. Other interesting in-vivo hydrolysable esters include, for example, $R^A$C(O)O($C_{1-6}$)alkyl-CO—, wherein $R^A$ is for example, benzyloxy-($C_{1-4}$)alkyl, or phenyl). Suitable substituents on a phenyl group in such esters include, for example, 4-($C_{1-4}$)piperazino-($C_{1-4}$)alkyl, piperazino-($C_{1-4}$)alkyl and morpholino-($C_{1-4}$)alkyl.

In this specification the term "alkyl" includes both straight-chain and branched-chain alkyl groups. However references to individual alkyl groups such as "propyl" are specific for the straight chain version only and references to individual branched-chain alkyl groups such as t-butyl are specific for the branched chain version only. For example, "$C_{1-3}$alkyl" includes methyl, ethyl, propyl and isopropyl and examples of "$C_{1-6}$alkyl" include the examples of "$C_{1-3}$alkyl" and additionally t-butyl, pentyl, 2,3-dimethylpropyl, 3-methylbutyl and hexyl. Examples of "$C_{1-8}$alkyl" include the examples of "$C_{1-6}$alkyl" and additionally heptyl, 2,3-dimethylpentyl, 1-propylbutyl and octyl. An analogous convention applies to other terms, for example "$C_{2-6}$alkenyl" includes vinyl, allyl, 1-propenyl, 2-butenyl, 3-butenyl, 3-methylbut-1-enyl, 1-pentenyl and 4-hexenyl and examples of "$C_{2-6}$alkynyl" includes ethynyl, 1-propynyl, 3-butynyl, 2-pentynyl and 1-methylpent-2-ynyl.

"$C_{3-7}$carbocyclyl" is a saturated, partially saturated or unsaturated, monocyclic ring containing 3 to 7 carbon ring atoms wherein a —$CH_2$— group can optionally be replaced by a —C(O)—. Suitable examples of "carbocyclyl" are cyclopropyl, cyclopentyl, cyclobutyl, cyclohexyl, cyclohexenyl, 4-oxocyclohex-1-yl and 3-oxocyclohept-5-en-1-yl.

The term "halo" refers to fluoro, chloro, bromo and iodo.

Examples of "$C_{1-6}$alkoxy" include methoxy, ethoxy, propoxy, isopropoxy, butyloxy, pentyloxy, 1-ethylpropoxy and hexyloxy. Examples of "$C_{1-6}$alkylamino" include methylamino, ethylamino, propylamino, butylamino and 2-methylpropylmino. Examples of "di($C_{1-6}$alkyl)amino" include dimethylamino, N-methyl-N-ethylamino, diethylamino, N-propyl-N-3-methylbutylamino. Examples of "N—($C_{1-6}$alkyl)-N-(phenyl)amino" include N-methyl-N-phenylamino, N-propyl-N-phenylamino and N-(2-methylbutyl)-N-phenylamino. Examples of "N—($C_{1-6}$alkyl)carbamoyl" are N-methylcarbamoyl, N-ethylcarbamoyl and N-(2-ethylbutyl)carbamoyl. Examples of "N—($C_{1-6}$alkyl)-N-(phenyl) carbamoyl" include N-methyl-N-phenylcarbamoyl, N-butyl-N-phenylcarbamoyl and N-(3-methylpentyl)-N-(phenyl)carbamoyl. Examples of "N N-di($C_{1-6}$alkyl)carbamoyl" include N,N-dimethylcarbamoyl, N-methyl-N-ethylcarbamoyl and N-propyl-N-(2-methylbutyl)carbamoyl. Examples of "$C_{1-6}$alkylthio" include methylthio, ethylthio, propylthio, butylthio and 2-methylbutylthio.

"Heteroaryl" is a monocyclic or bicyclic aryl ring, containing 5 to 10 ring atoms of which 1, 2, 3 or 4 ring atoms are chosen from nitrogen, sulphur or oxygen. Examples of heteroaryl include pyrrolyl, furanyl, thienyl, thiazolyl, isothiazolyl, oxazolyl, isoxazolyl, imidazolyl, pyrazolyl, triazolyl, tetrazolyl, isoxadiazolyl, oxadiazolyl, isothiadiazolyl, thiadiazolyl, pyridyl, pyrimidinyl, pyrazinyl, pyridazinyl, triazinyl, pyridinonyl, pyrimidindionyl, benzfuranyl, benzthieno, indolyl, benzimidazolyl, benzoxazolyl, benzthiazolyl, indazolyl, benzisoxazolyl, benzisothiazolyl, benztriazolyl, quinolinyl, isoquinolinyl, 4H-chromen-4-onyl, tetrahydroquinolinyl, tetrahydroisoquinolinyl, and naphthiridinyl. Conveniently heteroaryl is selected from imidazolyl, pyrazolyl, thiazolyl, isoxazolyl, furanyl, thienyl, isoxazolyl, or indazolyl. Fully saturated heterocyclic rings include examples such as oxetanyl, azetidinyl, pyrrolidinyl, tetrahydrofuranyl, isoxazolidinyl, tetrahydropyranyl, piperidinyl, piperazinyl, piperazinonyl, morpholinyl, thiomorpholinyl, thiomorpholinyl-1-oxide, thiomorpholinyl-1,1-dioxide, oxazinanonyl, quinuclidinyl, homopiperidinyl and homopiperazinyl, 9-methyl-3,9-diazabicyclo[4.2.1]nonanyl and tetrahydropyridinyl.

Examples of "a 3-8 membered ring optionally containing 1, 2 or 3 atoms selected from O, S and $NR^8$" include oxetanyl, azetidinyl, benzodiazolyl, pyrrolidinyl, tetrahydrofuranyl, isoxazolidinyl, tetrahydrothiophenyl, tetrahydropyranyl, piperidinyl, piperazinyl, piperazinonyl, morpholinyl, thiomorpholinyl, thiomorpholinyl-1-oxide, thiomorpholinyl-1,1-dioxide, oxazinanonyl, quinuclidinyl, homopiperidinyl and homopiperazinyl tetrahydrodioxanyl. Examples of "a 4- to 7-membered saturated heterocyclic ring system" include azetidinyl, pyrrolidinyl, isoxazolidinyl, piperidinyl, piperazinyl, piperazinonyl, homopiperazinyl, thiomorpholinyl, thiomorpholinyl-1-oxide, thiomorpholinyl-1,1-dioxide, oxazinanonyl, quinuclidinyl and morpholinyl, Where optional substituents are chosen from "1, 2 or 3" groups it is to be understood that this definition includes all substituents being chosen from one of the specified groups or the substituents being chosen from two or more of the specified groups. An analogous convention applies to substituents chosen from "1 or 2" groups.

Convenient values of $R^1$, $R^2$, $R^3$, and X are as follows:

$R^1$ is $C_{1-8}$allyl, wherein the group is substituted by phenyl optionally substituted by 1, 2 or 3 substituents independently selected from fluoro, chloro, bromo, methoxy, methyl and trifluoromethyl.

X is —$CH_2$—, a bond, oxygen, sulphur, sulphoxide, or sulphone;

$R^2$ is $C_{1-8}$alkyl wherein the group is optionally substituted by 1, 2 or 3 substituents independently selected from $C_{1-6}$alkoxy, hydroxy and fluoro; or $R^2$ is a 5-6 membered ring optionally containing 1, 2 or 3 heteroatoms selected from O, S, —$NR^8$ and whereby the ring is optionally substituted by —$OR^4$.

$R^3$ is $C_{3-7}$carbocyclyl, $C_{1-8}$allyl, —$NR^5R^6$, phenyl, monocyclic or bicyclic heteroaryl wherein a heterorring may be partially or fully saturated and one or more ring carbon atoms may form a carbonyl group, and wherein each phenyl or heteroaryl group is optionally substituted by 1, 2 or 3 substituents independently selected from cyano, heteroaryl, —$OR^4$, —$NR^5R^6$, —$CONR^5R^6$, —$COR^{7-}$, —$COR^{20}$, —NR$^8$COR$^9$, —SO$_2$R$^{10}$, —SO$_2$NR$^5$R$^6$, C$_{1-6}$alkyl [optionally further substituted by 1, 2 or 3 substituents independently selected from —OR$^{20}$, —COR$^{20}$, —NR$^{18}$R$^{19}$, —CONR$^{18}$R$^{19}$, phenyl or monocyclic or bicyclic heteroaryl, wherein a heteroring may be partially or fully saturated; and wherein each phenyl or heteroaryl group is optionally substituted by 1, 2 or 3 substituents independently selected from nitro, —OR$^{20}$, —NR$^5$R$^6$, —NR$^8$COR$^9$, heteroaryl, C$_{1-6}$alkyl (optionally further substituted by 1, 2 or 3 substituents independently selected from cyano, —OR$^{20}$).

Convenient values of R$^4$-R$^{17}$ are as follows:
R$^4$ is hydrogen or C$_{1-6}$alkyl;
R$^5$ and R$^6$ are a group selected from C$_{1-6}$alkyl or R$^5$ and R$^6$ together with the nitrogen atom to which they are attached form a 4- to 7-membered saturated heterocyclic ring optionally containing a further heteroatom selected from oxygen and nitrogen atoms.
R$^7$, R$^8$, R$^9$, R$^{11}$, R$^{12}$, R$^{13}$, R$^{14}$ R$^{15}$, R$^{16}$, R$^{17}$ are independently hydrogen, C$_{1-6}$alkyl or phenyl.

Convenient values of R$^{18}$-R$^{20}$ are as follows:
R$^{18}$, R$^{19}$ and R$^{20}$ are hydrogen, phenyl, heteroaryl, or C$_{1-6}$alkyl (optionally further substituted by NR$^8$R$^9$).

Preferred values of R$^1$, R$^2$, R$^3$, and X are as follows:
R$^1$ is C$_{1-3}$alkyl (such as —CH$_2$—, —(CH$_2$)$_2$—, —(CH$_2$)$_3$—, —CH$_2$(CH$_3$)— or —CH$_2$(CH$_3$)CH$_2$—) wherein the group is substituted by phenyl optionally substituted by 1, 2 or 3 substituents independently selected from fluoro and chloro. Benzyl is particularly preferred.

X is —CH$_2$—, a bond, oxygen, or sulphur. Oxygen is particularly preferred.

R$^2$ is C$_{1-8}$ alkyl, such as C$_{1-4}$ alkyl, wherein the group is optionally substituted by 1 or 2 substituents independently selected from C$_{1-3}$alkoxy (such as methoxy, ethoxy, cyclopropyloxy or isopropyloxy), hydroxy and fluoro, hydroxy is particularly preferred; or R$^2$ is a 5-membered ring optionally containing a heteroatom selected from 0 or —NR$^8$ and whereby the ring is optionally substituted by —OR$^4$.

R$^3$ is C$_{1-3}$allyl (such as methyl, ethyl, isopropyl or cyclopropyl) or —NR$^5$R$^6$ (such as azetidinyl, pyrrolidinyl, morpholinyl, piperidinyl, piperazinyl) or phenyl or a monocyclic or bicyclic heteroaryl group (such as 1-methylimidazolyl or 1,2-dimethylimidazolyl).

Preferred values of R$^4$-R$^{17}$ are as follows:
R$^4$ is hydrogen, or C$_{1-3}$alkyl (such as methyl, ethyl, cyclopropyl or isopropyl)
R$^5$ and R$^6$ are a group selected from C$_{1-2}$alkyl (such as methyl and ethyl) or R$^5$ and R$^6$ together with the nitrogen atom to which they are attached form a 4- to 6-membered saturated heterocyclic ring (such as azetidinyl, pyrrolidinyl, piperidinyl) or optionally containing a further heteroatom selected from oxygen (such as morpholinyl) or nitrogen (such as piperazinyl).
R$^7$, R$^8$, R$^9$, R$^{11}$, R$^{12}$, R$^{13}$, R$^{14}$ R$^{15}$, R$^{16}$, R$^{17}$ are independently hydrogen, or C$_{1-2}$alkyl (such as methyl or ethyl).

Preferred values of R$^{18}$-R$^{20}$ are as follows:
R$^{18}$, R$^{19}$ and R$^{20}$ are hydrogen or C$_{1-6}$alkyl (optionally further substituted by NR$^8$R$^9$).

Such values may be used where appropriate with any of the definitions, claims or embodiments defined hereinbefore or hereinafter.

Particular compounds of the invention include:
N-[2-[[(2,3-difluorophenyl)methyl]thio]-6-[2-hydroxy-1-(hydroxymethyl)ethoxy]-4-pyrimidinyl]-1-azetidinesulfonamide R,S)N-[2-[[(2,3-difluorophenyl)methyl]thio]-6-[3,4-dihydroxybutyl]pyrimidin-4-yl]azetidine-1-sulphonamide; and
N-[2-[[(2,3-difluorophenyl)methyl]thio]-6-[3-hydroxy-2-(hydroxymethyl)propyl]pyrimidin-4-yl]azetidine-1-sulphonamide
N-(2-[(2,3-difluorobenzyl)thio]-6-{[(1R,2R)-2-hydroxy-1-methylpropyl]oxy}pyrimidin-4-yl)azetidine-1-sulfonamide; and
N-(2-[(2,3-difluorobenzyl)thio]-6-{[(1S,2S)-2-hydroxy-1-methylpropyl]oxy}pyrimidin-4-yl)azetidine-1-sulfonamide
N-[2-[[(2,3-difluorophenyl)methyl]thio]-6-[[(2S)-2,3-dihydroxypropyl]oxy]-4-pyrimidinyl]-1-azetidinesulfonamide
N-[2-[[(2,3-difluorophenyl)methyl]thio]-6-[2-hydroxy-1-(hydroxymethyl)-1-methylethoxy]-4-pyrimidinyl]-1-azetidinesulfonamide
N-[2-[[(2,3-difluorophenyl)methyl]thio]-6-[(1R)-2-hydroxy-1-methylethoxy]-4-pyrimidinyl]-2-thiazolesulfonamide
N-[2-[[(2,3-difluorophenyl)methyl]thio]-6-[(1R)-2-hydroxy-1-methylethoxy]-4-pyrimidinyl]-4-pyridine sulfonamide
N-[2-[[(2,3-difluorophenyl)methyl]thio]-6-[(1R)-2-hydroxy-1-methylethoxy]-4-pyrimidinyl]-1-piperazinesulfonamide N-[2-[[(2,3-difluorophenyl)methyl]thio]-6-[(1R)-2-hydroxy-1-methylethoxy]-4-pyrimidinyl]-1,6-dihydro-1-methyl-6-oxo-3-pyridinesulfonamide
N-[2-[[(2,3-difluorophenyl)methyl]thio]-6-[(1R)-2-hydroxy-1-methylethoxy]-4-pyrimidinyl]-1-azetidine sulfonamide N-[2-[[(2,3-difluorophenyl)methyl]thio]-6-[(1R)-2-hydroxy-1-methylethoxy]-4-pyrimidinyl]-methanesulfonamide
N-[2-[[(2,3-difluorophenyl)methyl]thio]-6-[(1R)-2-hydroxy-1-methylethoxy]-4-pyrimidinyl]-4-morpholine sulfonamide
N-[2-[[(2,3-difluoro phenyl)methyl]thio]-6-[(1R)-2-hydroxy-1-methylethoxy]-4-pyrimidinyl]-1-pyrrolidinesulfonamide
N-[2-[[(2,3-difluorophenyl)methyl]thio]-6-[(1R)-2-hydroxy-1-methylethoxy]-4-pyrimidinyl]-cyclopropanesulfonamide
N-[2-[[(2,3-difluorophenyl)methyl]thio]-6-[(1R)-2-hydroxy-1-methylethoxy]-4-pyrimidinyl]-1-methyl-1H-imidazole-4-sulfonamide
N-[2-[[(2,3-Difluorophenyl)methyl]thio]-6-methoxypyrimidin-4-yl]azetidine-1-sulfonamide
N-[2-[[(2,3-Difluorophenyl)methyl]thio]-6-methoxypyrimidin-4-yl]piperazine-1-sulfonamide
N-[2-[[(2,3-Difluorophenyl)methyl]thio]-6-methoxypyrimidin-4-yl]-1-methyl-1H-imidazole-4-sulfonamide
N-[2-[[(2,3-Difluorophenyl)methyl]thio]-6-{[(1R,2R)-2,3-dihydroxy-1-methylpropyl]oxy}-4-pyrimidinyl]-1-azetidinesulfonamide
N-[2-[[(2,3-Difluorophenyl)methyl]thio]-6-[[(1R,2R)-2,3-dihydroxy-1-methylpropyl]oxy}-4-pyrimidinyl]-methanesulfonamide
N-[2-[[(2,3-Difluorophenyl)methyl]thio]-6-{[(1R,2S)-2,3-dihydroxy-1-methylpropyl]oxy}-4-pyrimidinyl]-1-azetidinesulfonamide
N-[2-[[(2,3-Difluorophenyl)methyl]thio]-6-{[(1R,2S)-2,3-dihydroxy-1-methylpropyl]oxy}-4-pyrimidinyl]-1-piperazinesulfonamide
5-(azetidin-1-ylcarbonyl)-N-{2-[(2,3-difluorobenzyl)thio]-6-[(1R)-2-hydroxy-1-methylethoxy]pyrimidin-4-yl}furan-2-sulfonamide Each of the above mentioned compounds and the pharmaceutically acceptable salts, solvates or in vivo hydrolysable esters thereof, taken individually is a particular aspect of the invention.

The present invention further provides a process for the preparation of compounds of formula (1) as defined above which comprises:
(a) treating a compound of formula (2a):

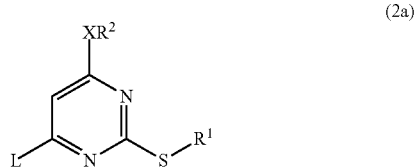

(2a)

wherein $R^1$, $R^2$ and X are as defined in formula (1) and L is a leaving group such as halogen with sulfonamides ($R^3SO_2NH_2$) where $R^3$ is as defined in formula (1).
and optionally thereafter (i), (iv), or (v) in any order:
i) removing any protecting groups;
ii) converting the compound of formula (1) into a further compound of formula (1)
iii) forming a salt
iv) forming a prodrug
v) forming an in vivo hydrolysable ester.

Reaction of compounds of formula (2a) wherein $R^1$, $R^2$ and X are as defined in formula (1) with sulfonamides ($R^3SO_2NH_2$), where $R^3$ is as defined in formula (1), can be carried out in the presence of a suitable base, solvent and catalyst heated thermally or by microwaves. Examples of suitable bases include metal carbonates such as those from cesium, potassium, lithium or sodium. Most preferably Cesium carbonate is used. Suitable solvents include toluene and ethers such as anisole, tetrahydrofuran, 1,4-dioxane, glyme and diglyme. Preferably 1,4-dioxane is used. The temperature of the reaction can be performed between 10° C. and 120° C., preferably at 100° C. Examples of suitable catalysts include a suitable palladium(0) source such as palladium tris(dibenzylideneacetone)dipalladium(0) ($Pd_2(dba)_3$), or tetrakistriphenylphosphinepalladium ($Pd(Ph_3)_4$) (either in 0.01-0.5 mol equivalents) in the presence of a suitable ligand such as (9,9-dimethyl-9H-xanthene-4,5-diyl)bis[diphenylphosphine (Xantphos), or 2-dicyclohexyl-phosphino-2'-(N,N-dimethylamino)biphenyl or 2-dicyclohexyl-phosphino-2',4',6'-tri-isopropyl,1,1'-biphenyl (XPHOS) (either in 0.01-0.5 mol equivalents). Preferably the catalyst combination is tris (dibenzylideneacetone)dipalladium(0) ($Pd_2(dba)_3$) with 2-dicyclohexyl-phosphino-2',4',6'-tri-isopropyl,1,1'-biphenyl (Xphos) in 0.01-0.5 mol equivalents in 1,4-dioxane at 100° C. with cesium carbonate as the base;
or (b) treating a compound of formula (2b):

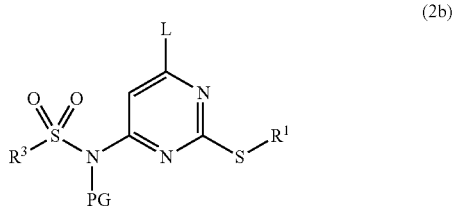

(2b)

wherein $R^1$ and $R^3$ are as defined in formula (1), L is a leaving group such as halogen, PG is a convenient protecting group or hydrogen and where X is oxygen or sulphur, with alcohols $HOR^2$ or thiols $HSR^2$ respectively wherein $R^2$ is as defined in formula (1) in the presence of a suitable base and solvent,
and optionally thereafter (i), (ii), (iv), or (v) in any order:
i) removing any protecting groups;
ii) converting the compound of formula (1) into a further compound of formula (1)
iii) forming a salt
iv) forming a prodrug
v) forming an in vivo hydrolysable ester.

Examples of suitable bases include the alkali metal hydrides such as Na or K, or metal alkoxides such as Li, Na or K-tert-butoxide, alkali metal hexamethyldisilazides such as Li, Na or K-hexamethyldisilazide, or metal carbonates such as Na, K, Cs. Suitable solvents include N,N-dimethylamides, 1-methyl-2-pyrrolidinone, toluene and ethers such as anisole, tetrahydrofuran, 1,4-dioxane, glyme and diglyme.

Also, compounds of formula (1) wherein W and $R^3$ are as defined in formula (1), L is a leaving group such as halogen, PG is a convenient protecting group or hydrogen and X is —$CH_2$— or a bond, can be prepared from compounds of formula (2b) wherein $R^2$ is as defined in formula (1) by treatment with a suitably protected alkene under "Heck coupling" type reaction conditions (Synlett, 2003, no 8 pp 1133-1136) or with a suitably protected boronic acid or ester under "Suzuki coupling" type reaction conditions (JACS, 1999, no 121, pp 9550-9561, JACS 2001, no 123, pp 10099-10100) in the presence of a suitable palladium catalyst, ligand, salt, base and solvent with thermal or microwave heating.

For "Heck" type couplings, examples of suitable palladium catalysts, salts, bases and solvents include tris(dibenzylideneacetone)dipalladium(0) ($Pd_2(dba)_3$), or palladium di-acatate ($Pd(OAc)_2$); added salts include potassium chloride, tetra-n-butylanamonium chloride; and bases include tri-n-butylamine or di-isopropylethylamine; and solvents include N,N-dimethylformamide or N-methyl-pyrrolidin-2-one.

For "Suzuki" type couplings, examples of suitable palladium catalysts, ligands, salts, bases and solvents include palladium di-acetate; with ligands tri-cyclohexylphosphine, or 2,2'bis-dicyclohexyl-phosphino-1,1'-biphenyl or di-t-butyl-phosphino-1,1'-biphenyl or tri-t-butylphosphine; with salts potassium phosphate ($K_3PO_4$) or potassium fluoride in solvents tetrahydrofuran or 1,4-dioxane.

Compounds of formula (2a) wherein $R^1$, and $R^2$ are as defined in formula (1), and X is oxygen or sulphur can be prepared from compounds of formula (3) wherein $R^1$ is as defined in formula (1) and L is a leaving group such as halogen by treatment with alcohols $HOR^2$ or thiols $HSR^2$ wherein $R^2$ is as defined in formula (1) in the presence of a suitable base and solvent.

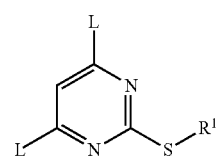

(3)

Examples of suitable bases include the alkali metal hydrides such as Na or K, or metal alkoxides such as Li, Na or K-tert-butoxide, alkali metal hexamethyldisilazides such as Li, Na or K-hexamethyldisilazide, or metal carbonates such as Na, K, Cs. Suitable solvents include N,N-dimethylamides, 1-methyl-2-pyrrolidinone, ethers such as tetrahydrofuran, 1,4-dioxane, glyme and diglyme. Preferably sodium hydride in tetrahydrofuran at ambient to reflux temperature is employed.

Also, compounds of formula (2a) wherein $R^1$ and $R^2$ are as defined in formula (1), and X is —$CH_2$— or a bond can be prepared from compounds of formula (3) wherein $R^1$ is as defined in formula (1) and L is a leaving group such as halogen, by treatment with a suitably protected alkene under "Heck coupling" type reaction conditions (Synlett, 2003, no 8 pp 1133-1136) or with a suitably protected boronic acid or ester under "Suzuki coupling" type reaction conditions (JACS, 1999, no 121, pp 9550-9561, JACS 2001, no 123, pp 10099-10100) in the presence of a suitable palladium catalyst, ligand, salt, base and solvent with thermal or microwave heating.

For "Heck" type couplings, examples of suitable palladium catalysts, salts, bases and solvents include tris(dibenzylideneacetone)dipalladium(0) ($Pd_2(dba)_3$), or palladium di-acatate ($Pd(OAc)_2$); added salts include potassium chloride, tetra-n-butylammonium chloride; and bases include tri-n-butylamine or di-isopropylethylamine; and solvents include N,N-dimethylformamide or N-methyl-pyrrolidin-2-one. Preferably palladium di-acetate, with salt tetra-n-butylammonium chloride, with base tri-n-butylamine in solvent NN-dimethylformamide at 95° C. is employed.

For "Suzuki" type couplings, Examples of suitable palladium catalysts, ligands, salts, bases and solvents include palladium di-acetate; with ligands tri-cyclohexylphosphine, or 2,2'bis-dicyclohexyl-phosphino-1,1'-biphenyl or di-t-butyl-phosphino-1,1'-biphenyl or tri-t-butylphosphine; with salts potassium phosphate ($K_3PO_4$) or potassium fluoride in solvents tetrahydrofuran or 1,4-dioxane. Preferably palladium di-acetate with ligand 2,2'bis-dicyclohexyl-phosphino-1,1'-biphenyl with salt potassium phosphate ($K_3PO_4$) in solvent tetrahydrofuran at reflux temperature is employed.

Compounds of formula (2b) wherein $R^1$ and $R^3$ are as defined in formula (1), L is a leaving group such as halogen and PG is a suitable protecting group or halogen may be prepared by reaction of compounds of formula (3), wherein $R^1$ is as defined in formula (1) and L is a leaving group such as halogen with sulfonamides ($R^3SO_2NHPG$) where $R^3$ is as defined in formula (1) and PG is a suitable protecting group or hydrogen, in the presence of a suitable base, solvent and catalyst heated thermally or by microwaves.
and optionally thereafter (i) or (ii) in any order:
i) adding any protecting groups;
ii) converting the compound of formula (2b) into a further compound of formula (2b)

Examples of suitable bases include the alkali metal hydrides such as Na or K, or metal alkoxides such as Li, Na or K-tert-butoxide, alkali metal hexamethyldisilazides such as Li, Na or K-hexamethyldisilazide, or metal carbonates such as Na, K, Cs. Suitable solvents include acetonitrile, tetrahydrofuran, 1,4-dioxane, glyme and diglyme. The temperature of the reaction can be performed between 10° C. and 120° C. Examples of suitable catalysts include a suitable palladium (0) source such as tetrakistriphenylphosphinepalladium (Pd($Ph_3$)$_4$) or tris(dibenzylideneacetone)dipalladium(0) ($Pd_2(dba)_3$) in the presence of a suitable ligand such as (9,9-dimethyl-9H-xanthene-4,5-diyl)bis[diphenyl-phosphine (Xantphos), or 2-dicyclohexyl-phosphino-2'-(N,N-dimethylamino)biphenyl or 2-dicyclohexyl-phosphino-2',4',6'-tri-isopropyl, 1,1'-biphenyl (XPHOS).

Compounds of formula (3) wherein $R^1$ is as defined in formula (1) and L is halogen may be prepared from compounds of formula (3) wherein $R^1$ is as defined in formula (1) and L is OH by reaction with a halogenating agent such as phosphorous oxychloride. The reaction may be carried out in the presence of N,N-dimethylaniline at reflux.

Compounds of formula (3) wherein $R^1$ is as defined in formula (1) and L is OH;

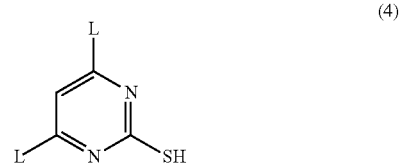

(4)

may be prepared from compounds of formula (4) wherein L is OH by reaction with alkylhalides ($R^1A$) where $R^1$ is as defined in formula (1) and A is halogen in the presence of a suitable base and solvent.

Examples of suitable bases include the alkali metal hydroxides such as Li, Na, or K, or metal carbonates such as Li, Na, K or Cs, or metal acetates such as Li, Na, K or Cs, or metal alkoxides such as Li, Na, K tert-butoxide. Suitable solvents include water, N,N-dimethylamides, 1-methyl-2-pyrrolidinone, ethers such as tetrahydrofuran, 1,4-dioxane, glyme and diglyme and alcohols such as methanol, ethanol and tert-butanol or acetonitrile. Preferably sodium acetate in acetonitrile and water at 40° C. temperature is used.

Compounds of formulae (4) are either commercially available, are well known in the literature or may be easily prepared using known techniques.

In each of the process variants outlined above for preparation of compounds of the formula 1 or a pharmaceutically acceptable salt, solvate, or in vivo hydrolysable ester thereof, each of the stated convenient or suitable materials or reaction conditions represents an individual and distinct aspect of the present invention.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (1) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wuts, Wiley-Interscience (1991).

Examples of convenient leaving groups are provided in standard chemistry textbooks such as "Organic Chemistry" by Jonathan Clayden et al, published by Oxford University Press (3$^{rd}$ Edn 2005) They include halogen, mesylate and tosylate groups. Halogen, such as chlorine is a preferred leaving group.

A compound of formula (1) may be prepared from another compound of formula (1) and a compound of formula (2b) may be prepared from a compound of formula (2b) by chemical modification. Examples of chemical modifications include standard alkylation, arylation, heteroarylation, acylation, sulphonylation, phosphorylation, aromatic halogenation and coupling reactions. These reactions may be used to add new substituents or to modify existing substituents. Alternatively, existing substituents in compounds of formula (1) and formula (2b) may be modified by, for example, oxidation, reduction, elimination, hydrolysis or other cleavage reactions to yield other compounds of formula (1) and formula (2b) respectively.

Compounds of the formula (2a)

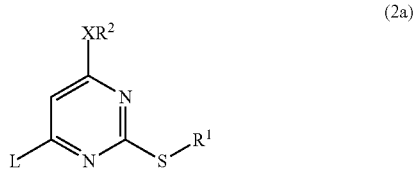

wherein $R^1$, $R^2$ and X are as defined in formula (1) and L is a leaving group such as halogen, provided that when $R^1$ is benzyl, X is oxygen, R2 is methyl then L is not chlorine or when $R^1$ is benzyl, X is a bond, R2 is propyl then L is not chlorine, represent a further aspect of the invention.

The compounds of formula (1) above may be converted to a pharmaceutically acceptable salt, solvate or in vivo hydrolysable ester thereof, as discussed above. The salt is preferably a basic addition salt.

The compounds of formula (1) have activity as pharmaceuticals, in particular as modulators of chemokine receptor (especially CXCR2) activity, and may be used in the treatment (therapeutic or prophylactic) of conditions/diseases in human and non-human animals which are exacerbated or caused by excessive or unregulated production of chemokines. Examples of such conditions/diseases include (each taken independently):

(1) the respiratory tract—obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) bone and joints—rheumatoid arthritis, seronegative spondyloarthropathies (including ankylosing spondylitis, psoriatic arthritis and Reiter's disease), Behchet's disease, Sjogren's syndrome and systemic sclerosis;

(3) skin—psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) gastrointestinal tract—Coeliac disease, proctitis, eosinopilic gastro-enteritis, mastocytosis, Crohn's disease, ulcerative colitis, indeterminate colitis, microscopic colitis, inflammatory bowel disease, irritable bowel syndrome, non-inflammatory diarrhea, food-related allergies which have effects remote from the gut, e.g., migraine, rhinitis and eczema;

(5) central and peripheral nervous system—Neurodegenerative diseases and dementia disorders, e.g. Alzheimer's disease, amyotrophic lateral sclerosis and other motor neuron diseases, Creutzfeldt-Jacob's disease and other prion diseases, HIV encephalopathy (AIDS dementia complex), Huntington's disease, frontotemporal dementia, Lewy body dementia and vascular dementia; polyneuropathies, e.g. Guillain-Barré syndrome, chronic inflammatory demyelinating polyradiculoneuropathy, multifocal motor neuropathy, plexopathies; CNS demyelination, e.g. multiple sclerosis, acute disseminated/haemorrhagic encephalomyelitis, and subacute sclerosing panencephalitis; neuromuscular disorders, e.g. myasthenia gravis and Lambert-Eaton syndrome; spinal disorders, e.g. tropical spastic paraparesis, and stiff-man syndrome: paraneoplastic syndromes, e.g. cerebellar degeneration and encephalomyelitis; CNS trauma; migraine; and stroke.

(6) other tissues and systemic disease—atherosclerosis, Acquired Immunodeficiency Syndrome (AIDS), lupus erythematosus, systemic lupus, erythematosus, Hashimoto's thyroiditis, type I diabetes, nephrotic syndrome, eosinophilia fascitis, hyper IgE syndrome, lepromatous leprosy, and idiopathic thrombocytopenia pupura; post-operative adhesions, and sepsis.

(7) allograft rejection—acute and chronic following, for example, transplantation of kidney, heart, liver, lung, bone marrow, skin and cornea; and chronic graft versus host disease;

(8) cancers—especially non-small cell lung cancer (NSCLC), malignant melanoma, prostate cancer and squamous sarcoma, and tumour metastasis, non melanoma skin cancer and chemoprevention metastases;

(9) diseases—in which angiogenesis is associated with raised CXCR2 chemokine levels (e.g. NSCLC, diabetic retinopathy);

(10) cystic fibrosis;

(11) burn wounds & chronic skin ulcers;

(12) reproductive diseases—for example disorders of ovulation, menstruation and implantation, pre-term labour, endometriosis;

(13) re-perfusion injury—in the heart, brain, peripheral limbs and other organs, inhibition of atherosclerosis.

Thus, the present invention provides a compound of formula (1), or a pharmaceutically-acceptable salt, solvate or an in vivo hydrolysable ester thereof, as hereinbefore defined for use in therapy.

Preferably the compounds of the invention are used to treat diseases in which the chemokine receptor belongs to the CXC chemokine receptor subfamily, more preferably the target chemokine receptor is the CXCR2 receptor.

Particular conditions which can be treated with the compounds of the invention are cancer, diseases in which angiogenesis is associated with raised CXCR2 chemokine levels, and inflammatory diseases such as asthma, allergic rhinitis, COPD, rheumatoid arthritis, psoriasis, inflammatory bowel diseases, osteoarthritis or osteoporosis.

As a further aspect of the present invention, the compounds of formula (1) may have utility as antagonists of the CX3CR1 receptor. Such compounds are expected to be particularly useful in the treatment of disorders within the central and peripheral nervous system and other conditions characterized by an activation of microglia and/or infiltration of leukocytes (e.g. stroke/ischemia and head trauma). In particular, the compounds are indicated for use in the treatment of neurodegenerative disorders or demyelinating disease in mammals including man. More particularly, the compounds are indicated for use in the treatment of multiple sclerosis. The compounds are also indicated to be useful in the treatment of pain, rheumatoid arthritis, osteoarthritis, stroke, atherosclerosis and pulmonary arterial hypertension.

The compounds of the invention may also be used to treat diseases in which the chemokine receptor belongs to the CCR chemokine receptor subfamily, more preferably the target chemokine receptor is the CCR2b receptor.

In a further aspect, the present invention provides a compound of formula (1), or a pharmaceutically acceptable salt, solvate or in vivo hydrolysable ester thereof, as hereinbefore defined for use as a medicament.

In a still further aspect, the present invention provides the use of a compound of formula (1), or a pharmaceutically acceptable salt, solvate or in vivo hydrolysable ester thereof, as hereinbefore defined for use as a medicament for the treatment of human diseases or conditions in which modulation of chemokine receptor activity is beneficial.

In a still further aspect, the present invention provides the use of a compound of formula (1), or a pharmaceutically acceptable salt, solvate or in vivo hydrolysable ester thereof, as hereinbefore defined for use as a medicament for the treatment of asthma, allergic rhinitis, cancer, COPD, rheumatoid arthritis, psoriasis, inflammatory bowel diseases, osteoarthritis or osteoporosis.

In a further aspect, the present invention provides the use of a compound of formula (1), or a pharmaceutically acceptable salt, solvate or in vivo hydrolysable ester thereof, as hereinbefore defined in the manufacture of a medicament for use in therapy.

In a still further aspect, the present invention provides the use of a compound of formula (1), or a pharmaceutically acceptable salt, solvate or in vivo hydrolysable ester thereof, as hereinbefore defined in the manufacture of a medicament for the treatment of human diseases or conditions in which modulation of chemokine receptor activity is beneficial.

In a still further aspect, the present invention provides the use of a compound of formula (1), or a pharmaceutically acceptable salt, solvate or in vivo hydrolysable ester thereof, as hereinbefore defined in the manufacture of a medicament for the treatment of asthma, allergic rhinitis, cancer, COPD, rheumatoid arthritis, psoriasis, inflammatory bowel diseases, osteoarthritis or osteoporosis.

In the context of the present specification, the term "therapy" also includes "prophylaxis" unless there are specific indications to the contrary. The terms "therapeutic" and "therapeutically" should be construed accordingly.

The invention still further provides a method of treating a chemokine mediated disease wherein the chemokine binds to a chemokine (especially CXCR2) receptor, which comprises administering to a patient a therapeutically effective amount of a compound of formula, or a pharmaceutically acceptable salt, solvate or in vivo hydrolysable ester, as hereinbefore defined.

The invention also provides a method of treating an inflammatory disease, especially asthma, allergic rhinitis, COPD, rheumatoid arthritis, psoriasis, inflammatory bowel diseases, osteoarthritis or osteoporosis, in a patient suffering from, or at risk of, said disease, which comprises administering to the patient a therapeutically effective amount of a compound of formula (1), or a pharmaceutically acceptable salt, solvate or in vivo hydrolysable ester thereof, as hereinbefore defined.

For the above-mentioned therapeutic uses the dosage administered will, of course, vary with the compound employed, the mode of administration, the treatment desired and the disorder indicated.

The compounds of formula (1) and pharmaceutically acceptable salts, solvates or in vivo hydrolysable esters thereof may be used on their own but will generally be administered in the form of a pharmaceutical composition in which formula (1) compound/salt/solvate/ester (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (1), or a pharmaceutically acceptable salt, solvate or in vivo hydrolysable ester thereof, as hereinbefore defined, in association with a pharmaceutically acceptable adjuvant, diluent or carrier.

The invention further provides a process for the preparation of a pharmaceutical composition of the invention which comprises mixing a compound of formula (1), or a pharmaceutically acceptable salt, solvate or in vivo hydrolysable ester thereof, as hereinbefore defined, with a pharmaceutically acceptable adjuvant, diluent or carrier. The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compounds of the invention are administered orally.

In addition to their use as therapeutic medicines, the compounds of formula (1) and their pharmaceutically acceptable salts, solvate or in vivo hydrolysable esters are also useful as pharmacological tools in the development and standardisation of in vitro and in vivo test systems for the evaluation of the effect of chemokine modulation activity in laboratory animals such as cats, dogs, rabbits, monkeys, rats and mice, as part of the search for new therapeutic agents.

The invention further relates to combination therapies wherein a compound of formula (1) or a pharmaceutically acceptable salts, solvate or in vivo hydrolysable ester thereof, or a pharmaceutical composition or formulation comprising a compound of formula (1) is administered concurrently or sequentially with therapy and/or an agent for the treatment of any one of asthma, allergic rhinitis, cancer, COPD, rheumatoid arthritis, psoriasis, inflammatory bowel disease, irritable bowel syndrome, osteoarthritis or osteoporosis.

In particular, for the treatment of the inflammatory diseases rheumatoid arthritis, psoriasis, inflammatory bowel disease, irritable bowel syndrome, COPD, asthma and allergic rhinitis the compounds of the invention may be combined with agents such as TNF-α inhibitors such as anti-TNF monoclonal antibodies (such as Remicade, CDP-870 and D.sub2.E.sub7.) and TNF receptor immunoglobulin molecules (such as Enbrel.reg.), non-selective COX-1/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin), COX-2 inhibitors (such as meloxicam, celecoxib, rofecoxib, valdecoxib and etoricoxib) low dose methotrexate, lefunomide; ciclesonide; hydroxychloroquine, d-penicillamine, auranofin or parenteral or oral gold. For inflammatory bowel disease and irritable bowel disorder further convenient agents include sulphasalazine and 5-ASAs, topical and systemic steroids, immunomodulators and immunosuppressants, antibiotics, probiotics and anti-integrins.

The present invention still further relates to the combination of a compound of the invention together with a leukotriene biosynthesis inhibitor, 5-lipoxygenase (5-LO) inhibitor or 5-lipoxygenase activating protein (FLAP) antagonist such as zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY×1005.

The present invention still further relates to the combination of a compound of the invention together with a receptor antagonist for leukotrienes $LTB_4$, $LTC_4$, $LTD_4$, and $LTE_4$ selected from the group consisting of the phenothiazin-3-ones such as L-651,392; amidino compounds such as CGS-25019c; benzoxalamines such as ontazolast; benzenecarboximidamides such as MIL 284/260; and compounds such as zafirlukast, ablukast, montelukast, pranlukast, verlukast (MK-679), RG-12525, Ro-245913, iralukast (CGP 45715A), and BAY×7195.

The present invention still further relates to the combination of a compound of the invention together with a PDE4 inhibitor including inhibitors of the isoform PDE4D.

The present invention still further relates to the combination of a compound of the invention together with a antihistaminic $H_1$ receptor antagonists such as cetirizine, loratadine, desloratadine, fexofenadine, astemizole, azelastine, and chlorpheniramine.

The present invention still further relates to the combination of a compound of the invention together with a gastroprotective $H_2$ receptor antagonist.

The present invention still further relates to the combination of a compound of the invention together with an $\alpha_1$- and $\alpha_2$-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of a compound of the invention together with anticholinergic agents such as ipratropium bromide; tiotropium bromide; oxitropium bromide; pirenzepine; and telenzepine.

The present invention still further relates to the combination of a compound of the invention together with a $\beta_1$- to $\beta_4$-adrenoceptor agonists such as metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the invention together with an insulin-like growth factor type I (IGF-1) mimetic.

The present invention still further relates to the combination of a compound of the invention together with an inhaled glucocorticoid with reduced systemic side effects, such as prednisone, prednisolone, flunisolide, triamcinolone acetonide, beclomethasone dipropionate, budesonide, fluticasone propionate, and mometasone furoate.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-12.

The present invention still further relates to the combination of a compound of the invention together with other modulators of chemokine receptor function such as CCR1, CCR2, CCR2A, CCR2B, CCR3, CCR4, CCR5, CCR6, CCR7, CCR8, CCR9, CCR10 and CCR11 (for the C—C family); CXCR1, CXCR3, CXCR4 and CXCR5 (for the C—X—C family) and $CX_3CR1$ for the C—$X_3$—C family.

The present invention still further relates to the combination of a compound of the invention together with antiviral agents such as Viracept, AZT, aciclovir and famciclovir, and antisepsis compounds such as Valant.

The present invention still further relates to the combination of a compound of the invention together with cardiovascular agents such as calcium channel blockers, lipid lowering agents such as statins, fibrates, beta-blockers, Ace inhibitors, Angiotensin-2 receptor antagonists and platelet aggregation inhibitors.

The present invention still further relates to the combination of a compound of the invention together with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metrifonate.

The present invention still further relates to the combination of a compound of the invention together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA-4 antagonists; (vi) cathepsins; (vii) MAP kinase inhibitors; (viii) glucose-6 phosphate dehydrogenase inhibitors; (ix) kinin-$B_1$- and $B_2$-receptor antagonists; (x) anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) transforming growth factor (TGFβ); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) Tachykinin $NK_1$ and $NK_3$ receptor antagonists selected from the group consisting of NKP-608C; SB-233412 (talnetant); and D-4418; (xx) elastase inhibitors selected from the group consisting of UT-77 and ZD-0892; (xxi) TNF☐ converting enzyme inhibitors (TACE); (xxii) induced nitric oxide synthase inhibitors (iNOS) or (xxiii) chemoattractant receptor-homologous molecule expressed on TH2 cells, (CRTH2 antagonists).

The compounds of the present invention may also be used in combination with osteoporosis agents such as roloxifene, droloxifene, lasofoxifene or fosomax and immunosuppressant agents such as FK-506, rapamycin, cyclosporine, azathioprine, and methotrexate.

The compounds of the invention may also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as cortico steroids and hyaluronic acids such as hyalgan and synvisc and P2X7 receptor antagonists.

The compounds of the invention can also be used in combination with existing therapeutic agents for the treatment of cancer. Suitable agents to be used in combination include:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel (Taxol®); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Pharmacological Data
Ligand Binding Assay

[$^{125}$I]IL-8 (human, recombinant) was purchased from Amersham, U.K. with a specific activity of 2,000Ci/mmol. All other chemicals were of analytical grade. High levels of hrCXCR2 were expressed in HEK 293 cells (human embryo kidney 293 cells ECACC No. 85120602) (Lee et al. (1992) *J. Biol. Chem.* 267, pp 16283-16291). hrCXCR2 cDNA was amplified and cloned from human neutrophil mRNA. The DNA was cloned into PCRScript (Stratagene) and clones were identified using DNA. The coding sequence was subcloned into the eukaryotic expression vector RcCMV (Invitrogen). Plasmid DNA was prepared using Quiagen Megaprep 2500 and transfected into HEK 293 cells using Lipofectamine reagent (Gibco BRL). Cells of the highest expressing clone were harvested in phosphate-buffered saline containing 0.2% (w/v) ethylenediaminetetraacetic acid (EDTA) and centrifuged (200 g, 5 min.). The cell pellet was resuspended in ice cold homogenisation buffer [10 mM HEPES (pH 7.4), 1 mM dithiothreitol, 1 mM EDTA and a panel of protease inhibitors (1 mM phenyl methyl sulphonyl fluoride, 2 μg/ml soybean trypsin inhibitor, 3 mM benzamidine, 0.5 μg/ml leupeptin and 100 μg/ml bacitracin)] and the cells left to swell for 10 minutes. The cell preparation was disrupted using a hand held glass mortar/PTFE pestle homogeniser and cell membranes harvested by centrifugation (45 minutes, 100,000 g, 4° C.). The membrane preparation was stored at −70° C. in homogenisation buffer supplemented with Tyrode's salt solution (137 mM NaCl, 2.7 mM KCl, 0.4 mM $NaH_2PO_4$), 0.1% (w/v) gelatin and 10% (v/v) glycerol.

All assays were performed in a 96-well MultiScreen 0.45 μm filtration plates (Millipore, U.K.). Each assay contained ~50 pM [$^{125}$I]IL-8 and membranes (equivalent to ~200,000 cells) in assay buffer [Tyrode's salt solution supplemented with 10 mM HEPES (pH 7.4), 1.8 mM $CaCl_2$, 1 mM $MgCl_2$, 0.125 mg/ml bacitracin and 0.1% (w/v) gelatin]. In addition, a compound of formula (1) according to the Examples was pre-dissolved in DMSO and added to reach a final concentration of 1% (v/v) DMSO. The assay was initiated with the addition of membranes and after 1.5 hours at room temperature the membranes were harvested by filtration using a Millipore MultiScreen vacuum manifold and washed twice with assay buffer (without bacitracin). The backing plate was removed from the MultiScreen plate assembly, the filters dried at room temperature, punched out and then counted on a Cobra γ-counter.

The compounds of formula (1) according to the Examples 1-156 were found to have $pIC_{50}$ values of greater than (>) 5.0.

Intracellular Calcium Mobilisation Assay

Human neutrophils were prepared from EDTA-treated peripheral blood, as previously described (Baly et al. (1997) Methods in Enzymology 287 pp 70-72), in storage buffer [Tyrode's salt solution (137 mM NaCl, 2.7 mM KCl, 0.4 mM $NaH_2PO_4$) supplemented with 5.7 mM glucose and 10 mM HEPES (pH 7.4)].

The chemokine GROα (human, recombinant) was purchased from R&D Systems (Abingdon, U.K.). All other chemicals were of analytical grade. Changes in intracellular free calcium were measured fluorometrically by loading neutrophils with the calcium sensitive fluorescent dye, fluo-3, as described previously (Merritt et al. (1990) Biochem. J. 269, pp 513-519). Cells were loaded for 1 hour at 37° C. in loading buffer (storage buffer with 0.1% (w/v) gelatin) containing 5 µM fluo-3 AM ester, washed with loading buffer and then resuspended in Tyrode's salt solution supplemented with 5.7 mM glucose, 0.1% (w/v) bovine serum albumin (BSA), 1.8 mM $CaCl_2$ and 1 mM $MgCl_2$. The cells were pipetted into black walled, clear bottom, 96 well micro plates (Costar, Boston, U.S.A.) and centrifuged (200 g, 5 minutes, room temperature).

A compound of formula (1) according to the Examples was pre-dissolved in DMSO and added to a final concentration of 0.1% (v/v) DMSO. Assays were initiated by the addition of an $A_{50}$ concentration of GRO□ and the transient increase in fluo-3 fluorescence ($\lambda_{Ex}$=490 nm and $\lambda_{Em}$=520 nm) monitored using a FLIPR (Fluorometric Imaging Plate Reader, Molecular Devices, Sunnyvale, U.S.A.).

The compounds of formula (1) according to the Examples were tested and found to be antagonists of the CXCR2 receptor in human neutrophils.

The invention will now be illustrated by the following non-limiting Examples in which, unless stated otherwise:
(i) when given Nuclear Magnetic Resonance (NMR) spectra were measured on a Varian Unity Inova 300 or 400 MHz spectrometer. $^1$H NMR data is quoted in the form of delta values for major diagnostic protons, given in parts per million (ppm) relative to tetramethylsilane (TMS) as an internal standard.
(ii) Mass Spectrometry (MS) spectra were measured on a Finnigan Mat SSQ7000 or Micromass Platform spectrometer.
(iii) the title and sub-titled compounds of the Examples and methods were named using the ACD/Name program (version 4.55) from Advanced Chemical Development Inc, Canada.
(iv) Normal phase column chromatography and normal phase HPLC was conducted using a silica column. Reverse phase High Pressure Liquid Chromatography (HPLC) purification was performed using either a Waters Micromass LCZ with a Waters 600 pump controller, Waters 2487 detector and Gilson FC024 fraction collector or a Waters Delta Prep 4000 or a Gilson Auto Purification System, using a Symmetry, NovaPak or Ex-Terra reverse phase silica column.
(v) The following abbreviations are used:
AcOH acetic acid
$CHCl_3$ chloroform
DCM dichloromethane
DMF N,N-dimethylformamide
DMSO dimethylsulfoxide
$Et_2O$ diethyl ether
EtOAc ethyl acetate
$MgSO_4$ magnesium sulfate
NMP 1-methylpyrrolidin-2-one
THF tetrahydrofuran
$H_2O$ water
$NH_3$ ammonia

EXAMPLE 1

N-[2-[[(2,3-difluorophenyl)methyl]thio]-6-[2-hydroxy-1-(hydroxymethyl)ethoxy]-4-pyrimidinyl]-1-azetidinesulfonamide

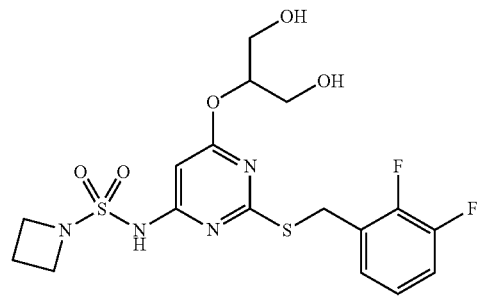

To a suspension of N-[2-[[(2,3-difluorophenyl)methyl] thio]-6-[(2-phenyl-1,3-dioxan-5-yl)oxy]-4-pyrimidinyl]-1-azetidinesulfonamide (the product of step iv) (220 mg) in methanol (5 ml)/water (0.1 ml) was added pyridinium p-toluenesulfonate (20 mg) and the mixture was stirred at ambient temperature for 1.5 hour, then at reflux for 20 hour. The reaction mixture was evaporated, suspended in water and extracted with ethyl acetate (×2). The combined organic layers were dried with magnesium sulfate, filtered and evaporated. The residue was purified by column chromatography on silica gel using a 98:2 mixture of methylene chloride and methanol as eluent to give the title compound as a white solid. Yield: 120 mg MS: APCI (+ve) 463, [M+H$^+$]

$^1$H NMR: (DMSO) δ 2.13 (quintet, 2H), 3.57 (m, 4H), 3.89 (t, 4), 4.44 (s, 2H), 4.78 (t, 2H), 5.13 (quintet, 1H), 6.15 (s, 1H), 7.17 (dq, 1H), 7.36 (dq, 1H), 7.45 (dt, 1H), 11.11 (bs, 1H);

The intermediates for this compound were prepared as follows:

i) 2-[(2,3-Difluorobenzyl)thio]pyrimidine-4,6-diol

To a slurry of 2-mercaptopyrimidine-4,6-diol (55.6 g) in water (735 ml) was added sodium acetate (47.4 g) with stirring forming a complete solution over 20 minutes. A solution of 2,3-difluorobenzyl bromide (80 g) in acetonitrile (73.5 ml) was then added dropwise over 15 minutes and the resulting mixture heated at 40° C. with stirring for 18 h. After cooling to ambient temperature the resulting precipitate was then filtered and washed with H₂O (1 L) before drying in vacuo at 100° C. to afford the subtitle compound as a cream solid.

Yield: 101.5 g.

¹H NMR: δ (DMSO) 7.74 (1H, s), 7.39-7.32 (2H, m), 7.21-7.15 (1H, m), 4.48 (2H, s).

ii) 4,6-Dichloro-2-[(2,3-difluorobenzyl)thio]pyrimidine

To a mixture of the subtitle product of step i) (101.5 g) with benzyltriethylammonium chloride (8.6 g) in 1,2-dimethoxyethane (550 ml) was added phosphorus oxychloride (70 ml) and the mixture heated at 85° C. for 5 h. The reaction was allowed to cool and solvents and excess phosphorus oxychloride were removed in vacuo before partitioning between ethyl acetate and ice water. The layers were separated and the dried (MgSO₄) organics concentrated in vacuo to afford the crude product as a pale brown oil which solidified on standing. The crude product was purified by column chromatography (4% EtOAc/iso-hexane) to yield the subtitle compound as a white solid. Yield: 90 g.

¹H NMR: δ (DMSO) 7.74 (1H, s), 7.39-7.32 (2H, m), 7.21-7.15 (1H, m) 4.48 (2H, s)

iii) 4-chloro-2-[[(2,3-difluorophenyl)methyl]thio]-6-[(2-phenyl-1,3-dioxan-5-yl)oxy]-pyrimidine To a solution of 2-phenyl-1,3-dioxan-5-ol (484 mg) in anhydrous tetrahydrofuran (10 ml) at 0° C. was added 60% sodium hydride (110 mg) and the mixture was heated to reflux for 25 minutes. On allowing to cool to ambient temperature 4,6-Dichloro-2-[(2,3-difluorobenzyl)thio]pyrimidine (the product of step (ii) (75 mg) was added and the reaction was heated to reflux for a further 90 minutes. The reaction mixture was allowed to cool, diluted with water and extracted with ethyl acetate (×3). The combined organic layers were dried with magnesium sulfate, filtered and evaporated. The residue was purified by column chromatography on silica using a 95:5 to 90:10 mixture of iso-hexane and ethyl acetate as eluent to give the sub-title compound as a white solid. Yield: 350 mg MS: APCI (+ve) 451 [M+H⁺]

iv) N-[2-[[(2,3-difluorophenyl)methyl]thio]-6-[(2-phenyl-1,3-dioxan-5-yl)oxy]-4-pyrimidinyl]-1-azetidinesulfonamide A mixture of azetidine-1-sulphonamide (420 mg), tris(dibenzylideneacetone)dipalladium (0) (71 mg), 2-dicyclohexylphosphino-2',4',6'-tri-isopropyl-1,1'-biphenyl (XPHOS) (37 mg), cesium carbonate (380 mg) and 4-chloro-2-[[(2,3-difluorophenyl)methyl]thio]-6-[(2-phenyl-1,3-dioxan-5-yl)oxy]-pyrimidine (350 mg) in anhydrous dioxane (8 ml) was heated to reflux in a microwave at 100° C., 300 W, open vessel with cooling for 10 minutes. The reaction mixture was diluted with methylene chloride, filtered through arbocel and the filtrate evaporated. The residue was purified by column chromatography on silica using a 80:20 to 70:30 mixture of iso-hexane and ethyl acetate as eluent to give the sub-title compound as a white solid.

Yield: 220 mg.

MS: APCI (+ve) 551 [M+H⁺]

EXAMPLE 2

(R,S)N-[2-[[(2,3-difluorophenyl)methyl]thio]-6-[3,4-dihydroxybutyl]pyrimidin-4-yl]azetidine-1-sulphonamide

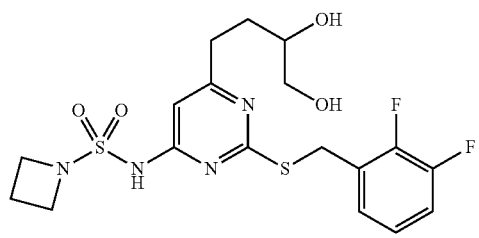 [SMILES: O=S(=O)(Nc1cc(CCC(O)CO)nc(SCc2cccc(F)c2F)n1)N1CCC1]

A solution of N-[2-[[(2,3-difluorophenyl)methyl]thio]-6-[2-(2,2-dimethyl[1,3]dioxolan-4yl)-ethyl]-pyrimidin-4-yl]azetidine-1-sulphonamide (the product of step (43 mg) and pyridinium para-toluenesulphonate (43 mg) in methanol (1 ml) and one drop of water was heated at 60° C. for 1.5 h. The solution was cooled and the solvent evaporated under reduced pressure. The residue was dissolved in dichloromethane and washed with water, dried (MgSO₄) and the solvent evaporated under reduced pressure. The residual yellow solid was purified by preparative plate chromatography eluting with ethyl acetate. The isolated product was dissolved in dichloromethane and the solvent evaporated at room temperature under reduced pressure to give the title product as a white solid. Yield 20 mg.

MS: APCI (−ve) 459 [M−1]

¹H NMR: δ (DMSO) 11.18 (s, 1H), 7.44 (t, 1H), 7.33 (q, 1H), 7.14 (m, 1H), 6.66 (s, 1H), 4.57 (d, 1H), 4.51 (t, 1H), 4.45 (s, 2H), 3.93 (t, 4H), 3.41 (m, 1H), 3.26 (m, 1H), 2.71 (m, 1H), 2.65 (m, 1H), 2.12 (p, 2H), 1.82 (m, 1H), 1.53 (m, 1H).

The intermediates for this compound were prepared as follows:

i) (cis/trans) 4-Chloro-2-[[(2,3-difluorophenyl)methyl]thio]-6-[2-(2,2-dimethyl[1,3]dioxolan-4-yl)-vinyl]-pyrimidine A mixture of 4,6-dichloro-2-[(2,3-difluorobenzyl)thio]pyrimidine (product of example 1 step ii) (0.5 g), tris(dibenzylideneacetone)dipalladium(0) (45 mg), 2,2-dimethyl-4-vinyl-1,3-dioxolane (630 mg), tri-n-butylamine (610 mg) and tetra-n-butylammonium chloride (460 mg) in anhydrous N,N-dimethylformamide (6.5 ml) were heated at 90° C. for 3 h. then stirred at room temperature overnight. The reaction mixture was partitioned between ethyl acetate and water. The organic phase was washed with water and brine, dried (MgSO₄) and the solvent evaporated under reduced pressure. The residue was purified by flash silica-gel chromatography eluting with 10% diethyl ether in iso-hexane to give the sub-title compound as a yellow viscous oil. Yield: 98 mg.

MS: APCI (+ve) 399 [M+1]

ii) (R,S) 4-Chloro-2-[[(2,3-difluorophenyl)methyl]thio]-6-[2-(2,2-dimethyl[1,3]dioxolan-4-yl)ethyl]-pyrimidine A solution of the product of step i) (96.8 mg) in ethanol (10 ml) was hydrogenated over platinum oxide (5 mg) at 3 atmospheres over 2 days. Further platinum oxide (20 mg) was added and the mixture was hydrogenated for further 3 days at 5 atmospheres. The catalyst was filtered (Celite) and the filtrate evaporated under reduced pressure. The residue was purified by flash silica-gel chromatography eluting with 10% diethyl ether in iso-hexane to give the sub-title compound as a viscous oil. Yield: 33 mg.

MS: APCI (+ve) 401 [M+1]

iii) (R,S)N-[2-[[(2,3-difluorophenyl)methyl]thio]-6-[2-(2,2-dimethyl[1,3]dioxolan-4yl)-ethyl]-pyrimidin-4-yl]azetidine-1-sulphonamide A solution of the product of step ii) (47 mg), tris(dibenzylideneacetone)dipalladium(0) (6 mg), azetidine-1-sulphonamide (62 mg), 2-dicyclohexyl-phosphino-2',4',6'-tri-isopropyl, 1,1'-biphenyl (XPHOS) (6 mg) and cesium carbonate (52 mg) in anhydrous dioxane (1 ml) was heated at 100° C. for 45 min. The reaction mixture was partitioned between ethyl acetate and water. Acetic acid (0.2 ml) was added and the separated organic phase was washed with water and brine, dried (MgSO₄) and the solvent evaporated under reduced pressure. The residue was purified by flash silica-gel chromatography eluting with 40% ethyl acetate in iso-hexane to give the sub-title compound as a yellow viscous oil. Yield: 46 mg.

MS: APCI (+ve) 501 [M+1]

EXAMPLE 3

N-[2-[[(2,3-difluorophenyl)methyl]thio]-6-[3-hydroxy-2-(hydroxymethyl)propyl]pyrimidin-4-yl]azetidine-1-sulphonamide

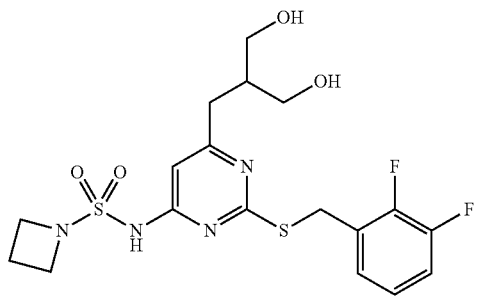 [SMILES: O=S(=O)(Nc1cc(CC(CO)CO)nc(SCc2cccc(F)c2F)n1)N1CCC1]

A solution of N-[2-[[(2,3-difluorophenyl)methyl]thio]-6-[(2,2-dimethyl-1,3-dioxan-5-yl)methyl]-4-pyrimidinyl]azetidine-1-sulphonamide (the product of step ii) (78 mg) and pyridinium para-toluenesulphonate (79 mg) in methanol (1.8 ml) and one drop of water was heated at 60° C. for 15 min. The solution was cooled and the solvent evaporated under reduced pressure. The residue was dissolved in dichloromethane and washed with 2N hydrochloric acid and water, dried (MgSO₄) and the solvent evaporated under reduced pressure to give a viscous yellow oil (17 mg). The aqueous washings were combined, the pH adjusted to 5 with aqueous sodium bicarbonate and then extracted with ethyl acetate. The organic solution was dried (MgSO₄) and the solvent evaporated under reduced pressure. The residual viscous oil was dissolved in dichloromethane and the solvent evaporated at room temperature under reduced pressure to give the title product as a white solid. Yield 62 mg.

MS: APCI (−ve) 459 [M−1]

¹H NMR: δ (DMSO) 11.17 (s, 1H), 7.44 (t, 1H), 7.33 (m, 1H), 7.14 (m, 1H), 6.65 (s, 1H), 4.45 (s, 4H), 3.92 (t, 4H), 3.38 (m, 4H), 2.57 (d, 2H), 2.12 (p, 2H), 1.98 (m, 1H)

The intermediates for this compound were prepared as follows:

i) 4-chloro-2-[[(2,3-difluorophenyl)methyl]thio]-6-[(2,2-dimethyl-1,3-dioxan-5-yl)methyl]pyrimidine A solution of 0.5M 9-borabicyclo[3.3.1]nonane (9-BBN) in tetrahydrofuran (17.12 ml) and 2,2-dimethyl-5-methylene-1,3-dioxane. (Tet. Lett. (1988) 29 (45) 5703-5706) (1.3 g) was heated at 45° C. for 18 h. The solution was cooled and added to mixture of palladium(II) acetate, potassium phosphate (1.16 g), (biphenyl-2-yl)dicyclohexyl-phosphine (0.14 g) and 4,6-dichloro-2-[(2,3-difluorobenzyl)thio]pyrimidine (1.5 g) stirred under nitrogen. The mixture was heated in a microwave at 70° C., 250 W for a total of 1.5 h, then 70° C. on a hot-plate for 2 days. The reaction mixture was adsorbed onto silica-gel, the solvent evaporated under reduced pressure and the residue purified by flash silica-gel chromatography eluting with 20% ethyl acetate in iso-hexane to give a yellow oil. The oil was further purified by flash silica-gel chromatography eluting with dichloromethane to give the sub-title product as a viscous oil.

Yield: 110 mg.
MS: APCI (−ve) 399 [M−1]

ii) N-[2-[[(2,3-difluorophenyl)methyl]thio]-6-[(2,2-dimethyl-1,3-dioxan-5-yl)methyl]-4-pyrimidinyl]azetidine-1-sulphonamide A solution of the product of step i) (109 mg), tris(dibenzylideneacetone)dipalladium(0) (14 mg), azetidine-1-sulphonamide (145 mg), 2-dicyclohexyl-phosphino-2',4',6'-tri-isopropyl, 1,1'-biphenyl(XPHOS) (14 mg) and cesium carbonate (120 mg) in anhydrous dioxane (2.3 ml) was heated at 100° C. for 45 min. The reaction mixture was partitioned between ethyl acetate and water. Acetic acid (0.2 ml) was added and the separated organic phase was washed with water and brine, dried (MgSO₄) and the solvent evaporated under reduced pressure. The residue was purified by flash silica-gel chromatography eluting with 40% ethyl acetate in iso-hexane to give the sub-title compound as a yellow viscous oil.

Yield: 78 mg.
MS: APCI (−ve) 499 [M−1]

EXAMPLE 4

N-(2-[(2,3-difluorobenzyl)thio]-6-{[(1R,2R)-2-hydroxy-1-methylpropyl]oxy}pyrimidin-4-yl)azetidine-1-sulfonamide

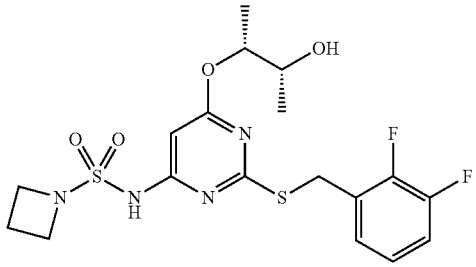 [SMILES: C[C@@H](O)[C@@H](C)Oc1cc(NS(=O)(=O)N2CCC2)nc(SCc2cccc(F)c2F)n1]

The title compound was prepared according to the procedure outlined in example 1 step (iv) using a mixture of azetidine-1-sulfonamide (150 mg), tris(dibenzylideneacetone)dipalladium (0) (25 mg), 2-dicyclohexylphosphino-2',4',6'-triisopropyl-1,1'-biphenyl (XPHOS) (25 mg), cesium carbonate (244 mg) and (2R,3R)-3-({6-chloro-2-[(2,3-difluorobenzyl)thio]pyrimidin-4-yl}oxy)butan-2-ol (200 mg) in anhydrous dioxane (10 ml). Purification was by reverse phase HPLC eluting with acetonitrile/aq. 0.1% ammonium acetate mixtures to give title compound as a white solid. Yield: 79 mg MS: APCI (+ve) 461 [M+1]

$^1$H NMR: δ (CDCl$_3$) 7.26-7.22 (1H, m), 7.10-6.99 (2H, m), 6.33 (1H, s), 5.07-5.00 (1H, m), 4.37 (2H, s), 4.02 (4H, t), 3.89-3.82 (1H, m), 2.25 (2H, quintet), 1.26-1.21 (6H, m)

The intermediates for this compound were prepared as follows:

i) (2R,3R)-3-({6-chloro-2-[(2,3-difluorobenzyl)thio]pyrimidin-4-yl}oxy)butan-2-ol To a solution of (2R,3R)-butane-2,3-diol (250 mg) and 4,6-Dichloro-2-[(2,3-difluorobenzyl)thio]pyrimidine (the product of example 1 step (ii)) (427 mg) in anhydrous tetrahydrofuran (20 ml) at ambient temperature was added 60% sodium hydride (33.4 mg). After stirring for 15 minutes the reaction mixture was partitioned between aq. ammonium chloride solution and ethyl acetate. The organics collected, dried (MgSO$_4$) and solvents removed under vacuo to give the subtitle compound as colourless gum. Yield: 525 mg.

MS: APCI (+ve) 361 [M+H$^+$]

EXAMPLE 5

N-(2-[(2,3-difluorobenzyl)thio]-6-{[(1S,2S)-2-hydroxy-1-methylpropyl]oxy}pyrimidin-4-yl)azetidine-1-sulfonamide

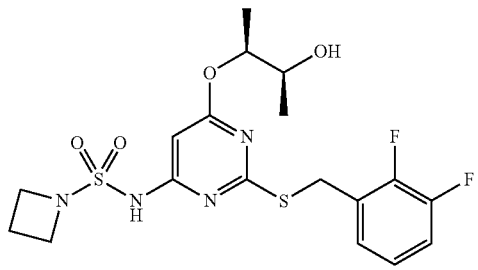 [SMILES: C[C@H](O)[C@H](C)Oc1cc(NS(=O)(=O)N2CCC2)nc(SCc2cccc(F)c2F)n1]

The title compound was prepared according to the procedure outlined in example 4 using a mixture of azetidine-1-sulfonamide (150 mg), tris(dibenzylideneacetone)dipalladium (0) (25 mg), 2-dicyclohexylphosphino-2',4',6'-triisopropyl-1,1'-biphenyl (XPHOS) (25 mg), cesium carbonate (244 mg) and (2S,3S)-3-({6-chloro-2-[(2,3-difluorobenzyl)thio]pyrimidin-4-yl}oxy)butan-2-ol (200 mg) in anhydrous dioxane (10 ml). Purification was by reverse phase HPLC eluting with acetonitrile/aq. 0.1% ammonium acetate mixtures to give title compound as a white solid. Yield: 60 mg MS: APCI (+ve) 461 [M+1]

$^1$H NMR: δ (CDCl$_3$) 7.25-7.21 (1H, m), 7.10-6.99 (2H, m), 6.32 (1H, s), 5.07-5.00 (1H, m), 4.37 (2H, s), 4.02 (4H, t), 3.88-3.81 (1H, m), 2.26 (2H, quintet), 1.26-1.21 (6H, m)

The intermediates for this compound were prepared as follows:

i) (2S,3S)-3-({6-chloro-2-[(2,3-difluorobenzyl)thio]pyrimidin-4-yl}oxy)butan-2-ol The subtitle compound was prepared according to the procedure outlined in example 4 step (i) using (2S,3S)-butane-2,3-diol (250 mg) and 4,6-Dichloro-2-[(2,3-difluorobenzyl)thio]pyrimidine (the product of example 1 step (ii)) (427 mg) in anhydrous tetrahydrofuran (20 ml) and 60% sodium hydride (33.4 mg) to give the subtitle compound as a colourless gum. Yield: 440 mg.

MS: APCI (+ve) 361 [M+H$^+$]

EXAMPLE 6

N-[2-[[(2,3-difluorophenyl)methyl]thio]-6-[[(2R)-2,3-dihydroxypropyl]oxy]-4-pyrimidinyl]-1-azetidinesulfonamide

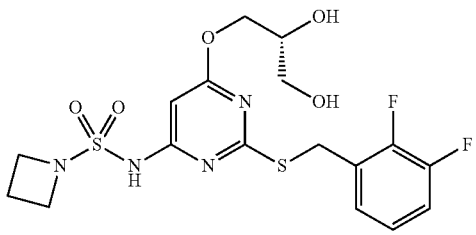 [SMILES: O=S(=O)(Nc1cc(OC[C@H](O)CO)nc(SCc2cccc(F)c2F)n1)N1CCC1]

To a solution of N-[2-[[(2,3-difluorophenyl)methyl]thio]-6-[(2S)-1,4-dioxaspiro[4.5]dec-2-ylmethoxy]-4-pyrimidinyl]-1-azetidinesulfonamide (the product of step ii) (0.34 g) in methanol (5 mL)/H$_2$O (0.1 mL) was added pyridinium p-toluenesulfonate (78 mg) and the mixture was stirred at reflux for 2 h and then ambient temperature for 20 h. The reaction mixture was evaporated, suspended in H$_2$O and extracted with EtOAc (×2). The combined organic layers were dried (MgSO$_4$), filtered and evaporated. The residue was purified by column chromatography on silica gel using DCM/MeOH (98:2) as eluent to give the title compound as a white solid. Yield: 0.15 g MS: APCI (+ve) 463 [M+H$^+$]

$^1$H NMR: δ (DMSO) 2.13 (quintet, 2H), 3.42 (m, 2H), 3.77 (m, 1H), 3.82 (t, 4H), 4.16 (dd, 1H), 4.35 (dd, 1H), 4.46 (s, 2H), 4.67 (t, 1H), 4.97 (d, 1H), 6.16 (s, 1H), 7.17 (m, 1H), 7.35 (m, 1H), 7.44 (m, 1H), 11.13 (br s, 1H);

The intermediates for this compound were prepared as follows:

i) 4-chloro-2-[[(2,3-difluorophenyl)methyl]thio]-6-[(2.5)-1,4-dioxaspiro[4.5]dec-2-ylmethoxy]-pyrimidine The subtitle compound was prepared according to the procedure outlined in example 1 step iii) using (2S)-1,4-dioxaspiro[4.5]decane-2-methanol (0.46 g) and 4,6-Dichloro-2-[(2,3-difluorobenzyl)thio]pyrimidine (the product of example 1 step (ii)) (0.75 g) in THF (8 mL) and 60% sodium hydride (39 mg) to give the subtitle compound as a pale yellow solid. Yield: 0.70 g.

MS: APCI (+ve) 403/405 [M+H$^+$]

ii) N-[2-[[(2,3-difluorophenyl)methyl]thio]-6-[(2S)-1,4-dioxaspiro[4.5]dec-2-ylmethoxy]-4-pyrimidinyl]-1-azetidinesulfonamide The subtitle compound was prepared according to the procedure outlined in example 1 step iv) using a mixture of azetidine-1-sulfonamide (prepared according to patent WO 2004/011443, 0.25 g), tris(dibenzylideneacetone)dipalladium (0) (83 mg), 2-dicyclohexylphosphino-2',4',6'-tri-isopropyl-1,1'-biphenyl (XPHOS) (43 mg), cesium carbonate (0.44 g) and 4-chloro-2-[[(2,3-difluorophenyl)methyl]thio]-6-[(2S)-1,4-dioxaspiro[4.5]dec-2-ylmethoxy]-pyrimidine (0.40 g) in dioxane (8 mL). Purification was by column chromatography on silica gel using EtOAC/isohexane (1:9 to 1:2 gradient) as eluent to give the subtitle compound as a pale yellow oil. Yield: 0.34 g MS: APCI (+ve) 543 [M+H$^+$]

EXAMPLE 7

N-[2-[[(2,3-difluorophenyl)methyl]thio]-6-[[(2S)-2,3-dihydroxypropyl]oxy]-4-pyrimidinyl]-1-azetidinesulfonamide

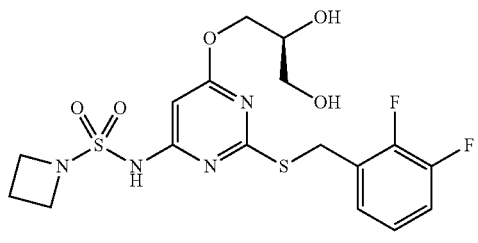 [SMILES: O=S(=O)(Nc1cc(OC[C@@H](O)CO)nc(SCc2cccc(F)c2F)n1)N1CCC1]

To a solution of N-[2-[[(2,3-difluorophenyl)methyl]thio]-6-[[(4R)-2,2-dimethyl-1,3-dioxolan-4-yl]methoxy]-4-pyrimidinyl]-1-azetidinesulfonamide (the product of step (0.48 g) in methanol (5 mL)/H$_2$O (0.1 mL) was added pyridinium p-toluenesulfonate (0.12 g) and the mixture was stirred at reflux for 2 h. The reaction mixture was evaporated, suspended in H$_2$O and extracted with EtOAc (×2). The combined organic layers were dried (MgSO$_4$), filtered and evaporated. The residue was triturated with DCM to give the title compound as a white solid. Yield: 0.30 g MS: APCI (+ve) 463 [M+H$^+$]

$^1$H NMR: δ (DMSO) 2.15 (quintet, 2H), 3.42 (m, 2H), 3.77 (m, 1H), 3.90 (t, 4H), 4.17 (dd, 1H), 4.35 (dd, 1H), 4.46 (s, 2H), 4.67 (t, 1H), 4.98 (d, 1H), 6.16 (s, 1H), 7.16 (m, 1H), 7.34 (m, 1H), 7.44 (m, 1H), 11.13 (br s, 1H);

The intermediates for this compound were prepared as follows:

1) 4-chloro-2-[[(2,3-difluorophenyl)methyl]thio]-6-[[(4R)-2,2-dimethyl-1,3-dioxolan-4-yl]methoxy]-pyrimidine The subtitle compound was prepared according to the procedure outlined in example 1 step iii) using 2,2-dimethyl-(4R)-1,3-dioxolane-4-methanol (0.26 g) and 4,6-Dichloro-2-[(2,3-difluorobenzyl)thio]pyrimidine (the product of example 1 step ii) (0.50 g) in THF (5 mL) and 60% sodium hydride (79 mg) to give the subtitle compound as a clear, colourless oil. Yield: 0.47 g.

MS: APCI (+ve) 403/405 [M+H$^+$]

ii) N-[2-[[(2,3-difluorophenyl)methyl]thio]-6-[[(4R)-2,2-dimethyl-1,3-dioxolan-4-yl]methoxy]-4-pyrimidinyl]-1-azetidinesulfonamide The subtitle compound was prepared according to the procedure outlined in example 1 step iv) using a mixture of azetidine-1-sulfonamide (prepared according to patent WO 2004/011443, 0.24 g), tris(dibenzylideneacetone)dipalladium (0) (0.11 g), 2-dicyclohexylphosphino-2',4',6'-tri-iso-propyl-1,1'-biphenyl (XPHOS) (55 mg), cesium carbonate (0.57 g) and 4-chloro-2-[[(2,3-difluorophenyl)methyl]thio]-6-[[(4R)-2,2-dimethyl-1,3-dioxolan-4-yl]methoxy]-pyrimidine (0.47 g) in dioxane (8 mL). Purification was by column chromatography on silica using EtOAc/isohexane (3:7) as eluent to give the subtitle compound as a pale yellow solid. Yield: 0.49 g MS: APCI (+ve) 503 [M+H$^+$]

EXAMPLE 8

N-[2-[[(2,3-difluorophenyl)methyl]thio]-6-[[(2R)-2,3-dihydroxy-1,1-dimethylpropyl]oxy]-4-pyrimidinyl]-1-azetidinesulfonamide

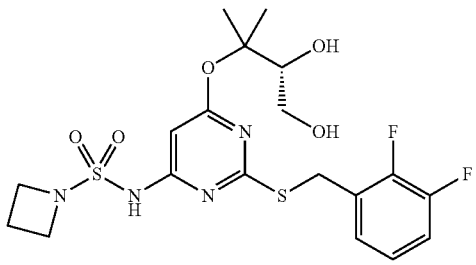 [SMILES: CC(C)(Oc1cc(NS(=O)(=O)N2CCC2)nc(SCc2cccc(F)c2F)n1)[C@H](O)CO]

To a suspension of N-[2-[[(2,3-difluorophenyl)methyl]thio]-6-[1-[(4R)-2,2-dimethyl-1,3-dioxolan-4-yl]-1-methylethoxy]-4-pyrimidinyl]-1-azetidinesulfonamide (the product from step iii) 0.34 g) in DCM (9 mL) was added iron (III) chloride hexahydrate (0.61 g) and the mixture was stirred at ambient temperature for 35 min. The reaction mixture was diluted with sat. sodium hydrogencarbonate solution and extracted with DCM (×3). The combined organic layers were dried (MgSO$_4$), filtered and evaporated. The residue was purified by column chromatography on silica gel using MeOH/DCM (99:1 to 98:2 gradient) as eluent to give the title compound as a white foam. Yield: 0.20 g MS: APCI (+ve) 489 [M+H$^+$]

$^1$H NMR: δ (DMSO) 1.41 (s, 3H), 1.44 (s, 3H), 2.16 (quintet, 2H), 3.32 (m, 1H), 3.56 (m, 1H), 3.87 (m, 1H), 3.91 (t, 4H), 4.46 (m, 3H), 4.98 (d, 1H), 6.06 (s, 1H), 7.18 (m, 1H), 7.37 (m, 1H), 7.42 (m, 1H), 11.06 (br s, 1H)

The intermediates for this compound were prepared as follows:

i) α,α-2,2-tetramethyl-(4R)-1,3-dioxolane-4-methanol

To anhydrous cerium (III) chloride (8.1 g of heptahydrate dried under high vacuum at 150° C. for 20 h) was added THF (10 mL) then methyllithium (1.6M, 11.7 mL) and the reaction mixture was stirred at ambient temperature for 10 min. A solution of 2,2-dimethyl-(4R)-1,3-dioxolane-4-carboxylic acid methyl ester (1 g) in THF (5 mL) was added and the mixture was stirred at ambient temperature for 1.5 h. The reaction mixture was quenched by a slow addition of H$_2$O (10 mL) and then extracted with Et$_2$O (×2). The combined organic layers were dried (MgSO$_4$), filtered and evaporated to afford the subtitle compound as a yellow oil. Yield: 0.40 g.

$^1$H NMR: δ (CDCl$_3$) 1.16 (s, 3H), 1.24 (s, 3H), 1.37 (s, 3H), 1.46 (s, 3H), 3.83 (m, 1H), 3.96 (m, 2H)

ii) 4-chloro-2-[[(2,3-difluorophenyl)methyl]thio]-6-[1-[(4R)-2,2-dimethyl-1,3-dioxolan-4-yl]-1-methyl-ethoxy]-pyrimidine The subtitle compound was prepared according to the procedure outlined in example 1 step iii) using α,α-2,2-tetramethyl-(4R)-1,3-dioxolane-4-methanol (0.32 g) and 4,6-Dichloro-2-[(2,3-difluorobenzyl)thio]pyrimidine (the product of example 1 step ii) (0.56 g) in THF (5 mL) and 60% sodium hydride (80 mg) to give the subtitle compound as a pale yellow oil. Yield: 0.43 g.

$^1$H NMR: δ (CDCl$_3$) 1.16 (s, 3H), 1.24 (s, 3H), 1.55 (s, 3H), 1.57 (s, 3H), 3.87 (dd, 1H), 4.02 (dd, 1H), 4.35 (t, 1H), 4.41 (s, 2H), 6.38 (s, 1H), 7.04 (m, 2H), 7.26 (m, 1H)

iii) N-[2-[[(2,3-difluorophenyl)methyl]thio]-6-[1-[(4R)-2,2-dimethyl-1,3-dioxolan-4-yl]-1-methyl-ethoxy]-4-pyrimidinyl]-1-azetidinesulfonamide The subtitle compound was prepared according to the procedure outlined in example 1 step iv) using a mixture of azetidine-1-sulfonamide (prepared according to patent WO 2004/011443, 0.20 g), tris(dibenzylideneacetone)dipalladium (0) (91 mg), 2-dicyclohexylphosphino-2',4',6'-tri-isopropyl-1,1'-biphenyl (XPHOS) (42 mg), cesium carbonate (0.49 g) and 4-chloro-2-[[(2,3-difluorophenyl)methyl]thio]-6-[1-[(4R)-2,2-dimethyl-1,3-dioxolan-4-yl]-1-methyl-ethoxy]-pyrimidine (0.43 g) in dioxane (8 mL). Purification was by column chromatography on silica gel using EtOAc/isohexane (2:8) as eluent to give the subtitle compound as a pale yellow foam. Yield: 0.43 g MS: APCI (−ve) 529 [M+H$^+$]

EXAMPLE 9

N-[2-[[(2,3-difluorophenyl)methyl]thio]-6-[[(2,5)-2,3-dihydroxy-1,1-dimethylpropyl]oxy]-4-pyrimidinyl]-1-azetidinesulfonamide

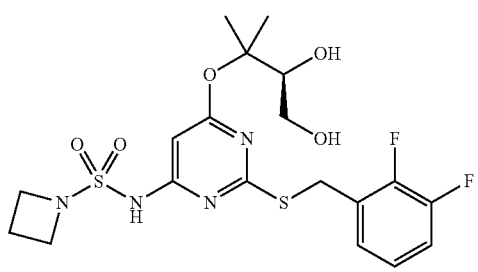 [SMILES: CC(C)(Oc1cc(NS(=O)(=O)N2CCC2)nc(SCc2cccc(F)c2F)n1)[C@@H](O)CO]

To a suspension of N-[2-[[(2,3-difluorophenyl)methyl]thio]-6-[1-[(4S)-2,2-dimethyl-1,3-dioxolan-4-yl]-1-methyl-ethoxy]-4-pyrimidinyl]-1-azetidinesulfonamide (the product from step (0.37 g) in DCM (10 mL) was added iron (III) chloride hexahydrate (0.66 g) and the mixture was stirred at ambient temperature for 1 h. The reaction mixture was diluted with sat. sodium hydrogencarbonate solution and extracted with DCM (×3). The combined organic layers were dried (MgSO$_4$), filtered and evaporated. The residue was purified by column chromatography on silica gel using a MeOH/DCM (99:1 to 98:2 gradient) as eluent to give the title compound as a white solid. Yield: 0.16 g MS: APCI (+ve) 489 [M+H$^+$]

$^1$H NMR: δ (DMSO) 1:42 (s, 3H), 1.44 (s, 3H), 2.15 (quintet, 2H), 3.33 (m, 1H), 3.56 (m, 1H), 3.87 (m, 1H), 3.90 (t, 4H), 4.44 (m, 3H), 4.98 (d, 1H), 6.06 (s, 1H), 7.17 (m, 1H), 7.36 (m, 1H), 7.41 (m, 1H), 11.06 (br s, 1H)

The intermediates for this compound were prepared as follows:

i) α,α-2,2-tetramethyl-(4S)-1,3-dioxolane-4-methanol

To anhydrous cerium (III) chloride (8.1 g of heptahydrate dried under high vacuum at 150° C. for 20 h) was added THF (10 mL) then methyllithium (1.6M, 11.7 mL) and the reaction mixture was stirred at ambient temperature for 10 min. A solution of 2,2-dimethyl-1-(4S)-1,3-dioxolane-4-carboxylic acid methyl ester (1 g) in THF (5 mL) was added and the mixture was stirred at ambient temperature for 1.5 h. The reaction mixture was quenched by a slow addition of H$_2$O (10 mL) and then extracted with Et$_2$O (×2). The combined organic layers were dried (MgSO$_4$), filtered and evaporated to afford the subtitle compound as a yellow oil. Yield: 0.75 g.

$^1$H NMR: δ (CDCl$_3$) 1.15 (s, 3H), 1.24 (s, 3H), 1.38 (s, 3H), 1.43 (s, 3H), 3.84 (m, 1H), 3.97 (m, 2H)

ii) 4-chloro-2-[[(2,3-difluorophenyl)methyl]thio]-6-[1-[(4S)-2,2-dimethyl-1,3-dioxolan-4-yl]-1-methyl-ethoxy]-pyrimidine The subtitle compound was prepared according to the procedure outlined in example 1 step iii) using α,α-2,2-tetramethyl-(4S)-1,3-dioxolane-4-methanol (0.32 g) and 4,6-Dichloro-2-[(2,3-difluorobenzyl)thio]pyrimidine (the product of example 1 step (0.56 g) in THF (5 mL) and 60% sodium hydride (80 mg) to give the subtitle compound as a colourless oil. Yield: 0.37 g.

$^1$H NMR: δ (CDCl$_3$) 1.15 (s, 3H), 1.24 (s, 3H), 1.55 (s, 3H), 1.57 (s, 3H), 3.88 (dd, 1H), 4.02 (dd, 1H), 4.35 (t, 1H), 4.41 (s, 2H), 6.38 (s, 1H), 7.03 (m, 2H), 7.26 (m, 1H)

iii) N-[2-[[(2,3-difluorophenyl)methyl]thio]-6-[1-[(4S)-2,2-dimethyl-1,3-dioxolan-4-yl]-1-methyl-ethoxy]-4-pyrimidinyl]-1-azetidinesulfonamide The subtitle compound was prepared according to the procedure outlined in example 1 step iv) using a mixture of azetidine-1-sulfonamide (prepared according to patent WO 2004/011443, 0.17 g), tris(dibenzylideneacetone)dipalladium (0) (78 mg), 2-dicyclohexylphosphino-2',4',6'-tri-isopropyl-1,1'-biphenyl (XPHOS) (40 mg), cesium carbonate (0.42 g) and 4-chloro-2-[[(2,3-difluorophenyl)methyl]thio]-6-[1-[(4S)-2,2-dimethyl-1,3-dioxolan-4-yl]-1-methyl-ethoxy]-pyrimidine (0.37 g) in dioxane (8 mL). Purification was by column chromatography on silica gel using EtOAc/isohexane (2:8 to 3:7 gradient) as eluent to give the subtitle compound as a pale yellow oil. Yield: 0.37 g MS: APCI (−ve) 529 [M+H$^−$]

EXAMPLE 10

N-[2-[[(2,3-difluorophenyl)methyl]thio]-6-[2-hydroxy-1-(hydroxymethyl)-1-methylethoxy]-4-pyrimidinyl]-1-azetidinesulfonamide

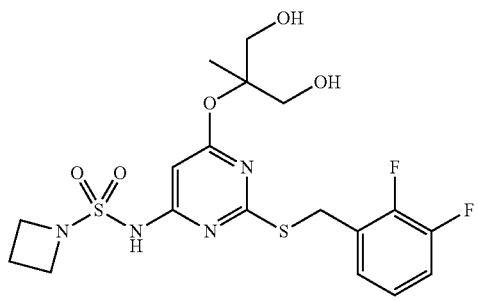 [SMILES: CC(CO)(CO)Oc1cc(NS(=O)(=O)N2CCC2)nc(SCc2cccc(F)c2F)n1]

To a suspension of N-[2-[[(2,3-difluorophenyl)methyl]thio]-6-[(2,2,5-trimethyl-1,3-dioxan-5-yl)oxy]-4-pyrimidinyl]-1-azetidinesulfonamide (the product from step (0.46 g) in DCM (15 mL) was added iron (III) chloride hexahydrate (0.85 g) and the mixture was stirred and ambient temperature for 30 min. A saturated solution of sodium hydrogencarbonate was added and then extracted with DCM (×4). The combined organic layers were dried (MgSO$_4$), filtered and evaporated. The residue was purified by column chromatography on silica gel using a MeOH/DCM (99:1 to 98:2 gradient) as eluent to give the title compound as a white foam. Yield: 100 mg MS: APCI (−ve) 475 [M+H$^+$]

$^1$H NMR: δ (DMSO) 1.43 (s, 3H), 2.15 (quintet, 2H), 3.63 (dd, 2H), 3.73 (dd, 2H), 3.92 (t, 4H), 4.44 (s, 2H), 4.78 (t, 2H), 6.09 (s, 1H), 7.17 (m, 1H), 7.36 (m, 1H), 7.43 (m, 1H), 11.06 (s, 1H)

The intermediates for this compound were prepared as follows:

i) 4-chloro-2-[[(2,3-difluorophenyl)methyl]thio]-6-[(2,2,5-trimethyl-1,3-dioxan-5-yl)oxy]-pyrimidine The subtitle compound was prepared according to the procedure outlined in example 1 step iii) using 2,2,5-trimethyl-1,3-dioxan-5-ol (as prepared in Synthesis, 1998, p 879) (0.29 g) and 4,6-Dichloro-2-[(2,3-difluorobenzyl)thio]pyrimidine (the product of example 1 step (0.51 g) in THF (5 mL) and 60% sodium hydride (80 mg) to give the subtitle compound as a yellow oil. Yield: 0.44 g.

$^1$H NMR: δ (CDCl$_3$) 1.16 (s, 3H), 1.24 (s, 3H), 1.53 (s, 3H), 3.85 (d, 2H), 4.14 (d, 2H), 4.38 (s, 2H), 6.48 (s, 1H), 7.04 (m, 2H), 7.26 (m, 1H)

ii) N-[2-[[(2,3-difluorophenyl)methyl]thio]-6-[(2,2,5-trimethyl-1,3-dioxan-5-yl)oxy]-4-pyrimidinyl]-1-azetidinesulfonamide The subtitle compound was prepared according to the procedure outlined in example 1 step (iv) using a mixture of azetidine-1-sulfonamide (prepared according to patent WO 2004/011443, 0.22 g), tris(dibenzylideneacetone)dipalladium (0) (97 mg), 2-dicyclohexylphosphino-2',4',6'-tri-isopropyl-1,1'-biphenyl (XPHOS) (50 mg), cesium carbonate (0.52 g) and 4-chloro-2-[[(2,3-difluorophenyl)methyl]thio]-6-[(2,2,5-trimethyl-1,3-dioxan-5-yl)oxy]-pyrimidine (0.44 g) in dioxane (10 mL). Purification was by column chromatography on silica gel using EtOAc/isohexane (2:8 to 3:7 gradient) as eluent to give the subtitle compound as a pale yellow oil. Yield: 0.46 g MS: APCI (+ve) 517 [M+H$^+$]

EXAMPLE 11

N-[2-[[(2,3-difluorophenyl)methyl]thio]-6-[(1R)-2-hydroxy-1-methylethoxy]-4-pyrimidinyl]-2-thiazolesulfonamide

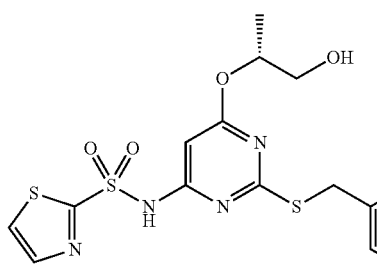

To a solution of 2-[[2-[[(2,3-difluorophenyl)methyl]thio]-6-[(2-thiazolylsulfonyl)amino]-4-pyrimidinyl]oxy]-(2R)-propanoic acid ethyl ester (the product from step ii) (0.11 g) in THF (3 mL) was added lithium borohydride (2M solution in THF, 0.23 mL) and the mixture was mixture was stirred at ambient temperature for 20 h. The reaction mixture was cooled to 0° C., quenched with 0.5M HCl solution and the aqueous was extracted with EtOAc (×2). The combined organic layers were dried (MgSO$_4$), filtered and evaporated. The residue was purified by column chromatography on silica gel using MeOH/DCM (99:1 to 98:2 gradient) as eluent to give the title compound as a white solid. Yield: 15 mg MS: APCI (+ve) 475 [M+H$^+$]

$^1$H NMR: δ (CDCl$_3$) 1.44 (d, 3H), 3.72 (m, 2H), 4.34 (q, 2H), 5.25 (m, 1H), 5.29 (s, 1H), 6.43 (s, 1H), 7.03 (m, 2H), 7.17 (t, 1H), 7.66 (s, 1H), 7.98 (s, 1H)

The intermediates for this compound were prepared as follows:

i) 2-[[6-chloro-2-[[(2,3-difluorophenyl)methyl]thio]-4-pyrimidinyl]oxy]-(2R)-propanoic acid ethyl ester The subtitle compound was prepared according to the procedure outlined in example 1 step iii) using 2-hydroxy-(2R)-propanoic acid ethyl ester (1.45 mL) and 4,6-Dichloro-2-[(2,3-difluorobenzyl)thio]pyrimidine (the product of example 1 step (3 g) in THF (40 mL) and 60% sodium hydride (0.55 g) to give the subtitle compound as a clear, colourless oil. Yield: 2.85 g.

MS: APCI (+ve) 389/391 [M+H$^+$]

ii) 2-[[2-[[(2,3-difluorophenyl)methyl]thio]-6-[(2-thiazolylsulfonyl)amino]-4-pyrimidinyl]oxy]-(2R)-propanoic acid ethyl ester The subtitle compound was prepared according to the procedure outlined in example 1 step (iv) using a mixture of 2-thiazolesulfonamide (0.17 g), tris(dibenzylideneacetone) dipalladium (0) (64 mg), 2-dicyclohexylphosphino-2',4',6'-tri-isopropyl-1,1'-biphenyl (XPHOS) (33 mg), cesium carbonate (0.34 g) and 2-[[6-chloro-2-[[(2,3-difluorophenyl)

methyl]thio]-4-pyrimidinyl]oxy]-(2R)-propanoic acid ethyl ester (0.27 g) in dioxane (5 mL). Purification was by column chromatography on silica using EtOAc/isohexane (1:9 to 1:1 gradient) as eluent to give the subtitle compound as a pale yellow oil. Yield: 0.11 g MS: APCI (+ve) 517 [M+H$^+$]

EXAMPLE 12

N-[6-(difluoromethoxy)-2-[[(2,3-difluorophenyl)methyl]thio]-4-pyrimidinyl]-1-azetidinesulfonamide

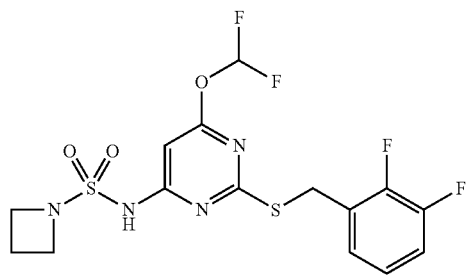 [SMILES: O=S(=O)(Nc1cc(OC(F)F)nc(SCc2cccc(F)c2F)n1)N1CCC1]

The title compound was prepared according to the procedure outlined in example 1 step (iv) using a mixture of azetidine-1-sulphonamide (prepared according to patent WO 2004/011443, 0.11 g), tris(dibenzylideneacetone)dipalladium (0) (0.10 g), 2-dicyclohexylphosphino-2',4',6'-tri-isopropyl-1,1'-biphenyl (XPHOS) (60 mg), cesium carbonate (0.26 g), 4-chloro-6-(difluoromethoxy)-2-[[(2,3-difluorophenyl)methyl]thio]-pyrimidine (product of step (0.18 g) and anhydrous dioxane (5 mL). Purification was by column chromatography on silica gel using EtOAc/isohexane (3:7) as eluent and the relevant fractions were evaporated. The resulting oil was triturated with diethyl ether/iso-hexane to give the title compound as a white solid. Yield: 70 mg MS: APCI (+ve) 439 [M+H$^+$]

$^1$H NMR: δ (DMSO) 2.13 (quintet, 2H), 3.93 (t, 4H), 4.50 (s, 2H), 6.30 (s, 1H), 7.19-7.12 (m, 1H), 7.45-7.30 (m, 2H), 7.79 (t, 1H), 11.53 (s, 1H)

The intermediates for this compound were prepared as follows:

i) 6-(difluoromethoxy)-2-[[(2,3-difluorophenyl)methyl]thio]-4-pyrimidinol

To a solution of 2-[[(2,3-difluorophenyl)methyl]thio]-4,6-pyrimidinediol (3 g) in DMF (30 mL), cesium carbonate (4.3 g) and chlorodifluoro-acetic acid sodium salt (1.9 g) was added. The resulting mixture was heated at 100° C. for 2 h. The reaction mixture was cooled then diluted with H$_2$O and extracted with EtOAc. The organic layer was washed with H$_2$O and dried (MgSO$_4$), filtered and evaporated. Purification was by column chromatography on silica gel using EtOAc/isohexane (2:8) as eluent to give the subtitle compound as a white solid. Yield: 0.4 g MS: APCI (+ve) 421 [M+H$^+$]

$^1$H NMR: δ (DMSO) 4.53 (s, 2H), 7.13-7.22 (m, 1H), 7.30-7.42 (m, 2H), 7.75 (t, 1H)

ii) 4-chloro-6-(difluoromethoxy)-2-[[(2,3-difluorophenyl)methyl]thio]-pyrimidine To a solution of 6-(difluoromethoxy)-2-[[(2,3-difluorophenyl)methyl]thio]-4-pyrimidinol (product of step i) (0.4 g) in 1,2-dimethoxyethane was added benzyltriethylammonium chloride (3 mg) and phosphorous oxychloride (0.23 mL). The resulting mixture was heated to reflux for 16 hours. The reaction mixture was cooled then diluted with H$_2$O and extracted with EtOAc. The organic layer was washed with H$_2$O and dried (MgSO$_4$), filtered and evaporated. Purification was by column chromatography on silica gel using EtOAc/isohexane (2:8) as eluent to give the subtitle compound as a clear, colourless oil. Yield: 0.35 g $^1$H NMR: δ (DMSO) 4.54 (s, 2H), 7.12-7.22 (m, 2H), 7.25 (s, 1H), 7.30-7.42 (m, 2H), 7.81 (t, 1H)

EXAMPLE 13

N-[2-[[(2,3-difluorophenyl)methyl]thio]-6-[(1R)-2-hydroxy-1-methylethoxy]-4-pyrimidinyl]-4-pyridinesulfonamide

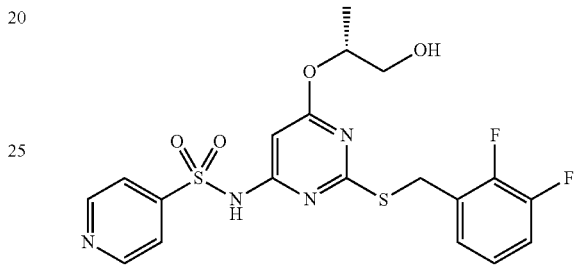

To a solution of N-[2-[[(2,3-difluorophenyl)methyl]thio]-6-[(1R)-1-methyl-2-(triphenylmethoxy)ethoxy]-4-pyrimidinyl]-4-pyridinesulfonamide (the product from step iv). (100 mg) in MeOH (10 mL) was added p-toluenesulfonic acid (31 mg) and anisole (0.15 g). The reaction was then stirred at room temperature for 18 h. The reaction was partitioned between EtOAc (100 mL) and H$_2$O (100 mL). The aqueous layer was then further extracted with EtOAc (2×100 mL). The combined organic layers were dried (MgSO$_4$), filtered and evaporated. The residue was purified by reverse phase HPLC using a TFA (0.2%)/MeCN to give the title compound as a white solid. Yield: 50 mg.

MS: APCI (+ve) 496 [M+H$^+$]

$^1$H NMR: δ (DMSO) 1.13 (d, 3H), 4.30 (s, 2H), 5.06-5.12 (m, 1H), 6.0 (s, 1H), 7.07-7.38 (m, 3H), 7.84 (d, 2H), 8.86 (d, 2H)

The intermediates for this compound were prepared as follows:

i) 4-pyridinesulfonamide

A solution of 4-pyridinethione (3.33 g) in c.HCl (22.5 mL) and H$_2$O (6 mL) was bubbled with chlorine gas at room temperature for 3 h. The reaction mixture was then poured onto ice (15 g), and the slurry was then transferred to ice-cold 0.88 ammonia (120 mL). This mixture was then stirred at room temperature overnight before being concentrated in vacuo until solid began to precipitate. At this point the reaction mixture was cooled overnight in the refrigerator and the solid collected by filtration as a yellow solid. Yield: 1.51 g.

$^1$H NMR: δ (DMSO) 7.73 (s, 2H), 7.75 (d, 2H), 8.84 (d, 2H)

ii) (2R)-1-(triphenylmethoxy)-2-propanol

To a suspension of (2R)-1,2-propanediol (1.9 mL) in toluene (20 mL) was added triethylamine (8.3 mL) and 4-dimethylaminopyridine (32 mg). The mixture was ice-cooled and 1,1',1''-(chloromethylidyne)tris-benzene (6.6 g) was added and the mixture stirred at ambient temperature for 20 h. The reaction mixture was diluted with toluene then extracted with ammonium chloride solution (×2), then brine (×1) and the organic layer was dried (MgSO$_4$), filtered and evaporated. The resulting oil was triturated with iso-hexane to give subtitle compound as a white solid. Yield: 4 g $^1$H NMR: δ (CDCl$_3$) 1.09 (d, 3H), 2.34 (d, 1H), 2.97 (dt, 1H), 3.15 (dd, 1H), 3.97 (m, 1H), 7.23 (m, 3H), 7.28 (m, 6H), 7.45 (m, 6H)

iii) 4-chloro-2-[[(2,3-difluorophenyl)methyl]thio]-6-[(1R)-1-methyl-2-(triphenylmethoxy)ethoxy]-pyrimidine The subtitle compound was prepared according to the procedure outlined in example 1 step (iii) using (2R)-1-(triphenylmethoxy)-2-propanol (1.35 g) and 4,6-Dichloro-2-[(2,3-difluorobenzyl)thio]pyrimidine (the product of example 1 step (ii) (1 g) in THF (15 mL) and 60% sodium hydride (0.18 g) to give the subtitle compound as a pale yellow oil. Yield: 1.8 g.

MS: APCI (+ve) 589 [M+H$^+$]

iv) N-[2-[[(2,3-difluorophenyl)methyl]thio]-6-[(1R)-1-methyl-2-(triphenylmethoxy)ethoxy]-4-pyrimidinyl]-4-pyridinesulfonamide A mixture of 4-pyridinesulfonamide (the product from step i) (0.21 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.66 g) and 4-chloro-2-[[(2,3-difluorophenyl)methyl]thio]-6-[(1R)-1-methyl-2-(triphenylmethoxy)ethoxy]-pyrimidine (the product from step iii) (0.40 g) in dioxane (20 mL) was heated at reflux in a microwave at 100° C., 300 W, open vessel with cooling for 3 h. The reaction mixture was diluted with DCM, filtered through arbocel and the filtrate evaporated. The residue was purified by reverse phase HPLC using a TFA (0.2%)/MeCN system to give the title compound as a yellow solid. Yield: 0.21 g.

MS: APCI (+ve) 711 [M+H$^+$]
$^1$H NMR: δ (DMSO) 8.85-8.76 (m, 2H), 7.83-7.73 (m, 2H), 7.26-7.17 (m, 18H), 6.03 (s, 1H), 5.44-5.35 (m, 1H), 4.29 (s, 2H), 3.08-3.01 (m, 2H), 1.22-1.14 (m, 3H)

EXAMPLE 14

N-[2-[[(2,3-difluorophenyl)methyl]thio]-6-ethoxy-4-pyrimidinyl]-1-azetidinesulfonamide

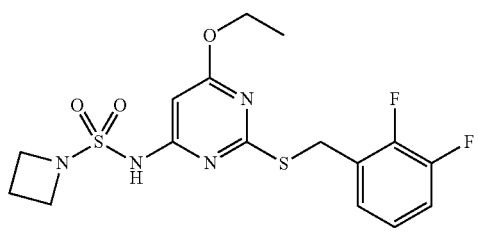 [SMILES: CCOc1cc(NS(=O)(=O)N2CCC2)nc(SCc2cccc(F)c2F)n1]

The title compound was prepared according to the procedure outlined in example 1 step iv) using a mixture of azetidine-1-sulfonamide (prepared according to patent WO 2004/011443, 0.17 g), tris(dibenzylideneacetone)dipalladium (0) (75 mg), 2-dicyclohexylphosphino-2',4',6'-tri-isopropyl-1,1'-biphenyl (XPHOS) (40 mg), cesium carbonate (0.40 g) 4-chloro-2-[[(2,3-difluorophenyl)methyl]thio]-6-ethoxy-pyrimidine (the product from step i) (0.26 g)) in dioxane (5 mL). Purification was by column chromatography on silica gel using EtOAc/isohexane (1:9) as eluent to give the title compound as a white solid. Yield: 0.17 g MS: APCI (−1-ve) 417 [M+H$^+$]
$^1$H NMR: δ (DMSO) 1.27 (t, 3H), 2.13 (quintet, 2H), 3.90 (t, 4H), 4.34 (q, 2H), 4.47 (s, 2H), 6.12 (s, 1H), 7.15 (m, 1H), 7.33 (m, 1H), 7.42 (m, 1H), 11.11 (br s, 1H)

The intermediate for this compound was prepared as follows:

i) 4-chloro-2-[[(2,3-difluorophenyl)methyl]thio]-6-ethoxy-pyrimidine

To a solution of 4,6-Dichloro-2-[(2,3-difluorobenzyl)thio] pyrimidine (0.50 g) in ethanol (5 mL) was added 60% sodium hydride (72 mg) and the reaction mixture was stirred at ambient temperature for 6 h. The mixture was diluted with H$_2$O and extracted with EtOAc (×2). The combined organic layers were dried (MgSO$_4$), filtered and evaporated to give the subtitle compound as a clear, colourless oil. Yield: 0.53 g MS: APCI (±ve) 317/319 [M+H$^+$]

EXAMPLE 15

N-[2-[[(2,3-difluorophenyl)methyl]thio]-6-ethoxy-4-pyrimidinyl]-1-piperazinesulfonamide

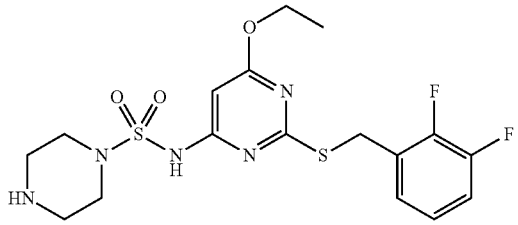

To a solution of 4-[[[2-[[(2,3-difluorophenyl)methyl]thio]-6-ethoxy-4-pyrimidinyl]amino]sulfonyl]-1-piperazinecarboxylic acid-1,1-dimethylethyl ester (the product from step ii) (0.24 g) in DCM (2 mL) was added trifluoroacetic acid (2 mL) and the reaction mixture was stirred at ambient temperature for 2.5 h. The reaction mixture was evaporated, the residue was azeotroped with DCM (×2) and then purified by reverse phase HPLC eluting with acetonitrile/aq. 0.2% trifluoroacetic acid mixtures to give title compound as a white solid. Yield: 0.18 g MS: APCI (−ve) 446 [M+H$^+$]
$^1$H NMR: δ (DMSO) 1.28 (t, 3H), 3.18 (m, 4H), 3.44 (m, 4H), 4.36 (q, 2H), 4.47 (s, 2H), 6.05 (s, 1H), 7.18 (m, 1H), 7.37 (m, 2H), 8.73 (br s, 1H), 11.33 (br s, 1H)

The intermediate for this compound was prepared as follows:

i) 4-(aminosulfonyl)-1,1-dimethylethyl ester-1-piperazinecarboxylic acid

To a solution of 1,1-dimethylethyl ester-1-piperazinecarboxylic acid (2.94 g) in dioxane (40 mL) was added sulfamide (4.0 g). The reaction mixture was then heated at reflux for 24 h. The reaction mixture was allowed to cool before being reduced in vacuo. The residue was separated between EtOAc (300 mL) and H$_2$O (300 mL) and the aqueous was further extracted (2×300 mL) with EtOAc. Combined organic layers were dried (MgSO$_4$), filtered and evaporated. The residue was purified by column chromatography on silica gel using EtOAc/isohexane (1:1) as eluent to give the subtitle compound as a white solid. Yield: 2.03 g.

$^1$H NMR: δ (DMSO) 1.41 (s, 9H), 2.89 (t, 4H), 3.40 (t, 4H), 6.81 (s, 2H)

ii) 4-[[[2-[[(2,3-difluorophenyl)methyl]thio]-6-ethoxy-4-pyrimidinyl]amino]sulfonyl]-1-piperazinecarboxylic acid-1,1-dimethylethyl ester The subtitle compound was prepared according to the procedure outlined in example 1 step (iv) using a mixture of 4-(aminosulfonyl)-1-piperazinecarboxylic acid-1,1-dimethylethyl ester (the product from step i) (0.29 g), tris(dibenzylideneacetone)dipalladium (0) (67 mg), 2-dicyclohexylphosphino-2',4',6'-tri-isopropyl-1,1'-biphenyl (XPHOS) (35 mg), cesium carbonate (0.36 g) and 4-chloro-2-[[(2,3-difluorophenyl)methyl]thio]-6-ethoxy-pyrimidine (the product from example 14, step i) (0.23 g) in dioxane (5 mL). Purification was by column chromatography on silica using EtOAc/isohexane (1:9 to 1:3 gradient) as eluent to give the subtitle compound as a yellow oil. Yield: 0.25 g MS: APCI (−ve) 544 [M+H$^+$]

EXAMPLE 16

N-[2-[[(2,3-difluorophenyl)methyl]thio]-6-(2,2,2-trifluoroethoxy)-4-pyrimidinyl]-1-azetidinesulfonamide

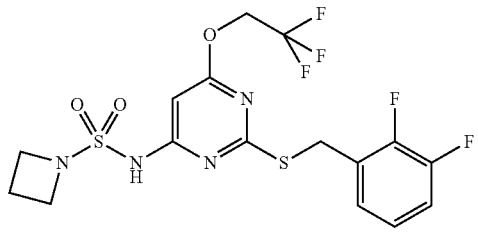 [SMILES: O=S(=O)(Nc1cc(OCC(F)(F)F)nc(SCc2cccc(F)c2F)n1)N1CCC1]

The title compound was prepared according to the procedure outlined in example 1 step iv) using a mixture of azetidine-1-sulfonamide (prepared according to patent WO 2004/011443, 0.14 g), tris(dibenzylideneacetone)dipalladium (0) (60 mg), 2-dicyclohexylphosphino-2',4',6'-tri-isopropyl-1,1'-biphenyl (XPHOS) (30 mg), cesium carbonate (0.32 g) 4-chloro-2-[[(2,3-difluorophenyl)methyl]thio]-6-(2,2,2-trifluoroethoxy)-pyrimidine (the product from step i) (0.24 g) in dioxane (5 mL). Purification was by column chromatography on silica gel using EtOAc/isohexane (1:9 to 2:8 gradient) as eluent to give the title compound as a white solid. Yield: 0.11 g MS: APCI (+ve) 471 [M+H$^+$]

$^1$H NMR: δ (DMSO) 2.1 (quintet, 2H), 3.83 (t, 4H), 4.51 (s, 2H), 5.03 (q, 2H), 6.22 (s, 1H), 7.16 (m, 1H), 7.36 (m, 1H), 7.42 (m, 1H), 11.33 (s, 1H)

The intermediate for this compound was prepared as follows:

i) 4-chloro-2-[[(2,3-difluorophenyl)methyl]thio]-6-(2,2,2-trifluoroethoxy)-pyrimidine The subtitle compound was prepared according to the procedure outlined in example 1 step iii) using 2,2,2-trifluoroethanol (0.16 mL) and 4,6-Dichloro-2-[(2,3-difluorobenzyl)thio]pyrimidine (the product of example 1 step ii) (0.60 g) in THF (6 mL) and 60% sodium hydride (94 mg) to give the subtitle compound as a clear, colourless oil. Yield: 0.6 g $^1$H NMR: δ (DMSO) 4.54 (s, 2H, 5.14 (m, 2H), 7.13 (s, 1H), 7.19 (m, 1H), 7.37 (m, 2H)

EXAMPLE 17

N-[2-[[(2,3-difluorophenyl)methyl]thio]-6-(2,2,2-trifluoroethoxy)-4-pyrimidinyl]-1-piperazinesulfonamide

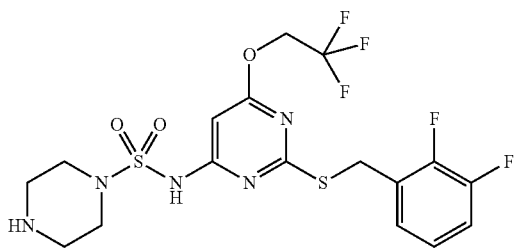 [SMILES: O=S(=O)(Nc1cc(OCC(F)(F)F)nc(SCc2cccc(F)c2F)n1)N1CCNCC1]

To a solution of 4-[[[2-[[(2,3-difluorophenyl)methyl]thio)-6-(2,2,2-trifluoroethoxy)-4-pyrimidinyl]amino]sulfonyl]-1-piperazinecarboxylic acid-1,1-dimethylethyl ester (the product from step i) (0.21 g) in DCM (2 mL) was added trifluoroacetic acid (2 mL) and the reaction mixture was stirred at ambient temperature for 4 h. The reaction mixture was evaporated, the residue was azeotroped with Et$_2$O (×2) and then purified by reverse phase HPLC eluting with acetonitrile/aq. 0.2% trifluoroacetic acid mixtures to give title compound as a white solid. Yield: 0.14 g MS: APCI (+ve) 500 [M+H$^+$]

$^1$H NMR: δ (DMSO) 3.17 (m, 4H), 3.50 (m, 4H), 4.51 (s, 2H), 5.06 (q, 2H), 6.17 (s, 1H), 6.96-7.42 (m, 3H), 8.82 (br s, 2H)

The intermediate for this compound was prepared as follows:

i) 4-[[[2-[[(2,3-difluorophenyl)methyl]thio]-6-(2,2,2-trifluoroethoxy)-4-pyrimidinyl]amino]sulfonyl]-1-piperazinecarboxylic acid-1,1-dimethylethyl ester The subtitle compound was prepared according to the procedure outlined in example 1 step (iv) using a mixture of 4-(aminosulfonyl)-1-piperazinecarboxylic acid-1,1-dimethylethyl ester (the product from example 15, step i), 0.40 g), tris(dibenzylideneacetone)dipalladium (0) (91 mg), 2-dicyclohexylphosphino-2',4',6'-tri-isopropyl-1,1'-biphenyl (XPHOS) (48 mg), cesium carbonate (0.49 g) and 4-chloro-2-[[(2,3-difluorophenyl)methyl]thio]-6-(2,2,2-trifluoroethoxy)-pyrimidine (the product from example 16, step i) (0.37 g) in dioxane (6 mL). Purification was by column chromatography on silica gel using EtOAc/isohexane (1:9 to 2:8 gradient) as eluent to give the subtitle compound as a yellow solid. Yield: 0.22 g MS: APCI (−ve) 598 [M+H$^−$]

EXAMPLE 18

N-[2-[[(2,3-difluorophenyl)methyl]thio]-6-(1,1-dimethylethoxy)-4-pyrimidinyl]-1-azetidinesulfonamide

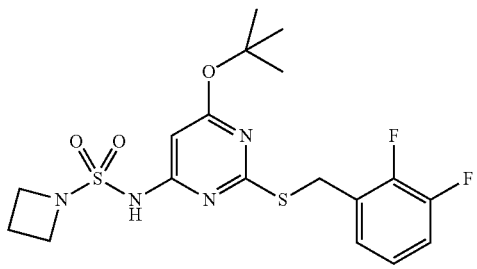 [SMILES: CC(C)(C)Oc1cc(NS(=O)(=O)N2CCC2)nc(SCc2cccc(F)c2F)n1]

The title compound was prepared according to the procedure outlined in example 1 step iv) using a mixture of azetidine-1-sulfonamide (prepared according to patent WO 2004/011443, 0.16 g), tris(dibenzylideneacetone)dipalladium (0) (70 mg), 2-dicyclohexylphosphino-2',4',6'-tri-isopropyl-1,1'-biphenyl (XPHOS) (36 mg), cesium carbonate (0.37 g) and 4-chloro-2-[[(2,3-difluorophenyl)methyl]thio]-6-(1,1-dimethylethoxy)-pyrimidine (the product from step i) (0.26 g) in dioxane (6 mL). Purification was by column chromatography on silica gel using EtOAc/isohexane (1:9 to 2:8 gradient) as eluent to give the title compound as a white solid.

Yield: 0.28 g

MS: APCI (−ve) 443 [M+H$^-$]

$^1$H NMR: δ (DMSO) 1.48 (s, 9H), 2.16 (quintet, 2H), 3.92 (t, 4H), 4.46 (s, 2H), 6.03 (s, 1H), 7.17 (m, 1H), 7.35 (m, 1H), 7.42 (m, 1H), 11.05 (br s, 1H)

The intermediate for this compound was prepared as follows:

i) 4-chloro-2-[[(2,3-difluorophenyl)methyl]thio]-6-(1,1-dimethylethoxy)-pyrimidine To a solution of 4,6-Dichloro-2-[(2,3-difluorobenzyl)thio] pyrimidine (the product of example 1 step (2 g) in THF (20 mL) was added potassium tert-butoxide (0.8 g) and the reaction mixture was stirred at ambient temperature for 20 h. Further potassium tert-butoxide (0.8 g) was added and the reaction mixture was stirred at ambient temperature for 4 1. The mixture was diluted with H$_2$O and extracted with EtOAc (×3). The combined organic layers were washed with H$_2$O and dried (MgSO$_4$), filtered and evaporated. The resulting oil was purified by column chromatography on silica gel using MeOH/DCM (99:1 to 98:2 gradient) as eluent to give the subtitle compound as a clear, colourless oil. Yield: 0.68 g $^1$H NMR: δ (DMSO) 1.50 (s, 9H), 4.47 (s, 2H), 6.70 (s, 1H), 7.19 (m, 1H), 7.37 (m, 2H)

EXAMPLE 19

N-[2-[[(2,3-difluorophenyl)methyl]thio]-6-[[2-hydroxy-1-(hydroxymethyl)ethyl]thio]-pyrimidin-4-yl]azetidine-1-sulfonamide

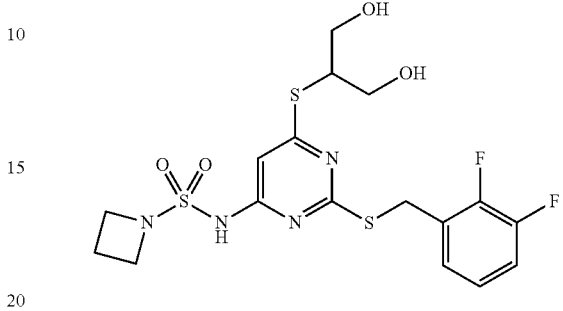

A solution of N-[2-[[(2,3-difluorophenyl)methyl]thio]-6-[(2-phenyl-1,3-dioxan-5-yl)thio]pyrimidin-4-yl]azetidine-1-sulfonamide (the product of step (0.11 g) and pyridinium para-toluenesulfonate (99 mg) in methanol (5 mL) and H$_2$O (2 drops) was heated at 60° C. for 1 h. The solution was cooled and the solvent evaporated under reduced pressure. The residue was dissolved in EtOAc, washed with H$_2$O, dried (MgSO$_4$) and filtered. The solvent was evaporated under reduced pressure and the residue was purified by flash chromatography on silica gel, eluting with EtOAc/iso-hexane (8:2) to give the subtitle product as a yellow gum. The gum was dissolved in DCM and methanol, filtered through charcoal and the filtrate evaporated under reduced pressure. The residual solid was dried under high vacuum at 40° C. to give the title product as a white solid. Yield: 50 mg MS: APCI (−ve) 477 [M−H]

$^1$H NMR: δ (DMSO) 2.13 (m, 2H), 3.66 (octet, 4H), 3.92 (t, 5H), 4.49 (s, 2H), 4.99 (t, 2H), 6.65 (s, 1H), 7.17 (m, 1H), 7.36 (m, 2H), 11.18 (s, 1H).

The intermediates for this compound were prepared as follows:

i) 4-Chloro-2-[[(2,3-difluorophenyl)methyl]thio]-6-[(2-phenyl-1,3-dioxan-5-yl)thio]pyrimidine Sodium methoxide (0.1 mL of 25-30% methanol solution) was added to a solution of ethyl S-(2-phenyl-1,3-dioxan-5-yl)ethanethioate (0.12 g; prepare according to the procedure in *Chem. Pharm. Bull.*, 2000, 48, (5), p 694-707) in THF (2 mL). After stirring for 15 min, the product of Example 1, step (0.12 g) was added. The reaction mixture was stirred at room temperature for 18 h. The solvent was evaporated under reduced pressure and the residue purified by flash chromatography on silica gel, eluting with Et$_2$O/iso-hexane (1:9) to give the subtitle product as a beige solid. Yield: 0.18 g.

MS: APCI (+ve) 467/469 [M+H]

ii) N-[2-[[(2,3-Difluorophenyl)methyl]thio]-6-[(2-phenyl-1,3-dioxan-5-yl)thio]pyrimidin-4-yl]azetidine-1-sulfonamide The subtitle compound was prepared from azetidine-1-sulfonamide (prepared according to patent WO 2004/011443, 0.11 g) and 4-Chloro-2-[[(2,3-difluorophenyl)methyl]thio]-6-[(2-phenyl-1,3-dioxan-5-yl)thio]pyrimidine (the product of step i) (0.17 g) according to the procedure outlined in Example 1, step iv). The residue was purified by flash chromatography on silica gel, eluting with EtOAc/iso-hexane (2:8) to give the subtitle compound as a colourless oil. Yield: 0.11 g MS: APCI (+ve) 567 [M+H]

EXAMPLE 20

N-[2-[[(2,3-difluorophenyl)methyl]thio]-6-[(1R)-2-hydroxy-1-methylethoxy]-4-pyrimidinyl]-1-piperazinesulfonamide

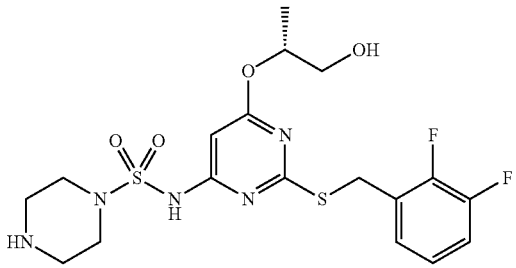 [SMILES: C[C@H](CO)Oc1cc(NS(=O)(=O)N2CCNCC2)nc(SCc2cccc(F)c2F)n1]

To a solution of 4-[[[2-[[(2,3-difluorophenyl)methyl]thio]-6-[(1R)-2-hydroxy-1-methylethoxy]-4-pyrimidinyl]amino]sulfonyl], 1,1-dimethylethyl ester1-piperazinecarboxylic acid (the product of step ii) (0.23 g) in DCM (3 mL) was added trifluoroacetic acid (3 mL). The reaction mixture was then stirred at room temperature for 1 h. The solvent was removed and the residue purified by reverse phase HPLC using a TFA (0.2%)/MeCN method to give the title compound as a white solid. Yield: 77 mg MS: APCI (+ve) 476 [M+H⁺]

$^1$H NMR: δ (DMSO) 1.13 (d, 3H), 3.01-3.05 (m, 4H), 3.13-3.17 (m, 4H), 4.34-4.41 (m, 2H), 4.79 (s, 1H), 4.97-5.05 (m, 1H), 5.84 (s, 1H), 7.10-7.16 (m, 1H), 7.27-7.34 (m, 1H), 7.39-7.45 (m, 1H)

The intermediates for this compound were prepared as follows:

(i) 4-[[[2-[[(2,3-difluorophenyl)methyl]thio]-6-[(1R)-2-ethoxy-1-methyl-2-oxoethoxy]-4-pyrimidinyl]amino]sulfonyl], 1,1-dimethylethyl ester1-piperazinecarboxylic acid A mixture of 4-(aminosulfonyl)-1,1-dimethylethyl ester-1-piperazinecarboxylic acid (the product of example 15 step i) (0.40 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (1 g) and (2R)-propanoic acid-2-[[6-chloro-2-[[(2,3-difluorophenyl)methyl]thio]-4-pyrimidinyl]oxy]-, ethyl ester (the product from example 11 step i) (0.40 g) in dioxane (20 mL) was heated at reflux in a microwave at 100° C., 300 W, open vessel with cooling for 20 min. The reaction was filtered through arbocel and then separated between EtOAc (200 mL) and H$_2$O (200 mL) and the aqueous was then further extracted with EtOAc (2×200 mL). The combined organic layers were dried (MgSO$_4$), filtered and evaporated to give the subtitle compound as a clear oil.

Yield: 0.93 g.

MS: APCI (+ve) 618 [M+H⁺]

(ii), 4-[[[2-[[(2,3-difluorophenyl)methyl]thio]-6-[(1R)-2-hydroxy-1-methylethoxy]-4-pyrimidinyl]amino]sulfonyl]-, 1,1-dimethylethyl ester1-piperazinecarboxylic acid To a solution of 4-[[[2-[[(2,3-difluorophenyl)methyl]thio]-6-[(1R)-2-hydroxy-1-methylethoxy]-4-pyrimidinyl]amino]sulfonyl], 1,1-dimethylethyl ester-1-piperazinecarboxylic acid (the product from step i) (0.93 g) in THF (20 mL) was added 2M LiBH$_4$ in THF (3.0 mL). The reaction mixture was then heated in a microwave at 50° C., 300 W, open vessel with cooling for 10 min. The reaction mixture was then quenched with 2N HCl and the volatiles evaporated. The residue was then separated between EtOAc (200 mL) and H$_2$O (200 mL), the aqueous was then further extracted with EtOAc (2×200 mL). The combined organic layers were dried (MgSO$_4$), filtered and evaporated and the residue purified by reverse phase HPLC using a TFA (0.2%)/MeCN method to give the title compound as a clear oil.

Yield: 0.23 g.

MS: APCI (+ve) 576 [M+H⁺]

EXAMPLE 21

N-[6-(difluoromethoxy)-2-[[(2,3-difluorophenyl)methyl]thio]-4-pyrimidinyl]-1-methyl-1H-imidazole-4-sulfonamide

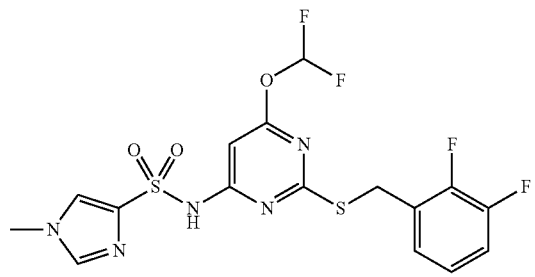 [SMILES: Cn1cnc(S(=O)(=O)Nc2cc(OC(F)F)nc(SCc3cccc(F)c3F)n2)c1]

The title compound was prepared according to the procedure outlined in example 1 step (iv) using a mixture of 1-methyl-1H-imidazole-4-sulfonamide (0.25 g), tris(dibenzylideneacetone)dipalladium (0) (0.10 g), 2-dicyclohexylphosphino-2',4',6'-tri-isopropyl-1,1'-biphenyl (XPHOS) (60 mg), cesium carbonate (0.26 g), 4-chloro-6-(difluoromethoxy)-2-[[(2,3-difluorophenyl)methyl]thio]-pyrimidine (product of example 12, step (0.18 g) and anhydrous dioxane (5 ml). Purification was by tituration with methanol/DCM. The resulting white solid was diluted with H$_2$O and extracted with EtOAc. The organic layer was washed with H$_2$O (×2) then brine and dried (MgSO$_4$), filtered and evaporated. The resulting oil was triturated with methanol/DCM to give the title compound as a white solid. Yield: 15 mg MS: APCI (+ve) 464 [M+H⁺]

$^1$H NMR: δ (DMSO) 3.67 (s, 3H), 4.45 (s, 2H), 6.38 (s, 1H), 7.10-7.18 (m, 1H), 7.30-7.40 (m, 2H), 7.70 (t, 1H), 7.82 (s, 1H), 8.08 (s, 1H)

EXAMPLE 22

N-[2-[[(2,3-difluorophenyl)methyl]thio]-6-[(1R)-2-hydroxy-1-methylethoxy]-4-pyrimidinyl]-1,6-dihydro-1-methyl-6-oxo-3-pyridinesulfonamide

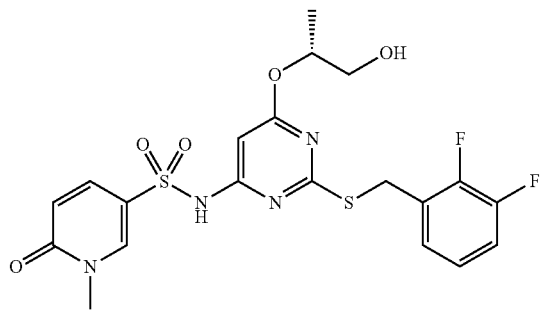 [SMILES: C[C@H](CO)Oc1cc(NS(=O)(=O)c2ccc(=O)n(C)c2)nc(SCc2cccc(F)c2F)n1]

To a solution of N-[2-[[(2,3-difluorophenyl)methyl]thio]-6-[(1R)-1-methyl-2-(triphenylmethoxy)ethoxy]-4-pyrimidinyl]-1,6-dihydro-1-methyl-6-oxo-3-pyridinesulfonamide (the product from step ii) (0.16 g) in MeOH (10 mL) was added p-toluenesulfonic acid (50 mg) and anisole (0.22 g). The reaction was then stirred at room temperature for 18 h. The reaction was partitioned between EtOAc (100 mL) and H₂O (100 mL). The aqueous layer was then further extracted with EtOAc (2×100 mL). Combined organic layers were dried (MgSO₄), filtered and evaporated. The residue was purified by reverse phase HPLC using TFA (0.2%)/MeCN to give a white solid. Yield: 9 mg.

MS: APCI (+ve) 499 [M+H⁺]

¹H NMR: δ (CD₃OD) 1.12 (d, 3H), 3.47 (s, 3H), 3.50-3.53 (m, 2H), 4.30-4.33 (m, 2H), 5.08-5.19 (m, 1H), 5.95 (s, 1H), 6.45 (d, 1H), 6.93-7.11 (m, 2H), 7.14-7.21 (m, 1H), 7.69-7.74 (m, 1H), 8.39 (d, 1H)

The intermediates for this compound were prepared as follows:

i) [(1,6-dihydro-1-methyl-6-oxo-3-pyridinyl)sulfonyl]-, 1,1-dimethylethyl ester carbamic acid Chlorosulfonyl isocyanate (6 mL) was added dropwise to a solution of 2-methyl-2-propanol (6.5 mL) in DCM (75 mL) at 0° C. After 5 min, 1-methyl-2(1H)-pyridinone (9 mL) was added dropwise followed by N,N-diisopropylethylamine (14.5 mL) also added dropwise. The reaction mixture was then allowed to warm to room temperature over 18 h. H₂O (100 mL) was added to the reaction mixture and the organic layer was separated. The aqueous was then further extracted with DCM (2×100 mL). The combined organic layers were dried (MgSO₄), filtered and evaporated to give the subtitle compound as a pale yellow oil. Yield: 7 g ¹H NMR: δ (CDCl₃) 1.45 (s, 9H), 3.62 (s, 3H), 6.60-6.64 (m, 1H), 7.69-7.74 (m, 1H), 8.21-8.24 (m, 1H)

ii) 4-pyridinesulfonamide-N-[2-[[(2,3-difluorophenyl)methyl]thio]-6-[(1R)-1-methyl-2-(triphenylmethoxy)ethoxy]-4-pyrimidinyl]

A mixture of [(1,6-dihydro-1-methyl-6-oxo-3-pyridinyl)sulfonyl]-, 1,1-dimethylethyl ester carbamic acid (the product from step i) (0.60 g), tris(dibenzylideneacetone)dipalladium (0) (50 mg), 2-dicyclohexylphosphino-2',4',6'-triisopropyl-1,1'-biphenyl (XPHOS) (50 mg), cesium carbonate (1 g) and 4-chloro-2-[[(2,3-difluorophenyl)methyl]thio]-6-[(1R)-1-methyl-2-(triphenylmethoxy)ethoxy]-pyrimidine (the product of example 13 step iii), 0.40 g) in dioxane (20 mL) was heated at reflux in a microwave at 100° C., 300 W, open vessel with cooling for 3 h. The reaction mixture was diluted with DCM, filtered through arbocel and the filtrate evaporated. The residue was purified by reverse phase HPLC using a TFA (0.2%)/MeCN system to give the subtitle compound as a yellow solid. Yield: 0.12 g.

MS: APCI (+ve) 741 [M+H⁺]

¹H NMR: δ (DMSO) 1.16-1.23 (m, 3H), 3.06 (d, 2H), 3.35 (s, 3H), 4.33-4.41 (m, 2H), 5.39-5.47 (m, 1H), 6.06 (s, 1H), 6.47 (d, 1H), 7.04-7.11 (m, 2H), 7.17-7.34 (m, 17H), 7.67-7.71 (m, 1H), 8.54-8.56 (m, 1H)

EXAMPLE 23

2-[[6[(1-azetidinylsulfonyl)amino]-2-[[(2,3-difluorophenyl)methyl]thio]-4-pyrimidinyl]oxy]-(2R)-propanoic acid ethyl ester

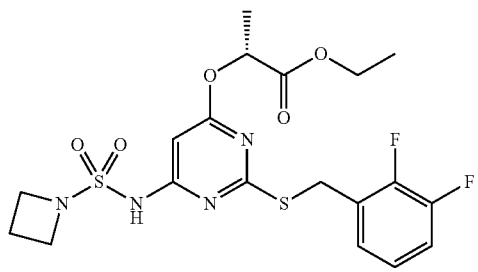 [SMILES: CCOC(=O)[C@@H](C)Oc1cc(NS(=O)(=O)N2CCC2)nc(SCc2cccc(F)c2F)n1]

The title compound was prepared according to the procedure outlined in example 1 step (iv) using a mixture of azetidine-1-sulfonamide (prepared according to patent WO 2004/011443, 0.61 g), tris(dibenzylideneacetone)dipalladium (0) (0.15 g), 2-dicyclohexylphosphino-2',4',6'-tri-isopropyl-1,1'-biphenyl (XPHOS) (105 mg), cesium carbonate (0.77 g), 2-[[6-chloro-2-[[(2,3-difluorophenyl)methyl]thio]-4-pyrimidinyl]oxy]-(2R)-propanoic acid ethyl ester (the product of example 11, step i) (0.61 g) and dioxane (15 mL). Purification was by column chromatography on silica gel using MeOH/DCM (5:95) as eluent, followed by reverse phase HPLC (symmetry as the stationary phase and TFA/acetonitrile as the mobile phase) to give the title compound as a white solid. Yield: 46 mg MS: APCI (+ve) 489 [M+H⁺]

¹H NMR: δ (DMSO) 1.12 (t, 3H), 1.49 (d, 3H), 2.14 (quintet, 2H), 3.92 (t, 4H), 4.05-4.16 (m, 2H), 4.42 (dd, 2H), 5.26 (q, 1H), 6.21 (s, 1H), 7.12-7.21 (m, 1H), 7.31-7.41 (m, 2H), 11.24 (s, 1H)

EXAMPLE 24

N-[2-[[(2,3-difluorophenyl)methyl]thio]-6-[(1R)-2-hydroxy-1-methylethoxy]-4-pyrimidinyl]-1-azetidinesulfonamide

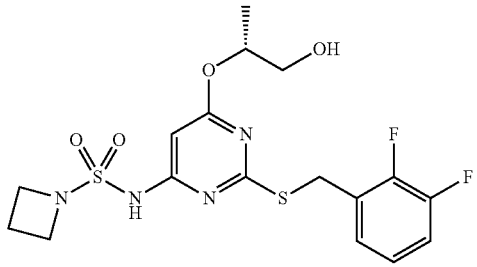 [SMILES: C[C@H](CO)Oc1cc(NS(=O)(=O)N2CCC2)nc(SCc2cccc(F)c2F)n1]

To a suspension of 2-[[6-[(1-azetidinylsulfonyl)amino]-2-[[(2,3-difluorophenyl)methyl]thio]-4-pyrimidinyl]oxy]-(2R)-propanoic acid ethyl ester, (the product of example 23) (0.40 g) in TI-IF (10 mL) was added 2M lithium borohydride in THF (0.82 mL) dropwise and the mixture was stirred at ambient temperature for 20 h. The reaction mixture was cooled to 0° C. and quenched with 1M aqueous hydrochloric acid. The resulting mixture was extracted with EtOAc (×2). The combined organic layers were washed with 1M aqueous hydrochloric acid then brine and was dried (MgSO$_4$), filtered and evaporated. The residue was purified by column chromatography on silica gel using EtOAc/isohexane (1:1) as eluent. The resulting oil was triturated with DCM to give the title compound as a white solid. Yield: 0.25 g MS: APCI (−ve) 445 [M−H$^-$]

$^1$H NMR δ (CD$_3$OD) 1.15 (d, 3H), 2.11 (quintet, 2H), 3.54 (d, 2H), 3.88 (t, 4H), 4.36 (dd, 2H), 5.16 (dt, 1H), 6.12 (s, 1H), 6.93-7.12 (m, 2H), 7.22-7.31 (m, 1H)

EXAMPLE 25

N-[2-[[(2,3-difluorophenyl)methyl]thio]-6-[(1S)-2-hydroxy-1-methylethoxy]-4-pyrimidinyl]-1-azetidinesulfonamide

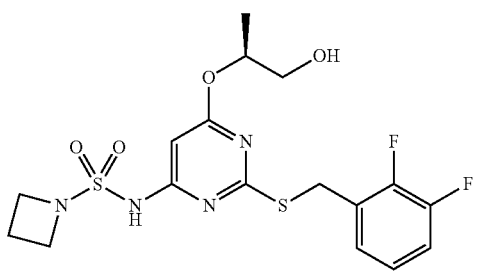 [SMILES: C[C@@H](CO)Oc1cc(NS(=O)(=O)N2CCC2)nc(SCc2cccc(F)c2F)n1]

The title compound was prepared according to the procedure outlined in example 24 using 2-[[6-[(1-azetidinylsulfonyl)amino]-2-[[(2,3-difluorophenyl)methyl]thio]-4-pyrimidinyl]oxy]-(2S)-propanoic acid, ethyl ester, (the product of step ii) (0.28 g), THF (8 mL) and 2M lithium borohydride in THF (0.57 mL). Purification was by column chromatography on silica using EtOAc/isohexane (2:3) as eluent to give the title compound as a white solid. Yield: 0.15 g MS: APCI (−ve) 445 [M−H$^-$]

$^1$H NMR: δ (CD$_3$OD) 1.27 (d, 3H), 2.23 (quintet, 2H), 3.66 (d, 2H), 4.00 (t, 4H), 4.48 (dd, 2H), 5.28 (q, 1H), 6.24 (s, 1H), 7.05-7.23 (m, 2H), 7.33-7.43 (m, 1H)

The intermediates for this compound were prepared as follows:

i) 2-[[6-chloro-2-[[(2,3-difluorophenyl)methyl]thio]-4-pyrimidinyl]oxy]-(2S)-propanoic acid ethyl ester The subtitle compound was prepared according to the procedure outlined in example 1 step iii) using 4,6-Dichloro-2-[(2,3-difluorobenzyl)thio]pyrimidine (product of example 1 step ii) (0.77 g), THF (15 mL), 2-hydroxy-(2S)-propanoic acid ethyl ester (0.40 mL) and 60% sodium hydride (0.14 g) to give the subtitle compound as a clear, colourless oil. Yield: 1 g MS: APCI (+ve) 389/391 [M+H$^+$]

$^1$H NMR: δ (DMSO) 1.13 (t, 3H), 1.51 (d, 3H), 3.99-4.17 (m, 2H), 4.37-4.50 (m, 2H), 5.28-5.38 (m, 1H), 7.02 (s, 1H), 7.13-7.23 (m, 1H), 7.28-7.42 (m, 2H)

ii) 2-[[6-[(1-azetidinylsulfonyl)amino]-2-[[(2,3-difluorophenyl)methyl]thio]-4-pyrimidinyl]oxy]-(2S)-propanoic acid ethyl ester The subtitle compound was prepared according to the procedure outlined in example 1 step (iv) using a mixture of azetidine-1-sulfonamide (prepared according to patent WO 2004/011443, 0.13 g), tris(dibenzylideneacetone)dipalladium (0) (58 mg), 2-dicyclohexylphosphino-2',4',6'-tri-isopropyl-1,1'-biphenyl (XPHOS) (42 mg), cesium carbonate (0.31 g), 2-[[6-chloro-2-[[(2,3-difluorophenyl)methyl]thio]-4-pyrimidinyl]oxy]-(2S)-propanoic acid ethyl ester (product of step i) (0.25 g) and dioxane (10 mL). Purification was by column chromatography on silica gel using EtOAc/isohexane (3:7) as eluent to give the subtitle compound as clear, colourless oil. Yield: 0.28 g MS: APCI (+ve) 489 [M+H$^+$]

EXAMPLE 26

2-[[6-[(1-azetidinylsulfonyl)amino]-2-[[(2,3-difluorophenyl)methyl]thio]-4-pyrimidinyl]oxy]-(2R)-propanamide

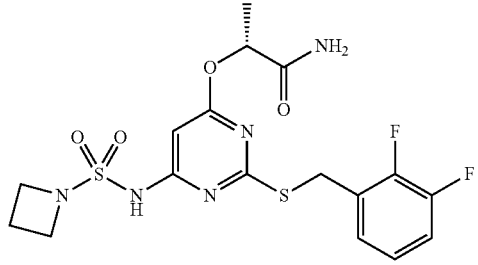 [SMILES: C[C@@H](Oc1cc(NS(=O)(=O)N2CCC2)nc(SCc2cccc(F)c2F)n1)C(N)=O]

To a solution of 2-[[6-chloro-2-[[(2,3-difluorophenyl)methyl]thio]-4-pyrimidinyl]oxy]-(2R)-propanoic acid ethyl ester (the product of example 23) (103 mg) in methanol (8 mL) ammonia gas was bubbled through at 0° C. The resulting mixture was stirred in a sealed tube at ambient temperature for 48 h. The solvent was evapourated under reduced pressure and the resulting solid was triturated with ether to give the title compound was a white solid. Yield: 88 mg MS: APCI (+ve) 460 [M+H$^+$]

¹H NMR: δ (DMSO) 1.43 (d, 3H), 2.13 (quintet, 2H), 3.91 (t, 4H), 4.45 (dd, 2H), 5.21 (q, 1H), 6.23 (s, 1H), 7.13-7.20 (m, 2H), 7.31-7.43 (m, 2H), 7.59 (s, 1H), 11.17 (s, 1H)

EXAMPLE 27

2-[[6-[(1-azetidinylsulfonyl)amino]-2-[[(2,3-difluorophenyl)methyl]thio]-4-pyrimidinyl]oxy]-N-methyl-(2R)-propanamide

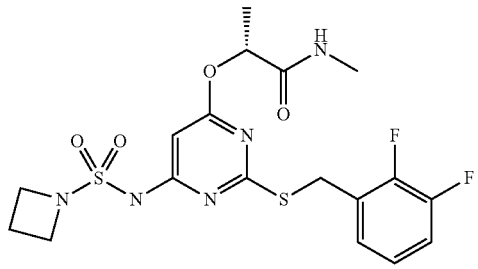 [SMILES: CNC(=O)[C@@H](C)Oc1cc(NS(=O)(=O)N2CCC2)nc(SCc2cccc(F)c2F)n1]

To a solution of 2-[[6-chloro-2-[[(2,3-difluorophenyl)methyl]thio]-4-pyrimidinyl]oxy]-(2R)-propanoic acid ethyl ester (the product of example 23) (100 mg) in ethanol (1.5 mL) was added 8M methylamine in ethanol. The resulting mixture was stirred in a sealed tube at ambient temperature for 16 h. The solvent was evaporated under reduced pressure. Purification was by reverse phase HPLC (symmetry as the stationary phase and TFA/acetonitrile as the mobile phase) to give the title compound as a white solid. Yield: 60 mg MS: APCI (+ve) 474 [M+H⁺]

¹H NMR: δ (DMSO) 1.41 (d, 3H), 2.14 (quintet, 2H), 2.57 (d, 3H), 3.92 (t, 4H), 4.43 (dd, 2H), 5.26 (q, 1H), 6.23 (s, 1H), 7.12-7.21 (m, 1H), 7.30-7.41 (m, 2H), 8.00-8.07 (m, 1H), 11.18 (s, 1H)

EXAMPLE 28

2-[[6-[(1-azetidinylsulfonyl)amino]-2-[[(2,3-difluorophenyl)methyl]thio]-4-pyrimidinyl]oxy]-(2R)-propanoic acid

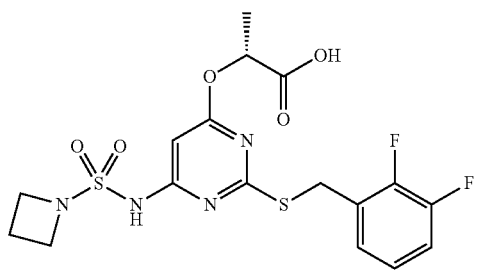 [SMILES: C[C@@H](Oc1cc(NS(=O)(=O)N2CCC2)nc(SCc2cccc(F)c2F)n1)C(=O)O]

To a solution of 2-[[6-chloro-2-[[(2,3-difluorophenyl)methyl]thio]-4-pyrimidinyl]oxy]-(2R)-propanoic acid ethyl ester (the product of example 23) (0.24 g) in methanol (1 mL) was added 1M aqueous sodium hydroxide (1 mL). The resulting mixture was stirred at ambient temperature for 16 h. The reaction mixture was acidified using 2M aqueous HCl, then extracted with EtOAc (×2). The combined organics were washed with brine then dried (MgSO₄), filtered and evaporated. The resulting oil was triturated with DCM/iso-hexane to give the title compound was a white solid. Yield: 0.20 g MS: APCI (−ve) 459 [M−H⁻]

¹H NMR: δ (DMSO) 1.49 (d, 3H), 2.13 (quintet, 2H), 3.91 (t, 4H), 4.43 (dd, 2H), 5.23 (q, 1H), 6.19 (s, 1H), 7.12-7.21 (m, 1H), 7.30-7.42 (m, 2H)

EXAMPLE 29

N-[2-[[(2,3-difluorophenyl)methyl]thio]-6-[(1R)-2-hydroxy-1-methylethoxy]-4-pyrimidinyl]-methanesulfonamide

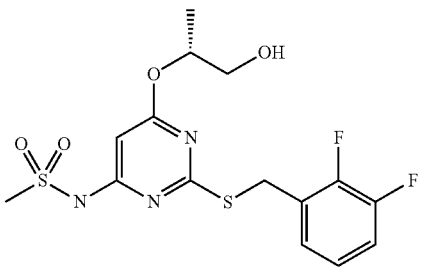 [SMILES: C[C@H](CO)Oc1cc(NS(C)(=O)=O)nc(SCc2cccc(F)c2F)n1]

The title compound was prepared according to the procedure outlined in example 24 using a mixture of 2-[[2-[[(2,3-difluorophenyl)methyl]thio]-6-[(methylsulfonyl)amino]-4-pyrimidinyl]oxy]-(2R)-propanoic acid ethyl ester, (the product of step i) (0.28 g), THF (8 mL) and 2M lithium borohydride in THF (1.3 mL). Purification was by reverse phase HPLC (symmetry as the stationary phase and TFA/acetonitrile as the mobile phase). The resulting oil was triturated with toluene, DCM, then ether/iso-hexane to give the title compound as a white solid. Yield: 0.18 g MS: APCI (−ve) 440 [M−H⁻]

¹H NMR: δ (DMSO) 1.17 (d, 3H), 3.29 (s, 3H), 3.47-3.50 (m, 3H), 4.47 (dd, 2H), 5.09-5.18 (m, 1H), 5.99 (s, 1H), 7.13-7.21 (m, 1H), 7.29-7.43 (m, 2H), 11.14 (s, 1H)

The intermediate for this compound was prepared as follows:

i) 2-[[2-[[(2,3-difluorophenyl)methyl]thio]-6-[(methylsulfonyl)amino]-4-pyrimidinyl]oxy]-(2R)-propanoic acid ethyl ester The subtitle compound was prepared according to the procedure outlined in example 1 step iv) using a mixture of methanesulfonamide (93 mg), tris(dibenzylideneacetone)dipalladium (0) (71 mg), 2-dicyclohexylphosphino-2',4',6'-triisopropyl-1,1'-biphenyl (XPHOS) (52 mg), cesium carbonate (0.38 g), 2-[[6-chloro-2-[[(2,3-difluorophenyl)methyl]thio]-4-pyrimidinyl]oxy]-(2R)-propanoic acid ethyl ester (the product of Example 23 step i) (0.30 g) and dioxane (10 mL). Purification was by column chromatography on silica using EtOAc/isohexane (1:1) as eluent to give the subtitle compound as an oil. Yield: 0.28 g MS: APCI (+ve) 448 [M+H⁺]

EXAMPLE 30

N-[2-[[(2,3-difluorophenyl)methyl]thio]-6-[(1R)-2-hydroxy-1-methylethoxy]-4-pyrimidinyl]-4-morpholinesulfonamide

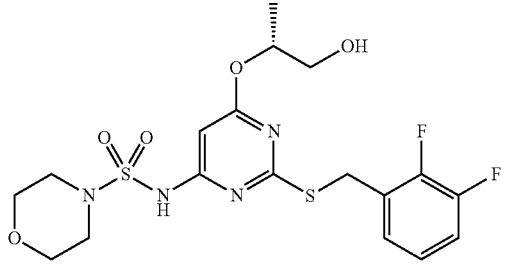 [SMILES: C[C@H](CO)Oc1cc(NS(=O)(=O)N2CCOCC2)nc(SCc2cccc(F)c2F)n1]

The title compound was prepared according to the procedure outlined in example 24 using a mixture of 2-[[2-[[(2,3-difluorophenyl)methyl]thio]-6-[(4-morpholinylsulfonyl)amino]-4-pyrimidinyl]oxy]-(2R)-propanoic acid ethyl ester, (the product of step i) (0.34 g), THF (8 mL) and 2M lithium borohydride in THF (1 mL). Purification was by reverse phase HPLC (symmetry as the stationary phase and ammonium acetate/acetonitrile as the mobile phase) to give the title compound as a white solid. Yield: 0.25 g MS: APCI (−ve) 475 [M−H−]

$^1$H NMR: δ (DMSO) 1.16 (d, 3H), 3.11 (s, 4H), 3.42-3.53 (m, 2H), 3.59 (t, 4H), 4.43 (dd, 2H), 4.84 (t, 1H), 5.10 (q, 1H), 5.98 (s, 1H), 7.12-7.19 (m, 1H), 7.29-7.37 (m, 1H), 7.39-7.45 (m, 1H)

The intermediate for this compound was prepared as follows:

i) 2-[[2-[[(2,3-difluorophenyl)methyl]thio]-6-[(4-morpholinylsulfonyl)amino]-4-pyrimidinyl]oxy]-(2R)-propanoic acid ethyl ester The subtitle compound was prepared according to the procedure outlined in example 1 step iv) using a mixture of 4-morpholinesulfonamide (prepared according to patent WO 2004/011443, 0.19 g), tris(dibenzylideneacetone)dipalladium (0) (71 mg), 2-dicyclohexylphosphino-2',4',6'-tri-isopropyl-1,1'-biphenyl (XPHOS) (52 mg), cesium carbonate (0.38 g), 2-[[6-chloro-2-[[(2,3-difluorophenyl)methyl]thio]-4-pyrimidinyl]oxy]-(2R)-propanoic acid ethyl ester (the product of Example 23 step i) (0.30 g) and dioxane (10 mL). Purification was by column chromatography on silica gel using EtOAc/isohexane (1:1) as eluent to give the subtitle compound as an oil. Yield: 0.34 g MS: APCI (+ve) 519 [M+H+]

EXAMPLE 31

N-[2-[[(2,3-difluorophenyl)methyl]thio]-6-[(1R)-2-hydroxy-1-methylethoxy]-4-pyrimidinyl]-1-pyrrolidinesulfonamide

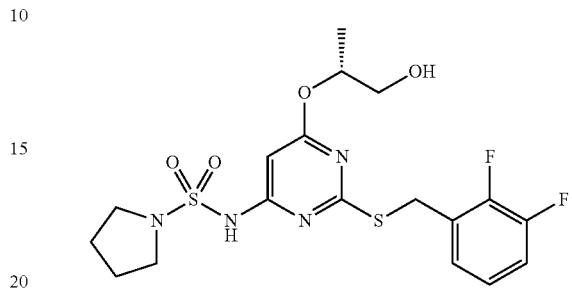

The title compound was prepared according to the procedure outlined in example 24 using a mixture of 2-[[2-[[(2,3-difluorophenyl)methyl]thio]-6-[(1-pyrrolidinylsulfonyl)amino]-4-pyrimidinyl]oxy]-(2R)-propanoic acid ethyl ester, (the product of step i) (0.38 g), THF (8 mL) and 2M lithium borohydride in THF (1.3 mL). Purification was by reverse phase HPLC (symmetry as the stationary phase and TFA/acetonitrile as the mobile phase). The resulting oil was titurated with methanol, toluene, DCM, then ether/iso-hexane to give the title compound as a white solid. Yield: 0.15 g MS: APCI (−ve) 459 [M−H−]

$^1$H NMR: δ (DMSO) 1.16 (d, 3H), 1.75-1.82 (m, 4H), 3.27-3.38 (m, 4H), 3.44-3.51 (m, 2H), 4.45 (dd, 2H), 5.10-5.18 (m, 1H), 5.97 (s, 1H), 7.13-7.20 (m, 1H), 7.29-7.42 (m, 2H), 10.91 (s, 1H)

The intermediate for this compound was prepared as follows:

i) 2-[[2-[[(2,3-difluorophenyl)methyl]thio]-6-[(1-pyrrolidinylsulfonyl)amino]-4-pyrimidinyl]oxy]-(2R)-propanoic acid ethyl ester The subtitle compound was prepared according to the procedure outlined in example 1, step iv) using a mixture of 1-pyrrolidinesulfonamide (prepared according to patent WO 2004/011443, 0.19 g), tris(dibenzylideneacetone)dipalladium (0) (71 mg), 2-dicyclohexylphosphino-2',4',6'-tri-isopropyl-1,1'-biphenyl (XPHOS) (52 mg), cesium carbonate (0.38 g), 2-[[6-chloro-2-[[(2,3-difluorophenyl)methyl]thio]-4-pyrimidinyl]oxy]-(2R)-propanoic acid ethyl ester (the product of Example 23 step i) (0.30 g) and dioxane (10 mL). Purification was by column chromatography on silica gel using EtOAc/isohexane (1:1) as eluent to give the subtitle compound as an oil. Yield: 0.38 g MS: APCI (+ve) 475 [M+H+]

EXAMPLE 32

N-[2-[[(2,3-difluorophenyl)methyl]thio]-6-[(1R)-2-hydroxy-1-methylethoxy]-4-pyrimidinyl]-cyclopropanesulfonamide

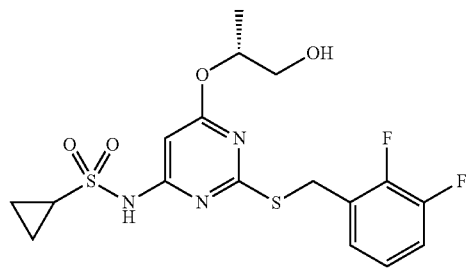 [SMILES: C[C@H](CO)Oc1cc(NS(=O)(=O)C2CC2)nc(SCc2cccc(F)c2F)n1]

The title compound was prepared according to the procedure outlined in example 24 using 2-[[6-[(cyclopropylsulfonyl)amino]-2-[[(2,3-difluorophenyl)methyl]thio]-4-pyrimidinyl]oxy]-(2R)-propanoic acid ethyl ester, (the product of step i) (0.30 g), THF (8 mL) and 2M lithium borohydride in THF (2 mL). Purification was by reverse phase HPLC (symmetry as the stationary phase and TFA/acetonitrile as the mobile phase). The resulting oil was triturated with methanol, toluene, DCM, then ether/iso-hexane to give the title compound as a white solid. Yield: 0.20 g MS: APCI (−ve) 430 [M−h⁻]

$^1$H NMR: δ (DMSO) 1.00-1.10 (m, 4H), 1.17 (d, 3H), 2.93-3.04 (m, 1H), 3.47-3.50 (m, 2H), 4.47 (s, 2H), 5.08-5.20 (m, 1H), 6.06 (s, 1H), 7.11-7.21 (m, 1H), 7.28-7.45 (m, 2H), 11.10 (s, 1H)

The intermediate for this compound was prepared as follows:

i) 2-[[6[(cyclopropylsulfonyl)amino]-2-[[(2,3-difluorophenyl)methyl]thio]-4-pyrimidinyl]oxy]-(2R)-propanoic acid ethyl ester The subtitle compound was prepared according to the procedure outlined in example 1, step iv) using a mixture of cyclopropanesulfonamide (prepared according to patent WO 2003/099274, 0.14 g), tris(dibenzylideneacetone)dipalladium (0) (71 mg), 2-dicyclohexylphosphino-2',4',6'-tri-isopropyl-1,1'-biphenyl (XPHOS) (52 mg), cesium carbonate (0.38 g), 2-[[6-chloro-2-[[(2,3-difluorophenyl)methyl]thio]-4-pyrimidinyl]oxy]-(2R)-propanoic acid ethyl ester (the product of Example 23 step i) (0.30 g) and dioxane (10 mL). Purification was by column chromatography on silica gel using EtOAc/isohexane (1:1) as eluent to give the subtitle compound as an oil. Yield: 0.30 g MS: APCI (+ve) 503 [M+H⁺]

EXAMPLE 33

N-[2-[[(2,3-difluorophenyl)methyl]thio]-6-[(1R)-2-hydroxy-1-methylethoxy]-4-pyrimidinyl]-1-methyl-1H-imidazole-4-sulfonamide

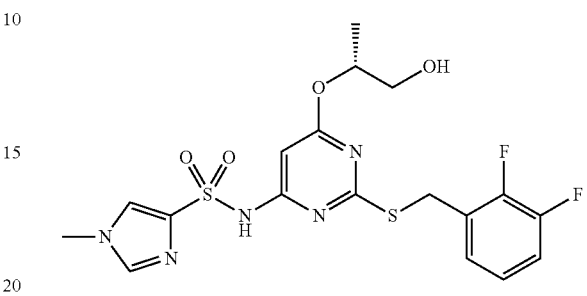

The title compound was prepared according to the procedure outlined in example 24 using 2-[2-[[(2,3-difluorophenyl)methyl]thio]-6-[[(1-methyl-1H-imidazol-4-yl)sulfonyl]amino]-4-pyrimidinyl]oxy]-(2R)-propanoic acid ethyl ester (the product of step i) (0.28 g), THF (8 mL) and 2M lithium borohydride in THF (0.81 mL). Purification was by reverse phase HPLC (symmetry as the stationary phase and TFA/acetonitrile as the mobile phase). The resulting oil was triturated with toluene, methanol, then ether/iso-hexane to give the title compound as a white solid. Yield: 0.12 g MS: APCI (−ve) 470 [M−H⁻]

$^1$H NMR: δ (DMSO) 1.14 (d, 3H), 3.46 (m, 2H), 3.67 (s, 3H), 4.39 (t, 2H), 5.01-5.14 (m, 1H), 6.17 (s, 1H), 7.09-7.19 (m, 1H), 7.27-7.42 (m, 2H), 7.80 (s, 1H), 8.01 (s, 1H), 11.55 (s, 1H)

The intermediate for this compound was prepared as follows:

i) 2-[[2-[[(2,3-difluorophenyl)methyl]thio]-6-[[(1-methyl-1H-imidazol-4-yl)sulfonyl]amino]-4-pyrimidinyl]oxy]-(2R)-propanoic acid ethyl ester The subtitle compound was prepared according to the procedure outlined in example 1, step iv) using a mixture of 1-methyl-1H-imidazole-4-sulfonamide (0.19 g), tris(dibenzylideneacetone)dipalladium (0) (71 mg), 2-dicyclohexylphosphino-2',4',6'-tri-isopropyl-1,1'-biphenyl (XPHOS) (52 mg), cesium carbonate (0.38 g), 2-[[6-chloro-2-[[(2,3-difluorophenyl)methyl]thio]-4-pyrimidinyl]oxy]-(2R)-propanoic acid ethyl ester (the product of Example 23 step i) (0.30 g) and dioxane (10 mL). Purification was by column chromatography on silica gel using EtOAc/isohexane (1:1) as eluent to give the subtitle compound as an oil. Yield: 0.28 g MS: APCI (+ve) 514 [M+H⁺]

EXAMPLE 34

N-[2-[[(2,3-difluorophenyl)methyl]thio]-6-[(1S)-2-ethoxy-1-(hydroxymethyl)ethoxy]-4-pyrimidinyl]-1-azetidinesulfonamide

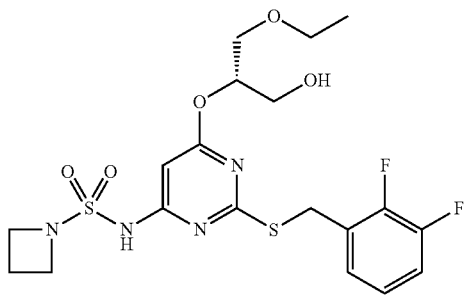 [SMILES: CCOC[C@H](CO)Oc1cc(NS(=O)(=O)N2CCC2)nc(SCc2cccc(F)c2F)n1]

To a solution of N-[2-[[(2,3-difluorophenyl)methyl]thio]-6-[(1R)-2-[[(1,1-dimethylethyl)dimethylsilyl]oxy]-1-(ethoxymethyl)ethoxy]-4-pyrimidinyl]-1-azetidinesulfonamide, (product from step v) (0.79 g) in THF (10 mL) was added a 1M solution of tetrabutylammoniumfluoride in THF (2.4 mL) with stirring, at ambient temperature, for 72 h. The reaction mixture was diluted with $H_2O$ and extracted with EtOAc (×2). The organic layer was washed with $H_2O$ then brine and dried ($MgSO_4$), filtered and evaporated. The resulting oil was purified by reverse phase HPLC (symmetry as the stationary phase and TFA/acetonitrile as the mobile phase) then titurated with DCM followed by ether/iso-hexane to give the title compound as a white solid. Yield: 0.28 g MS: APCI (−ve) 489 [M−H⁻]

¹H NMR: δ (DMSO) 1.06 (t, 3H), 2.13 (quintet, 2H), 3.36-3.46 (m, 2H), 3.54-3.59 (m, 4H), 3.91 (t, 4H), 4.46 (dd, 2H), 4.88 (t, 1H), 5.25 (quintet, 1H), 6.12 (s, 1H), 7.12-7.19 (m, 1H), 7.30-7.38 (m, 1H), 7.40-7.45 (m, 1H), 11.14 (s, 1H)

The intermediates for this compound were prepared as follows:

i) (4R)-4-(ethoxymethyl)-2,2-dimethyl-1,3-dioxolane

To a solution of 2,2-dimethyl-1,3-dioxolane-4-methanol (1.5 g), in dimethylfomylamide (30 mL), 60% sodium hydride (0.50 g) was added portion-wise at 0° C. then warmed to ambient temperature. Iodoethane (3.5 mL) was added to the mixture at 0° C. then stirred for 16 h at room temperature. The reaction mixture was filtered then the filtrate was diluted with $H_2O$ and extracted with EtOAc. The organic layer was washed with $H_2O$ (×2) then brine and dried ($MgSO_4$), filtered and evaporated. Purification was by column chromatography on silica gel using EtOAc/$Et_2O$ (1:1) as eluent to give the subtitle compound as clear, colourless oil. Yield: 1 g ¹H NMR: δ (DMSO) 1.10 (t, 3H), 1.27 (s, 3H), 1.32 (s, 3H), 3.32-3.50 (m, 4H), 3.54-3.62 (m, 1H), 3.93-4.01 (m, 1H), 4.11-4.20 (m, 1H)

ii) (2S)-3-ethoxy-1,2-propanediol

A solution of (4R)-4-(ethoxymethyl)-2,2-dimethyl-1,3-dioxolane (product from step i) (1 g) in 80% glacial acetic acid (30 mL) was stirred at ambient temperature for 48 h. The solvent was evaporated, azeotroped with methanol, ethanol and toluene then redissolved in DCM, dried ($MgSO_4$), filtered and evaporated to give the subtitle compound as a yellow oil. Yield: 0.55 g ¹H NMR: δ (DMSO) 1.10 (t, 3H), 3.22-3.44 (m, 6H), 3.54 (quintet, 1H), 4.45 (t, 1H), 4.58 (d, 1H)

iii) (2R)-1-[[(1,1-dimethylethyl)dimethylsilyl]oxy]-3-ethoxy-2-propanol

To a solution of (2S)-3-ethoxy-1,2-propanediol (product from step (0.50 g) in DCM (30 mL) was added tert-butyldimethylsilyl chloride (0.88 g), triethylamine (0.43 mL) and 4-(dimethylamino)pyridine (31 mg) at 0° C. The solution was then warmed to ambient temperature and stirred for 16 h. The reaction mixture diluted with $H_2O$ and extracted with EtOAc. The organic layer was washed with brine and evaporated. Purification was by column chromatography on silica gel using EtOAc/isohexane (2:8) as eluent to give the subtitle compound as an oil. Yield: 0.69 g ¹H NMR: δ (DMSO) 0.07 (s, 6H), 0.90 (s, 9H), 1.14 (t, 3H), 3.28-3.65 (m, 7H), 4.70 (d, 1H)

iv) 4-chloro-2-[[(2,3-difluorophenyl)methyl]thio]-6-[(1R)-2-[[(1,1-dimethylethyl)dimethylsilyl]oxy]-1-(ethoxymethyl)ethoxy]-pyrimidine The subtitle compound was prepared according to the procedure outlined in example 1 step iv) using 4,6-Dichloro-2-[(2,3-difluorobenzyl)thio]pyrimidine (product of example 1 step ii) (0.43 g), (2R)-1-[[(1,1-dimethylethyl)dimethylsilyl]oxy]-3-ethoxy-2-propanol (product of step iii) (0.47 g), THF (20 mL) and 60% sodium hydride (67 mg), to give the subtitle compound as a colourless oil. Yield: 0.7 g MS: APCI (+ve) 505/507 [M+H⁺]

¹H NMR: δ (DMSO) 0.03 (s, 6H), 0.80 (s, 9H), 1.09 (t, 3H), 3.39-3.50 (m, 2H), 3.60 (d, 2H), 3.75-3.81 (m, 2H), 4.49 (s, 2H), 5.35-5.44 (m, 1H), 6.90 (s, 1H), 7.14-7.23 (m, 1H), 7.32-7.43 (m, 2H)

v) N-[2-[[(2,3-difluorophenyl)methyl]thio]-6-[(1R)-2-[[(1,1-dimethylethyl)dimethylsilyl]oxy]-1-(ethoxymethyl)ethoxy]-4-pyrimidinyl]-1-azetidinesulfonamide The subtitle compound was prepared according to the procedure outlined in example 1 step (iv) using a mixture of azetidine-1-sulfonamide (prepared according to patent WO 2004/011443, 0.29 g), tris(dibenzylideneacetone)dipalladium (0) (0.13 g), 2-dicyclohexylphosphino-2',4',6'-tri-isopropyl-1,1'-biphenyl (XPHOS) (93 mg), cesium carbonate (0.68 g), 4-chloro-2-[[(2,3-difluorophenyl)methyl]thio]-6-[(1R)-2-[[(1,1-dimethylethyl)dimethylsilyl]oxy]-1-(ethoxymethyl)ethoxy]-pyrimidine (the product of step iv) (0.70 g) and dioxane (15 mL). Purification was by column chromatography on silica gel using EtOAc/isohexane (3:7) 70:30 as eluent, to give the title compound as a white solid.

Yield: 0.22 g

MS: APCI (+ve) 605 [M+H⁺]

¹H NMR: δ (DMSO) 0.02 (s, 6H), 0.84 (s, 9H), 1.04-1.11 (m, 3H), 2.08-2.18 (m, 2H), 3.53-3.59 (m, 2H), 3.72-3.77 (m, 2H), 3.86-3.94 (m, 4H), 3.99-4.07 (m, 2H), 4.49 (s, 2H), 5.34 (s, 1H), 6.14 (s, 1H), 7.10-7.20 (m, 1H), 7.29-7.45 (m, 2H), 11.17 (s, 1H)

EXAMPLE 35

N-[2-[[(2,3-Difluorophenyl)methyl]thio]-6-methoxypyrimidin-4-yl]azetidine-1-sulfonamide

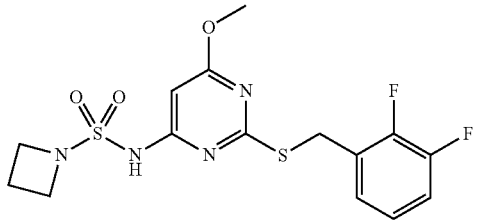

The title compound was prepared according to the procedure outlined in example 1, step iv). A mixture of azetidine-1-sulfonamide (prepared according to patent WO 2004/011443, 0.15 g), tris(dibenzylideneacetone)dipalladium (0) (44 mg), 2-dicyclohexylphosphino-2'4'6'-tri-iso-propyl-1,1'biphenyl (44 mg), cesium carbonate (0.36 g) and 4-chloro-2-[[(2,3-difluorophenyl)methyl]thio]-6-methoxypyrimidine (the product of step i) (0.23 g) in dioxane (7.2 mL). Acetic acid (0.67 mL) was added and the reaction mixture was extracted with EtOAc (×3). The combined organic layers were washed with $H_2O$, dried ($MgSO_4$), filtered and the solvent evaporated under reduced pressure. The residue was purified by flash column chromatography on silica gel using EtOAc/isohexane (3:7) as eluent. The resulting solid was further purified by trituration with iso-hexane and dried under high vacuum at 40° C. to give the title compound as a pale yellow solid. Yield: 0.29 g.

MS: APCI (+ve) 403 [M+H]

$^1$H NMR: δ (DMSO) 2.12 (m, 2H), 3.9 (m, 7H), 4.49 (s, 2H), 6.15 (s, 1H), 7.16 (m, 1H), 7.39 (m, 2H), 11.12 (s, 1H).

The intermediate for this compound was prepared as follows:

i) 4-Chloro-2-[[(2,3-difluorophenyl)methyl]thio]-6-methoxypyrimidine

To a stirred solution of 4,6-Dichloro-2-[(2,3-difluorobenzyl)thio]pyrimidine (the product of Example 1, step (5 g) in dry methanol (40 mL) was added 60% sodium hydride (0.68 g) batchwise over 5 min. The reaction mixture was stirred for 5 h, $H_2O$ added and the solvents were partially evaporated. The residue was extracted with EtOAc which was washed with $H_2O$, dried ($MgSO_4$) and the solvent evaporated under reduced pressure. The residue was purified by flash chromatography on silica gel, eluting with $Et_2O$/iso-hexane (5:95) to give the subtitle compound as a white solid. Yield: 4.05 g.

MS: APCI (+ve) 303/305 [M+H]

EXAMPLE 36

N-[2-[[(2,3-Difluorophenyl)methyl]thio]-6-methoxypyrimidin-4-yl]piperazine-1-sulfonamide, trifluoroacetate salt

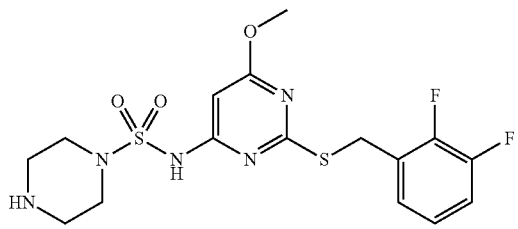 [SMILES: COc1cc(NS(=O)(=O)N2CCNCC2)nc(SCc2cccc(F)c2F)n1]

1,1-Dimethylethyl 4-[2-[[(2,3-difluorophenyl)methyl]thio]-6-methoxypyrimidin-4-yl sulfamoyl]piperazine-1-carboxylate (the product of step i) (0.36 g) and trifluoroacetic acid (1 mL) in dichloromethane (4 mL) were stirred at room temperature for 30 min. The solvent was evaporated under reduced pressure and the residue was azeotroped with toluene (3×). The residual pale yellow solid was triturated with EtOAc, filtered and dried at 40° C. under high vacuum to give the title compound as a cream solid. Yield: 0.24 g.

MS: APCI (+ve) 432 [M+H]

$^1$H NMR: δ (DMSO) 3.17 (m, 4H), 3.40 (m, 4H), 3.90 (s, 3H), 4.49 (s, 2H), 6.08 (s, 1H), 7.18 (m, 1H), 7.38 (m, 2H).

The intermediates for this compound were prepared as follows:

i) 1,1-Dimethylethyl 4-[2-[[(2,3-difluorophenyl)methyl]thio]-6-methoxy pyrimidin-4-yl sulfamoyl]piperazine-1-carboxylate The subtitle compound was prepared from 1,1-dimethylethyl 4-sulfamoylpiperazine-1-carboxylate (the product of example 15, step i), 0.22 g) and 4-Chloro-2-[[(2,3-difluorophenyl)methyl]thio]-6-methoxypyrimidine (the product of Example 35, step i) (0.25 g) according to the procedure outlined in Example 1, step iv). The crude material was purified by column chromatography on silica gel using EtOAc/isohexane (2:8) as eluent. Yield: 0.36 g MS: APCI (−ve) 530 [M−H]

$^1$H NMR: δ ($CDCl_3$) 1.45 (s, 9H), 3.27 (t, 4H), 3.48 (t, 4H), 3.94 (s, 3H), 4.40 (s, 2H), 6.23 (s, 1H), 7.04 (m, 2H), 7.22 (m, 1H).

EXAMPLE 37

4-Acetyl-N-[2-[[(2,3-difluorophenyl)methyl]thio]-6-methoxypyrimidin-4-yl]piperazine-1-sulfonamide

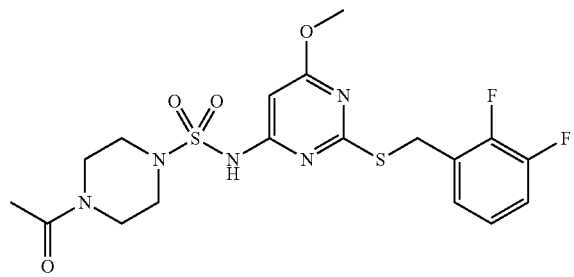 [SMILES: COc1cc(NS(=O)(=O)N2CCN(C(C)=O)CC2)nc(SCc2cccc(F)c2F)n1]

Acetic anhydride (0.78 mL) was added to a mixture of N-[2-[[(2,3-Difluorophenyl)methyl]thio]-6-methoxypyrimidin-4-yl]piperazine-1-sulfonamide, trifluoroacetate salt (the title product of Example 36, 0.84 g) and N,N-diisopropylethylamine (1 mL) in DCM (5 mL). The reaction mixture was stirred at room temperature for 30 min and the solvent evaporated under reduced pressure. The residue was dissolved in EtOAc which was washed with aqueous citric acid, $H_2O$, dried ($MgSO_4$) and the solvent evaporated under reduced pressure. The residue was purified by flash chromatography on silica gel, eluting with EtOAc to give the title compound as a white solid. Yield: 78 mg.

MS: APCI (+ve) 474 [M+H]

$^1$H NMR: δ (DMSO) 1.98 (s, 3H), 3.20 (m, 4H), 3.87 (s, 3H), 3.32 (br d, 4H), 4.48 (s, 2H), 6.07 (s, 1H), 7.17 (m, 1H), 7.33 (m, 1H), 7.42 (t, 1H), 11.18 (s, 1H).

EXAMPLE 38

N-[2-[[(2,3-Difluorophenyl)methyl]thio]-6-methoxy-pyrimidin-4-yl]morpholine-4-sulfonamide

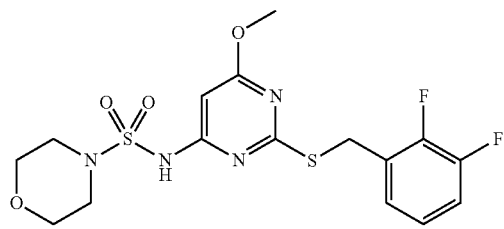

The title compound was prepared from morpholine-4-sulfonamide (prepared according to patent WO 2004/011443, 0.20 g) and 4-Chloro-2-[[(2,3-difluorophenyl)methyl]thio]-6-methoxypyrimidine (the product of Example 35, step i) (0.25 g) according to the procedure outlined in Example 1, step iv). The crude material was purified by column chromatography using EtOAc/isohexane (2:8) as eluent. Yield: 0.26 g.

MS: APCI (+ve) 433 [M+H]

$^1$H NMR: δ (DMSO) 3.17 (t, 4H), 3.59 (t, 4H), 3.88 (s, 3H), 4.48 (s, 2H), 6.09 (s, 1H), 7.17 (m, 1H), 7.34 (m, 1H), 7.43 (t, 1H), 11.17 (s, 1H).

EXAMPLE 39

N-[2-[[(2,3-Difluorophenyl)methyl]thio]-6-methoxy-pyrimidin-4-yl]methane-sulfonamide

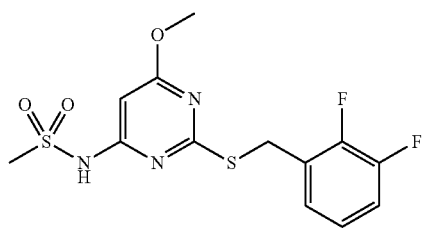 [SMILES: COc1cc(NS(C)(=O)=O)nc(SCc2cccc(F)c2F)n1]

The title compound was prepared from methane sulfonamide (0.11 g) and 4-Chloro-2-[[(2,3-difluorophenyl)methyl]thio]-6-methoxypyrimidine (the product of Example 35, step i) (0.25 g) according to the procedure outlined in Example 1, step iv). The crude material was purified by column chromatography using EtOAc/isohexane (2:8) as eluent. Yield: 0.12 g.

MS: APCI (+ve) 362 [M+H]

$^1$H NMR: δ (DMSO) 3.28 (s, 3H), 3.87 (s, 3H), 4.49 (s, 2H), 6.03 (s, 1H), 7.17 (m, 1H), 7.37 (m, 2H), 11.14 (s, 1H).

EXAMPLE 40

N-[2-[[(2,3-Difluorophenyl)methyl]thio]-6-methoxy-pyrimidin-4-yl]-1-methyl-1H-imidazole-4-sulfonamide

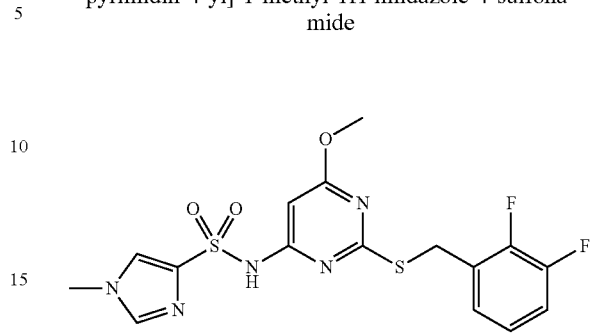

The title compound was prepared from 1-methyl-1H-imidazole-4-sulfonamide (0.19 g) and 4-Chloro-2-[[(2,3-difluorophenyl)methyl]thio]-6-methoxypyrimidine (the product of Example 35, step i) (0.25 g) according to the procedure outlined in Example 1, step iv). The crude material was purified by column chromatography using EtOAc/isohexane (2:8) as eluent.

Yield: 0.11 g.

MS: APCI (+ve) 428 [M+H]

$^1$H NMR: δ (DMSO) 3.67 (s, 3H), 3.83 (s, 3H), 4.41 (s, 2H), 6.20 (s, 1H), 7.15 (m, 1H), 7.36 (m, 2H), 7.78 (s, 1H), 8.00 (s, 1H), 11.55 (s, 1H)

EXAMPLE 41

N-[2-[[(2,3-Difluorophenyl)methyl]thio]-6-[(S)-isoxazolidin-4-yl)oxy]pyrimidin-4-yl]azetidine-1-sulfonamide

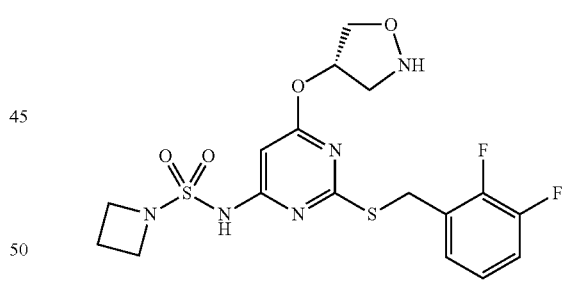

1,1-Dimethylethyl (S)-4-[6-(azetidine-1-sulfonylamino)-2-[[(2,3-difluorophenyl)methyl]thio]pyrimidin-4-yloxy]isoxazolidine-2-carboxylate (the product of step (0.14 g) and trifluoroacetic acid (1 mL) in dichloromethane (2 mL) were stirred at room temperature for 30 min. The solvent was evaporated under reduced pressure and the residue was azeotroped with toluene (3×). The residue was purified by reverse phase HPLC eluting with acetonitrile/0.1% aqueous ammonium acetate mixtures to give the title compound as a white solid. Yield: 80 mg.

MS: APCI (+ve) 458 [M+H]

$^1$H NMR: δ (DMSO) 7.37 (m, 2H), 7.18 (m, 1H), 6.16 (s, 1H), 5.65 (bm, 1H), 4.49 (s, 2H), 3.91-3.81 (bs+t, 6H), 3.01 (bs, 1H), 2.13 (m, 2H).

The intermediates for this compound were prepared as follows:

i) 1,1-Dimethylethyl (S)-4-[6-chloro-2-[[(2,3-difluorophenyl)methyl]thio]pyrimidin-4-yloxy]-isoxazolidine-2-carboxylate To a stirred solution of 4,6-Dichloro-2-[(2,3-difluorobenzyl)thio]pyrimidine (the product of Example 1, step ii) (0.25 g) and 1,1-dimethylethyl (S)-4-hydroxyisoxazolidine-2-carboxylate (0.16 g) in dry THF (5 mL) was added 60% Sodium hydride (0.034 g) over 5 min. The reaction mixture was stirred and heated at 60° C. for 7 days, H$_2$O was added and the solvents were partially evaporated. The residue was extracted with EtOAc which was washed with H$_2$O, dried (MgSO$_4$) and the solvent evaporated under reduced pressure. The residue was purified by flash chromatography on silica gel, eluting with Et$_2$O/iso-hexane (1:9) to give the subtitle compound as a gum. Yield: 0.15 g.

MS: APCI (+ve) 460/462 [M+H]

ii) 1,1-Dimethylethyl (S)-4-[6-(azetidine-1-sulfonylamino)-2-[[(2,3-difluorophenyl)methyl]thio]pyrimidin-4-yloxy]isoxazolidine-2-carboxylate The subtitle compound was prepared from azetidine-1-sulfonamide (prepared according to patent WO 2004/011443, 0.22 g) and 1,1-Dimethylethyl (S)-4-[6-chloro-2-[[(2,3-difluorophenyl)methyl]thio]pyrimidin-4-yloxy]isoxazolidine-2-carboxylate (the product of step i) (0.13 g) according to the procedure outlined in Example 1, step iv). The crude material was purified by column chromatography using EtOAc/isohexane (2:8) as eluent. Yield: 0.14 g MS: APCI (-ve) 558 [M-H]

EXAMPLE 42

N-[6-((R)-2-amino-1-methylethoxy)-2-[[(2,3-Difluorophenyl)methyl]thio]pyrimidin-4-yl]azetidine-1-sulfonamide

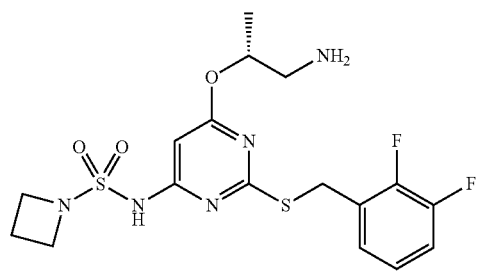

The title compound was prepared from 1,1-dimethylethyl [(R)-2-[6-azetidine-1-sulfonyl amino)-2-[[(2,3-difluorophenyl)methyl]thio]pyrimidin-4-yloxy]propyl}carbamate (0.26 g) (the product of step ii) according to the procedure outlined in Example 41. The crude material was purified by column chromatography using EtOAc/isohexane (2:8) as eluent. Yield: 0.11 g MS: APCI (+ve) 446 [M+H]

$^1$H NMR: δ (DMSO) 1.19 (d, 3H), 1.97 (m, 2H), 2.99 (m, 2H), 3.58 (t, 4H), 4.38 (q, 2H), 5.15 (s, 1H), 5.97 (s, 1H), 7.12 (m, 1H), 7.30 (m, 1H), 7.43 (t, 1H), 7.49 (br s, 3H).

The intermediates for this compound were prepared as follows:

i) 1,1-Dimethylethyl [(R)-2-[6-chloro-2-[[(2,3-difluorophenyl)methyl]thio]pyrimidin-4-yloxy]propyl]carbamate The subtitle compound was prepared from 1,1-dimethylethyl ((R)-2-hydroxypropyl) carbamate (0.15 g) and 4,6-Dichloro-2-[(2,3-difluorobenzyl)thio]pyrimidine (the product of Example 1, step (0.25 g) according to the procedure outlined in Example 41, step i) with heating at 45° C. for 18 h. The crude material was purified by column chromatography using EtOAc/isohexane (2:8) as eluent. Yield: 0.23 g.

MS: APCI (-ve) 444/446 [M-H]

ii) 1,1-Dimethylethyl [(R)-2-[6-azetidine-1-sulfonylamino)-2-[[(2,3-difluorophenyl)methyl]thio]pyrimidin-4-yloxy]propy]carbamate The subtitle compound was prepared from azetidine-1-sulfonamide (prepared according to patent WO 2004/011443, 0.11 g) and 1,1-Dimethylethyl [(R)-2-[6-chloro-2-[[(2,3-difluorophenyl)methyl]thio]pyrimidin-4-yloxy]propyl]carbamate (the product of step i) (0.2 g) according to the procedure outlined in Example 1, step iv). The crude material was purified by column chromatography using EtOAc/isohexane (2:8) as eluent. Yield: 0.14 g MS: APCI (-ve) 544 [M-H]

EXAMPLE 43

N—[(R)-2-[6-[azetidine-1-sulfonylamino]-2-[[(2,3-difluorophenyl)methyl]thio]pyrimidin-4-yloxy]propyl]acetamide

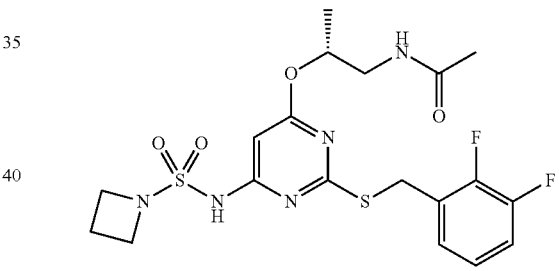

To a suspension of N-[6-((R)-2-amino-1-methylethoxy)-2-[[(2,3-Difluorophenyl)methyl]thio]pyrimidin-4-yl]azetidine-1-sulfonamide (the title product of Example 42) (0.05 g) in dichloromethane (10 mL) was added pyridine (0.02 mL), followed by acetic anhydride (0.02 mL). The mixture was stirred overnight at room temperature. Pyridine (0.02 mL) and acetic anhydride (0.02 mL) were added and the reaction mixture was stirred for a further 2 h Pyridine (1.0 mL) and acetic anhydride (0.50 mL) were added and the reaction mixture was stirred for a further 2 h. The reaction mixture was diluted with dichloromethane, washed with aqueous citric acid, H$_2$O, dried (MgSO$_4$), filtered and the solvent evaporated under reduced pressure. The residue was purified by flash column chromatography on silica gel using 40% EtOAc in isohexane as eluent. The isolated product was further purified by reverse phase HPLC eluting with acetonitrile/aq. 0.1% ammonium acetate mixtures to give the title compound as a white solid. Yield: 55 mg.

MS: APCI (-ve) 486 [M-H]

$^1$H NMR: δ (DMSO) 1.11 (d, 3H), 1.80 (s, 3H), 1.96 (m, 2H), 3.20 (m, 2H), 3.55 (t, 4H), 4.34 (q, 2H), 5.02 (m, 1H), 5.88 (s, 1H), 7.12 (m, 1H), 7.29 (m, 1H), 7.41 (t, 1H), 7.99 (t, 1H).

EXAMPLE 44

N-[2-[[(2,3-Difluorophenyl)methyl]thio]-6-[(R,S)-2-dimethylamino-1-methylethoxy]pyrimidin-4-yl]azetidine-1-sulfonamide

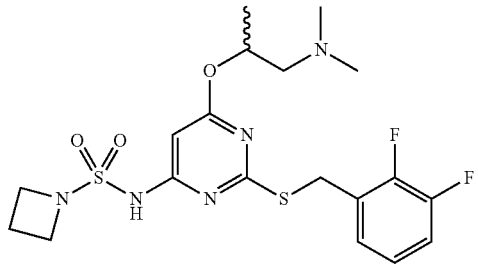 [SMILES: CC(CN(C)C)Oc1cc(NS(=O)(=O)N2CCC2)nc(SCc2cccc(F)c2F)n1]

The title compound was prepared from azetidine-1-sulfonamide (prepared according to patent WO 2004/011443, 0.15 g) and 2-[[6-chloro-2-[[(2,3-difluorophenyl)methyl]thio]-4-pyrimidinyl]oxy]-N,N-dimethyl-1-propanamine (the product of step i) (0.29 g) according to the procedure outlined in Example 1, step iv). The reaction product was purified by reverse phase HPLC eluting with acetonitrile/aq. 0.1% ammonium acetate mixtures to give the title compound as a pale yellow solid. Yield: 0.30 g MS: APCI (+ve) 474 [M+H]

$^1$H NMR: δ (DMSO) 1.17 (d, 3H), 2.07 (m, 2H), 2.24 (s, 6H), 2.44 (m, 1H), 2.64 (m, 1H), 3.79 (t, 4H), 4.24 (t, 2H), 5.27 (m, 1H), 6.00 (s, 1H), 7.15 (m, 1H), 7.33 (m, 1H), 7.42 (t, 1H).

The intermediate for this compound was prepared as follows:

i) 2-[[6-chloro-2-[[(2,3-difluorophenyl)methyl]thio]-4-pyrimidinyl]oxy]-N,N-dimethyl-1-propanamine The subtitle compound was prepared according to the procedure outlined in Example 41 step i) using 1-dimethylamino-2-propanol (80 mg), 4,6-Dichloro-2-[(2,3-difluorobenzyl)thio]pyrimidine (the product of Example 1 step (0.25 g) and 60% sodium hydride (30 mg) in THF (2 mL) at room temperature for 2 d to give the subtitle compound as a pale yellow gum. Yield: 0.29 g.

MS: APCI (+ve) 374 [M+H]

EXAMPLE 45

N-[2-[[(2,3-Difluorophenyl)methyl]thio]-6-{[(1R,2R)-2,3-dihydroxy-1-methylpropyl]oxy}-4-pyrimidinyl]-1-azetidinesulfonamide

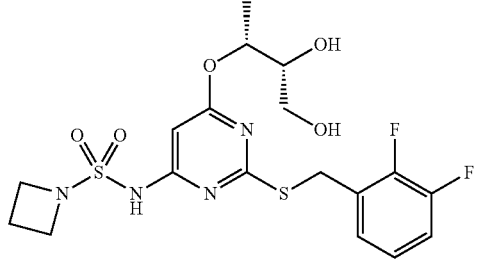 [SMILES: C[C@@H](Oc1cc(NS(=O)(=O)N2CCC2)nc(SCc2cccc(F)c2F)n1)[C@H](O)CO]

To a solution of N-[2-[[(2,3-difluorophenyl)methyl]thio]-6-[(1R)-1-[(4R)-2,2-dimethyl-1,3-dioxolan-4-yl]ethoxy]-4-pyrimidinyl]-1-azetidinesulfonamide (the product of step vi) (0.13 g) in DCM (5 mL) was added iron (III) chloride hexahydrate (0.26 g). The reaction mixture was stirred at ambient temperature for 1.5 h, then saturated aqueous sodium bicarbonate (1 mL) was added. The layers were separated and the aqueous material extracted with DCM (×3) and ethyl acetate (×3). The combined organic extracts were washed with saturated aqueous sodium chloride, dried (MgSO$_4$), filtered and evaporated. The residual pale yellow solid was slowly precipitated from DCM, filtered and the resulting material washed with minimal cold DCM (2×1 mL) to afford the title compound as a white powder. Yield: 64 mg.

MS: APCI (+ve) 477 [M+H$^+$]

$^1$H NMR: δ (CDCl$_3$) 1.33 (d, 3H), 2.27 (quintet, 2H), 2.55 (d, 1H), 3.61-3.70 (m, 2H), 3.74-3.82 (m, 1H), 4.02 (t, 4H), 4.31-4.41 (m, 2H), 5.32 (quintet, 1H), 6.34 (s, 1H), 6.98-7.24 (m, 3H).

The intermediates for this compound were prepared as follows:

i) (2S,3R)-3-(Benzyloxy)-2-hydroxybutanoic acid

To a solution of (2S,3R)-2-amino-3-benzyloxy-butyric acid (1.1 g) in 2M sulfuric acid (6.31 mL) was added dropwise over 2 h a solution of sodium nitrite (0.65 g) in water (6 mL), keeping the internal temperature of the reaction below 0° C. The reaction mixture was stirred at −5° C. for 6 h then allowed to warm to room temperature overnight. The mixture was adjusted to pH 4 with 50% aqueous sodium hydroxide then ethyl acetate was added. The mixture was stirred vigorously and acidified to pH 2 with concentrated sulfuric acid. The layers were separated and the aqueous layer extracted with further ethyl acetate (×2). The combined organic extracts were washed with saturated aqueous sodium chloride, dried (MgSO$_4$), filtered and evaporated to give the subtitle compound as a yellow crystalline solid which was used without further purification. Yield: 0.84 g.

MS: APCI (+ve) 211, [M+H$^+$]

$^1$H NMR: δ (300 MHz, CDCl$_3$) 1.31 (d, 3H), 3.99-4.05 (m, 1H), 4.16 (d, 1H), 4.51 (d, 1H), 4.69 (d, 1H), 7.22-7.38 (m, 5H).

ii) (2R,3R)-3-(Benzyloxy)butane-1,2-diol

To a solution of (2S,3R)-3-(benzyloxy)-2-hydroxybutanoic acid (the product of step i) (0.79 g) and trimethyl borate (0.67 mL) in anhydrous tetrahydrofuran (4 mL) at 0° C. was added dropwise borane-dimethyl sulfide complex (3 mL, 2M in tetrahydrofuran). The reaction mixture was stirred at room temperature overnight, then further borane-dimethyl sulfide complex (3 mL, 2M in tetrahydrofuran) was added at 0° C. and the reaction mixture stirred at room temperature for a further 2 d. The mixture was cooled to 0° C. and methanol (10 mL) slowly added. When effervescence had ceased, the volatiles were evaporated, further methanol added and the mixture concentrated again to give the subtitle compound as a yellow oil which was used without further purification. Yield: 0.68 g.

MS: APCI (+ve) 197, [M+H$^+$]

$^1$H NMR: δ (CDCl$_3$) 1.25 (d, 3H), 2.17 (t, 1H), 2.77 (d, 1H), 3.52-3.77 (m, 4H), 4.43 (d, 1H), 4.69 (d, 1H), 7.27-7.39 (m, 5H).

iii) (4R)-4-[(1R)-1-(Benzyloxy)ethyl]-2,2-dimethyl-1,3-dioxolane

A stirred solution of (2R,3R)-3-(benzyloxy)butane-1,2-diol (the product of step ii) (0.68 g), p-toluene sulfonic acid monohydrate (34 mg) and 2,2-dimethoxypropane (0.43 mL) in toluene (10 mL) was heated to reflux for 30 min, then anhydrous sodium sulfate was added and reflux continued for 2.5 h. The reaction mixture was allowed to cool and diluted with EtOAc and saturated aqueous sodium bicarbonate and the layers separated. The organic extract was washed with brine, dried (MgSO$_4$), filtered and evaporated. The residue was purified by column chromatography on silica gel using EtOAc/isohexane (1:9 to 1:1 gradient) as eluent to give the subtitle compound as a colourless liquid. Yield: 0.46 g.

$^1$H NMR: δ (CDCl$_3$) 1.13 (d, 3H), 1.37 (s, 3H), 1.42 (s, 3H), 3.60 (quintet, 1H), 3.71 (dd, 1H), 3.99 (dd, 1H), 4.15 (quintet, 1H), 4.64 (d, 1H), 4.67 (d, 1H), 7.24-7.38 (m, 5H).

iv) (1R)-1-[(4R)-2,2-Dimethyl-1,3-dioxolan-4-yl]ethanol

Ammonia (c. 50 mL) was condensed at −78° C. into a three-necked flask which had been oven-dried overnight, and to it was added a solution of (4R)-4-[(1R)-1-(benzyloxy)ethyl]-2,2-dimethyl-1,3-dioxolane (the product of step iii) (0.39 g) in tetrahydrofuran (7.5 mL). Sodium was added in small pieces until the reaction mixture was dark blue, then it was allowed to warm to −40° C. and kept at this temperature for 1.5 h, during which time further sodium was added when the blue colour faded. The reaction mixture was quenched with excess solid ammonium chloride and allowed to warm to room temperature. Ether (20 mL) was added followed by water, cautiously (10 mL). The layers were separated and the aqueous layer extracted with further ether (×3). The combined organic extracts were washed with saturated aqueous sodium chloride, dried (MgSO$_4$), filtered and evaporated to give the subtitle compound as a pale yellow liquid which was used without further purification. Yield: 0.24 g.

$^1$H NMR: δ (CDCl$_3$) 1.16 (d, 3H), 1.37 (s, 3H), 1.44 (s, 3H), 3.67-3.77 (m, 2H), 3.93 (q, 1H), 4.00-4.05 (m, 1H).

v) 4-Chloro-2-[(2,3-difluorophenyl)methylthio]-6-{(1R)-1-[(4R)-2,2-dimethyl-1,3-dioxolan-4-yl]ethoxy}pyrimidine To a solution of (1R)-1-[(4R)-2,2-dimethyl-1,3-dioxolan-4-yl]ethanol (the product of step iv) (0.24 g) in dry THF (10 mL) at 0° C. was added in portions sodium hydride (91 mg as 60% dispersion in mineral oil) followed in portions by 4,6-dichloro-2-[(2,3-difluorobenzyl)thio]pyrimidine (the product of example 1 step ii) (0.50 g). The reaction mixture was stirred at room temperature for 48 h then quenched with saturated aqueous ammonium chloride (10 mL) and diluted with ethyl acetate. The layers were separated and the aqueous layer extracted with further ethyl acetate. The combined organic extracts were washed with brine, dried (MgSO$_4$), filtered and evaporated. The residue was purified by column chromatography on silica gel using EtOAc/isohexane (1:19 to 1:9 gradient) as eluent to give the subtitle compound as a pale yellow solid. Yield: 0.42 g.

MS: APCI (+ve) 417/419 [M+H$^+$]

$^1$H NMR: δ (CDCl$_3$) 1.24 (d, 3H), 1.36 (s, 3H), 1.40 (s, 3H), 3.74 (dd, 1H), 4.03 (dd, 1H), 4.21 (q, 1H), 4.40 (s, 2H), 5.28 (quintet, 1H), 6.44 (s, 1H), 6.98-7.11 (m, 2H), 7.26-7.31 (m, 1H).

vi) N-[2-[[(2,3-Difluorophenyl)methyl]thio]-6-[(1R)-1-[(4R)-2,2-dimethyl-1,3-dioxolan-4-yl]ethoxy]-4-pyrimidinyl]-1-azetidinesulfonamide A mixture of azetidine-1-sulphonamide (prepared according to patent WO 2004/011443, 0.20 g), tris(dibenzylideneacetone)-dipalladium (0) (33 mg), 2-dicyclohexylphosphino-2',4',6'-tri-isopropyl-1,1'-biphenyl (XPHOS) (17 mg), cesium carbonate (0.18 g) and 4 chloro-2-[[(2,3-difluorophenyl)methyl]thio]-6-[(1R)-1-[(4R)-2,2-dimethyl-1,3-dioxolan-4-yl]ethoxy]-pyrimidine (the product of step v) (0.15 g) in dioxane (5 mL) was heated at reflux in a microwave at 100° C., 300 W, open vessel with cooling for 25 min. Saturated aqueous ammonium chloride was added and the resulting mixture extracted with ethyl acetate. The combined organic extracts were washed with brine, dried (MgSO$_4$), filtered and evaporated. The residue was purified by column chromatography on silica gel using EtOAc/isohexane (1:19 to 3:7 gradient) as eluent to give the subtitle compound as a yellow oil. Yield: 0.14 g.

MS: APCI (+ve) 517 [M+H$^+$]

$^1$H NMR: δ (CDCl$_3$) 1.23 (d, 3H), 1.38 (s, 3H), 1.43 (s, 3H), 2.25 (quintet, 2H), 3.77 (dd, 1H), 3.98-4.09 (m, 5H), 4.24 (q, 1H), 4.37 (s, 2H), 5.30 (quintet, 1H), 6.32 (s, 1H), 6.98-7.11 (m, 2H), 7.20-7.26 (m, 1H).

EXAMPLE 46

N-[2-[[(2,3-Difluorophenyl)methyl]thio]-6-[[(1R,2R)-2,3-dihydroxy-1-methylpropyl]oxy]-4-pyrimidinyl]-methanesulfonamide

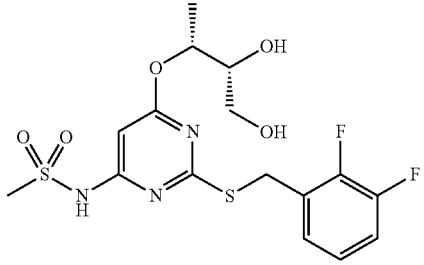 [SMILES: C[C@@H](Oc1cc(NS(C)(=O)=O)nc(SCc2cccc(F)c2F)n1)[C@H](O)CO]

To a solution of N-[2-[[(2,3-difluorophenyl)methyl]thio]-6-[(1R)-1-[(4R)-2,2-dimethyl-1,3-dioxolan-4-yl]ethoxy]-4-pyrimidinyl]-methanesulfonamide (the product of step i) (0.23 g) in DCM (5 mL) was added iron (III) chloride hexahydrate (0.25 g). The reaction mixture was stirred at ambient temperature for 2 h then saturated aqueous sodium bicarbonate (2 mL) was added. The layers were separated and the aqueous material extracted with DCM (×3) and ethyl acetate (×3). The combined organic extracts were washed with brine, dried (MgSO$_4$), filtered and evaporated. The residual yellow solid was precipitated from 10% DCM in Et$_2$O, filtered and the resulting material washed with minimal Et$_2$O (2×1 mL) to afford the title compound as a white powder. Yield: 24 mg.

MS: APCI (+ve) 436, [M+H$^+$]

$^1$H NMR: δ (DMSO) 1.19 (d, 3H), 3.29 (s, 3H), 3.36-3.40 (m, 2H), 3.46-3.53 (m, 1H), 4.43 (d, 1H), 4.48 (d, 1H), 4.54-4.57 (m, 1H), 4.88 (d, 1H), 5.16-5.24 (m, 1H), 5.98 (s, 1H), 7.12-7.19 (m, 1H), 7.29-7.43 (m, 2H), 11.10 (s, 1H).

The intermediate for this compound was prepared as follows:

i) N-[2-[[(2,3-difluorophenyl)methyl]thio]-6-[(1R)-1-[(4R)-2,2-dimethyl-1,3-dioxolan-4-yl]ethoxy]-4-pyrimidinyl]-methanesulfonamide A mixture of methanesulfonamide (0.11 g), tris(dibenzylideneacetone)dipalladium (0) (26 mg), 2-dicyclohexylphosphino-2',4',6'-tri-isopropyl-1,1'-biphenyl (XPHOS) (14 mg), cesium carbonate (0.14 g) and 4 chloro-2-[[(2,3-difluorophenyl)methyl]thio]-6-[(1R)-1-[(4R)-2,2-dimethyl-1,3-dioxolan-4-yl]ethoxy]-pyrimidine (the subtitle product of example 45 step v) (0.12 g) in dioxane (6 mL) was heated at reflux in a microwave at 100° C., 300 W, open vessel with cooling for 15 min. Saturated aqueous ammonium chloride was added and the resulting mixture extracted with ethyl acetate. The combined organic extracts were washed with brine, dried (MgSO$_4$), filtered and evaporated. The residue was purified by column chromatography on silica gel using EtOAc/isohexane (1:19 to 3:7 gradient) as eluent to give the subtitle compound as a yellow oil. Yield: 0.12 g.

MS: APCI (+ve) 476 [M+H$^+$]

$^1$H NMR (CDCl$_3$) δ 1.23 (d, 3H), 1.37 (s, 3H), 1.42 (s, 3H), 3.22 (s, 3H), 3.76 (dd, 1H), 4.04 (dd, 1H), 4.23 (q, 1H), 4.38 (s, 2H), 5.30 (quintet, 1H), 6.23 (s, 1H), 6.97-7.11 (m, 2H), 7.22-7.28 (m, 1H).

EXAMPLE 47

N-[2-[[(2,3-Difluorophenyl)methyl]thio]-6-{[(1R, 2S)-2,3-dihydroxy-1-methylpropyl]oxy}-4-pyrimidinyl]-1-azetidinesulfonamide

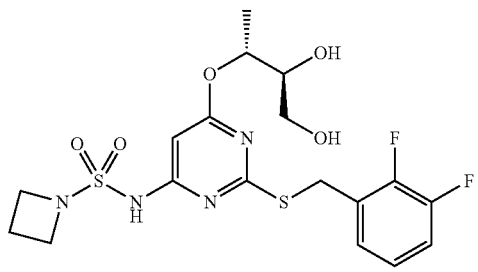 [SMILES: C[C@@H](Oc1cc(NS(=O)(=O)N2CCC2)nc(SCc2cccc(F)c2F)n1)[C@@H](O)CO]

To a solution of N-[2-[[(2,3-difluorophenyl)methyl]thio]-6-[(1R)-1-[(4S)-2,2-dimethyl-1,3-dioxolan-4-yl]ethoxy]-4-pyrimidinyl]-1-azetidinesulfonamide (the product of step (0.13 g) in DCM (5 mL) was added iron (III) chloride hexahydrate (0.24 g). The reaction mixture was stirred at ambient temperature for 1 h, then saturated aqueous sodium bicarbonate (10 mL) was added. The layers were separated and the aqueous material extracted with DCM (3×10 mL) and EtOAc (3×10 mL). The combined organic extracts were washed with saturated sodium chloride, dried (MgSO$_4$), filtered and evaporated. The residual pale yellow solid was slowly precipitated from DCM, filtered and the resulting material washed with minimal cold DCM (2×1 mL) to afford the title compound as a white powder. Yield: 45 mg.

MS: APCI (+ve) 477 [M+H$^+$]

$^1$H NMR: δ (CDCl$_3$) 1.36 (d, 3H), 2.27 (quintet, 2H), 2.34 (br s, 1H), 2.67 (d, 1H), 3.59-3.65 (m, 1H), 3.67-3.78 (m, 2H), 4.02 (t, 4H), 4.36 (s, 2H), 5.23 (quintet, 1H), 6.31 (s, 1H), 7.00-7.10 (m, 2H), 7.19-7.23 (m, 1H).

The intermediates for this compound were prepared as follows:

i) 4-chloro-2-[(2,3-difluorobenzyl)thio]-6-{(1R)-1-[(4S)-2,2-dimethyl-1,3-dioxolan-4-yl]ethoxy}pyrimidine The subtitle compound was prepared according to the procedure outlined in example 1 step (iii) using (1R)-1-[(4S)-2,2-dimethyl-1,3-dioxolan-4-yl]ethanol (prepared according to *Liebigs. Ann. Chem.* 1987, 7-14) (0.25 g) and 4,6-Dichloro-2-[(2,3-difluorobenzyl)thio]pyrimidine (the product of example 1 step ii) (0.53 g) in THF (20 mL) and 60% sodium hydride (80 mg). Crude material was purified by column chromatography on silica gel using EtOAc/isohexane (1:3) as eluent to give the subtitle compound as a clear, colourless oil. Yield: 0.37 g.

MS: APCI (+ve) 417/419 [M+H$^+$]

ii) N-[2-[[(2,3-Difluorophenyl)methyl]thio]-6-[(1R)-1-[(4S)-2,2-dimethyl-1,3-dioxolan-4-yl]ethoxy]-4-pyrimidinyl]-1-azetidinesulfonamide A mixture of azetidine-1-sulphonamide (prepared according to patent WO 2004/011443, 0.16 g), tris(dibenzylideneacetone)-dipalladium (0) (33 mg), 2-dicyclohexylphosphino-2',4',6'-tri-isopropyl-1,1'-biphenyl (XPHOS) (17 mg), cesium carbonate (0.28 g) and 4 chloro-2-[[(2,3-difluorophenyl)methyl]thio]-6-[1R)-1-[(4S)-2,2-dimethyl-1,3-dioxolan-4-yl]ethoxy]-pyrimidine (the product of step i) (0.25 g) in dioxane (10 mL) was heated at reflux in a microwave at 100° C., 300 W, open vessel with cooling for 20 min. Saturated ammonium chloride was added and the resulting mixture extracted with EtOAc. The combined organic extracts were washed with saturated aqueous sodium chloride, dried (MgSO$_4$), filtered and evaporated. The residue was purified by column chromatography on silica gel using EtOAc/isohexane (3:7) as eluent to give the subtitle compound as a yellow oil. Yield: 0.13 g.

MS: APCI (+ve) 517 [M+H$^+$]

EXAMPLE 48

N-[2-[[(2,3-Difluorophenyl)methyl]thio]-6-{[(1R, 2S)-2,3-dihydroxy-1-methylpropyl]oxy}-4-pyrimidinyl]-1-piperazinesulfonamide

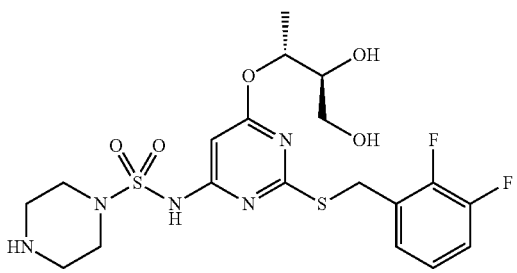 [SMILES: C[C@@H](Oc1cc(NS(=O)(=O)N2CCNCC2)nc(SCc2cccc(F)c2F)n1)[C@@H](O)CO]

A solution of tert-butyl 4-{[(2-[(2,3-difluorobenzyl)thio]-6-{(1R)-1-[(4S)-2,2-dimethyl-1,3-dioxolan-4-yl]ethoxy}pyrimidin-4-yl)amino]sulfonyl}piperazine-1-carboxylate (the product of step i) (0.23 g) in 10% trifluoroacetic acid/DCM (5 mL) was stirred at room temperature for 1 h. The mixture was evaporated to dryness in vacuo. The resulting crude oil was purified by reverse phase HPLC (75% to 5% gradient of 0.1% aqueous ammonium acetate in acetonitrile as eluent) to give the title compound as a white solid. Yield: 40 mg.

MS: APCI (+ve) 506 [M+H$^+$]

$^1$H NMR δ (DMSO) 1.14 (d, 3H), 2.99-3.05 (m, 4H), 3.11-3.17 (m, 4H), 3.25-3.40 (m, 2H), 3.54-3.61 (m, 1H), 4.34 (d, 1H), 4.41 (d, 1H), 4.54 (br s, 1H), 4.81 (d, 1H), 5.03 (dq, 1H), 5.82 (s, 1H), 7.09-7.16 (m, 1H), 7.26-7.35 (m, 1H), 7.43 (dd, 1H)

The intermediate for this compound was prepared as follows:

i) tert-butyl 4-{[(2-[(2,3-difluorobenzyl)thio]-6-{(1R)-1-[(4S)-2,2-dimethyl-1,3-dioxolan-4-yl]ethoxy}pyrimidin-4-yl)amino]sulfonyl}piperazine-1-carboxylate The subtitle compound was prepared from 1,1-dimethylethyl 4-sulfamoylpiperazine-1-carboxylate (the product of example 15, step i), 0.26 g) and 4-chloro-2-[(2,3-difluorobenzyl)thio]-6-{(1R)-1-[(4S)-2,2-dimethyl-1,3-dioxolan-4-yl]ethoxy}pyrimidine (the product of Example 47, step i) (0.21 g) according to the procedure outlined in Example 1, step iv). Yield: 0.28 g
MS: APCI (−ve) 644 [M−H]

EXAMPLE 49

5-(azetidin-1-ylcarbonyl)-N-{2-[(2,3-difluorobenzyl)thio]-6-[(1R)-2-hydroxy-1-methylethoxy]pyrimidin-4-yl}furan-2-sulfonamide

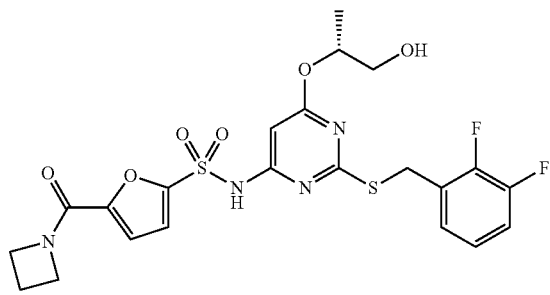 [SMILES: C[C@H](CO)Oc1cc(NS(=O)(=O)c2ccc(C(=O)N3CCC3)o2)nc(SCc2cccc(F)c2F)n1]

To a solution of 5-(azetidin-1-ylcarbonyl)-N-{2-[(2,3-difluorobenzyl)thio]-6-[(1R)-1-methyl-2-(triphenylmethyloxy)ethoxy]pyrimidin-4-yl}furan-2-sulfonamide (the product of step iv) (0.24 g) in methanol (5 mL) was added para-toluenesulfonic acid hydrate (58 mg) and anisole (0.34 mL). After stirring at room temperature for 2 d, H$_2$O (5 mL) was added and the mixture extracted with EtOAc (3×10 mL). The combined organic layers were washed with brine (10 mL), dried (MgSO$_4$), filtered and evaporated to dryness in vacuo. The resulting crude solid was purified by reverse phase HPLC (50% to 5% gradient of 0.1% aqueous ammonium acetate in acetonitrile as eluent) to give the title compound as a white solid. Yield: 10 mg.
MS: APCI (+ve) 541 [M+H$^+$]
$^1$H NMR δ (CDCl$_3$) 1.28 (d, 3H), 2.39 (quintet, 2H), 3.70 (dd, 1H), 3.76 (dd, 1H), 4.20 (t, 4H), 4.33 (d, 1H), 4.37 (d, 1H), 4.51 (t, 2H), 5.31 (dquintet, 1H), 6.41 (s, 1H), 6.99-7.08 (m, 2H), 7.11 (d, 1H), 7.17-7.22 (m, 1H), 7.21 (d, 1H)

The intermediates for this compound were prepared as follows:

i) methyl 5-[(tert-butylamino)sulfonyl]-2-furoate

To a solution of methyl 5-(chlorosulfonyl)-2-furoate (3.0 g) in DCM (100 mL) was added tert-butylamine (3.6 mL). After stirring at room temperature for 2 days the mixture was filtered through a pad of celite, washing with DCM (2×10 mL). The filtrate was evaporated to dryness in vacuo. The resulting crude residue was purified by column chromatography using EtOAc/isohexane (2:8) as eluent to give the subtitle compound as a foam. Yield: 2.75 g.
MS: APCI (−ve) 260 [M−H]

ii) 5-(azetidin-1-ylcarbonyl)-N-(tert-butyl)furan-2-sulfonamide

To a solution of methyl 5-[(tert-butylamino)sulfonyl]-2-furoate (the product of step i) (2.15 g) in methanol (80 mL) was added azetidine (1.15 mL). After stirring at room temperature for 5 h the mixture was evaporated to dryness in vacuo. The resulting residue was partitioned between EtOAc (50 mL) and H$_2$O (50 mL). The separated organic layer was dried (MgSO$_4$), filtered and evaporated to dryness in vacuo. The resulting crude material was purified by column chromatography (EtOAC as eluent) to give the subtitle compound as a pale yellow oil. Yield: 3 g.
MS: APCI (+ve) 287 [M+H$^+$]

iii) 5-(azetidin-1-ylcarbonyl)furan-2-sulfonamide

A solution of 5-(azetidin-1-ylcarbonyl)-N-(tert-butyl)furan-2-sulfonamide (the product of step ii) (3 g) in trifluoroacetic acid (90 mL) was stirred at room temperature. After 18 h the mixture was evaporated to dryness in vacuo. The resulting oil was triturated with Et$_2$O and filtered to give the subtitle compound as a white solid. Yield: 1.75 g.
MS: APCI (+ve) 231 [M+H$^+$]

iv) 5-(azetidin-1-ylcarbonyl)-N-{2-[(2,3-difluorobenzyl)thio]-6-[(1R)-1-methyl-2-(triphenylmethyloxy)ethoxy]pyrimidin-4-yl}furan-2-sulfonamide The subtitle compound was prepared from 5-(azetidin-1-ylcarbonyl)furan-2-sulfonamide (the product of step iii) (0.40 g) and 4-chloro-2-[[(2,3-difluorophenyl)methyl]thio]-6-[(1R)-1-methyl-2-(triphenylmethoxy)ethoxy]-pyrimidine (the product of Example 13, step iii) (0.41 g) according to the procedure outlined in Example 1, step iv). Yield: 0.25 g
MS: APCI (−ve) 781 [M−H]

EXAMPLE 50

N-(tert-butyl)-5-[({2-[(2,3-difluorobenzyl)thio]-6-[(1R)-2-hydroxy-1-methylethoxy]pyrimidin-4-yl}amino)sulfonyl]-2-furamide

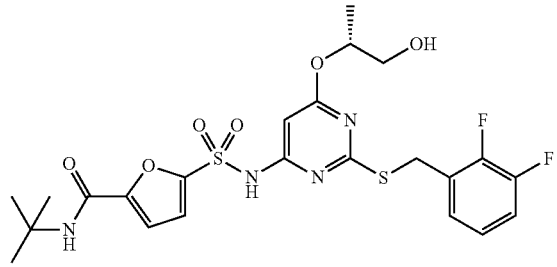 [SMILES: C[C@H](CO)Oc1cc(NS(=O)(=O)c2ccc(C(=O)NC(C)(C)C)o2)nc(SCc2cccc(F)c2F)n1]

To a solution of ethyl (2R)-2-({6-[({5-[(tert-butylamino)carbonyl]-2-furyl}sulfonyl)amino]-2-[(2,3-difluorobenzyl)thio]pyrimidin-4-yl}oxy)propanoate (the product of step iii) (0.25 g) in THF (10 mL) was added a solution of lithium borohydride (0.6 mL, 2.0M in hexanes) dropwise at 0° C. The mixture was warmed to room temperature and stirred for 18 h. After cooling to 0° C., 1N HCl (20 mL) was added slowly, and the mixture extracted with EtOAc (3×20 mL). The combined organic layers were dried (MgSO₄), filtered and evaporated to dryness in vacuo. The resulting crude oil was purified by reverse phase HPLC (75% to 5% gradient of 0.2% aqueous trifluoroacetic acid in acetonitrile as eluent) to give the title compound as a white solid. Yield: 90 mg.

MS: APCI (−ve) 555 [M−H]

¹H NMR δ (CDCl₃): 1.27 (d, 3H), 1.44 (s, 9H), 3.69 (dd, 1H), 3.75 (dd, 1H), 4.33 (d, 1H), 4.38 (d, 1H), 5.26-5.33 (m, 1H), 6.23 (br s, 1H), 6.32 (s, 1H), 6.98-7.08 (m, 2H), 7.09 (d, 1H), 7.17-7.21 (m, 1H), 7.23 (d, 1H)

The intermediates for this compound were prepared as follows:

i) N-(tert-butyl)-5-cyanofuran-2-sulfonamide

A solution of 5-formylfuran-2-sulfonic acid sodium salt (2.97 g), and hydroxylamine hydrochloride (1.05 g) in H₂O (1.35 mL) and acetic acid (21 mL) was heated at 60° C. for 4 h. After cooling to room temperature the solvent was removed in vacuo. The crude residue was triturated with Et₂O (3×50 mL) and dried under high vacuum to give a crude pale brown solid. A solution of this material (3.7 g) in phosphorusoxychloride (100 mL) was heated at 60° C. for 18 h. After cooling to room temperature the mixture was partitioned between ice-water (100 mL) and EtOAc (100 mL). The aqueous layer was separated and further extracted with EtOAc (2×100 mL). The combined organic phases were washed with brine (100 mL), dried (MgSO₄), filtered and evaporated to dryness in vacuo to give a crude brown oil. To a solution of this crude oil (1.6 g) in DCM (85 mL) was added tert-butylamine (1.8 mL). After stirring at room temperature for 2 days the mixture was filtered through celite, washing with DCM (2×20 mL). The filtrate was evaporated to dryness in vacuo. The resulting crude material was purified by column chromatography using EtOAc/isohexane (2:8) as eluent to give the subtitle compound as a pale yellow oil. Yield: 1.0 g.

MS: APCI (−ve) 227 [M−H]

ii) 5-(aminosulfonyl)-N-(tert-butyl)-2-furamide

A solution of N-(tert-butyl)-5-cyanofuran-2-sulfonamide (the product of step i) (1.0 g) in trifluoroacetic acid (30 mL) was stirred at room temperature for 24 h. The mixture was evaporated to dryness in vacuo to leave a crude yellow oil that was triturated with Et₂O and filtered to give the subtitle compound as a white solid. Yield: 0.25 g.

MS: APCI (−ve) 245 [M−H]

iii) ethyl (2R)-2-({6-[({5-[(tert-butylamino)carbonyl]-2-furyl}sulfonyl)amino]-2-[(2,3-difluorobenzyl)thio]pyrimidin-4-yl}oxy)propanoate The subtitle compound was prepared according to the procedure outlined in example 1 step (iv) using a mixture of 5-(aminosulfonyl)-N-(tert-butyl)-2-furamide (0.25 g), tris(dibenzylideneacetone)dipalladium (0) (58 mg), 2-dicyclohexylphosphino-2',4',6'-tri-isopropyl-1,1'-biphenyl (XPHOS) (30 mg), cesium carbonate (0.65 g) and 2-[[6-chloro-2-[[(2,3-difluorophenyl)methyl]thio]-4-pyrimidinyl]oxy]-(2R)-propanoic acid ethyl ester (product of Example 11 step i) (0.26 g) in dioxane (1.0 mL). Purification was trituration with Et₂O to give the subtitle compound as a white solid. Yield: 0.25 g MS: APCI (+ve) 599 [M+H⁺]

EXAMPLE 51

5-cyano-N-{2-[(2,3-difluorobenzyl)thio]-6-[(1R)-2-hydroxy-1-methylethoxy]pyrimidin-4-yl}furan-2-sulfonamide

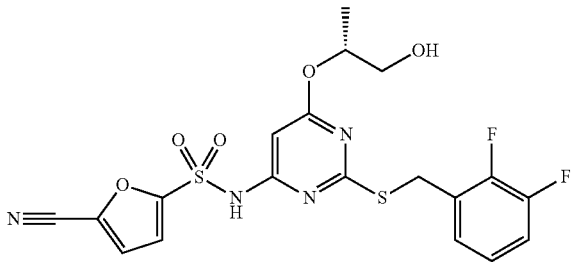 [SMILES: C[C@H](CO)Oc1cc(NS(=O)(=O)c2ccc(C#N)o2)nc(SCc2cccc(F)c2F)n1]

To a solution of 5-cyano-N-{2-[(2,3-difluorobenzyl)thio]-6-[(1R)-1-methyl-2-(triphenylmethyloxy)ethoxy]pyrimidin-4-yl}furan-2-sulfonamide (the product of step ii) (0.15 g) in methanol (5 mL) was added para-toluenesulfonic acid hydrate (39 mg) and anisole (0.23 mL). After stirring at room temperature for 5 h, H₂O (5 mL) was added and the mixture extracted with EtOAc (3×10 mL). The combined organic layers were washed with brine (10 mL), dried (MgSO₄), filtered and evaporated to dryness in vacuo. The resulting crude solid was purified by reverse phase HPLC (75% to 5% gradient of 0.1% aqueous ammonium acetate in acetonitrile as eluent) to give the title compound as a white solid. Yield: 20 mg.

MS: APCI (−ve) 481 [M+H⁻]

¹H NMR δ (CDCl₃): 1.28 (d, 3H), 3.71 (dd, 1H), 3.76 (dd, 1H), 4.34 (d, 1H), 4.38 (d, 1H), 5.29-5.33 (m, 1H), 6.31 (s, 1H), 7.00-7.11 (m, 2H), 7.15 (d, 1H), 7.18-7.21 (m, 1H), 7.24 (d, 1H)

The intermediates for this compound were prepared as follows:

i) 5-cyanofuran-2-sulfonamide

A solution of N-(tert-butyl)-5-cyanofuran-2-sulfonamide (the product of example 50, step i) (1.0 g) in trifluoroacetic acid (30 mL) was stirred at room temperature for 24 h. The mixture was evaporated to dryness in vacuo to leave a crude yellow oil that was triturated with Et₂O and filtered. The filtrate was evaporated to dryness in vacuo to give the subtitle compound as a pale yellow oil. Yield: 0.29 g.

MS: APCI (−ve) 171 [M−H⁻]

ii) 5-cyano-N-{2-[(2,3-difluorobenzyl)thio]-6-[(1R)-1-methyl-2-(triphenylmethyloxy)ethoxy]pyrimidin-4-yl}furan-2-sulfonamide The subtitle compound was prepared from 5-cyanofuran-2-sulfonamide (the product of step i) (0.29 g) and 4-chloro-2-[[(2,3-difluorophenyl)methyl]thio]-6-[(1R)-1-methyl-2-(triphenylmethoxy)ethoxy]-pyrimidine (the product of Example 13, step (0.15 g) according to the procedure outlined in Example 1, step iv). Purification was by column chromatography on silica gel using EtOAc/isohexane (1:4 to 2:3 gradient) to give the subtitle compound as a pale yellow solid. Yield: 0.25 g MS: APCI (−ve) 723 [M−H]

EXAMPLE 52

N-{2-[(2,3-Difluorobenzyl)thio]-6-methoxypyrimidin-4-yl}-4-pyrimidin-2-ylpiperazine-1-sulfonamide

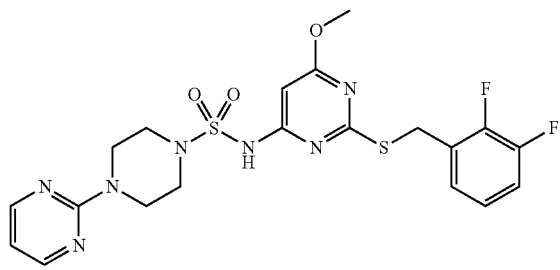 [SMILES: COc1cc(NS(=O)(=O)N2CCN(c3ncccn3)CC2)nc(SCc2cccc(F)c2F)n1]

The title compound was prepared according to the procedure outlined in example 1 step (iv) using a mixture of 4-pyrimidin-2-ylpiperazine-1-sulfonamide (0.24 g), tris(dibenzylideneacetone)dipalladium (0) (60 mg), 2-dicyclohexylphosphino-2',4',6'-tri-isopropyl-1,1'-biphenyl (XPHOS) (31 mg), cesium carbonate (0.32 g) and 4-Chloro-2-[[(2,3-difluorophenyl)methyl]thio]-6-methoxypyrimidine (the product of Example 35, step i) (0.20 g) in dioxane (6 ml). The crude material was purified by column chromatography using EtOAc/isohexane (2:8 to 1:1 gradient) as eluent to give the title compound as a pale yellow foam. Yield: 0.19 g.

MS: APCI (+ve) 510 [M+H]

$^1$H NMR: δ (DMSO) 3.26 (m, 4H), 3.77 (m, 4H), 3.86 (s, 3H), 4.47 (s, 2H), 6.08 (s, 1H), 6.67 (t, 1H), 7.13 (m, 1H), 7.33 (m, 1H), 7.40 (dt, 1H), 8.37 (d, 2H), 11.16 (bs, 1H)

The intermediate for this compound was prepared as follows:

i) 4-Pyrimidin-2-ylpiperazine-1-sulfonamide

The subtitle compound was prepared according to the procedure outlined in example 15 step i) using 2-piperazin-1-ylpyrimidine (3.0 g) and sulfamide (1.2 g) in dioxane (30 mL) to give the subtitle compound as a white solid. Yield: 2.06 g.

$^1$H NMR: δ (DMSO) 3.00 (t, 2H), 3.83 (t, 2H), 6.68 (t, 1H), 6.81 (bs, 1H), 8.39 (d, 2H)

EXAMPLE 53

N-{5-[({2-[(2,3-Difluorobenzyl)thio]-6-methoxypyrimidin-4-yl}amino)sulfonyl]-4-methyl-1,3-thiazol-2-yl}acetamide

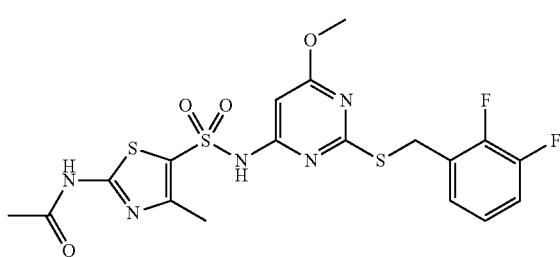 [SMILES: COc1cc(NS(=O)(=O)c2sc(NC(C)=O)nc2C)nc(SCc2cccc(F)c2F)n1]

The title compound was prepared according to the procedure outlined in example 1 step (iv) using a mixture of N-[5-(aminosulfonyl)-4-methyl-1,3-thiazol-2-yl]acetamide (0.25 g), tris(dibenzylideneacetone)dipalladium (0) (64 mg), 2-dicyclohexylphosphino-2',4',6'-tri-isopropyl-1,1'-biphenyl (XPHOS) (33 mg), cesium carbonate (0.69 g) and 4-Chloro-2-[[(2,3-difluorophenyl)methyl]thio]-6-methoxypyrimidine (the product of Example 35, step i) (0.21 g) in dioxane (6 ml). The crude material was purified by column chromatography using EtOAc/isohexane (2.5:7.5 to 4:6 gradient) as eluent to give the title compound as a pale yellow solid. Yield: 85 mg.

MS: APCI (+ve) 502 [M+H]

$^1$H NMR: δ (CDCl$_3$) 2.26 (s, 3H), 2.57 (s, 3H), 3.90 (s, 3H), 4.38 (s, 2H), 6.32 (s, 1H), 7.03 (m, 2H), 7.19 (dt, 1H)

The intermediates for this compound were prepared as follows:

i) N-{5-[(tert-Butylamino)sulfonyl]-4-methyl-1,3-thiazol-2-yl}acetamide

To a suspension of 2-(acetylamino)-4-methyl-1,3-thiazole-5-sulfonyl chloride (1.0 g) in DCM (10 ml) was added tert-butylamine (0.92 ml) and the mixture was stirred at room temperature for 2 d. The mixture was diluted with H$_2$O and extracted with DCM (×3). The combined organic extracts were dried (MgSO$_4$), filtered and evaporated to give the subtitle compound as a beige foam. Yield 1.1 g.

MS: APCI (+ve) 292 [M+H]

ii) N-[5-(Aminosulfonyl)-4-methyl-1,3-thiazol-2-yl]acetamide

A solution of N-{5-[(tert-butylamino)sulfonyl]-4-methyl-1,3-thiazol-2-yl}acetamide (1.1 g) in TFA (10 ml) was stirred at room temperature for 3 d. The mixture was evaporated, redissolved in TFA (10 ml) and stirred for a further 1d. On evaporation the resulting oil was azeotroped with DCM (×2) and triturated with Et$_2$O to give the subtitle compound as a beige solid. Yield 0.7 g.

MS: APCI (+ve) 236 [M+H]

EXAMPLE 54

2-Amino-N-{2-[(2,3-difluorobenzyl)thio]-6-methoxypyrimidin-4-yl}-4-methyl-1,3-thiazole-5-sulfonamide

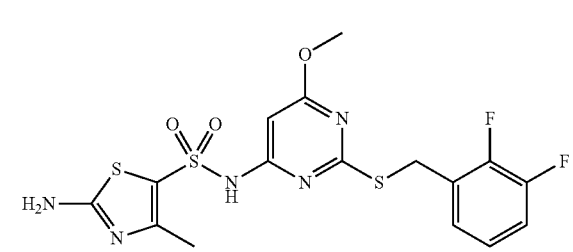 [SMILES: COc1cc(NS(=O)(=O)c2sc(N)nc2C)nc(SCc2cccc(F)c2F)n1]

The title compound was prepared according to the procedure outlined in example 1 step (iv) using a mixture of 2-amino-4-methyl-1,3-thiazole-5-sulfonamide (0.23 g), tris(dibenzylideneacetone)dipalladium (0) (73 mg), 2-dicyclohexylphosphino-2',4',6'-tri-isopropyl-1,1'-biphenyl (XPHOS) (38 mg), cesium carbonate (0.39 g) and 4-Chloro-2-[[(2,3-difluorophenyl)methyl]thio]-6-methoxypyrimidine (the product of Example 35, step i) (0.24 g) in dioxane (6 ml). The crude material was purified by column chromatography using EtOAc/isohexane (2:8 to 4.5:5.5 gradient) as eluent and trituration with Et$_2$O to give the title compound as a beige solid. Yield: 0.15 g.

MS: APCI (+ve) 460 [M+H]

$^1$H NMR: δ (DMSO) 2.42 (s, 3H), 3.91 (s, 3H), 4.56 (s, 2H), 6.07 (s, 1H), 7.18 (dq, 1H), 7.35 (m, 2H), 7.55 (bs, 2H), 11.91 (bs, 1H)

The intermediate for this compound was prepared as follows:

i) 2-Amino-4-methyl-1,3-thiazole-5-sulfonamide

A suspension of N-[5-(aminosulfonyl)-4-methyl-1,3-thiazol-2-yl]acetamide (the product from Example 53, step (0.44 g) in hydrazine hydrate (1.5 ml) was stirred at room temperature for 4 h. The mixture was diluted with $H_2O$ and extracted with EtOAc (×4). The combined organic extracts were dried (MgSO$_4$), filtered and evaporated to give the subtitle compound as an off-white solid. Yield 0.23 g.

MS: APCI (+ve) 194 [M+H]

EXAMPLE 55

N-(2-[(2,3-Difluorobenzyl)thio]-6-{[(1R,2S)-2,3-dihydroxy-1-methylpropyl]oxy}pyrimidin-4-yl)methanesulfonamide

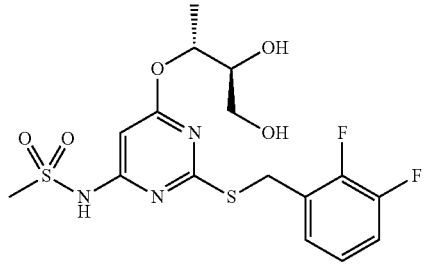 [SMILES: C[C@@H](Oc1cc(NS(C)(=O)=O)nc(SCc2cccc(F)c2F)n1)[C@@H](O)CO]

To a solution of N-(2-[(2,3-difluorobenzyl)thio]-6-{(1R)-1-[(4S)-2,2-dimethyl-1,3-dioxolan-4-yl]ethoxy}pyrimidin-4-yl)methanesulfonamide (0.23 g) in MeOH (2 ml) was added TFA (0.4 ml) and the reaction was stirred at room temperature for 20 h. The mixture was evaporated, suspended in saturated sodium carbonate solution and then re-acidified to pH5 with glacial acetic acid with stirring. The resulting solid was collected, washed with $H_2O$ and dried to give the title compound as a cream solid. Yield 0.17 g.

MS: APCI (+ve) 436 [M+H]

$^1$H NMR: δ (DMSO) 1.18 (d, 3H), 3.26 (s, 3H), 3.36 (t, 2H), 3.62 (quintet, 1H), 4.45 (quintet, 2H), 4.60 (t, 1H), 4.93 (d, 1H), 5.17 (quintet, 1H), 5.97 (s, 1H), 7.17 (m, 1H), 7.35 (m, 1H), 7.40 (m, 1H)

The intermediate for this compound was prepared as follows:

i) N-(2-[(2,3-Difluorobenzyl)thio]-6-{(1R)-1-[(4S)-2,2-dimethyl-1,3-dioxolan-4-yl]ethoxy}pyrimidin-4-yl)methanesulfonamide The subtitle compound was prepared according to the procedure outlined in example 1 step (iv) using a mixture of methane sulfonamide (0.25 g), tris(dibenzylideneacetone)dipalladium (0) (55 mg), 2-dicyclohexylphosphino-2',4',6'-tri-isopropyl-1,1'-biphenyl (XPHOS) (29 mg), cesium carbonate (0.30 g) and 4-chloro-2-[(2,3-difluorobenzyl)thio]-6-{(1R)-1-[(4S)-2,2-dimethyl-1,3-dioxolan-4-yl]ethoxy}pyrimidine (the product of Example 47, step i) (0.25 g) in dioxane (5 ml). The crude material was purified by column chromatography using EtOAc/isohexane (2:8) as eluent to give the subtitle compound as a yellow oil. Yield: 0.25 g.

MS: APCI (+ve) 476 [M+H]

EXAMPLE 56

N-(2-[(2,3-Difluorobenzyl)thio]-6-{[(1R,2S)-2,3-dihydroxy-1-methylpropyl]oxy}pyrimidin-4-yl)morpholine-4-sulfonamide

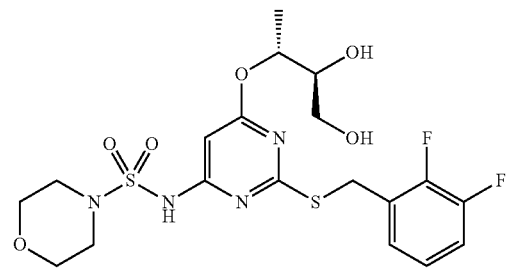 [SMILES: C[C@@H](Oc1cc(NS(=O)(=O)N2CCOCC2)nc(SCc2cccc(F)c2F)n1)[C@@H](O)CO]

To a solution of N-(2-[(2,3-difluorobenzyl)thio]-6-{(1R)-1-[(4S)-2,2-dimethyl-1,3-dioxolan-4-yl]ethoxy}pyrimidin-4-yl)morpholine-4-sulfonamide (0.20 g) in MeOH (2 ml) was added TFA (0.4 ml) and the reaction was stirred at room temperature for 20 h. The mixture was evaporated, suspended in saturated sodium carbonate solution and then re-acidified to pH5 with glacial acetic acid with stirring. The resulting solid was collected, washed with $H_2O$ and dried to give the title compound as a white solid. Yield 0.15 g.

MS: APCI (+ve) 507 [M+H]

$^1$H NMR: δ (DMSO) 1.18 (d, 3H), 3.18 (m, 4H), 3.33 (m, 2H), 3.60 (m, 5H), 4.44 (q, 2H), 4.60 (t, 1H), 4.89 (d, 1H), 5.20 (quintet, 1H), 6.03 (s, 1H), 7.16 (m, 1H), 7.38 (m, 2H), 11.13 (bs, 1H)

The intermediate for this compound was prepared as follows:

i) N-(2-[(2,3-Difluorobenzyl)thio]-6-{(1R)-1-[(4S)-2,2-dimethyl-1,3-dioxolan-4-yl]ethoxy}pyrimidin-4-yl)morpholine-4-sulfonamide The subtitle compound was prepared according to the procedure outlined in example 1 step (iv) using a mixture of 4-morpholine sulfonamide (prepared according to patent WO 2004/011443) (0.15 g), tris(dibenzylideneacetone)dipalladium (0) (55 mg), 2-dicyclohexylphosphino-2',4',6'-tri-isopropyl-1,1'-biphenyl (XPHOS) (29 mg), cesium carbonate (0.30 g) and 4-chloro-2-[(2,3-difluorobenzyl)thio]-6-{(1R)-1-[(4.5)-2,2-dimethyl-1,3-dioxolan-4-yl]ethoxy}pyrimidine (the product of Example 47, step i) (0.25 g) in dioxane (5 ml). The crude material was purified by column chromatography using EtOAc/isohexane (1:9 to 2.5:7.5 gradient) as eluent to give the subtitle compound as an off-white foam. Yield: 0.20 g.

MS: APCI (+ve) 547 [M+H]

EXAMPLE 57

N-[2-[(2,3-Difluorobenzyl)thio]-6-(methylthio)pyrimidin-4-yl]methanesulfonamide

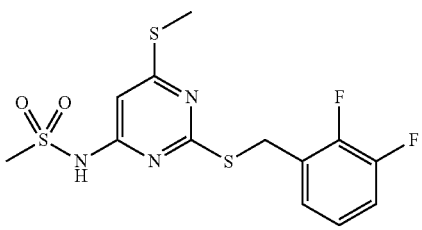

A mixture of methane sulfonamide (0.22 g), tris(dibenzylideneacetone)-dipalladium (0) (33 mg), 2-dicyclohexylphosphino-2',4',6'-tri-isopropyl-1,1'-biphenyl(XPHOS) (17 mg), cesium carbonate (0.58 g) and 4-chloro-2-[(2,3-difluorobenzyl)thio]-6-(methylthio)pyrimidine (the product of step i) (0.38 g) in dioxane (10 mL) was heated at 100° C. for 18 h. The mixture was cooled and saturated ammonium chloride was added and the resulting mixture extracted with EtOAc. The combined organic extracts were washed with saturated aqueous sodium chloride, dried (MgSO$_4$), filtered and evaporated. The residue was purified by reverse phase HPLC eluting with acetonitrile/aq. 0.1% TFA mixtures to give the title compound as a white solid. Yield: 30 mg.

MS: APCI (+ve) 378 [M+H$^+$]

$^1$H NMR (CDCl$_3$) δ 2.52 (3H, s), 3.21 (3H, s), 4.44 (2H, s), 6.73 (1H, s), 6.99-7.10 (2H, m), 7.21-7.24 (1H, m)

The intermediate for this compound was prepared as follows:

i) 4-chloro-2-[(2,3-difluorobenzyl)thio]-6-(methylthio)pyrimidine

To a solution of 4,6-dichloro-2-[(2,3-difluorobenzyl)thio]pyrimidine (the product of example 1 step (1.54 g) in THF (50 mL) was added sodium methanethiolate (0.39 g). The mixture was allowed to warm to room temperature and stirring continued for 2 h. Saturated ammonium chloride was added and the resulting mixture extracted with EtOAc. The combined organic extracts were washed with saturated aqueous sodium chloride, dried (MgSO$_4$), filtered and evaporated to give the subtitle compound as a pale yellow solid. Yield: 1.51 g.

MS: APCI (−ve) 317/319 [M−H$^-$]

EXAMPLE 58

N-[2-[(2,3-Difluorobenzyl)thio]-6-(methylthio)pyrimidin-4-yl]azetidine-1-sulfonamide

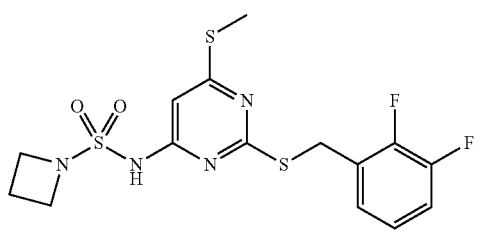 [SMILES: CSc1cc(NS(=O)(=O)N2CCC2)nc(SCc2cccc(F)c2F)n1]

A mixture of azetidine-1-sulfonamide (prepared according to patent WO 2004/011443, 0.32 g), tris(dibenzylideneacetone)-dipalladium (0) (33 mg), 2-dicyclohexylphosphino-2',4',6'-tri-isopropyl-1,1'-biphenyl (XPHOS) (17 mg), cesium carbonate (0.58 g) and 4-chloro-2-[(2,3-difluorobenzyl)thio]-6-(methylthio)pyrimidine (the product of example 57, step i) (0.38 g) in dioxane (10 mL) was heated at 100° C. for 18 h. The mixture was cooled and saturated ammonium chloride was added and the resulting mixture extracted with EtOAc. The combined organic extracts were washed with saturated aqueous sodium chloride, dried (MgSO$_4$), filtered and evaporated. The residue was purified by reverse phase HPLC eluting with acetonitrile/aq. 0.1% ammonium acetate mixtures to give the title compound as a white solid. Yield: 50 mg.

MS: APCI (+ve) 419 [M+H$^+$]

$^1$H NMR (CDCl$_3$) δ 2.25 (2H, quintet), 2.51 (3H, s), 4.01 (4H, t), 4.43 (2H, s), 6.81 (1H, s), 6.98-7.10 (2H, m), 7.21-7.24 (1H, m)

EXAMPLE 59

N-[2-[(2,3-Difluorobenzyl)thio]-6-(methylthio)pyrimidin-4-yl]morpholine-4-sulfonamide

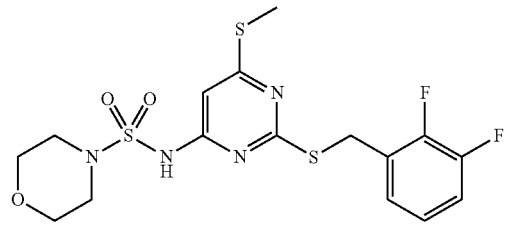

A mixture of 4-morpholinesulfonamide (prepared according to patent WO 2004/011443, 0.39 g), tris(dibenzylideneacetone)-dipalladium (0) (33 mg), 2-dicyclohexylphosphino-2',4',6'-tri-isopropyl-1,1'-biphenyl (XPHOS) (17 mg), cesium carbonate (0.58 g) and 4-chloro-2-[(2,3-difluorobenzyl)thio]-6-(methylthio)pyrimidine (the product of example 57, step i) (0.38 g) in dioxane (10 mL) was heated at 100° C. for 18 h. The mixture was cooled and saturated ammonium chloride was added and the resulting mixture extracted with EtOAc. The combined organic extracts were washed with saturated aqueous sodium chloride, dried (MgSO$_4$), filtered and evaporated. The residue was purified by reverse phase HPLC eluting with acetonitrile/aq. 0.1% ammonium acetate mixtures to give the title compound as a white solid. Yield: 30 mg.

MS: APCI (+ve) 449 [M+H$^+$]

$^1$H NMR (CDCl$_3$) δ 2.51 (3H, s), 3.30 (4H, t), 3.72 (4H, t), 4.43 (2H, s), 6.73 (1H, s), 7.00-7.10 (2H, m), 7.21-7.24 (1H, m)

EXAMPLE 60

N-[2-[[(2,3-Difluorophenyl)methyl]thio]-6-{[(1R,2R)-2,3-dihydroxy-1-methylpropyl]oxy}-4-pyrimidinyl]-1-morpholinesulfonamide

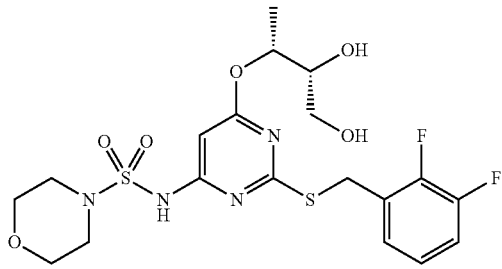 [SMILES: C[C@@H](Oc1cc(NS(=O)(=O)N2CCOCC2)nc(SCc2cccc(F)c2F)n1)[C@H](O)CO]

To a solution of N-[2-[[(2,3-difluorophenyl)methyl]thio]-6-[(1R)-1-[(4R)-2,2-dimethyl-1,3-dioxolan-4-yl]ethoxy]-4-pyrimidinyl]-1-morpholinesulfonamide (the product of step i) (0.17 g) in DCM (5 ml) was added iron (III) chloride hexahydrate (0.25 g). The reaction mixture was stirred at room temperature for 3 h after which time further iron (III) chloride hexahydrate (0.25 g) was added. After a further 3 h saturated aqueous sodium bicarbonate (1 ml) was added. The layers were separated and the aqueous material extracted with DCM (×3) and EtOAc (×3). The combined organic extracts were washed with saturated aqueous sodium chloride, dried with sodium sulfate, filtered and evaporated. The residual solid was purified by reverse phase HPLC (gradient 25-95% acetonitrile in 0.2% aqueous TFA) to afford the title compound as a white powder. Yield: 23 mg MS: APCI (+ve) 507 [M+H$^+$]

$^1$H NMR: δ (400 MHz, CDCl$_3$) 1.31 (d, 3H), 3.29-3.32 (m, 4H), 3.60-3.80 (m, 7H), 4.36 (½Abq, 1H), 4.36 (½Abq, 1H), 5.31 (quintet, 1H), 6.23 (s, 1H), 6.99-7.10 (m, 2H), 7.20-7.23 (m, 1H).

The intermediate for this compound was prepared as follows:

i) N-[2-[[(2,3-Difluorophenyl)methyl]thio]-6-[(1R)-1-[(4R)-2,2-dimethyl-1,3-dioxolan-4-yl]ethoxy]-4-pyrimidinyl]-4-morpholinesulfonamide A mixture of morpholine-4-sulfonamide (prepared according to patent WO 2004/011443, 0.239 g), tris(dibenzylideneacetone)-dipalladium (0) (33 mg), 2-dicyclohexylphosphino-2',4',6'-tri-isopropyl-1,1'-biphenyl (XPHOS) (17 mg), cesium carbonate (0.176 g) and 4-chloro-2-[(2,3-difluorobenzyl)thio]-6-{(1R)-1-[(4R)-2,2-dimethyl-1,3-dioxolan-4-yl]ethoxy}pyrimidine (the product of example 45 step vi) (0.150 g) in anhydrous dioxane (6 ml) was heated at reflux in a microwave at 100° C., 300 W, open vessel with cooling for 20 min. Saturated aqueous ammonium chloride was added and the resulting mixture extracted with EtOAc. The combined organic extracts were washed with saturated aqueous sodium chloride, dried with sodium sulfate, filtered and evaporated. The residue was purified by column chromatography on silica using a 1:19 to 2:3 mixture of EtOAc and iso-hexane as eluent to give the subtitle compound as a yellow gum. Yield: 0.165 g MS: APCI(+ve) 547 [M+H$^+$]

EXAMPLE 61

N-[2-[[(2,3-Difluorophenyl)methyl]thio]-6-{[(1S,2R)-2,3-dihydroxy-1-methylpropyl]oxy}-4-pyrimidinyl]-1-azetidinesulfonamide

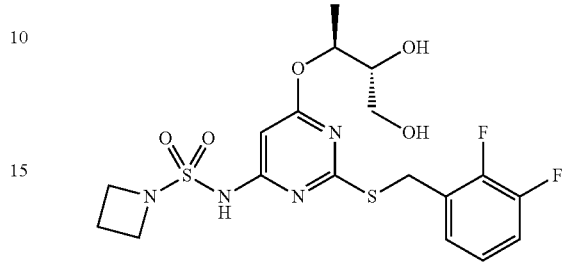

To a solution of N-(2-[(2,3-difluorobenzyl)thio]-6-{(1S)-1-[(2R)-1,4-dioxaspiro[4.5]dec-2-yl]ethoxy}pyrimidin-4-yl)azetidine-1-sulfonamide (the product of step (43 mg) in DCM (4 ml) was added iron (III) chloride hexahydrate (73 mg). The reaction mixture was stirred at room temperature for 2 h after which time further iron (III) chloride hexahydrate (40 mg) was added. After 3 d at −18° C., H$_2$O and DCM were added. The layers were separated and the aqueous material extracted with further DCM. The combined organic extracts were washed with saturated aqueous sodium chloride, dried with sodium sulfate, filtered and evaporated. TFA (1 ml) and DCM (4 ml) were added to the residue and the reaction mixture stirred at room temperature for 2 d. The mixture was partitioned between saturated aqueous sodium bicarbonate and DCM, then neutralised with 2M aqueous hydrochloric acid, the layers separated and the aqueous material extracted with further DCM. The DCM extracts were allowed to slowly evaporate and the resulting solid washed with minimal cold DCM to afford the title compound as a white powder. Yield: 11 mg MS: APCI (+ve) 477 [M+H$^+$]

$^1$H NMR: δ (300 MHz, CDCl$_3$) 1.36 (d, 3H), 2.27 (quintet, 2H), 3.59-3.65 (m, 1H), 3.68-3.78 (m, 2H), 4.02 (t, 4H), 4.37 (s, 2H), 5.23 (quintet, 1H), 6.31 (s, 1H), 6.99-7.11 (m, 2H), 7.19-7.23 (m, 1H).

The intermediates for this compound were prepared as follows:

i) 4-Chloro-2-[(2,3-difluorobenzyl)thio]-6-{(1S)-1-[(2R)-1,4-dioxaspiro[4.5]dec-2-yl]ethoxy}pyrimidine A solution of (1S)-1-[(2R)-1,4-dioxaspiro[4.5]dec-2-yl]ethanol (prepared according to J. Org. Chem. 1995, 60, 585-587, 0.183 g of −2:1 mixture of diastereomers) in dry THF (5 ml) was cooled to 0° C. and to it was added (in portions) sodium hydride (46 mg as 60% dispersion in mineral oil) followed in portions by 4,6-dichloro-2-(2,3-difluoro-benzylsulfanyl)-pyrimidine (product of example 1 step ii, 0.252 g). The reaction mixture was stirred at room temperature for 24 h then quenched with saturated aqueous ammonium chloride (2 ml) and diluted with EtOAc. The layers were separated and the aqueous layer extracted with further EtOAc. The combined organic extracts were washed with saturated aqueous sodium chloride, dried with sodium sulfate, filtered and evaporated to leave a yellow oil which was purified by column chromatography on silica using a 0.5 to 4% mixture of EtOAc in iso-hexane as eluent to afford the subtitle compound as a white solid. Yield: 0.10 g MS: APCI (+ve) 457/459 [M+H$^+$]

ii) N-(2-[(2,3-Difluorobenzyl)thio]-6-{(1S)-1-[(2R)-1,4-dioxaspiro[4.5]dec-2-yl]ethoxy}pyrimidin-4-yl)azetidine-1-sulfonamide A mixture of azetidine-1-sulfonamide (prepared according to patent WO 2004/011443, 0.131 g), tris(dibenzylideneacetone)-dipalladium (0) (22 mg), 2-dicyclohexylphosphino-2',4',6'-tri-isopropyl-1,1'-biphenyl (XPHOS) (11 mg), cesium carbonate (0.117 g) and 4-chloro-2-[(2,3-difluorobenzyl)thio]-6-{(1S)-1-[(2R)-1,4-dioxaspiro[4.5]dec-2-yl]ethoxy}pyrimidine (the product of step i) (0.100 g) in anhydrous dioxane (5 ml) was heated at reflux in a microwave at 100° C., 300 W, open vessel with cooling for 15 min. Saturated aqueous ammonium chloride was added and the resulting mixture extracted with EtOAc. The combined organic extracts were washed with saturated aqueous sodium chloride, dried with sodium sulfate, filtered and evaporated. The residue was purified by column chromatography on silica using a 1:19 to 3:7 mixture of EtOAc and iso-hexane as eluent and then by reverse phase HPLC (gradient 25-95% acetonitrile in 0.1% ammonium acetate) to give the subtitle compound as a colourless gum. Yield: 43 mg MS: APCI (+ve) 557 [M+H$^+$]

EXAMPLE 62

N-[2-[[(2,3-Difluorophenyl)methyl]thio]-6-methoxypyrimidin-4-yl]-4-ethanesulfonylpiperazine-1-sulfonamide

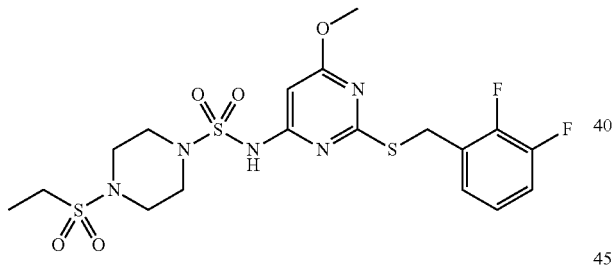

The title compound was prepared from 4-ethanesulfonylpiperazine-1-sulfonamide (the product of step i) (0.31 g) and 4-chloro-2-[[(2,3-difluorophenyl)methyl]thio]-6-methoxypyrimidine (the product of Example 35, step i) (0.25 g) according to the procedure outlined in Example 1, step iv). The crude material was purified by column chromatography using EtOAc/isohexane (1:1) as eluent. Yield: 0.37 g MS: APCI (+ve) 524 [M+H$^+$]
$^1$H NMR: δ (DMSO) 1.17 (t, 3H), 3.06 (q, 2H), 3.23 (d, 4H), 3.28 (d, 4H), 3.88 (s, 3H), 4.48 (s, 2H), 6.06 (s, 1H), 7.17 (m, 1H), 7.33 (m, 1H), 7.42 (t, 1H), 11.22 (bs, 1H).

The intermediate for this compound was prepared as follows:

i) 4-Ethanesulfonylpiperazine-1-sulfonamide

To a solution of 1-ethanesulfonylpiperazine (1.0 g) in dioxane (10 ml) was added sulfamide (0.51 g). The reaction was then heated at 100° C. for 24 h. The reaction was allowed to cool before being concentrated in vacuo. The residue was stirred in Et$_2$O for 4 h and the mixture filtered to give the product as a white solid. Yield: 1.3 g.

$^1$H NMR: δ (DMSO) 1.21 (t, 3H), 3.02 (t, 4H), 3.09 (q, 2H), 3.28 (t, 4H), 6.89 (s, 2H).

EXAMPLE 63

N-[2-[[(2,3-Difluorophenyl)methyl]thio]-6-methoxypyrimidin-4-yl]-3-oxopiperazine-1-sulfonamide

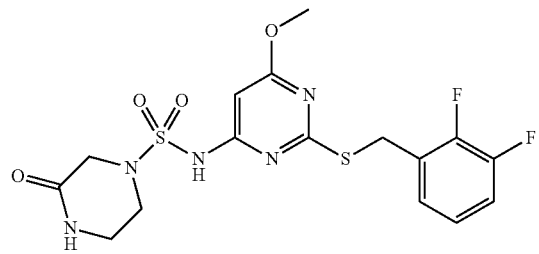 [SMILES: COc1cc(NS(=O)(=O)N2CCNC(=O)C2)nc(SCc2cccc(F)c2F)n1]

The title compound was prepared from 3-oxopiperazine-1-sulfonamide (the product of step i) (0.22 g) and 4-chloro-2-[[(2,3-difluorophenyl)methyl]thio]-6-methoxypyrimidine (the product of Example 35, step i) (0.25 g) according to the procedure outlined in Example 1, step iv). The crude material was purified by column chromatography using EtOAc/isohexane (1:1) as eluent to give a white solid. This solid was dissolved in EtOAc and Et$_2$O and extracted with 1N sodium hydroxide. The basic solution was washed with Et$_2$O, acidified with dilute hydrochloric acid and extracted with EtOAc. The organic solution was washed with H$_2$O, dried (MgSO$_4$) and the solvent evaporated in vacuo to give the product as a yellow foam.

Yield: 40 mg
MS: APCI (+ve) 446 [M+H$^+$]
$^1$H NMR: δ (DMSO) 3.19 (s, 2H), 3.43 (t, 2H), 3.80 (s, 2H), 3.88 (s, 3H), 4.48 (s, 2H), 6.03 (s, 1H), 7.17 (q, 1H), 7.34 (m, 1H), 7.41 (m, 1H), 8.07 (s, 1H), 11.29 (s, 1H).

The intermediate for this compound was prepared as follows:

i) 3-Oxopiperazine-1-sulfonamide

The subtitle compound was prepared according to the procedure outlined in Example 62 step i) using 2-oxopiperazine (0.5 g) and sulfamide (0.45 g) to give a beige solid. Yield: 0.83 g.

$^1$H NMR: δ (DMSO) 3.14 (t, 2H), 3.25 (t, 2H), 3.50 (s, 2H), 7.02 (s, 2H), 8.04 (s, 1H).

EXAMPLE 64

N-[2-[[(2,3-Difluorophenyl)methyl]thio]-6-methoxypyrimidin-4-yl]-1,1-dioxothiomorpholine-4-sulfonamide

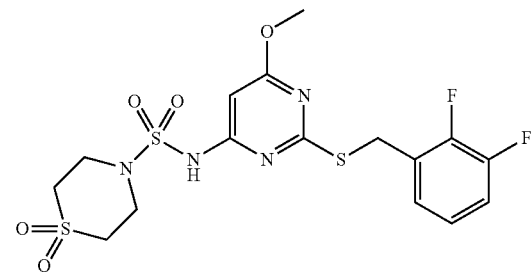 [SMILES: COc1cc(NS(=O)(=O)N2CCS(=O)(=O)CC2)nc(SCc2cccc(F)c2F)n1]

The title compound was prepared from 1,1-dioxothiomorpholine-4-sulfonamide (0.31 g, McManus, J. M. et al, J. Med. Chem (1965) 8 766-776) and 4-chloro-2-[[(2,3-difluorophenyl)methyl]thio]-6-methoxypyrimidine (the product of Example 35, step i) (0.25 g) according to the procedure outlined in Example 1, step iv). The crude material was purified by column chromatography using EtOAc/isohexane (1:1) as eluent. Yield: 0.48 g MS: APCI (+ve) 481 [M+H⁺]

¹H NMR: δ (DMSO) 3.24 (bt, 4H), 3.71 (bm, 4H), 3.89 (s, 3H), 4.49 (s, 2H), 6.01 (s, 1H), 7.17 (m, 1H), 7.34 (m, 1H), 7.40 (t, 1H).

EXAMPLE 65

4-O-{6-[(Azetidin-1-ylsulfonyl)amino]-2-[(2,3-difluorobenzyl)thio]pyrimidin-4-yl}-2,5-dideoxy-D-threo-pentitol

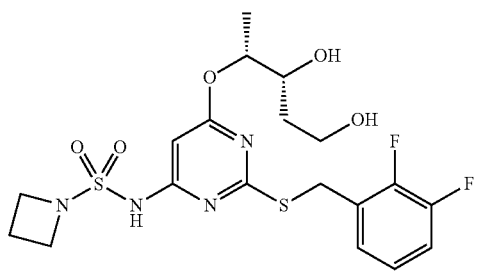 [SMILES: C[C@@H](Oc1cc(NS(=O)(=O)N2CCC2)nc(SCc2cccc(F)c2F)n1)[C@H](O)CCO]

To a solution of 4-O-{6-[(azetidin-1-ylsulfonyl)amino]-2-[(2,3-difluorobenzyl)thio]pyrimidin-4-yl}-2,5-dideoxy-1,3-O-(4-methoxybenzylidene)-D-threo-pentitol (the product from step vii) in MeOH (9 ml) was added TFA (1 ml) dropwise. The reaction mixture was stirred at room temperature for 18 h. The reaction mixture was reduced in vacuo and the residue redissolved in EtOAc (20 ml) before reducing in vacuo directly onto silica and purifying by column chromatography on silica gel 50% EtOAc/50% iso-hexane to give the title compound as a white solid. Yield: 32 mg MS: APCI (−ve) 489 [M+H⁻]

¹H NMR: δ (DMSO) 1.25-1.29 (m, 3H), 1.73-1.80 (m, 2H), 2.25 (q, 2H), 3.88-3.96 (m, 3H), 4.02 (t, 4H), 4.32-4.40 (m, 2H), 5.12-5.20 (m, 1H), 6.32 (s, 1H), 6.99-7.10 (m, 2H), 7.21-7.25 (m, 1H)

The intermediates for this compound were prepared as follows:

i) (2R)-2-{[tert-Butyl(diphenyl)silyl]oxy}propanoic acid

To a solution of (2R)-2-hydroxypropanoic acid (5 g) in DMF (20 ml) was added TBDPSCl (33.0 g) and imidazole (16.4 g). The reaction was then stirred overnight at RT. The reaction was partitioned between EtOAc (200 ml) and H₂O (200 ml). The organics were recovered and washed with 10% citric acid (200 ml), H₂O (200 ml) and finally brine (200 ml). The organics were then collected, dried (MgSO₄) before being reduced in vacuo. The residue was dissolved in MeOH (200 ml), cooled in an ice bath and potassium carbonate (6.9 g) in H₂O was added. After stirring at room temperature for 6 h the solvent was removed in vacuo and the residue diluted with H₂O (100 ml). The pH was then adjusted to pH 4 with 10% citric acid, and the aqueous extracted three times with EtOAc (3×200 ml). The organics were collected dried MgSO₄ before reducing in vacuo to give the subtitle compound as a colourless oil. Yield: 7.5 g MS: APCI (−ve) 327, [M+H⁻]

ii) Ethyl (4R)-4-{[tert-butyl(diphenyl)silyl]oxy}-3-oxopentanoate

To a solution of (2R)-2-{[tert-Butyl(diphenyl)silyl]oxy}propanoic acid (the product from step i, 7.85 g) in THF (300 ml) was added CDI (4.26 g) and the reaction was stirred at room temperature for approximately 15 mins. In a separate flask (71.7 ml) of a 1M heptane solution was added to a solution of ethyl hydrogen malonate (9.47 g) in THF (300 ml) at 0° C. This solution was then allowed to warm to RT. The acyl imidazole solution was then transferred to the flask which contained the magnesium salt and the reaction was monitored for the next 2 d. When the reaction was complete it was quenched by the addition of 250 ml of sat. aq NH₄Cl solution. The reaction mixture was then extracted with Et₂O (3×200 ml). The combined organics were dried (MgSO₄), filtered and reduced to yield a clear oil which was purified by column chromatography on silica gel 4% EtOAc/96% iso-hexane. This gave the subtitle compound as a colourless oil. Yield: 2.0 g ¹H NMR: δ (DMSO) 1.03 (m, 9H), 1.11-1.19 (m, 6H), 3.31 (s, 2H), 4.07 (q, 2H), 4.23-4.31 (m, 1H), 7.37-7.52 (m, 6H), 7.57-7.66 (m, 4H)

iii) 4-O-[tert-Butyl(diphenyl)silyl]-2,5-dideoxy-D-glycero-pentitol

To a solution of Ethyl (4R)-4-{([tert-butyl(diphenyl)silyl]oxy}-3-oxopentanoate (the product from step ii) (2.0 g) in THF (100 ml) was added 2M LiBH₄ in THF (12 ml) The reaction was then stirred at room temperature for 18 h. Saturated ammonium chloride (200 ml) was added to the reaction mixture to quench any remaining LiBH₄. The reaction mixture was then extracted using EtOAc (3×200 ml). The organics were recovered and dried (MgSO₄) before reducing in vacuo. The residue was purified by column chromatography on silica gel 30% EtOAc/70% iso-hexane to yield the subtitle compound as a clear oil. Yield: 540 mg ¹H NMR: δ (CDCl3) 1.00-1.03 (m, 3H), 1.07 (s, 9H), 1.61-1.68 (m, 2H), 3.63-3.84 (m, 4H), 7.36-7.47 (m, 6H), 7.65-7.70 (m, 4H)

iv) 4-O-[tert-Butyl(diphenyl)silyl]-2,5-dideoxy-1,3-O-(4-methoxybenzylidene)-D-glycero-pentitol To a solution of 4-O-[tert-butyl(diphenyl)silyl]-2,5-dideoxy-D-glycero-pentitol (the product from step (0.60 g) and 1-(dimethoxymethyl)-4-methoxybenzene (0.30 g) in DCM (60 ml) was added tosic acid (60 mg). The reaction was the stirred at room temperature for 3 h before addition of more 1-(dimethoxymethyl)-4-methoxybenzene (0.61 g) and a further 2 h stirring at RT. The reaction was worked up by reducing directly onto silica and purifying by flash column chromatography on silica gel 10% EtOAc/90% iso-hexane. This yielded the subtitle compound as a clear colourless oil. Yield: 0.45 g MS: APCI (+ve) 477, [M+H⁺]

v) (1R)-1-[2-(4-Methoxyphenyl)-1,3-dioxan-4-yl]ethanol

To a solution of 4-O-[tert-Butyl(diphenyl)silyl]-2,5-dideoxy-1,3-O-(4-methoxybenzylidene)-D-glycero-pentitol (the product from step iv, 0.40 g) in THF was added TBAF (2.76 ml). The reaction was then allowed to stir at room temperature for 18 h. The reaction mixture was then reduced directly onto silica and purified by column chromatography on silica gel 25% EtOAc/75% iso-hexane. This gave the subtitle compound as a clear colourless oil. Yield: 0.19 g MS: APCI (+ve) 239 [M+H]⁺ vi) 2-O-{6-Chloro-2-[(2,3-difluorobenzyl)thio]pyrimidin-4-yl}-1,4-dideoxy-3,5-O-(4-methoxybenzylidene)-D-threo-pentitol 4-O-{6-Chloro-2-[(2,3-difluorobenzyl)thio]pyrimidin-4-yl}-2,5-dideoxy-1,3-O-(4-methoxybenzylidene)-D-erythro-pentitol To a solution of (0.18 g) (1R)-1-[2-(4-Methoxyphenyl)-1,3-dioxan-4-yl]ethanol and 4,6-Dichloro-2-[(2,3-difluorobenzyl)thio]pyrimidine (the product of example 1 step (ii), 0.25 g) in anhydrous THF (10 ml) at room temperature was added 60% sodium hydride (38 mg). After stirring for 18 h the reaction mixture was partitioned between H₂O (50 ml) solution and EtOAc (150 ml). The organics were separated and the aqueous layer was re-extracted with EtOAc (2×150 ml) The organics collected, dried (MgSO₄) and solvents removed in vacuo to give the subtitle compound as a colourless oil. The residue was then purified by column chromatography on silica gel 10% EtOAc/90% iso-hex aneto separate the two diastereoisomers 2-O-{6-Chloro-2-[(2,3-difluorobenzyl)thio]pyrimidin-4-yl}-1,4-dideoxy-3,5-O-(4-methoxybenzylidene)-D-threo-pentitol ¹H NMR: δ (CDCl₃) 1.36 (d, 3H), 1.52-1.59 (m, 1H), 1.83-1.96 (m, 1H), 3.80 (s, 3H), 3.90-3.98 (m, 1H), 4.26-4.30 (m, 1H), 4.40 (s, 2H), 5.28-5.33 (m, 1H), 5.47 (s, 1H), 6.43 (s, 1H), 6.88 (d, 2H), 6.96-7.10 (m, 2H), 7.24-7.29 (m, 1H), 7.37 (d, 2H). Yield: 0.15 g.

4-O-{6-Chloro-2-[(2,3-difluorobenzyl)thio]pyrimidin-4-yl}-2,5-dideoxy-1,3-O-(4-methoxybenzylidene)-D-erythro-pentitol ¹H NMR: δ (CDCl₃) 1.32 (d, 3H), 1.52-1.59 (m, 1H), 1.86-1.98 (m, 1H), 3.79 (s, 3H), 3.91-4.01 (m, 1H), 4.26-4.31 (m, 1H), 4.40 (s, 2H), 5.35-5.41 (m, 1H), 5.46 (s, 1H), 6.43 (s, 1H), 6.86 (d, 2H), 6.96-7.09 (m, 2H), 7.25-7.30 (m, 1H), 7.34 (d, 2H). Yield: 0.20 g.

vii) 2-O-{6-[(Azetidin-1-ylsulfonyl)amino]-2-[(2,3-difluorobenzyl)thio]pyrimidin-4-yl}-1,4-dideoxy-3,5-O-(4-methoxybenzylidene)-D-threo-pentitol A mixture of Azetidine-1-sulfonamide (73 mg), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.14 g) and 2-O—(6-chloro-2-[(2,3-difluorobenzyl)thio]pyrimidin-4-yl)-1,4-dideoxy-3,5-O-(4-methoxybenzylidene)-D-threo-pentitol (the product of example 65 step vi the diastereoisomer which eluted first) (0.145 g) in dioxane (10 mL) was heated at reflux in a microwave at 100° C., 300 W, open vessel with cooling for 30 min. The reaction mixture was partitioned between aq. ammonium chloride solution (50 ml) and EtOAc (150 ml). The organics were separated and the aqueous layer was re-extracted with EtOAc (2×150 ml). The organics collected, dried (MgSO₄) and solvents removed in vacuo to give the subtitle compound as a yellow solid. Yield: 0.45 g.

MS: APCI (+ve) 609 [M+H]⁺

EXAMPLE 66

4-O-{6-[(Azetidin-1-ylsulfonyl)amino]-2-[(2,3-difluorobenzyl)thio]pyrimidin-4-yl}-2,5-dideoxy-D-erythro-pentitol

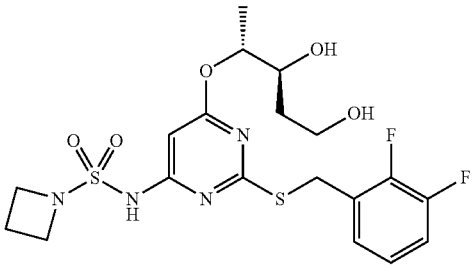 [SMILES: C[C@@H](Oc1cc(NS(=O)(=O)N2CCC2)nc(SCc2cccc(F)c2F)n1)[C@@H](O)CCO]

To a solution of 4-O-{6-[(azetidin-1-ylsulfonyl)amino]-2-[(2,3-difluorobenzyl)thio]pyrimidin-4-yl}-2,5-dideoxy-1,3-O-(4-methoxybenzylidene)-D-erythro-pentitol (the product from step i) in MeOH (9 ml) was added TFA (1 ml) dropwise. The reaction mixture was stirred at room temperature for 18 h. The reaction mixture was reduced in vacuo and the residue redissolved in EtOAc (20 ml) before reducing in vacuo directly onto silica and purifying by column chromatography on silica 50% EtOAc/50% iso-hexane to give the title compound as a white solid. Yield: 12 mg MS: APCI (+ve) 489 [M+H]⁺

¹H NMR: δ (DMSO) 1.29 (d, 3H), 1.72-1.77 (m, 2H), 2.26 (q, 2H), 3.83-3.94 (m, 2H), 3.99-4.07 (m, 5H), 4.37 (s, 2H), 5.18-5.24 (m, 1H), 6.32 (s, 1H), 6.99-7.10 (m, 2H), 7.20-7.24 (m, 1H)

The intermediate for this compound was prepared as follows:

i) 4-O-{6-[(Azetidin-1-ylsulfonyl)amino]-2-[(2,3-difluorobenzyl)thio]pyrimidin-4-yl}-2,5-dideoxy-1,3-O-(4-methoxybenzylidene)-D-erythro-pentitol A mixture of azetidine-1-sulfonamide (0.13 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.23 g) and 4-O-{(6-Chloro-2-[(2,3-difluorobenzyl)thio]pyrimidin-4-yl}-2,5-dideoxy-1,3-O-(4-methoxybenzylidene)-D-erythro-pentitol (the product of example 65 step vi the diastereoisomer which eluted second) (0.20 g) in dioxane (10 mL) was heated at reflux in a microwave at 100° C., 300 W, open vessel with cooling for 30 mins. The reaction mixture was partitioned between aq. ammonium chloride solution (50 ml) and EtOAc (150 ml). The organics were separated and the aqueous layer was re-extracted with EtOAc (2×150 ml). The organics collected, dried (MgSO₄) and solvents removed in vacuo to give the subtitle compound as a yellow solid. Yield: 0.50 g.

MS: APCI (+ve) 609.9 [M+H]⁺

EXAMPLE 67

N-[2-[[(2,3-Difluorophenyl)methyl]thio]-6-[(1R)-2-hydroxy-1-methylethoxy]-4-pyrimidinyl]4-methyl-piperazine-1-sulfonamide

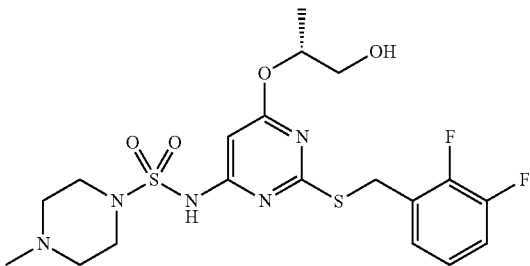 [SMILES: C[C@H](CO)Oc1cc(NS(=O)(=O)N2CCN(C)CC2)nc(SCc2cccc(F)c2F)n1]

To a solution of N-{2-[(2,3-difluorobenzyl)thio]-6-[(1R)-1-methyl-2-(trityloxy)ethoxy]pyrimidin-4-yl}-4-methylpiperazine-1-sulfonamide (the product from step (100 mg) in DCM (3 ml) was added TFA (3 ml) dropwise. The reaction was then allowed to stir at room temperature for the following 3 h until complete. The reaction was then reduced in vacuo and the resulting residue was purified by preparative HPLC to yield the title compound as a white solid. Yield: 45 mg MS: APCI (+ve) 490 [M+H$^+$]

$^1$H NMR: δ (DMSO) 1.27 (d, 3H), 2.31 (s, 3H), 2.50 (t, 4H), 3.36 (t, 4H), 3.67-3.77 (m, 2H), 4.31-4.41 (m, 2H), 5.26-5.32 (m, 1H), 6.24 (s, 1H), 7.00-7.10 (m, 2H), 7.19-7.24 (m, 1H)

The intermediates for this compound were prepared as follows:

i) 4-Methylpiperazine-1-sulfonamide

To a solution of 1-Methylpiperazine (1.58 g) in dioxane was added sulfamide (4.0 g) and the reaction mixture was then heated at reflux in dioxane for 18 h. The reaction mixture was then reduced in vacuo and the residue partitioned between EtOAc (100 ml) and H$_2$O (100 ml). The organics were separated and the aqueous layer was re-extracted with EtOAc (2×100 ml). Organics were combined, dried (MgSO$_4$) and reduced in vacuo to give the subtitle compound as a white solid. Yield: 640 mg $^1$H NMR: δ (DMSO) 2.18 (s, 3H), 2.37 (t, 4H), 2.94 (t, 4H), 6.74 (s, 2H)

ii) N-{2-[(2,3-Difluorobenzyl)thio]-6-[(1R)-1-methyl-2-(trityloxy)ethoxy]pyrimidin-4-yl}-4-methylpiperazine-1-sulfonamide A mixture of 4-Methylpiperazine-1-sulfonamide (the product from step i) (0.64 g), tris(dibenzylideneacetone)dipalladium (0) (50 mg), 2-dicyclohexylphosphino-2',4',6'-triisopropyl-1,1'-biphenyl (XPHOS) (50 mg), cesium carbonate (0.55 g) and 4-chloro-2-[[(2,3-difluorophenyl)methyl]thio]-6-[(1R)-1-methyl-2-(triphenylmethoxy)ethoxy]-pyrimidine ((the product of example 13 step 0.50 g) in dioxane (40 mL) was heated at reflux in a microwave at 100° C., 300 W, open vessel with cooling for 1 h. The reaction mixture was diluted with DCM, filtered through arbocel and the filtrate evaporated. The residue was purified by reverse phase HPLC using a TFA (0.2%)/MeCN system to give the subtitle compound as a yellow solid. Yield: 0.22 g.

$^1$H NMR: δ (CDCl$_3$) 1.27 (d, 3H), 2.21 (s, 3H), 2.33-2.47 (m, 4H), 3.24-3.35 (m, 4H), 4.29-4.42 (m, 2H), 5.42-5.54 (m, 1H), 6.26 (s, 1H), 6.93-7.08 (m, 2H), 7.18-7.31 (m, 10H), 7.37-7.41 (m, 6H)

EXAMPLE 68

N-[2-[[(2,3-Difluorophenyl)methyl]thio]-6-[(1R)-2-hydroxy-1-methylethoxy]-4-pyrimidinyl]-1,4-diazepane-1-sulfonamide

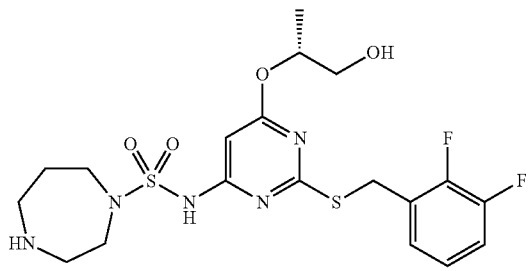 [SMILES: C[C@H](CO)Oc1cc(NS(=O)(=O)N2CCCNCC2)nc(SCc2cccc(F)c2F)n1]

To a solution of N-[2-[[(2,3-Difluorophenyl)methyl]thio]-6-[(1R)-1-methyl-2-(trityloxy)ethoxy]-4-pyrimidinyl]-sulfamoyl-1,4-diazepane-1-carboxylic acid tert-butyl ester (the product of step ii, 100 mg) in DCM (3 ml) was added TFA (3 ml) dropwise. The reaction was then allowed to stir at room temperature for the following 3 h until complete. The reaction was then reduced in vacuo and the resulting residue was purified by preparative HPLC to yield the title compound as a white solid. Yield: 62 mg MS: APCI (+ve) 490 [M+H$^+$]

$^1$H NMR: δ (DMSO) 1.13 (d, 3H), 1.90-1.97 (m, 2H), 3.34-3.55 (m, 10H), 4.36-4.42 (m, 2H), 5.02-5.08 (m, 1H), 5.77 (s, 1H)), 7.11-7.18 (m, 1H), 7.29-7.36 (m, 1H), 7.37-7.44 (m, 1H)

The intermediates for this compound were prepared as follows:

i) 4-Sulfamoyl-1,4-diazepane-1-carboxylic acid tert-butyl ester

To a solution of 1,4-Diazepane-1-carboxylic acid tert-butyl ester (3.16 g) in dioxane (40 ml) was added sulfamide (4.0 g) and the reaction mixture was then heated at reflux for 18 h. The reaction mixture was then reduced in vacuo and the residue partitioned between EtOAc (100 ml) and H$_2$O (100 ml). The organics were separated and the aqueous layer was re-extracted with EtOAc (2×100 ml). Organics were combined, dried (MgSO$_4$) and reduced in vacuo to give the subtitle compound as a white solid. Yield: 4.27 g $^1$H NMR: (DMSO) δ 1.40 (s, 9H), 1.70-1.77 (m, 2H), 3.12-3.23 (m, 4H), 3.32-3.44 (m, 2H), 6.72 (s, 2H)

ii) N-{2-[(2,3-Difluorobenzyl)thio]-6-[(1R)-1-methyl-2-(trityloxy)ethoxy]pyrimidin-4-yl}-4-pyrimidinyl]sulfamoyl-1,4-diazepane-1-carboxylic acid tert-butyl ester A mixture of 4-Sulfamoyl-1,4-diazepane-1-carboxylic acid tert-butyl ester (the product from step i) (0.84 g), tris (dibenzylideneacetone)dipalladium (0) (50 mg), 2-dicyclohexylphosphino-2',4',6'-tri-isopropyl-1,1'-biphenyl (XPHOS) (50 mg), cesium carbonate (0.55 g) and 4-chloro-2-[[(2,3-difluorophenyl)methyl]thio]-6-[(1R)-1-methyl-2-

(triphenylmethoxy)ethoxy]-pyrimidine (the product of example 13 step iii), 0.50 g) in dioxane (20 mL) was heated at reflux in a microwave at 100° C., 300 W, open vessel with cooling for 3 h. The reaction mixture was then reduced in vacuo and the residue partitioned between EtOAc (100 ml) and H$_2$O (100 ml). The organics were separated and the aqueous layer was re-extracted with EtOAc (2×100 ml). Organics were combined, dried (MgSO$_4$) and reduced in vacuo and the resulting residue was purified by prep HPLC to give the subtitle compound as a clear colourless oil. Yield: 0.11 g $^1$H NMR: (CDCl$_3$) δ 1.27 (d, 3H), 1.43 (s, 9H), 1.88 (quintet, 2H), 3.09-3.16 (m, 1H), 3.24-3.30 (m, 1H), 3.34-3.53 (m, 8H), 4.28-4.44 (m, 2H), 5.47-5.54 (m, 1H), 6.03-6.11 (m, 2H), 6.93-7.08 (m, 2H), 7.18-7.30 (m, 10H), 7.35-7.41 (m, 6H)

EXAMPLE 69

N-[2-[[(2,3-Difluorophenyl)methyl]thio]-6-[(1R)-2-hydroxy-1-methylethoxy]-4-pyrimidinyl]-4-ethyl-piperazine-1-sulfonamide

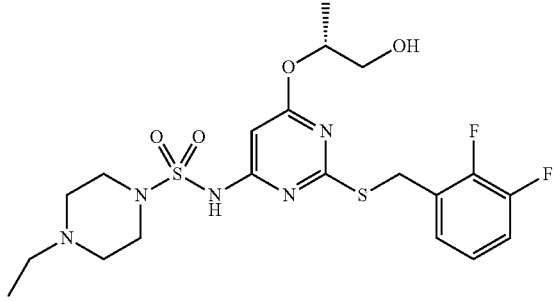 [SMILES: CCN1CCN(S(=O)(=O)Nc2cc(O[C@H](C)CO)nc(SCc3cccc(F)c3F)n2)CC1]

To a solution of ethyl(2R)-2-[(2-[(2,3-Difluorobenzyl)thio]-6-{[(4-ethylpiperazin-1-yl)sulfonyl]amino}pyrimidin-4-yl)oxy]propanoate (the product from step i) (0.72 g) in THF (10 ml) was added 2M LiBH$_4$ in TI-IF (1.3 ml). The reaction was then stirred for 18 h at RT. Saturated NH$_4$Cl (150 ml) was then added to the reaction mixture which was extracted with DCM (3×150 ml). Organics were combined, dried (MgSO$_4$) and reduced in vacuo and the resulting residue was purified by prep HPLC to give the title compound as a white solid.

Yield: 45 mg
MS: APCI (+ve) 504 [M+H$^+$]
$^1$H NMR: (CDCl$_3$) δ 1.15 (d, 3H), 1.24 (t, 3H), 3.13 (q, 2H), 2.50 (t, 4H), 3.36 (t, 4H), 3.67-3.77 (m, 2H), 4.31-4.41 (m, 2H), 5.32-5.26 (m, 1H), 6.24 (s, 1H), 7.00-7.10 (m, 2H), 7.19-7.24 (m, 1H)

The intermediate for this compound was prepared as follows:

i) Ethyl (2R)-2-[(2-[(2,3-difluorobenzyl)thio]-6-{[(4-ethylpiperazin-1-yl)sulfonyl]amino}pyrimidin-4-yl)oxy]propanoate To a solution of 1-Ethylpiperazine (1 g) in dioxane (10 ml) was added sulfamide (0.746 g) and the reaction mixture was then heated at reflux in dioxane for 72 h. The reaction mixture was purified by loading onto SCX and eluting with (200 ml) MeOH/NH$_3$. The eluent was then reduced in vacuo to yield 4-Ethylpiperazine-1-sulfonamide as a white solid. A mixture of 4-ethylpiperazine-1-sulfonamide (0.289 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.628 g) and 2-[[6-chloro-2-[[(2,3-difluorophenyl)methyl]thio]-4-pyrimidinyl]oxy]-(2R)-propanoic acid ethyl ester ((the product of example 5 step i), 0.50 g) in dioxane (10 mL) was heated at reflux in a microwave at 100 C, 300 W, open vessel with cooling for 30 min. The reaction mixture was then reduced in vacuo and the residue was partitioned between EtOAc (150 ml) and H$_2$O (100 ml). The organics were separated and the aqueous layer was re-extracted with EtOAc (2×150 ml). Organics were combined, dried (MgSO$_4$) and reduced in vacuo to give the subtitle compound as a yellow solid. Yield: 0.720 g MS: APCI (+ve) 546 [M+H$^+$]

EXAMPLE 70

N-[2-[[(2,3-Difluorophenyl)methyl]thio]-6-[(1R)-2-hydroxy-1-methylethoxy]-4-pyrimidinyl]-4-(4-pyridyl)piperazine-1-sulfonamide

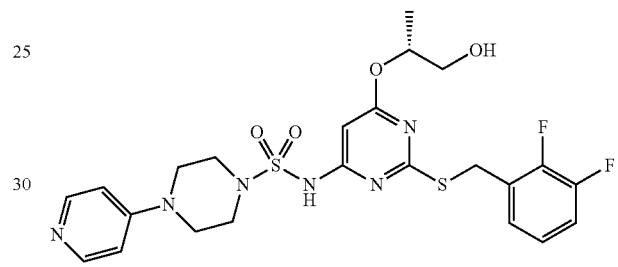

To a solution of ethyl(2R)-2-[(2-[(2,3-Difluorobenzyl)thio]-6-{[(4-pyridin-4-ylpiperazine)sulfonyl]amino}pyrimidin-4-yl)oxy]propanoate (the product from step i) (0.72 g) in THF (10 ml) was added 2M LiBH$_4$ in THF (1.3 ml). The reaction was then stirred for 18 h at RT. Saturated NH$_4$Cl (150 ml) was then added to the reaction mixture which was extracted with DCM (3×150 ml). Organics were combined, dried (MgSO$_4$) and reduced in vacuo and the resulting residue was purified by prep HPLC to give the title compound as a white solid. Yield: 10 mg MS: APCI (+ve) 553 [M+H$^+$]
$^1$H NMR: (DMSO) δ 1.16 (d, 3H), 3.37-3.41 (m, 4H), 3.46-3.51 (m, 2H), 3.75-3.79 (m, 4H), 4.40-4.48 (m, 2H), 5.11-5.17 (m, 1H), 6.01 (s, 1H), 7.13-7.21 (m, 3H), 7.31-7.39 (m, 2H), 8.28 (d, 2H)

The intermediate for this compound was prepared as follows:

i) Ethyl (2R)-2-[(2-[(2,3-difluorobenzyl)thio]-6-{[(4-pyridin-4-ylpiperazin-1-yl)sulfonyl]amino}pyrimidin-4-yl)oxy]propanoate To a solution of 1-pyridin-4-ylpiperazine (1.23 g) in dioxane (10 ml) was added sulfamide (0.746 g) and the reaction mixture was then heated at reflux in dioxane for 72 h. The reaction mixture was purified by loading onto SCX and eluting with (200 ml) MeOH/NH$_3$. The eluent was then reduced in vacuo to yield 4-pyridin-4-ylpiperazine-1-sulfonamide as a white solid. A mixture of 4-pyridin-4-ylpiperazine-1-sulfonamide (0.260 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.438 g) and 2-[[6-chloro-2-[[(2,3-difluorophenyl)methyl]thio]-4-pyrimidinyl]oxy]-(2R)-propanoic acid ethyl ester ((the product of example 5 step i), 0.350 g) in dioxane (10 ml) was heated at reflux in a microwave at 100 C, 300 W, open vessel with cooling for 30 mins. The reaction mixture was then reduced in vacuo and the residue was partitioned between EtOAc (150 ml) and H₂O (100 ml). The organics were separated and the aqueous layer was re-extracted with EtOAc (2×150 ml). Organics were combined, dried (MgSO₄) and reduced in vacuo to give the subtitle compound as a yellow solid. Yield: 0.720 g MS: APCI (+ve) 595 [M+H⁺]

EXAMPLE 71

N-[2-[[(2,3-Difluorophenyl)methyl]thio]-6-[(1R)-2-hydroxy-1-methylethoxy]-4-pyrimidinyl]-(3R)-3-ethylpiperazine-1-sulfonamide

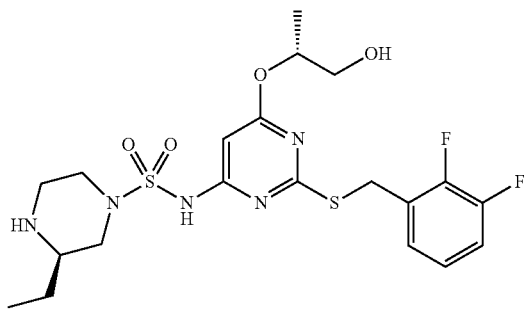 [SMILES: CC[C@@H]1CN(S(=O)(=O)Nc2cc(O[C@H](C)CO)nc(SCc3cccc(F)c3F)n2)CCN1]

To a solution of ethyl (2R)-2-[[2-[[(2,3-difluorophenyl)methyl]thio]-6-[[[(3R)-3-ethyl-1-piperazinyl]sulfonyl]amino]-4-pyrimidinyl]oxy]propanoate (the product from step i) (0.71 g) in THF (10 ml) was added 2M LiBH₄ in THF (1.3 ml). The reaction was then stirred for 18 h at RT. Saturated NH₄Cl (150 ml) was then added to the reaction mixture which was extracted with DCM (3×150 ml). Organics were combined, dried (MgSO₄) and reduced in vacuo and the resulting residue was purified by prep HPLC to give the title compound as a white solid. Yield: 70 mg MS: APCI (+ve) 504 [M+H⁺]

¹H NMR: (CDCl₃) δ 0.87 (t, 3H), 1.28 (d, 3H), 1.53-1.63 (m, 1H), 1.63-1.73 (m, 1H), 2.79-2.88 (m, 1H), 2.95-3.08 (m, 2H), 3.61-3.80 (m, 4H), 3.97-4.05 (m, 1H), 4.08-4.16 (m, 1H), 4.33-4.44 (m, 2H), 5.28-5.36 (m, 1H), 6.28 (m, 1H), 6.99-7.12 (m, 2H), 7.19-7.24 (m, 1H)

The intermediate for this compound was prepared as follows:

i) Ethyl (2R)-2-[(2-[(2,3-difluorobenzyl)thio]-6-{[((3R)-3-ethylpiperazine-1-sulfonamide)sulfonyl]amino}pyrimidin-4-yl)oxy]propanoate To a solution of (3R)-3-ethylpiperazine (0.5 g) in dioxane (10 ml) was added sulfamide (0.373 g) and the reaction mixture was then heated at reflux in dioxane for 3 d. The reaction mixture was purified by loading onto SCX and eluting with (200 ml) MeOH/NH₃. The eluent was then reduced in vacuo to yield (3R)-3-ethylpiperazine-1-sulfonamide as a white solid. A mixture of (3R)-3-ethylpiperazine-1-sulfonamide (0.260 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.438 g) and 2-[[6-chloro-2-[[(2,3-difluorophenyl)methyl]thio]-4-pyrimidinyl]oxy]-(2R)-propanoic acid ethyl ester ((the product of example 5 step i), 0.350 g) in dioxane (10 ml) was heated at reflux in a microwave at 100 C, 300 W, open vessel with cooling for 30 min. The reaction mixture was then reduced in vacuo and the residue was partitioned between EtOAc (150 ml) and H₂O (100 ml). The organics were separated and the aqueous layer was re-extracted with EtOAc (2×150 ml). Organics were combined, dried (MgSO₄) and reduced in vacuo to give the subtitle compound as a yellow solid. Yield: 0.705 g MS: APCI (+ve) 546 [M+H⁺]

EXAMPLE 72

N-[2-[[(2,3-Difluorophenyl)methyl]thio]-6-[(1R)-2-hydroxy-1-methylethoxy]-4-pyrimidinyl]-(3R,5S)-3,5-dimethylpiperazine-1-sulfonamide

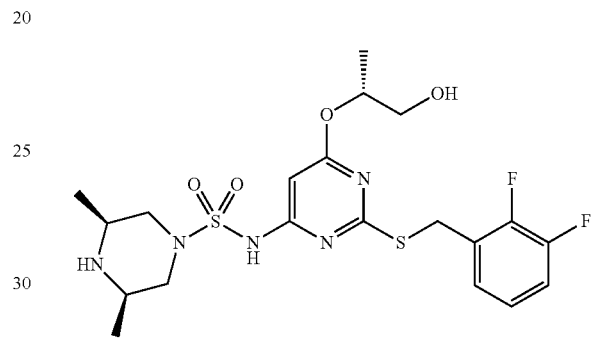

To a solution of Ethyl(2R)-2-[(2-[(2,3-difluorobenzyl)thio]-6-{[((3R,5S)-3,5-dimethylpiperazine)sulfonyl]amino}pyrimidin-4-yl)oxy]propanoate (the product from step i), 0.50 g) in THF (10 ml) was added 2M LiBH₄ in THF (0.9 ml). The reaction was then stirred for 18 h at RT. Saturated NH₄Cl (150 ml) was then added to the reaction mixture which was extracted with DCM (3×150 ml). Organics were combined, dried (MgSO₄) and reduced in vacuo and the resulting residue was purified by prep HPLC to give the title compound as a white solid. Yield: 80 mg MS: APCI (+ve) 504 [M+H⁺]

¹H NMR: (DMSO) δ 1.13 (d, 6H), 3.01-3.21 (m, 2H), 3.37-3.57 (m, 4H), 4.33-4.43 (m, 2H), 4.76-4.81 (m, 2H), 4.97-5.05 (m, 1H), 5.81 (s, 1H), 7.09-7.17 (m, 1H), 7.26-7.35 (m, 1H), 7.39-7.45 (m, 1H)

The intermediate for this compound was prepared as follows:

i) Ethyl (2R)-2-[(2-[(2,3-difluorobenzyl)thio]-6-{[((3R,5S)-3,5-dimethylpiperazine)sulfonyl]amino}pyrimidin-4-yl)oxy]propanoate To a solution of (2R,6S)-2,6-dimethylpiperazine (1 g) in dioxane (10 ml) was added sulfamide (0.746 g) and the reaction mixture was then heated at reflux in dioxane for 72 h. The reaction mixture was partitioned between EtOAc (150 ml) and H₂O (150 ml) and the aqueous re-extracted with EtOAc (2×150 ml). Organics were collected dried and reduced in vacuo to yield (3R,5S)-3,5-dimethylpiperazine-1-sulfonamide as a white solid (0.29 g). A mixture of (3R,5S)-3,5-dimethylpiperazine-1-sulfonamide (0.29 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.628 g) and 2-[[6- chloro-2-[[(2,3-difluorophenyl)methyl]thio]-4-pyrimidinyl]oxy]-(2R)-propanoic acid ethyl ester (the product of example 5 step i), 0.5 g) in dioxane (10 mL) was heated at reflux in a microwave at 100° C., 300 W, open vessel with cooling for 30 min. The reaction mixture was then reduced in vacuo and the residue was partitioned between EtOAc (150 ml) and H$_2$O (100 ml). The organics were separated and the aqueous layer was re-extracted with EtOAc (2×150 ml). Organics were combined, dried (MgSO$_4$) and reduced in vacuo to give the subtitle compound as a yellow solid. Yield: 0.940 g MS: APCI (+ve) 546 [M+H$^+$]

EXAMPLE 73

N-{2-[(2,3-Difluorobenzyl)thio]-6-[(1R)-2-hydroxy-1-methylethoxy]pyrimidin-4-yl}-9-methyl-3,9-diazabicyclo[4.2.1]nonane-3-sulfonamide

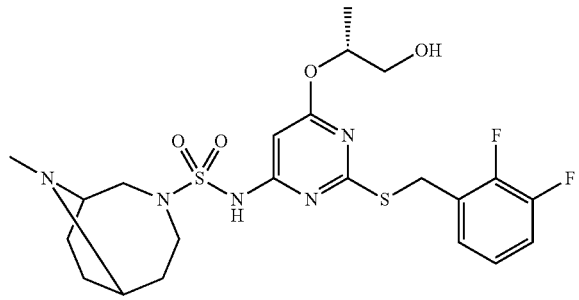 [SMILES: C[C@H](CO)Oc1cc(NS(=O)(=O)N2CCC3CCC(C2)N3C)nc(SCc2cccc(F)c2F)n1]

To a solution of ethyl (2R)-2-[(2-[(2,3-difluorobenzyl)thio]-6-{[(9-methyl-3,9-diazabicyclo[4.2.1]non-3-yl)sulfonyl]amino}pyrimidin-4-yl)oxy]propanoate (the product from step i), 0.35 g) in THF (10 ml) was added 2M LiBH$_4$ in THF (0.6 ml). The reaction was then stirred for 18 h at room temperature. Saturated NH$_4$Cl (150 ml) was then added to the reaction mixture which was extracted with DCM (3×150 ml). Organics were combined, dried (MgSO$_4$) and reduced in vacuo and the resulting residue was purified by prep HPLC to give the title compound as a white solid. Yield 20 mg MS: APCI (+ve) 530 [M+H$^+$]

$^1$H NMR: (CDCL$_3$) δ 1.27 (d, 3H), 1.32-1.40 (m, 2H), 1.65-1.80 (m, 4H), 2.54 (s, 3H), 2.91-3.05 (m, 2H), 3.39-3.48 (m, 2H), 3.65-3.75 (m, 2H), 4.03-4.11 (m, 1H), 4.16-4.24 (m, 1H), 4.32-4.46 (m, 2H), 5.22-5.28 (m, 1H), 6.19 (s, 1H), 6.98-7.08 (m, 2H), 7.20-7.32 (m, 1H)

The intermediate for this compound was prepared as follows:

i) Ethyl (2R)-2-[(2-[(2,3-difluorobenzyl)thio]-6-{[(9-methyl-3,9-diazabicyclo[4.2.1]non-3-yl)sulfonyl]amino}pyrimidin-4-yl)oxy]propanoate To a solution of 9-methyl-3,9-diazabicyclo[4.2.1]nonane (0.56 g) in 1,4-dioxane (10 ml) was added sulfamide (0.37 g) and the reaction mixture was then heated at reflux in 1,4-dioxane for 72 h. The reaction mixture was purified by loading onto SCX and eluting with 7N NH$_3$/MeOH (200 ml). The eluent was then reduced in vacuo to yield 9-methyl-3,9-diazabicyclo[4.2.1]nonane-3-sulfonamide (0.13 g) as a yellow solid. A mixture of 9-methyl-3,9-diazabicyclo[4.2.1]nonane-3-sulfonamide (0.13 g), tris(dibenzylideneacetone)dipalladium (0) (50 mg), 2-dicyclohexylphosphino-2',4',6'-tri-iso-propyl-1,1'-biphenyl (XPHOS) (50 mg), cesium carbonate (0.31 g) and 2-[[6-chloro-2-[[(2,3-difluorophenyl)methyl]thio]-4-pyrimidinyl]oxy]-(2R)-propanoic acid ethyl ester (the product of example 5 step i), 0.25 g) in 1,4-dioxane (10 mL) was heated at reflux in a microwave at 100° C., 300 W, open vessel with cooling for 30 min. The reaction mixture was then reduced in vacuo and the residue was partitioned between EtOAc (150 ml) and H$_2$O (100 ml). The organics were separated and the aqueous layer was re-extracted with EtOAc (2×150 ml). Organics were combined, dried (MgSO$_4$) and reduced in vacuo to give the subtitle compound as a yellow solid. Yield 0.35 g MS: APCI (+ve) 572 [M+H$^+$]

EXAMPLE 74

N-[2-[[(2,3-Difluorophenyl)methyl]thio]-6-[(1R)-2-hydroxy-1-methylethoxy]-4-pyrimidinyl]-(3S)-3-methylpiperazine-1-sulfonamide

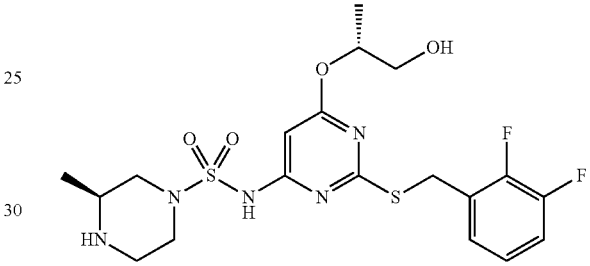

To a solution of Ethyl (2R)-2-[(2-[(2,3-difluorobenzyl)thio]-6-{[((3S)-3-methylpiperazine-1-sulfonamide)sulfonyl]amino}pyrimidin-4-yl)oxy]propanoate (the product from step i) (0.94 g) in THF (10 ml) was added 2M LiBH$_4$ in THF (1.8 ml). The reaction was then stirred for 18 h at RT. Saturated NH$_4$Cl (150 ml) was then added to the reaction mixture which was extracted with DCM (3×150 ml). Organics were combined, dried (MgSO$_4$) and reduced in vacuo and the resulting residue was purified by prep HPLC to give the title compound as a white solid. Yield: 35 mg MS: APCI (+ve) 490 [M+H$^+$]

$^1$H NMR: (CDCl$_3$) δ 1.36 (d, 3H), 1.61 (d, 3H), 2.81-3.03 (m, 3H), 3.20-3.39 (m, 4H), 3.67-3.84 (m, 2H), 4.22-4.44 (m, 2H), 5.29-5.37 (m, 1H), 6.18 (s, 1H), 7.02-7.11 (m, 2H), 7.13-7.19 (m, 1H)

The intermediate for this compound was prepared as follows:

i) Ethyl (2R)-2-[(2-[(2,3-difluorobenzyl)thio]-6-{[(3S)-3-methylpiperazine)sulfonyl]amino}pyrimidin-4-yl)oxy]propanoate To a solution of (2S)-2-methylpiperazine (0.914 g) in dioxane (10 ml) was added sulfamide (0.746 g) and the reaction mixture was then heated at reflux in dioxane for 3 d. The reaction mixture was partitioned between EtOAc (150 ml) and H$_2$O (150 ml) and the aqueous re-extracted with EtOAc (2×150 ml). Organics were collected dried and reduced in vacuo to yield (3S)-3-methylpiperazine-1-sulfonamide as a white solid (0.27 g). A mixture of (3S)-3-methylpiperazine-1-sulfonamide (0.27 g), tris(dibenzylideneacetone)dipalladium (0) (50 mg), 2-dicyclohexylphosphino-2',4',6'-tri-iso-propyl-1,1'-biphenyl (XPHOS) (50 mg), cesium carbonate (0.628 g) and 2-[[6-chloro-2-[[(2,3-difluorophenyl)methyl]

thio]-4-pyrimidinyl]oxy]-(2R)-propanoic acid ethyl ester ((the product of example 5 step i), 0.50 g) in dioxane (20 mL) was heated at reflux in a microwave at 100° C., 300 W, open vessel with cooling for 30 mins. The reaction mixture was then reduced in vacuo and the residue was partitioned between EtOAc (150 ml) and H₂O (100 ml). The organics were separated and the aqueous layer was re-extracted with EtOAc (2×150 ml). Organics were combined, dried (MgSO₄) and reduced in vacuo to give the subtitle compound as a yellow solid. Yield: 0.940 g MS: APCI (+ve) 532 [M+H⁺]

EXAMPLE 75

N-(2-[(2,3-Difluorobenzyl)thio]-6-{[(1R,2R)-2-hydroxy-methylpropyl]oxy}pyrimidin-4-yl)-1,4-diazepane-1-sulfonamide

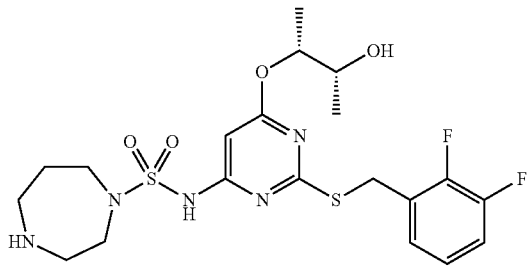 [SMILES: C[C@@H](O)[C@@H](C)Oc1cc(NS(=O)(=O)N2CCCNCC2)nc(SCc2cccc(F)c2F)n1]

N-(2-[(2,3-Difluorobenzyl)thio]-6-{[(1R,2R)-2-hydroxy-methylpropyl]oxy}pyrimidin-4-yl)-tert-butyl 4-(aminosulfonyl)-1,4-diazepane-1-carboxylate (1.6 g) was dissolved in DCM (30 ml) and stirred until in solution. To this solution was added TFA (30 ml). The reaction was then allowed to stir at room temperature overnight. The reaction was then reduced in vacuo and the resulting yellow residue purified by HPLC to give the title compound as a white solid.

Yield: 76 mg

MS: APCI (+ve) 504 [M+H⁺]

¹H NMR: (DMSO) δ 1.04 (d, 3H), 1.14 (d, 3H), 1.96-2.02 (m, 2H), 3.16-3.24 (m, 2H), 3.41-3.45 (m, 4H), 3.66-3.74 (m, 2H), 4.41-4.49 (m, 2H), 4.99-5.05 (m, 1H), 5.09 (s, 1H), 7.14-7.23 (m, 1H), 7.31-7.40 (m, 2H), 8.65-8.72 (m, 2H)

The intermediate for this compound was prepared as follows:

i) N-(2-[(2,3-Difluorobenzyl)thio]-6-{[(1R,2R)-2-hydroxy-methylpropyl]oxy}pyrimidin-4-yl)-tert-butyl 4-(aminosulfonyl)-1,4-diazepane-1-carboxylate A mixture of 4-sulfamoyl-1,4-diazepane-1-carboxylic acid tert-butyl ester (the product from example 68 step i) (0.541 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.55 g) and (2R,3R)-3-({6-chloro-2-[(2,3-difluorobenzyl)thio]pyrimidin-4-yl}oxy)butan-2-ol (the product of example 4 step i), 0.541 g) in dioxane (40 mL) was heated at reflux in a microwave at 100° C., 300 W, open vessel with cooling for 15 mins. The reaction mixture was then reduced in vacuo and the residue separated between DCM (200 ml) and H₂O (150 ml). The organics were separated and the aqueous layer was re-extracted with DCM (2×200 ml). Organics were combined, dried (MgSO₄) and reduced in vacuo and the resulting residue was purified by prep HPLC to give the subtitle compound as a yellow oil. Yield: 1.6 g MS: APCI (+ve) 604 [M+H⁺]

EXAMPLE 76

N-(2-[(2,3-Difluorobenzyl)thio]-6-{[(1R,2R)-2-hydroxy-methylpropyl]oxy}pyrimidin-4-yl)-(3R,5S)-3,5-dimethylpiperazine-1-sulfonamide

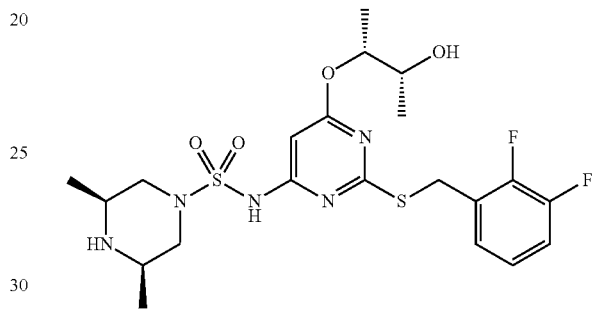

To a solution of (2R,6S)-2,6-Dimethylpiperazine (1 g) in dioxane (10 ml) was added sulfamide (0.746 g) and the reaction mixture was then heated at reflux in dioxane for 3 d. The reaction mixture was partitioned between EtOAc (150 ml) and H₂O (150 ml) and the aqueous re-extracted with EtOAc (2×150 ml). Organics were collected dried and reduced in vacuo to yield (3R,5S)-3,5-dimethylpiperazine-1-sulfonamide as a white solid (1.05 g). A mixture of (3R,5S)-3,5-dimethylpiperazine-1-sulfonamide (0.541 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.731 g) and (2R,3R)-3-({6-chloro-2-[(2,3-difluorobenzyl)thio]pyrimidin-4-yl}oxy)butan-2-ol ((the product of example 4 step i), 0.541 g) in dioxane (40 mL) was heated at reflux in a microwave at 100° C., 300 W, open vessel with cooling for 20 min. The reaction mixture was then reduced in vacuo and the residue separated between DCM (200 ml) and H₂O (200 ml). The organics were separated and the aqueous layer was re-extracted with DCM (2×200 ml). Organics were combined, dried (MgSO₄) and reduced in vacuo and the resulting residue was purified by prep HPLC to give the title compound as a white solid. Yield: 80 mg MS: APCI (+ve) 518 [M+H⁺]

¹H NMR: (CD₃OD) δ 1.16 (d, 3H), 1.22 (d, 3H), 1.33 (d, 6H), 2.89-2.96 (m, 2H), 3.37-3.48 (m, 2H), 3.78-3.85 (m, 1H), 3.99-4.04 (m, 2H), 4.40-4.50 (m, 2H), 5.09-5.16 (m, 1H), 5.99 (s, 1H), 7.07-7.21 (m, 2H), 7.30-7.36 (m, 2H)

EXAMPLE 77

N-(2-[(2,3-Difluorobenzyl)thio]-6-{[(1R,2R)-2-hydroxymethylpropyl]oxy}pyrimidin-4-yl)-piperazine-1-sulfonamide

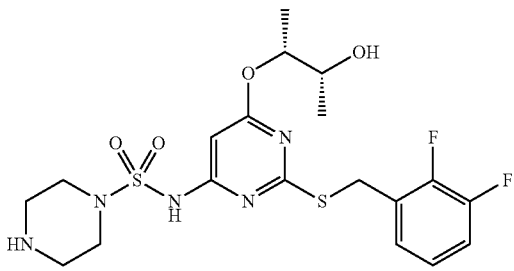

N-(2-[(2,3-difluorobenzyl)thio]-6-{[(1R,2R)-2-hydroxymethylpropyl]oxy}pyrimidin-4-yl) tert-butyl 4-(aminosulfonyl)piperazine-1-carboxylate (1.45 g) was dissolved in DCM (10 ml) and allowed to stir at room temperature until homogeneous. TFA (10 ml) was then slowly added and the reaction mixture stirred overnight. The reaction mixture was reduced in vacuo, dissolved in MeOH and purified by prep HPLC to give the title compound as a white solid Yield: 25 mg MS: APCI (+ve) 490 [M+H$^+$]

$^1$H NMR: (DMSO) δ 1.02 (d, 3H), 1.09 (d, 3H), 3.01-3.05 (m, 4H), 3.14-3.18 (m, 4H), 3.64-3.71 (m, 2H), 4.32-4.42 (m, 2H), 4.69-4.73 (m, 1H), 4.87-4.94 (m, 1H), 5.84 (s, 1H), 7.10-7.17 (m, 1H), 7.27-7.34 (m, 1H), 7.40-7.46 (m, 1H)

The intermediate for this compound was prepared as follows:

i) N-(2-[(2,3-Difluorobenzyl)thio]-6-{[(1R,2R)-2-hydroxymethylpropyl]oxy}pyrimidin-4-yl)tert-butyl 4-(aminosulfonyl)piperazine-1-carboxylate A mixture of 4-(Aminosulfonyl)-1,1-dimethylethyl ester-1-piperazinecarboxylic acid (0.663 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.731 g) and (2R,3R)-3-([6-chloro-2-[(2,3-difluorobenzyl)thio]pyrimidin-4-yl}oxy)butan-2-ol ((the product of example 4 step i), 0.541 g) in dioxane (40 mL) was heated at reflux in a microwave at 100° C., 300 W, open vessel with cooling for 1.5 h. The reaction mixture was then reduced in vacuo and the residue partitioned between EtOAc (200 ml) and H$_2$O (200 ml). The organics were separated and the aqueous layer was re-extracted with EtOAc (2×200 ml). Organics were combined, dried (MgSO$_4$) and reduced in vacuo to give the subtitle compound as a yellow solid. Yield: 1.45 g MS: APCI (+ve) 590 [M+H$^+$]

EXAMPLE 78

N-(2-[(2,3-Difluorobenzyl)thio]-6-{[(1R,2R)-2-hydroxymethylpropyl]oxy}pyrimidin-4-yl)-1,2,3,4-tetrahydroisoquinoline-7-sulfonamide

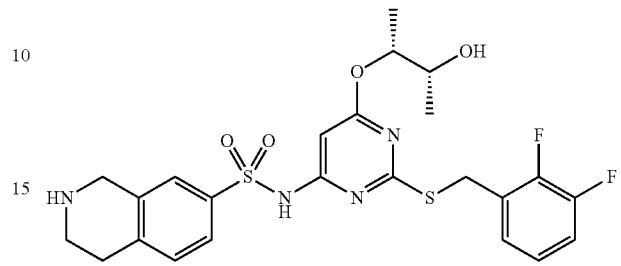

N-(2-[(2,3-Difluorobenzyl)thio]-6-{[(1R,2R)-2-hydroxymethylpropyl]oxy}pyrimidin-4-yl) 2-(trifluoroacetyl)-1,2,3,4-tetrahydroisoquinoline-7-sulfonamide (the product from step 0.54 g) was added to a solution of 7N NH$_3$ in MeOH (20 ml), sealed and stirred at room temperature for 1 h. The reaction was reduced in vacuo and the resulting residue purified by prep HPLC to give the title compound as a white solid. Yield: 180 mg MS: APCI (+ve) 537 [M+H$^+$]

$^1$H NMR: (DMSO) δ 0.98 (d, 3H), 1.04 (d, 3H), 2.95 (t, 2H), 3.30 (t, 2H), 3.60-3.67 (m, 1H), 4.22 (s, 2H), 4.25-4.27 (m, 2H), 4.78-4.85 (m, 1H), 5.63 (s, 1H), 7.09-7.15 (m, 1H), 7.21-7.23 (m, 1H), 7.26-7.39 (m, 2H), 7.56-7.61 (m, 2H)

The intermediates for this compound were prepared as follows:

i) N-(tert-Butyl)-2-(trifluoroacetyl)-1,2,3,4-tetrahydroisoquinoline-7-sulfonamide To a solution of 2-(trifluoroacetyl)-1,2,3,4-tetrahydroisoquinoline-7-sulfonyl chloride (3 g) in DCM (50 ml) was added 2-methylpropan-2-amine (1.73 g). The reaction was then allowed to stir at room temperature 18 h. The reaction was partitioned between H$_2$O (100 ml) and DCM (100 ml). The organics were separated and the aqueous layer was re-extracted with DCM (2×200 ml). Organics were combined, dried (MgSO$_4$) and reduced in vacuo to give the subtitle compound as colourless oil. Yield: 3.56 g $^1$H NMR: (DMSO) δ 1.10 (s, 9H), 2.95-3.02 (m, 2H), 3.80-3.86 (m, 2H), 4.79-4.86 (m, 2H), 7.37-7.49 (m, 2H), 7.63-7.72 (m, 1H)

ii) 1,2,3,4-Tetrahydroisoquinoline-7-sulfonamide

N-(tert-Butyl)-2-(trifluoroacetyl)-1,2,3,4-tetrahydroisoquinoline-7-sulfonamide (the product from step i), 1.78 g) was dissolved in TFA and stirred at room temperature for 96 h. The reaction was reduced in vacuo and the residue purified by column chromatography on silica gel 50% EtOAc/50% iso-hexane to give the subtitle compound as a white solid. Yield: 0.65 g $^1$H NMR: (DMSO) δ 2.95-3.02 (m, 2H), 3.80-3.86 (m, 2H), 4.80-4.85 (m, 2H), 7.38-7.43 (m, 1H), 7.64-7.77 (m, 2H)

iii) N-(2-[(2,3-Difluorobenzyl)thio]-6-{[(1R,2R)-2-hydroxymethylpropyl]oxy}pyrimidin-4-yl)2-(trifluoroacetyl)-1,2,3,4-tetrahydroisoquinoline-7-sulfonamide A mixture of 1,2,3,4-Tetrahydroisoquinoline-7-sulfonamide (the product from step 0.65 g), tris(dibenzylideneacetone)dipalladium (0) (50 mg), 2-dicyclohexylphosphino-2', 4',6'-tri-isopropyl-1,1'-biphenyl (XPHOS) (50 mg), cesium carbonate (0.731 g) and (2R,3R)-3-({6-chloro-2-[(2,3-difluorobenzyl)thio]pyrimidin-4-yl}oxy)butan-2-ol (the product of example 4 step i), 0.432 g) in dioxane (40 mL) was heated at reflux in a microwave at 100° C., 300 W, open vessel with cooling for 20 min. The reaction mixture was then reduced in vacuo and the residue separated between DCM (100 ml) and H$_2$O (100 ml). The organics were separated and the aqueous layer was re-extracted with DCM (2×100 ml). Organics were combined, dried (MgSO$_4$) and reduced in vacuo and the resulting residue was purified by column chromatography on silica 50% EtOAc/50% iso-hexane to give the subtitle compound as a clear oil. Yield: 0.54 g MS: APCI (+ve) 633 [M+H$^+$]

EXAMPLE 79

N-{2-[(2,3-Difluorobenzyl)thio]-6-[(1S)-2-hydroxy-1-(isopropoxymethyl)ethoxy]pyrimidin-4-yl}-1-methyl-1H-imidazole-4-sulfonamide

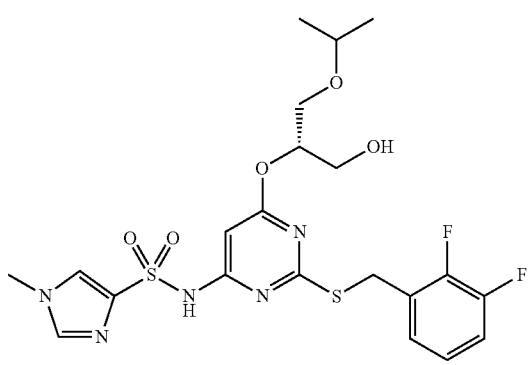 [SMILES: CC(C)OC[C@H](CO)Oc1cc(NS(=O)(=O)c2cn(C)cn2)nc(SCc2cccc(F)c2F)n1]

The title compound was prepared according to the procedure outlined in example 34 using N-{6-[(1R)-2-{[tert-butyl(dimethyl)silyl]oxy}-1-(isopropoxymethyl)ethoxy]-2-[(2,3-difluorobenzyl)thio]pyrimidin-4-yl}-1-methyl-1H-imidazole-4-sulfonamide (the product from step (v) (90 mg) in THF (5 mL) and 1M solution of tetrabutylammoniumfluoride in THF (0.28 mL) to give the title compound as a white solid. Yield: 30 mg.

MS: APCI (+ve) 530 [M+H$^+$]

$^1$H NMR: (DMSO) δ 0.98-1.04 (m, 6H), 3.47-3.56 (m, 4H), 3.67 (s, 3H), 4.40 (s, 2H), 5.14 (q, 1H), 6.17 (s, 1H), 7.07-7.18 (m, 1H), 7.28-7.41 (m, 2H), 7.79 (d, 1H), 8.00 (d, 1H), 11.57 (s, 1H)

The intermediates for this compound were prepared as follows:

i) (4R)-4-(isoPropoxymethyl)-2,2-dimethyl-1,3-dioxolane

To a solution of 2,2-dimethyl-1,3-dioxolane-4-methanol (2 g), in DMSO (50 mL), powdered potassium hydroxide was added portionwise at 0° C. then warmed to room temperature. 2-Iodo-propane (43 mL) was added to the mixture at 0° C. then stirred for 72 h at room temperature. The reaction mixture was diluted with H$_2$O and extracted with EtOAc. The organic layer was washed with H$_2$O then brine (×2) and dried (MgSO$_4$), filtered and evaporated to give the subtitle compound as clear, colourless oil. Yield: 2 g $^1$H NMR: (DMSO) δ 1.08 (d, 6H), 1.26 (d, 3H), 1.31 (s, 3H), 3.30-3.43 (m, 2H), 3.51-3.61 (m, 2H), 3.94-4.00 (m, 1H), 4.08-4.15 (m, 1H)

ii) (2S)-3-isoPropoxypropane-1,2-diol

Acetyl chloride was added dropwise into a solution of MeOH (30 mL) at 0° C. with stirring for min. A solution of (4R)-4-(isopropoxymethyl)-2,2-dimethyl-1,3-dioxolane (1.7 g) (the product from step (i), in MeOH (30 mL), was added dropwise to the reaction mixture. The solution was then warmed to room temperature and stirred for 2 h. The reaction mixture was evaporated to give the subtitle compound as clear oil. Yield: 0.8 g $^1$H NMR: (DMSO) δ 1.07 (dd, 6H), 3.21-3.37 (m, 4H), 3.47-3.55 (m, 2H)

iii) (2R)-1-{[tert-Butyl(dimethyl)silyl]oxy}-3-isopropoxypropan-2-ol

The subtitle compound was prepared according to the procedure outlined in example 34 step iii) using (2S)-3-isopropoxypropane-1,2-diol (0.80 g) (the product from step (ii) in DCM (10 mL), tert-butyldimethylsilyl chloride (1.59 g), triethylamine (1.43 mL) and 4-(dimethylamino)pyridine (50 mg) at 0° C. to give the subtitle compound as a clear, colourless oil. Yield: 1.86 g $^1$H NMR: (DMSO) δ 0.07 (s, 6H), 0.91 (s, 9H), 1.11 (d, 6H), 3.26-3.35 (m, 2H), 3.37-3.45 (m, 2H), 3.49-3.61 (m, 2H), 4.63 (d, 1H)

iv) 4-[(1R)-2-{[tert-Butyl(dimethyl)silyl]oxy}-1-(isopropoxymethyl)ethoxy]-6-chloro-2[(2,3-difluorobenzyl)thio]pyrimidine The subtitle compound was prepared according to the procedure outlined in example 1 step iii) using 4,6-Dichloro-2-[(2,3-difluorobenzyl)thio]pyrimidine (product of example 1 step ii) (0.46 g), (2R)-1-{[tert-butyl(dimethyl)silyl]oxy}-3-isopropoxypropan-2-ol (product of step (0.66 g), THF (5 mL) and 60% sodium hydride (80 mg), to give the subtitle compound as a colourless oil. Yield: 0.56 g MS: APCI (+ve) 519/521 [M+H$^+$]

v) N-{6-[(1R)-2-{[tert-Butyl(dimethyl)silyl]oxy}-1-(isopropoxymethyl)ethoxy]-2-[(2,3-difluorobenzyl)thio]pyrimidin-4-yl}-1-methyl-1H-imidazole-4-sulfonamide The subtitle compound was prepared according to the procedure outlined in example 1 step (iv) using a mixture of azetidine-1-sulfonamide (prepared according to patent WO 2004/011443) (0.19 g), tris(dibenzylideneacetone)dipalladium (0) (0.53 g), 2-dicyclohexylphosphino-2',4',6'-tri-isopropyl-1,1'-biphenyl (XPHOS) (39 mg), cesium carbonate (0.28 g), 4-[(1R)-2-{[tert-butyl(dimethyl)silyl]oxy}-1-(isopropoxymethyl)ethoxy]-6-chloro-2-[(2,3-difluorobenzyl)thio]pyrimidine (the product of step iv) (0.3 g) and dioxane (15 mL). Purification was by column chromatography on silica gel using EtOAc/iso-hexane (2:8) 50:70 as eluent, to give the title compound as a white solid. Yield: 90 mg MS: APCI (+ve) 645 [M+H$^+$]

EXAMPLE 80

N-{2-[(2,3-Difluorobenzyl)thio]-6-[(1R)-2-hydroxy-1-methylethoxy]pyrimidin-4-yl}-1,2-dimethyl-1H-imidazole-4-sulfonamide

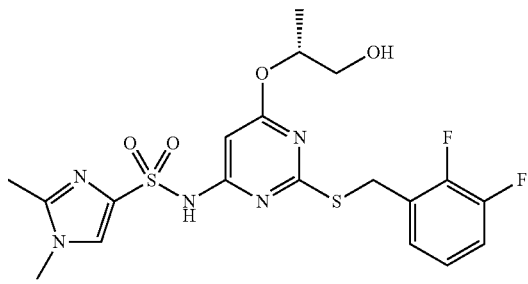 [SMILES: Cc1nc(S(=O)(=O)Nc2cc(O[C@H](C)CO)nc(SCc3cccc(F)c3F)n2)cn1C]

The title compound was prepared according to the procedure outlined in example 11 using a mixture of ethyl (2R)-2-[2-[(2,3-difluorobenzyl)thio]-6-{[(1,2-dimethyl-1H-imidazol-4-yl)sulfonyl]amino}pyrimidin-4-yl)oxy]propanoate (the product from step (i) (0.25 g), lithium borohydride (2M solution in THF, 0.48 mL) and THF (6 mL). Purification was by reverse phase HPLC (symmetry as the stationary phase and TFA/acetonitrile as the mobile phase) then titurated with Toluene, DCM and then Et₂O/iso-hexane to give the title compound as a white solid. Yield: 44 mg MS: APCI (+ve) 486 [M+H⁺]

¹H NMR: (DMSO) δ 1.14 (d, 3H), 2.27 (s, 3H), 3.44-3.49 (m, 2H), 3.56 (s, 3H), 4.41 (s, 2H), 5.02-5.14 (m, 1H), 6.11 (s, 1H), 7.08-7.20 (m, 1H), 7.25-7.43 (m, 2H), 7.92 (s, 1H), 11.44 (s, 1H)

The intermediate for this compound was prepared as follows:

i) Ethyl (2R)-2-[(2-[(2,3-difluorobenzyl)thio]-6-{[(1,2-dimethyl-1H-imidazol-4-yl)sulfonyl]amino}pyrimidin-4-yl)oxy]propanoate The subtitle compound was prepared according to the procedure outlined in example 1 step (iv) using a mixture of 1,2-Dimethyl-1H-imidazole-4-sulfonic acid amide (0.19 g), tris(dibenzylideneacetone)dipalladium (0) (56 mg), 2-dicyclohexylphosphino-2',4',6'-tri-isopropyl-1,1'-biphenyl (XPHOS) (41 mg), cesium carbonate (0.32 g), 2-[[6-chloro-2-[[(2,3-difluorophenyl)methyl]thio]-4-pyrimidinyl]oxy]-(2R)-propanoic acid ethyl ester (the product of example 11 step i) (0.24 g) and dioxane (20 mL). Purification was by column chromatography on silica gel using DCM/MeOH (100:1 to 90:10 gradient) as eluent, to give the title compound as a pale yellow solid. Yield: 0.25 g MS: APCI (+ve) 528 [M+H⁺]

EXAMPLE 81

2-{4-[2-(2,3-Difluoro-benzylsulfanyl)-6-methoxy-pyrimidin-4-ylsulfamoyl]-piperazin-1-yl}-N,N-dimethyl-acetamide

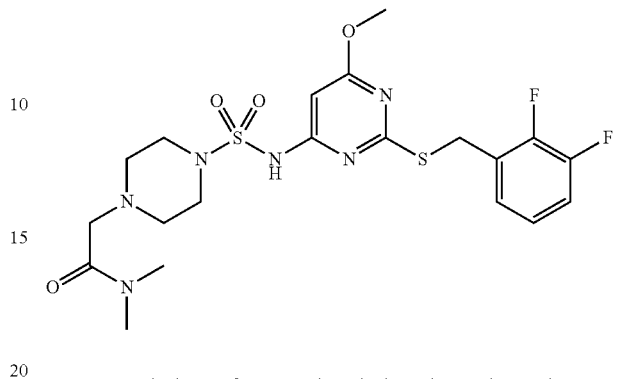

To a solution of N,N-Dimethyl-2-piperazin-1-yl-acetamide (0.51 g), in dioxane (20 mL) was added sulfamide (0.29 g). The reaction mixture was then heated at reflux for 24 h. The reaction mixture was allowed to cool before being reduced in vacuo to give the intermediate compound as an off white solid. Yield: 0.65 g The title compound was prepared according to the procedure outlined in example 1 step (iv) using a mixture of the above intermediate compound (0.38 g), tris(dibenzylideneacetone)dipalladium (0) (92 mg), 2-dicyclohexylphosphino-2',4',6'-tri-isopropyl-1,1'-biphenyl (XPHOS) (67 mg), cesium carbonate (0.49 g), 4-Chloro-2-[[(2,3-difluorophenyl)methyl]thio]-6-methoxypyrimidine (the product of example 35 step i) (0.30 g) and dioxane (10 mL). Purification was by reverse phase HPLC (symmetry as the stationary phase and TFA/acetonitrile as the mobile phase) then titurated with MeOH followed by DCM to give the title compound as a white solid. Yield: 0.24 g MS: APCI (+ve) 517 [M+H⁺]

¹H NMR: (CD₃OD) δ 3.00 (s, 3H), 3.02 (s, 3H), 3.41-3.53 (m, 4H), 3.64-3.80 (m, 4H), 3.97 (s, 3H), 4.29 (s, 2H), 4.54 (s, 2H), 6.09 (s, 1H), 7.08-7.25 (m, 2H), 7.33-7.41 (m, 1H)

EXAMPLE 82

4-Pyridin-4-ylmethyl-piperazine-1-sulfonic acid [2-(2,3-difluoro-benzylsulfanyl)-6-methoxy-pyrimidin-4-yl]-amide

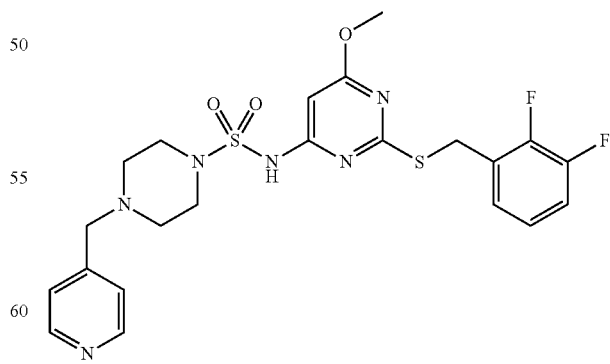

The title compound was prepared according to the procedure outlined in example 81 using a mixture of 1-Pyridin-4-ylmethyl-piperazine (0.53 g), sulfamide (0.29 g) and dioxane (20 mL). Followed by tris(dibenzylideneacetone)dipalladium (0) (92 mg), 2-dicyclohexylphosphino-2',4',6'-tri-isopropyl-1,1'-biphenyl (XPHOS) (67 mg), cesium carbonate (0.49 g), 4-Chloro-2-[[(2,3-difluorophenyl)methyl]thio]-6-methoxypyrimidine (the product of example 35 step i) (0.30 g) and dioxane (10 mL). Purification was by reverse phase HPLC (symmetry as the stationary phase and TFA/acetonitrile as the mobile phase) then titurated with MeOH followed by DCM to give the title compound as a white solid. Yield: 0.23 g MS: APCI (+ve) 523 [M+H⁺]

¹H NMR: (CD₃OD) δ 2.77 (t, 4H), 3.47 (t, 4H), 3.96 (s, 3H), 4.01 (s, 2H), 4.51 (s, 2H), 6.13 (s, 1H), 7.07-7.24 (m, 2H), 7.34-7.42 (m, 1H), 7.99 (d, 2H), 8.76 (d, 2H)

EXAMPLE 83

4-(Tetrahydro-furan-2-ylmethyl)-piperazine-1-sulfonic acid [2-(2,3-difluoro-benzylsulfanyl)-6-methoxy-pyrimidin-4-yl]-amide

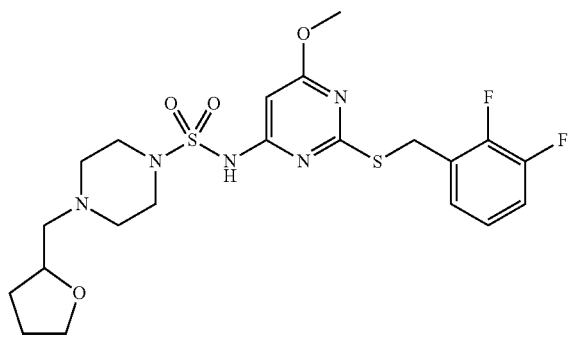 [SMILES: COc1cc(NS(=O)(=O)N2CCN(CC3CCCO3)CC2)nc(SCc2cccc(F)c2F)n1]

The title compound was prepared according to the procedure outlined in example 81 using a mixture of 1-(tetrahydrofuran-2-yl)-1-piperazine (0.51 g), sulfamide (0.29 g) and dioxane (20 mL). Followed by tris(dibenzylideneacetone) dipalladium (0) (92 mg), 2-dicyclohexylphosphino-2',4',6'-tri-isopropyl-1,1'-biphenyl (XPHOS) (67 mg), cesium carbonate (0.49 g), 4-Chloro-2-[[(2,3-difluorophenyl)methyl]thio]-6-methoxypyrimidine (the product of example 35 step i) (0.30 g) and dioxane (10 mL). Purification was by reverse phase HPLC (symmetry as the stationary phase and TFA/acetonitrile as the mobile phase) then titurated with Toluene, MeOH followed by DCM to give the title compound as a white solid.

Yield: 0.15 g

MS: APCI (+ve) 516 [M+H⁺]

¹H NMR: (CD3OD) δ 1.53-1.67 (m, 2H), 1.92-2.03 (m, 2H), 2.10-2.22 (m, 1H), 3.13-3.96 (m, 11H), 3.99 (s, 3H), 4.21-4.34 (m, 1H), 4.55 (s, 2H), 6.08 (s, 1H), 7.08-7.25 (m, 2H), 7.32-7.40 (m, 1H)

EXAMPLE 84

4-(3-Dimethylamino-propyl)-piperazine-1-sulfonic acid [2-(2,3-difluoro-benzylsulfanyl)-6-methoxy-pyrimidin-4-yl]-amide

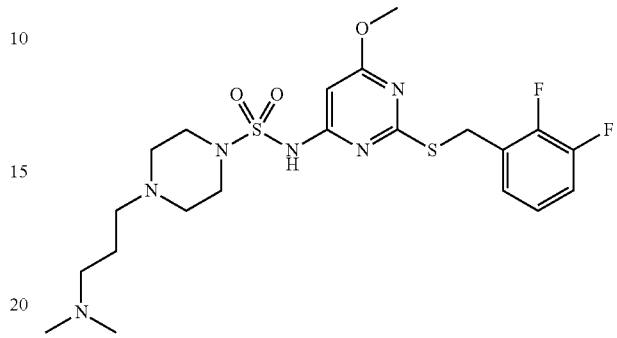

The title compound was prepared according to the procedure outlined in example 81 using a mixture of N,N-dimethyl-3-piperazi-1-ylpropan-1-amine (0.51 g), sulfamide (0.29 g) and dioxane (20 mL). Followed by tris(dibenzylideneacetone)dipalladium (0) (92 mg), 2-dicyclohexylphosphino-2',4',6'-tri-isopropyl-1,1'-biphenyl (XPHOS) (67 mg), cesium carbonate (0.49 g), 4-Chloro-2-[[(2,3-difluorophenyl)methyl]thio]-6-methoxypyrimidine (the product of example 35 step i) (0.30 g) and dioxane (10 mL). Purification was by reverse phase HPLC (symmetry as the stationary phase and TFA/acetonitrile as the mobile phase) then titurated with Toluene, MeOH followed by DCM to give the title compound as a white solid.

Yield: 0.14 g

MS: APCI (+ve) 517 [M+H⁺]

¹H NMR: (DMSO) δ 1.85-2.00 (m, 2H), 2.48-2.53 (m, 10H), 2.78 (s, 6H), 3.02-3.11 (m, 2H), 3.90 (s, 3H), 4.49 (s, 2H), 6.12 (s, 1H), 7.13-7.22 (m, 1H), 7.30-7.44 (m, 2H)

EXAMPLE 85

Piperazine-1,4-disulfonic acid [2-(2,3-difluoro-benzylsulfanyl)-6-methoxy-pyrimidin-4-yl]-amide dimethylamide

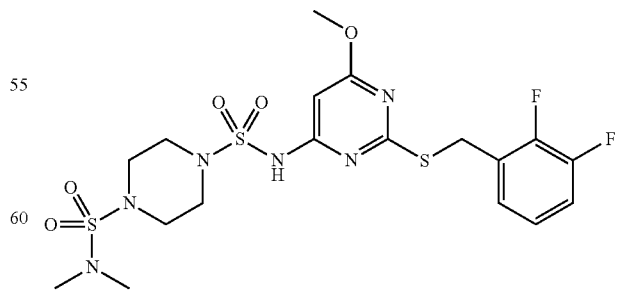

The title compound was prepared by adding dimethyl sulfamoyl chloride to a solution of N-[2-[[(2,3-Difluorophenyl)methyl]thio]-6-methoxypyrimidin-4-yl]piperazine-1-sulfonamide, trifluoroacetate salt (the product from example 36) (0.25 g) in DCM (5 mL). Purification was by reverse phase HPLC (symmetry as the stationary phase and TFA/acetonitrile as the mobile phase) then titurated with Toluene, DCM followed by Et$_2$O to give the title compound as a white solid. Yield: 0.11 g MS: APCI (+ve) 539 [M+H$^+$]

$^1$H NMR: (DMSO) δ 2.73 (s, 6H), 3.16-3.30 (m, 8H), 3.88 (s, 3H), 4.48 (s, 2H), 6.07 (s, 1H), 7.11-7.20 (m, 1H), 7.29-7.45 (m, 2H), 11.28 (s, 1H)

EXAMPLE 86

{4-[2-(2,3-Difluoro-benzylsulfanyl)-6-methoxy-pyrimidin-4-ylsulfamoyl]-piperazin-1-yl}-acetic acid

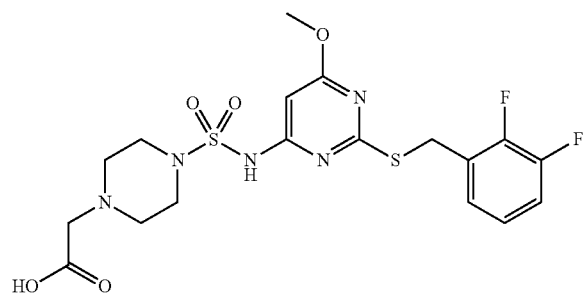 [SMILES: COc1cc(NS(=O)(=O)N2CCN(CC(=O)O)CC2)nc(SCc2cccc(F)c2F)n1]

The title compound was prepared by adding 1M NaOH (1 mL) to a solution of {4-[2-(2,3-Difluoro-benzylsulfanyl)-6-methoxy-pyrimidin-4-ylsulfamoyl]-piperazin-1-yl}-acetic acid ethyl ester (the product from step i) (0.31 g) in MeOH (1 mL). Purification was by reverse phase HPLC (symmetry as the stationary phase and TFA/acetonitrile as the mobile phase) then titurated with Toluene, DCM followed by Et$_2$O to give the title compound as a white solid. Yield: 85 mg MS: APCI (+ve) 490 [M+H$^+$]

$^1$H NMR: (CD3OD) δ 2.99-3.05 (m, 4H), 3.39 (s, 2H), 3.46-3.53 (m, 4H), 3.92 (s, 3H), 4.47 (s, 2H), 6.10 (s, 1H), 7.05-7.24 (m, 3H), 7.35 (t, 1H)

The intermediate for this compound was prepared as follows:

i) {4-[2-(2,3-Difluoro-benzylsulfanyl)-6-methoxy-pyrimidin-4-ylsulfamoyl]-piperazin-1-yl}-acetic acid ethyl ester The subtitle compound was prepared by adding 60% sodium hydride (0.18 g) portionwise to a solution of N-[2-[[(2,3-Difluorophenyl)methyl]thio]-6-methoxypyrimidin-4-yl]piperazine-1-sulfonamide, trifluoroacetate salt (the product from example 36) (0.53 g) and ethyl 2-bromoacetate (0.36 mL) in THF (10 mL). The reaction mixture was diluted with H$_2$O and extracted with EtOAc. The organic layer was washed with brine and evaporated to give the subtitle compound as an oil.

MS: APCI (+ve) 518 [M+H$^+$]

EXAMPLE 87

4-(2-Hydroxy-ethyl)-piperazine-1-sulfonic acid [2-(2,3-difluoro-benzylsulfanyl)-6-methoxy-pyrimidin-4-yl]-amide

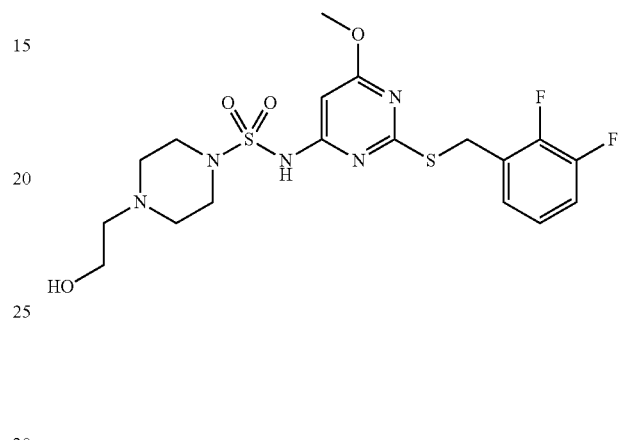

The title compound was prepared according to the procedure outlined in example 24 using a mixture of {4-[2-(2,3-Difluoro-benzylsulfanyl)-6-methoxy-pyrimidin-4-ylsulfamoyl]-piperazin-1-yl}-acetic acid ethyl ester (the product from example 86 step i) (0.31 g) lithium borohydride (1M solution in THF (1.2 mL) in THF (5 mL). Purification was by reverse phase HPLC (symmetry as the stationary phase and NH$_4$OAc/acetonitrile as the mobile phase) then titurated with Toluene, MeOH followed by DCM to give the title compound as a white solid.

Yield: 13 mg

MS: APCI (+ve) 476 [M+H$^+$]

$^1$H NMR: (CD3OD) δ 2.52-2.61 (m, 6H), 3.34 (t, 4H), 3.65 (t, 2H), 3.91 (s, 3H), 4.47 (s, 2H), 6.14 (s, 1H), 7.04-7.19 (m, 2H), 7.35 (t, 1H)

SYNTHESIS OF EXAMPLES 88-107

Examples 88-107 were synthesised using the following procedure:—

To a solution of the aldehyde (0.2 mmol) in NMP (0.8 mL), N-[2-[[(2,3-Difluorophenyl)methyl]thio]-6-methoxypyrimidin-4-yl]piperazine-1-sulfonamide trifluoroacetate salt (the product from example 36) (65 mg) was added as an NMP solution (0.4 ml) followed by resin bound cyanoborohydride (88 mg) and acetic acid (1.8 µL). The reaction mixture was agitated for 48 h, then filtered to remove the resin followed by centrifugal evaporation to dryness. The product was purified by LCMS directed purification (XTerra as the stationary phase and ammonia/acetonitrile as the mobile phase) to give the title compound.

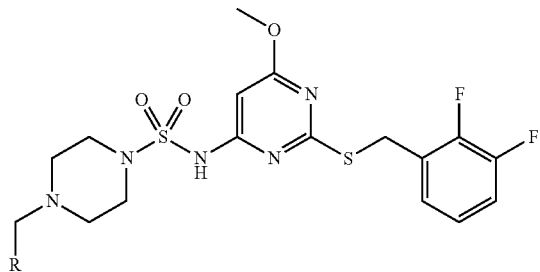

| Example number | Example | R | M/Z [M + H] |
|---|---|---|---|
| 88 | N-{2-[(2,3-Difluorobenzyl)thio]-6-methoxypyrimidin-4-yl}-4-(1H-imidazol-2-ylmethyl)piperazine-1-sulfonamide | | 512 |
| 89 | N-[4-({4-[({2-[(2,3-Difluorobenzyl)thio]-6-methoxypyrimidin-4-yl}amino)sulfonyl]piperazin-1-yl}methyl)phenyl]acetamide | | 578 |
| 90 | N-{2-[(2,3-Difluorobenzyl)thio]-6-methoxypyrimidin-4-yl}-4-(2,3-dihydroxypropyl)piperazine-1-sulfonamide | | 505 |
| 91 | N-{2-[(2,3-Difluorobenzyl)thio]-6-methoxypyrimidin-4-yl}-4-(3-furylmethyl)piperazine-1-sulfonamide | | 511 |
| 92 | N-{2-[(2,3-Difluorobenzyl)thio]-6-methoxypyrimidin-4-yl}-4-(1,3-thiazol-2-ylmethyl)piperazine-1-sulfonamide | | 528 |
| 93 | N-{2-[(2,3-Difluorobenzyl)thio]-6-methoxypyrimidin-4-yl}-4-[(4-oxo-4H-chromen-3-yl)methyl]piperazine-1-sulfonamide | | 589 |
| 94 | N-{2-[(2,3-Difluorobenzyl)thio]-6-methoxypyrimidin-4-yl}-4-(1H-pyrazol-3-ylmethyl)piperazine-1-sulfonamide | | 511 |
| 95 | N-{2-[(2,3-Difluorobenzyl)thio]-6-methoxypyrimidin-4-yl}-4-[3-(dimethylamino)-2,2-dimethylpropyl]piperazine-1-sulfonamide | | 544 |
| 96 | N-{2-[(2,3-Difluorobenzyl)thio]-6-methoxypyrimidin-4-yl}-4-(1,2,3-thiadiazol-4-ylmethyl)piperazine-1-sulfonamide | | 529 |

-continued

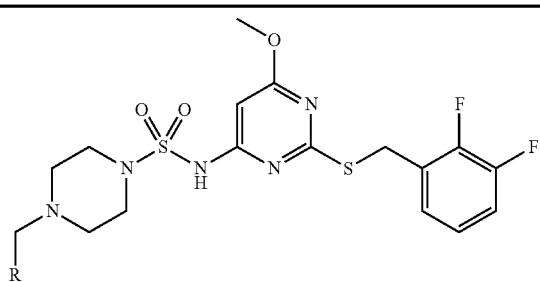

| Example number | Example | R | M/Z [M + H] |
|---|---|---|---|
| 97 | 4-{[1-(2-Cyanoethyl)-1H-pyrrol-2-yl]methyl}-N-{2-[(2,3-difluorobenzyl)thio]-6-methoxypyrimidin-4-yl}piperazine-1-sulfonamide | | 563 |
| 98 | N-{2-[(2,3-Difluorobenzyl)thio]-6-methoxypyrimidin-4-yl}-4-[4-hydroxy-3-(hydroxymethyl)benzyl]piperazine-1-sulfonamide | | 567 |
| 99 | N-{2-[(2,3-Difluorobenzyl)thio]-6-methoxypyrimidin-4-yl}-4-[(1,3,6-trimethyl-2,4-dioxo-1,2,3,4-tetrahydropyrimidin-5-yl)methyl]piperazine-1-sulfonamide | | 597 |
| 100 | N-{2-[(2,3-Difluorobenzyl)thio]-6-methoxypyrimidin-4-yl}-4-{[2-(dimethylamino)pyrimidin-5-yl]methyl}piperazine-1-sulfonamide | | 566 |
| 101 | N-{2-[(2,3-Difluorobenzyl)thio]-6-methoxypyrimidin-4-yl}-4-[(3-morpholin-4-yl-1H-pyrazol-5-yl)methyl]piperazine-1-sulfonamide | | 596 |
| 102 | N-{2-[(2,3-Difluorobenzyl)thio]-6-methoxypyrimidin-4-yl}-4-[(1-methyl-1H-1,2,4-triazol-5-yl)methyl]piperazine-1-sulfonamide | | 526 |
| 103 | N-{2-[(2,3-Difluorobenzyl)thio]-6-methoxypyrimidin-4-yl}-4-(5-hydroxy-2-nitrobenzyl)piperazine-1-sulfonamide | | 582 |

-continued

| Example number | Example | R | M/Z [M + H] |
|---|---|---|---|
| 104 | N-{2-[(2,3-Difluorobenzyl)thio]-6-methoxypyrimidin-4-yl}-4-(1H-imidazol-4-ylmethyl)piperazine-1-sulfonamide | 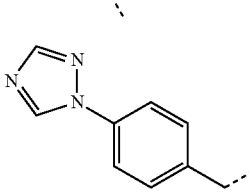 | 511 |
| 105 | N-{2-[(2,3-Difluorobenzyl)thio]-6-methoxypyrimidin-4-yl}-4-[4-(1H-1,2,4-triazol-1-yl)benzyl]piperazine-1-sulfonamide | 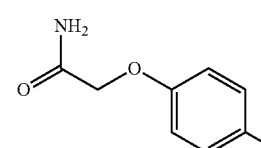 | 588 |
| 106 | 2-[4-({4-[({2-[(2,3-Difluorobenzyl)thio]-6-methoxypyrimidin-4-yl}amino)sulfonyl]piperazin-1-yl}methyl)phenoxy]acetamide | 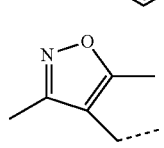 | 594 |
| 107 | N-{2-[(2,3-Difluorobenzyl)thio]-6-methoxypyrimidin-4-yl}-4-[(3,5-dimethylisoxazol-4-yl)methyl]piperazine-1-sulfonamide | 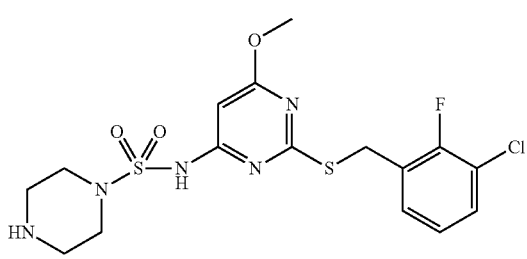 | 540 |

EXAMPLE 108

N-{2-[(3-Chloro-2-fluorobenzyl)thio]-6-methoxypyrimidin-4-yl}piperazine-1-sulfonamide The title compound was prepared according to the procedure outlined in example 15 using tert-butyl 4-[({2-[(3-chloro-2-fluorobenzyl)thio]-6-methoxypyrimidin-4-yl}amino)sulfonyl]piperazine-1-carboxylate (the product from step ii) (0.26 g), trifluoroacetic acid (0.5 mL) and DCM (10 mL). Purification was by reverse phase HPLC (Symmetry as the stationary phase and TFA/acetonitrile as the mobile phase) then triturated with MeOH followed by Et$_2$O to give the title compound as a white solid. Yield: 40 mg MS: APCI (+ve) 448 [M+H$^+$]

$^1$H NMR: (DMSO) δ 3.15-3.24 (m, 4H), 3.36-3.48 (m, 4H), 3.92 (s, 3H), 4.50 (s, 2H), 6.10 (s, 1H), 7.22 (t, 1H), 7.49-7.63 (m, 2H), 8.74 (s, 1H)

The intermediates for this compound were prepared as follows:

i) 4-Chloro-2-[(3-chloro-2-fluorobenzyl)thio]-6-methoxypyrimidine

The subtitle compound was prepared according to the procedure outlined in example 35 Step (i) using 4,6-dichloro-2-[(3-chloro-2-fluorobenzyl)thio]pyrimidine (prepared according to patent WO 2004/011443) (0.65 g), methanol (8 mL) and 60% sodium hydride (88 mg). Yield: 0.57 g.

$^1$H NMR: (CDCl$_3$) δ 3.93 (s, 3H), 4.41-4.43 (m, 2H), 6.43 (s, 1H), 6.99-7.05 (m, 1H), 7.25-7.32 (m, 1H), 7.40-7.46 (m, 1H)

ii) tert-Butyl 4-[({2-[(3-chloro-2-fluorobenzyl)thio]-6-methoxypyrimidin-4-yl}amino)sulfonyl]piperazine-1-carboxylate The subtitle compound was prepared according to the procedure outlined in example 1 step (iv) using 4-chloro-2-[(3-chloro-2-fluorobenzyl)thio]-6-methoxypyrimidine (the product from step i) (0.26 g), 4-(aminosulfonyl)-1,1-dimethylethyl ester-1-piperazinecarboxylic acid (the product of example 15 step i) (0.23 g), tris(dibenzylideneacetone)dipalladium (0) (73 mg), 2-dicyclohexylphosphino-2',4',6'-tri-isopropyl-1,1'-biphenyl (XPHOS) (53 mg), cesium carbonate (0.33 g), and dioxane (8 mL). Purification was by column chromatography on silica gel using EtOAc/isohexane (2:8 to 3:7 gradient) as eluent to give the subtitle compound as a white solid. Yield: 0.26 g MS: APCI (−ve) 546 [M−H⁻]

EXAMPLE 109

N-{2-[(2,3-Difluorobenzyl)thio]-6-methoxypyrimidin-4-yl}-3-hydroxyazetidine-1-sulfonamide

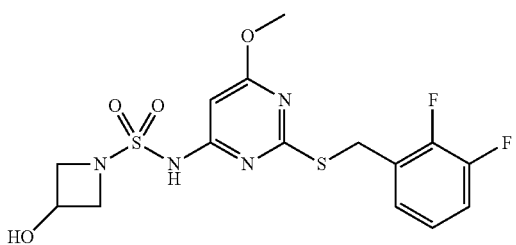 [SMILES: COc1cc(NS(=O)(=O)N2CC(O)C2)nc(SCc2cccc(F)c2F)n1]

The title compound was prepared according to the procedure outlined in example 34 using 3-{[tert-butyl(diphenyl)silyl]oxy}-N-{2-[(2,3-difluorobenzyl)thio]-6-methoxypyrimidin-4-yl}azetidine-1-sulfonamide (the product from step ii) (0.29 g) and 1M solution of tetrabutylammoniumfluoride in THF (5 mL). Purification was by reverse phase HPLC (symmetry as the stationary phase and TFA/acetonitrile as the mobile phase) then triturated with MeOH, Et₂O followed by iso-hexane to give the title compound as a white solid. Yield: 40 mg MS: APCI (+ve) 419 [M+H⁺]

¹H NMR: (DMSO) δ 3.70 (t, 2H), 3.86 (s, 3H), 3.97 (t, 2H), 4.29-4.39 (m, 1H), 4.46 (s, 2H), 5.79 (d, 1H), 6.16 (s, 1H), 7.10-7.18 (m, 1H), 7.32 (q, 1H), 7.41 (t, 1H), 11.23 (s, 1H)

The intermediates for this compound were prepared as follows:

i) 3-(tert-Butyl-diphenyl-silanyloxy)-azetidine-1-sulfonamide

The subtitle compound was prepared according to the procedure outlined in example 15 step (i) using 3-(tert-butyl-diphenyl-silanyloxy)-azetidine (prepared according to patent WO 2003/072557) (0.93 g), dioxane (20 mL) and sulfamide (0.34 g). Isolation was by filtration to remove excess sulfamide, the filtrate was then reduced in vacuo to give the subtitle compound as a brown oil. Yield: 1.2 g MS: APCI (−ve) 389 [M−H⁻]

ii) 3-{[tert-Butyl(diphenyl)silyl]oxy}-N-{2-[(2,3-difluorobenzyl)thio]-6-methoxypyrimidin-4-yl}azetidine-1-sulfonamide The subtitle compound was prepared according to the procedure outlined in example 1 step (iv) using a mixture of 4-Chloro-2-[[(2,3-difluorophenyl)methyl]thio]-6-methoxypyrimidine (the product of example 35 step i) (0.16 g), 3-(tert-butyl-diphenyl-silanyloxy)-azetidine-1-sulfonamide (the product from step i) (0.17 g), tris(dibenzylideneacetone)dipalladium (0) (33 mg), 2-dicyclohexylphosphino-2',4',6'-tri-isopropyl-1,1'-biphenyl (XPHOS) (24 mg), cesium carbonate (0.16 g) and dioxane (8 mL). Purification was by column chromatography on silica gel using EtOAc/isohexane (1:9 to 2:8 gradient) as eluent to give the subtitle compound as a yellow oil. Yield: 0.12 g MS: APCI (+ve) 657 [M+H⁺]

EXAMPLE 110

N'-{2-[(2,3-Difluorobenzyl)thio]-6-methoxypyrimidin-4-yl}-N-[2-(dimethylamino)ethyl]-N-methylsulfamide

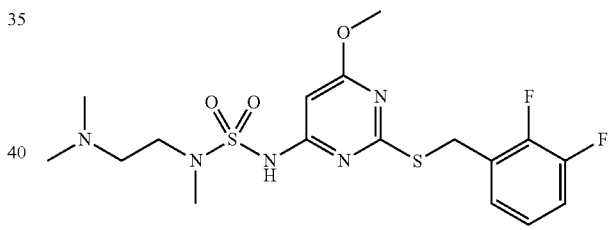

The title compound was prepared according to the procedure outlined in example 1 step (iv) using a mixture of 4-Chloro-2-[[(2,3-difluorophenyl)methyl]thio]-6-methoxypyrimidine (the product of example 35 step i) (0.35 g), N-[2-(dimethylamino)ethyl]-N-methylsulfamide (prepared according to procedure outlined in Org. Letts 2004, 6 (16), 2705-2708) (0.18 g), tris(dibenzylideneacetone)dipalladium (0) (73 mg), 2-dicyclohexylphosphino-2,4',6'-tri-isopropyl-1,1'-biphenyl (XPHOS) (53 mg), cesium carbonate (0.39 g) and dioxane (20 mL). Purification was by reverse phase HPLC (symmetry as the stationary phase and TFA/acetonitrile as the mobile phase) then titurated with MeOH followed by Et₂O to give the title compound as a white solid. Yield: 0.12 g MS: APCI (+ve) 448 [M+H⁺]

¹H NMR (DMSO) δ 2.84 (6H, s), 2.86 (3H, s), 3.33 (2H, t), 3.57 (2H, t), 3.93 (3H, s), 4.53 (2H, s), 6.05 (1H, s), 7.16-7.24 (1H, m), 7.32-7.45 (2H, m)

EXAMPLE 111

N-(2-[(2,3-Difluorobenzyl)thio]-6-{[(1R,2R)-2-hydroxymethylpropyl]oxy}pyrimidin-4-yl)-(2S)-2-methylpiperazine-1-sulfonamide

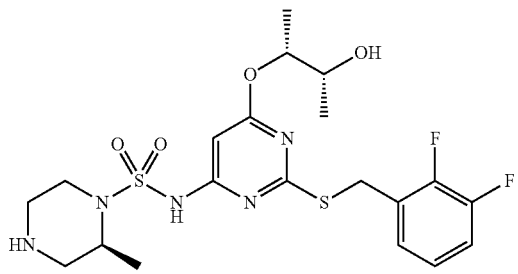 [SMILES: C[C@@H](O)[C@@H](C)Oc1cc(NS(=O)(=O)N2CCNC[C@@H]2C)nc(SCc2cccc(F)c2F)n1]

N-(2-[(2,3-difluorobenzyl)thio]-6-{[(1R,2R)-2-hydroxymethylpropyl]oxy}pyrimidin-4-yl) tert-butyl 4-(aminosulfonyl)piperazine-1-carboxylate (the product from step ii), 0.65 g was dissolved in DCM (15 ml) and allowed to stir at room temperature until homogeneous. TFA (15 ml) was then slowly added and the reaction mixture stirred overnight. The reaction mixture was reduced in vacuo, dissolved in MeOH and purified by prep HPLC to give the title compound as a white solid
Yield 105 mg
$^1$H NMR: (DMSO) δ 1.04 (d, 3H), 1.14 (d, 3H), 1.27 (d, 3H), 2.82-2.91 (m, 1H), 2.97-3.06 (m, 1H), 3.19-3.27 (m, 2H), 3.36-3.44 (m, 1H), 3.67-3.77 (m, 2H), 4.14-4.21 (m, 1H), 4.41-4.50 (m, 2H), 4.98-5.05 (m, 1H), 5.91 (s, 1H), 7.14-7.21 (m, 1H), 7.31-7.41 (m, 2H), 11.28 (s, 1H)
MS: APCI (+ve) 504.1 [M+H$^+$]
The intermediates for this compound were prepared as follows:

i) tert-Butyl (3S)-4-(aminosulfonyl)-3-methylpiperazine-1-carboxylate

To a solution of (2S)-2-methylpiperazine-1-sulfonamide (0.5 g) in dioxane (40 ml) was added sulfamide (0.288 g) and the reaction mixture was then heated at reflux in the microwave at 100° C., 300 W, open vessel with cooling for 4 h in dioxane. The reaction mixture was partitioned between DCM (100 ml) and H$_2$O (100 ml) and the aqueous re-extracted with DCM (2×100 ml). Organics were collected dried and reduced in vacuo to give the subtitle compound as a clear colourless oil (745 mg)
$^1$H NMR: (DMSO) δ 1.11 (d, 3H), 1.40 (s, 9H), 2.84-3.13 (m, 3H), 3.32 (s, 2H), 3.64-3.72 (m, 1H), 3.78-3.93 (m, 1H), 6.80 (s, 2H)

ii) N-(2-[(2,3-Difluorobenzyl)thio]-6-{[(1R,2R)-2-hydroxymethylpropyl]oxy}pyrimidin-4-yl)-tert-butyl (3S)-4-(aminosulfonyl)-3-methylpiperazine-1-carboxylate A mixture of tert-butyl (3S)-4-(aminosulfonyl)-3-methylpiperazine-1-carboxylate ((the product from step i), 0.373 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.488 g) and (2R,3R)-3-((6-chloro-2-[(2,3-difluorobenzyl)thio]pyrimidin-4-yl)oxy)butan-4-ol ((the product of example 4 step i), 0.361 g) in dioxane (20 ml) was heated at reflux in a microwave at 100° C., 300 W, open vessel with cooling for 1.5 h. The reaction mixture was then reduced in vacuo and the residue separated between EtOAc (200 ml) and H$_2$O (200 ml). The organics were separated and the aqueous layer was re-extracted with EtOAc (2×200 ml). Organics were combined, dried (MgSO$_4$) and reduced in vacuo to give the subtitle compound as a yellow solid
Yield 0.65 g
MS: APCI (+ve) 604.5 [M+H$^+$]

EXAMPLE 112

N-[2-[(2,3-Difluorobenzyl)thio]-6-(2-hydroxyethoxy)pyrimidin-4-yl]methanesulfonamide

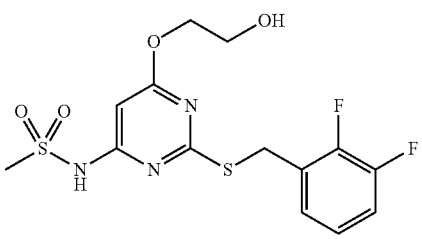 [SMILES: CS(=O)(=O)Nc1cc(OCCO)nc(SCc2cccc(F)c2F)n1]

A mixture of methanesulfonamide (0.228 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.585 g) and 2-({6-chloro-2-[(2,3-difluorobenzyl)thio]pyrimidin-4-yl}oxy)ethanol ((the product step i), 0.400 g) in dioxane (20 ml) was heated at reflux in a microwave at 100° C., 300 W, open vessel with cooling for 30 mins. The reaction mixture was then reduced in vacuo and the residue separated between DCM (150 ml) and H$_2$O (100 ml). The organics were separated and the aqueous layer was re-extracted with DCM (2×150 ml). Organics were combined, dried (MgSO$_4$) and reduced in vacuo and the resulting residue was purified by prep HPLC to give the title compound as a white solid. Yield: 102 mg
$^1$H NMR: (DMSO) δ 3.28 (s, 3H), 3.63-3.68 (m, 2H), 4.29 (t, 2H), 4.47 (s, 2H), 4.87 (t, 1H), 6.03 (s, 1H), 7.13-7.19 (m, 1H), 7.31-7.43 (m, 2H), 11.12 (s, 1H)
MS: APCI (+ve) 391.9 [M+H$^+$]
The intermediate for this compound was prepared as follows:

i) 2-({6-Chloro-2-[(2,3-difluorobenzyl)thio]pyrimidin-4-yl}oxy)ethanol

To a solution of 4,6-dichloro-2-[(2,3-difluorobenzyl)thio]pyrimidine ((the product of example 1 step ii) 5 g) and ethylene glycol (1.517 g) in THF (100 ml) was added NaH (1.3 g) slowly and the reaction was then allowed to stir overnight at RT. The reaction mixture was then partitioned between EtOAc (200 ml) and H$_2$O (200 ml). The organics were separated and the aqueous layer was re-extracted with EtOAc (2×200 ml). Organics were combined, dried (MgSO$_4$) and reduced in vacuo and the resulting residue was purified by column chromatography on silica gel 10% EtOAc/90% iso-Hex to give the subtitle compound as a clear oil. Yield: 2.4 g
MS: APCI (+ve) 332/334 [M+H$^+$]
$^1$H NMR: (DMSO) δ 3.90-3.95 (m, 2H), 4.42 (s, 2H), 4.45-4.48 (m, 2H), 6.48 (s, 1H), 6.98-7.10 (m, 2H), 7.24-7.30 (m, 1H)

EXAMPLE 113

N-[2-[(2,3-Difluorobenzyl)thio]-6-(2-hydroxy-ethoxy)pyrimidin-4-yl]piperazine-1-sulfonamide

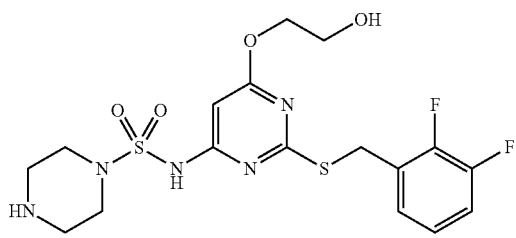 [SMILES: O=S(=O)(Nc1cc(OCCO)nc(SCc2cccc(F)c2F)n1)N1CCNCC1]

To a solution of N-[2-[(2,3-difluorobenzyl)thio]-6-(2-hydroxyethoxy)pyrimidin-4-yl]tert-butyl 4-(aminosulfonyl)piperazine-1-carboxylate ((the product from step i), 0.70 g) in DCM (20 ml) was added TFA (20 ml). The reaction was then stirred at room temperature for 18 h. The reaction was then reduced in vacuo and the residue dissolved in 7N $NH_3$/MeOH (20 ml) and stirred at room temperature for 1 h. The reaction was then reduced in vacuo and the residue purified by prep HPLC to give the title compound as a white solid. Yield: 33 mg MS: APCI (+ve) 462 [M+H$^+$]

$^1$H NMR: (DMSO) δ 3.01-3.05 (m, 4H), 3.13-3.17 (m, 4H), 3.60-3.64 (m, 2H), 4.16 (t, 2H), 4.38 (m, 2H), 4.79 (s, 1H), 5.87 (s, 1H), 7.09-7.17 (m, 1H), 7.26-7.35 (m, 1H), 7.41-7.46 (m, 1H)

The intermediate for this compound was prepared as follows:

i) N-[2-[(2,3-Difluorobenzyl)thio]-6-(2-hydroxy-ethoxy)pyrimidin-4-yl]tert-butyl 4-(aminosulfonyl)piperazine-1-carboxylate A mixture of 4-(aminosulfonyl)-1,1-dimethylethyl ester-1-piperazinecarboxylic acid (the product from example 15 step i) (0.637 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.385 g) and 2-({6-chloro-2-[(2,3-difluorobenzyl)thio]pyrimidin-4-yl}oxy)ethanol (the product from example 112 step i), 0.400 g) in dioxane (20 ml) was heated at reflux in a microwave at 100° C., 300 W, open vessel with cooling for 30 mins. The reaction mixture was then reduced in vacuo and the residue separated between DCM (150 ml) and $H_2O$ (100 ml). The organics were separated and the aqueous layer was re-extracted with DCM (2×150 ml). Organics were combined, dried (MgSO$_4$) and reduced in vacuo to give the subtitle compound as a yellow solid. Yield: 0.70 g MS: APCI (-ve) 560 [M-H$^-$]

$^1$H NMR: (DMSO) δ 3.28 (s, 3H), 3.63-3.68 (m, 2H), 4.29 (t, 2H), 4.47 (s, 2H), 4.87 (t, 1H), 6.03 (s, 1H), 7.13-7.19 (m, 1H), 7.31-7.43 (m, 2H), 11.12 (s, 1H)

EXAMPLE 114

N-[2-[(2,3-Difluorobenzyl)thio]-6-(2-hydroxy-ethoxy)pyrimidin-4-yl]morpholine-4-sulfonamide

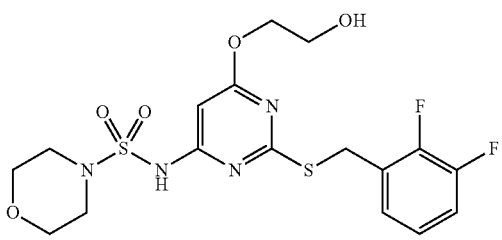 [SMILES: O=S(=O)(Nc1cc(OCCO)nc(SCc2cccc(F)c2F)n1)N1CCOCC1]

A mixture of morpholine-4-sulfonamide (prepared according to patent WO 2004/011443, 0.399 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.585 g) and 2-({6-chloro-2-[(2,3-difluorobenzyl)thio]pyrimidin-4-yl}oxy)ethanol (the product from example 112 step i), 0.400 g) in dioxane (20 ml) was heated at reflux in a microwave at 100° C., 300 W, open vessel with cooling for 30 mins. The reaction mixture was then reduced in vacuo and the residue separated between DCM (150 ml) and $H_2O$ (100 ml). The organics were separated and the aqueous layer was re-extracted with DCM (2×150 ml). Organics were combined, dried (MgSO$_4$) and reduced in vacuo and the resulting residue purified by prep HPLC to give the title compound as a white solid. Yield: 0.15 g MS: APCI (+ve) 463 [M+H$^+$]

$^1$H NMR: (DMSO) δ 3.18 (t, 4H), 3.60 (t, 4H), 3.66 (t, 2H), 4.30 (t, 2H), 4.47 (s, 2H), 4.88 (s, 1H), 6.10 (s, 1H), 7.13-7.20 (m, 1H), 7.31-7.38 (m, 1H), 7.39-7.44 (m, 1H)

EXAMPLE 115

N-[2-[(2,3-Difluorobenzyl)thio]-6-(2-hydroxy-ethoxy)pyrimidin-4-yl]-azetidine-1-sulfonamide

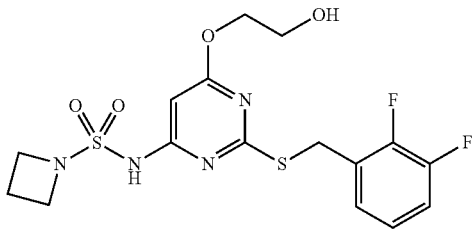 [SMILES: O=S(=O)(Nc1cc(OCCO)nc(SCc2cccc(F)c2F)n1)N1CCC1]

A mixture of azetidine-1-sulfonamide (0.33 g, prepared according to patent WO2004/011443), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.585 g) and 2-({6-chloro-2-[(2,3-difluorobenzyl)thio]pyrimidin-4-yl}oxy)ethanol ((the product from example 112 step ii), 0.400 g) in dioxane (20 ml) was heated at reflux in a microwave at 100° C., 300 W, open vessel with cooling for 30 mins. The reaction mixture was then reduced in vacuo and the residue separated between DCM (150 ml) and $H_2O$ (150 ml). The organics were separated and the aqueous layer was re-extracted with DCM (2×150 ml). Organics were combined, dried (MgSO$_4$) and reduced in vacuo and the resulting residue purified by prep HPLC to give the title compound as a white solid. Yield: 0.13 g MS: APCI (+ve) 433 [M+H⁺]

¹H NMR: (DMSO) δ2.13 (quintet, 2H), 3.65-3.68 (m, 2H), 3.91 (t, 4H), 4.30 (t, 2H), 4.47 (s, 2H), 4.91 (s, 1H), 6.16 (s, 1H), 7.13-7.19 (m, 1H), 7.30-7.38 (m, 1H), 7.40-7.45 (m, 1H), 11.13 (s, 1H)

EXAMPLE 116

N-{2-[(2,3-Difluorobenzyl)thio]-6-isopropoxypyrimidin-4-yl}azetidine-1-sulfonamide

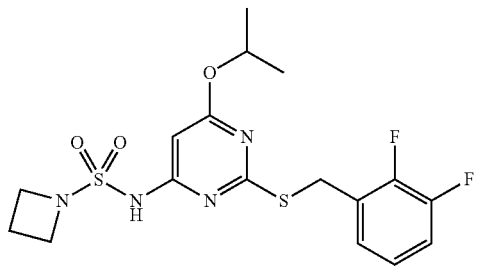 [SMILES: CC(C)Oc1cc(NS(=O)(=O)N2CCC2)nc(SCc2cccc(F)c2F)n1]

A mixture of azetidine-1-sulfonamide (0.327 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.585 g) and 4-chloro-2-[(2,3-difluorobenzyl)thio]-6-isopropoxypyrimidine (the product from step i), 0.400 g) in dioxane (20 ml) was heated at reflux in a microwave at 100° C., 300 W, open vessel with cooling for 30 mins. The reaction mixture was then reduced in vacuo and the residue separated between DCM (150 ml) and H₂O (150 ml). The organics were separated and the aqueous layer was re-extracted with DCM (2×150 ml). Organics were combined, dried (MgSO₄) and reduced in vacuo and the resulting residue purified by prep HPLC to give the title compound as a white solid. Yield: 0.18 g MS: APCI (+ve) 432 [M+H⁺]

¹H NMR: (DMSO) δ1.31 (d, 6H), 2.26 (quintet, 2H), 4.02 (t, 4H), 4.41 (s, 2H), 5.33 (septet, 1H), 6.32 (s, 1H), 6.98-7.10 (m, 2H), 7.18-7.28 (m, 1H)

The intermediate for this compound was prepared as follows:

i) 4-Chloro-2-[(2,3-difluorobenzyl)thio]-6-isopropoxypyrimidine

To a solution of 4,6-dichloro-2-[(2,3-difluorobenzyl)thio]pyrimidine ((the product of example 1 step ii), 3 g) in propan-2-ol (20 ml) was added NaH (0.43 g) slowly and the reaction was then allowed to stir overnight at RT. The reaction mixture was then partitioned between DCM (100 ml) and H₂O (100 ml). The organics were separated and the aqueous layer was re-extracted with DCM (2×100 ml). Organics were combined, dried (MgSO₄) and reduced in vacuo to give the subtitle compound as a pale yellow solid. Yield: 1.8 g ¹H NMR: (DMSO) δ 1.26 (d, 6H), 4.45 (s, 2H), 5.23-5.32 (m, 1H), 6.77 (s, 1H), 7.14-7.22 (m, 1H), 7.31-7.39 (m, 2H)

EXAMPLE 117

(3S)-3-Amino-N-{2-[(2,3-difluorobenzyl)thio]-6-methoxypyrimidin-4-yl}pyrrolidine-1-sulfonamide

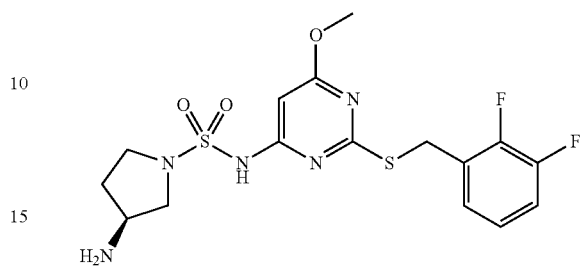

To a solution of tert-butyl {(3S)-1-[({2-[(2,3-difluorobenzyl)thio]-6-methoxypyrimidin-4-yl}amino)sulfonyl]pyrrolidin-3-yl}carbamate (the product from step ii), 0.75 g) in DCM (10 ml) was added TFA slowly. The reaction then stirred at room temperature for 18 h. The reaction was reduced in vacuo and the residue purified by prep HPLC to give the title compound as a white solid. Yield: 70 mg MS: APCI (+ve) 432 [M+H⁺]

¹H NMR: (DMSO) δ1.89-2.02 (m, 1H), 2.07-2.20 (m, 1H), 3.30-3.56 (m, 4H), 3.74-3.81 (m, 1H), 3.82 (s, 3H), 4.43 (s, 2H), 5.89 (s, 1H), 7.12-7.20 (m, 1H), 7.28-7.43 (m, 2H)

The intermediates for this compound were prepared as follows:

i) tert-Butyl [(3S)-1-(aminosulfonyl)pyrrolidin-3-yl]carbamate

To a solution of tert-butyl (3S)-pyrrolidin-3-ylcarbamate (1.3 g) in dioxane (50 ml) was added sulfamide (1.55 g) and the reaction was heated at 110° C. for 18 h. The reaction mixture was then partitioned between DCM (150 ml) and H₂O (100 ml). The organics were separated and the aqueous layer was re-extracted with DCM (2×150 ml). Organics were combined, dried (MgSO₄) and reduced in vacuo to give the subtitle compound as a pale yellow solid. Yield: 1.44 g ¹H NMR: (DMSO) δ 1.39 (s, 9H), 1.67-1.77 (m, 1H), 1.98-2.07 (m, 1H), 2.82-2.87 (m, 1H), 3.06-3.13 (m, 1H), 3.15-3.22 (m, 1H), 3.30-3.35 (m, 1H), 3.93-4.00 (m, 1H), 6.72 (s, 2H)

ii) tert-Butyl {(3S)-1-[({2-[(2,3-difluorobenzyl)thio]-6-methoxypyrimidin-4-yl}amino)sulfonyl]pyrrolidin-3-yl}carbamate A mixture of tert-butyl [(3S)-1-(aminosulfonyl)pyrrolidin-3-yl]carbamate (the product from step i), 0.525 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.429 g) and 4-Chloro-2-[[(2,3-difluorophenyl)methyl]thio]-6-methoxypyrimidine ((the product from example 35 step i), 0.400 g) in dioxane (20 ml) was heated at reflux in a microwave at 100° C., 300 W, open vessel with cooling for 40 mins. The reaction mixture was then reduced in vacuo and the residue separated between DCM (150 ml) and H₂O (150 ml). The organics were separated and the aqueous layer was re-extracted with DCM (2×150 ml). Organics were combined, dried (MgSO₄) and reduced in vacuo to give the subtitle compound as a yellow solid. Yield: 0.75 g MS: APCI (−ve) 530 [M−H⁻]

EXAMPLE 118

(3R)-3-Amino-N-{2-[(2,3-difluorobenzyl)thio]-6-methoxypyrimidin-4-yl}pyrrolidine-1-sulfonamide

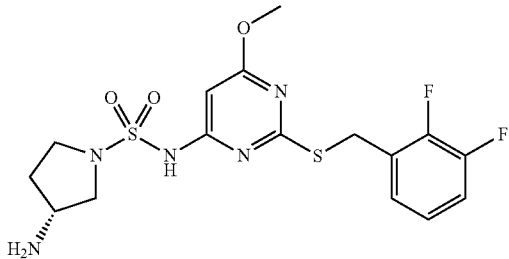 [SMILES: COc1cc(NS(=O)(=O)N2CC[C@@H](N)C2)nc(SCc2cccc(F)c2F)n1]

To a solution of tert-butyl {(3R)-1-[({2-[(2,3-difluorobenzyl)thio]-6-methoxypyrimidin-4-yl}amino)sulfonyl]pyrrolidin-3-yl}carbamate (0.75 g) in DCM (10 ml) was added TFA (10 ml) slowly. The reaction then stirred at room temperature for 18 h. The reaction was reduced in vacuo and the residue purified by prep HPLC to give the subtitle compound as a white solid.

Yield: 0.17 g $^1$H NMR: (DMSO) δ1.89-2.02 (m, 1H), 2.07-2.20 (m, 1H), 3.30-3.56 (m, 4H), 3.74-3.81 (m, 1H), 3.82 (s, 3H), 4.43 (s, 2H), 5.89 (s, 1H), 7.12-7.20 (m, 1H), 7.28-7.43 (m, 2H)

MS: APCI (+ve) 431.9 [M+H$^+$]

The intermediates for this compound were prepared as follows:

i) tert-Butyl [(3R)-1-(aminosulfonyl)pyrrolidin-3-yl]carbamate

To a solution of tert-butyl (3R)-pyrrolidin-3-ylcarbamate (1.3 g) in dioxane (50 ml) was added sulfamide (1.55 g) and the reaction was heated at 110° C. for 18 h. The reaction mixture was then partitioned between DCM (100 ml) and H$_2$O (100 ml). The organics were separated and the aqueous layer was re-extracted with DCM (2×100 ml). Organics were combined, dried (MgSO$_4$) and reduced in vacuo to give the subtitle compound as a pale yellow solid. Yield: 1.69 g $^1$H NMR: (DMSO) δ 1.39 (s, 9H), 1.68-1.76 (m, 1H), 1.98-2.07 (m, 1H), 2.82-2.87 (m, 1H), 3.06-3.13 (m, 1H), 3.15-3.22 (m, 1H), 3.29-3.35 (m, 1H), 3.92-4.00 (m, 1H), 6.72 (s, 2H)

ii) (3S)-3-Amino-N-{2-[(2,3-difluorobenzyl)thio]-6-methoxypyrimidin-4-yl}tert-butyl[(3S)-1-(aminosulfonyl)pyrrolidin-3-yl]carbamate A mixture of tert-butyl [(3S)-1-(aminosulfonyl)pyrrolidin-3-yl]carbamate (0.525 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.429 g) and 4-Chloro-2-[[(2,3-difluorophenyl)methyl]thio]-6-methoxypyrimidine (the product from example 35 step i), 0.400 g) in dioxane (20 ml) was heated at reflux in a microwave at 100° C., 300 W, open vessel with cooling for 40 mins. The reaction mixture was then reduced in vacuo and the residue separated between DCM (150 ml) and H$_2$O (150 ml). The organics were separated and the aqueous layer was re-extracted with DCM (2×150 ml). Organics were combined, dried (MgSO$_4$) and reduced in vacuo to give the title compound as a yellow solid. Yield: 0.77 g MS: APCI (−ve) 539 [M−H$^-$]

EXAMPLE 119

(3R)-3-Amino-N-{2-[(2,3-difluorobenzyl)thio]-6-methoxypyrimidin-4-yl}pyrrolidine-1-sulfonamide

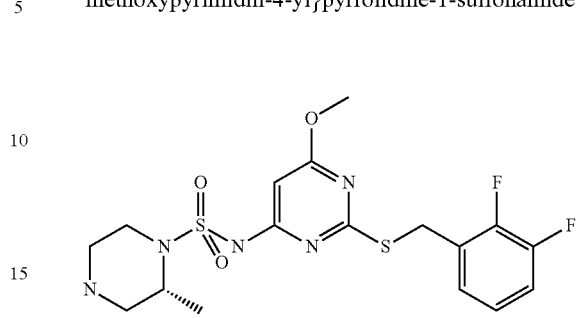

To a solution of tert-butyl (3R)-4-[({2-[(2,3-difluorobenzyl)thio]-6-methoxypyrimidin-4-yl}amino)sulfonyl]-3-methylpiperazine-1-carboxylate (0.75 g) in DCM (10 ml) was added TFA (10 ml) slowly. The reaction then stirred at room temperature for 18 h. The reaction was reduced in vacuo and the residue purified by prep HPLC to give the title compound as a white solid. Yield: 0.27 g MS: APCI (+ve) 446 [M+H$^+$]

$^1$H NMR: (CDCl$_3$) δ 1.43 (d, 3H), 3.07 (t, 1H), 3.15 (d, 1H), 3.26 (d, 1H), 3.33 (d, 1H), 3.60 (t, 1H), 3.86 (d, 1H), 3.95 (s, 3H), 4.30-4.37 (m, 1H), 4.42 (s, 2H), 6.01 (s, 1H), 6.99-7.10 (m, 2H), 7.19-7.22 (m, 1H)

The intermediates for this compound were prepared as follows:

i) tert-Butyl (3R)-3-methylpiperazine-1-carboxylate

To a solution of (2R)-2-methylpiperazine (1 g) in THF (10 ml) was added di-tert-butyl dicarbonate (1.45 g). The reaction mixture was allowed to stir at room temperature for 18 h. The reaction mixture was then partitioned between DCM (100 ml) and H$_2$O (100 ml). The organics were separated and the aqueous layer was re-extracted with DCM (2×150 ml). Organics were combined, dried (MgSO$_4$) and reduced in vacuo to give the subtitle compound as a clear oil. Yield: 1.1 g $^1$H NMR: (DMSO) δ 0.92 (d, 3H), 1.38 (s, 9H), 2.57-2.70 (m, 1H), 2.76-2.81 (m, 1H), 2.87-2.99 (m, 1H), 3.66-3.74 (m, 4H)

ii) tert-Butyl (3R)-4-(aminosulfonyl)-3-methylpiperazine-1-carboxylate

To a solution of tert-butyl (3R)-3-methylpiperazine-1-carboxylate ((the product from step i), 1.1 g) in dioxane (60 ml) was added sulfamide (1.06 g) and the reaction was heated at 110° C. for 18 h. The reaction mixture was then partitioned between DCM (150 ml) and H$_2$O (150 ml). The organics were separated and the aqueous layer was re-extracted with DCM (2×150 ml). Organics were combined, dried (MgSO$_4$) and reduced in vacuo to give the subtitle compound as a pale yellow oil. Yield: 1.44 g $^1$H NMR: (DMSO) δ 1.10 (d, 3H), 1.39 (s, 9H), 3.00-3.11 (m, 3H), 3.27-3.31 (m, 2H), 3.63-3.71 (m, 1H), 3.79-3.87 (m, 1H), 6.79 (s, 2H)

iii) tert-Butyl (3R)-4-[({2-[(2,3-difluorobenzyl)thio]-6-methoxypyrimidin-4-yl}amino)sulfonyl]-3-methylpiperazine-1-carboxylate A mixture of tert-butyl (3R)-4-(aminosulfonyl)-3-methylpiperazine-1-carboxylate ((the product from step 0.554 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.429 g) and 4-Chloro-2-[[(2,3-difluorophenyl)methyl]thio]-6-methoxypyrimidine (the product from example 35 step i), 0.400 g) in dioxane (20 ml) was heated at reflux in a microwave at 100° C., 300 W, open vessel with cooling for 60 mins. The reaction mixture was then reduced in vacuo and the residue separated between DCM (150 ml) and H₂O (100 ml). The organics were separated and the aqueous layer was re-extracted with DCM (3×150 ml). Organics were combined, dried (MgSO₄) and reduced in vacuo to give the subtitle compound as a yellow oil. Yield: 0.75 g MS: APCI (−ve) 543 [M−H⁻]

EXAMPLE 120

(3S)-3-Amino-N-{2-[(2,3-difluorobenzyl)thio]-6-methoxypyrimidin-4-yl}-(2S)-2-methylpiperizine-1-sulfonamide

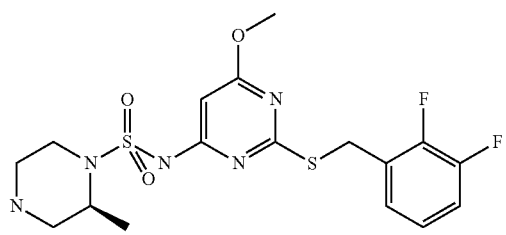 [SMILES: COc1cc(NS(=O)(=O)N2CCNC[C@@H]2C)nc(SCc2cccc(F)c2F)n1]

To a solution of tert-butyl (3S)-4-[({2-[(2,3-difluorobenzyl)thio]-6-methoxypyrimidin-4-yl}amino)sulfonyl]-3-methylpiperazine-1-carboxylate (0.75 g) in DCM (10 ml) was added TFA (10 ml) slowly. The reaction was then stirred at room temperature for 18 h. The reaction was reduced in vacuo and the residue purified by prep HPLC to give the title compound as a white solid. Yield: 0.18 g MS: APCI (+ve) 446 [M+H⁺]

¹H NMR: (CDCl₃) δ 1.43 (d, 3H), 3.07 (t, 1H), 3.15 (d, 1H), 3.26 (d, 1H), 3.33 (d, 1H), 3.60 (t, 1H), 3.86 (d, 1H), 3.95 (s, 3H), 4.30-4.37 (m, 1H), 4.42 (s, 2H), 6.01 (s, 1H), 6.99-7.10 (m, 2H), 7.19-7.22 (m, 1H)

The intermediates for this compound were prepared as follows:

i) tert-Butyl (3S)-4-(aminosulfonyl)-3-methylpiperazine-1-carboxylate

To a solution of tert-butyl (3S)-3-methylpiperazine-1-carboxylate (0.5 g) in dioxane (40 ml) was added sulfamide (0.29 g) and the reaction was heated at 110° C. for 18 h. The reaction mixture was then partitioned between DCM (150 ml) and H₂O (150 ml). The organics were separated and the aqueous layer was re-extracted with DCM (2×150 ml). Organics were combined, dried (MgSO₄) and reduced in vacuo to give the subtitle compound as a pale yellow oil. Yield: 0.66 g ¹H NMR: (DMSO) δ 1.10 (d, 3H), 1.40 (s, 9H), 3.00-3.11 (m, 3H), 3.26-3.34 (m, 2H), 3.63-3.71 (m, 1H), 3.79-3.87 (m, 1H), 6.79 (s, 2H)

ii) tert-Butyl (3S)-4-[({2-[(2,3-difluorobenzyl)thio]-6-methoxypyrimidin-4-yl}amino)sulfonyl]-3-methylpiperazine-1-carboxylate A mixture of tert-butyl (3S)-4-(aminosulfonyl)-3-methylpiperazine-1-carboxylate (0.372 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.286 g) and 4-Chloro-2-[[(2,3-difluorophenyl)methyl]thio]-6-methoxypyrimidine ((the product from example 35 step i), 0.373 g) in dioxane (20 ml) was heated at reflux in a microwave at 100° C., 300 W, open vessel with cooling for 60 min. The reaction mixture was then reduced in vacuo and the residue separated between DCM (150 ml) and H₂O (100 ml). The organics were separated and the aqueous layer was re-extracted with DCM (3×150 ml). Organics were combined, dried (MgSO₄) and reduced in vacuo to give the subtitle compound as a yellow solid. Yield: 0.65 g MS: APCI (−ve) 544 [M−H⁻]

EXAMPLE 121

N-[6-Methoxy-2-[(2-phenylethyl)thio]pyrimidin-4-yl]azetidine-1-sulfonamide

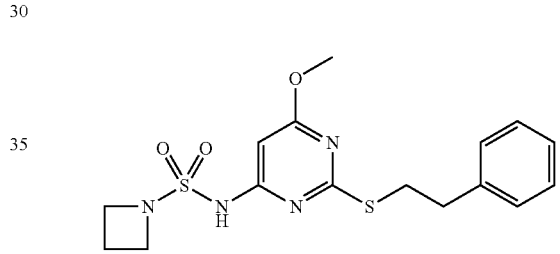

A solution of N-[(4-methoxyphenyl)methyl]-N-[6-methoxy-2-[(2-phenylethyl)thio]pyrimidin-4-yl]azetidine-1-sulfonamide (the product of step iii, 0.17 g) in DCM (1 ml) and TFA (2 ml) was stirred at room temperature for 18 h. The solvent was evaporated under reduced pressure. The residue was recrystallised from EtOAc and iso-hexane to give the title product as a white solid. Yield: 50 mg.

MS: APCI (+ve) 381 [M+H]

¹H NMR: δ (DMSO) 2.12 (quintet, 2H), 3.00 (m, 2H), 3.35 (m, 2H), 3.91 (t, 7H), 6.13 (s, 1H), 7.23 (m, 1H), 7.29 (m, 4H), 11.04 (bs, 1H).

The intermediates for this compound were prepared as follows:

i) N-[2-[[(2,3-Difluorophenyl)methyl]thio]-6-methoxypyrimidin-4-yl]-N-[(4-methoxyphenyl)methyl]azetidine-1-sulfonamide 60% Sodium hydride (0.42 g) was added to a solution of N-[2-[[(2,3-difluorophenyl)methyl]thio]-6-methoxypyrimidin-4-yl]azetidine-1-sulfonamide (the product of Example 35) (3.82 g) in anhydrous DMF (38 ml) stirred at 0° C. under nitrogen. The reaction mixture was stirred for a further 15 min when 4-methoxybenzylchloride (2.98 g) was added dropwise over one min followed by potassium iodide (1.66 g). After stirring at room temperature for 18 h. the reaction mixture was partitioned between EtOAc and H₂O. The aqueous layer was separated and further extracted with EtOAc (2×). The combined organic extracts were washed with H₂O, dried (MgSO₄), filtered and the solvent evaporated under reduced pressure. The residue was purified by flash column chromatography on silica gel using EtOAc/iso-hexane (2:8) as eluent. The product was further purified by flash column chromatography on silica gel using DCM/isohexane (6:4) as eluent to give the subtitle product as a white solid. Yield: 2.4 g.

MS: APCI (+ve) 523 [M+H]

ii) N-[2-[[(2,3-Difluorophenyl)methyl]sulfonyl)-6-methoxypyrimidin-4-yl]-N4(4-methoxyphenyl)methyl]azetidine-1-sulfonamide A mixture of the product of step i) (3.3 g) and mCPBA (1.1 g) in DCM was stirred at room temperature for 5 h. The reaction mixture was washed with aqueous sodium thiosulfate solution (3×100 ml; 15 g/100 ml), aqueous NaHCO₃, H₂O, dried (MgSO₄) and filtered. The solvent was evaporated under reduced pressure to give the subtitle product as a yellow foam.
Yield: 3.18 g.
MS: APCI (+ve) 555 [M+H]

iii) N-[(4-Methoxyphenyl)methyl]-N-[6-methoxy-2-[(2-phenylethyl)thio]pyrimidin-4-yl]azetidine-1-sulfonamide 60% Sodium hydride (29 mg) was added to a solution of the product of step (0.36 g) and 2-phenylethylthiol (0.1 g) in anhydrous DMF (4 ml) stirred under nitrogen. The reaction mixture was stirred for 18 h., diluted with EtOAc and washed with H₂O. The separated organic solution was dried (MgSO₄), filtered and the solvent evaporated under reduced pressure. The residue was purified by flash column chromatography on silica gel using Et₂O/isohexane (3:7) as eluent to give the product as a white solid. Yield: 0.17 g.
MS: APCI (+ve) 501 [M+H]

EXAMPLE 122

N-{6-Methoxy-2-[[(pyridin-4-yl)methyl]thio]pyrimidin-4-yl}azetidine-1-sulfonamide

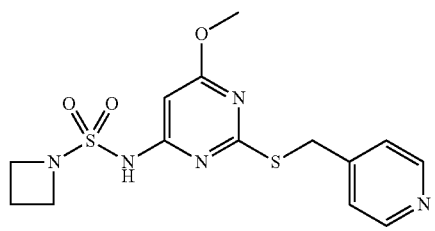 [SMILES: COc1cc(NS(=O)(=O)N2CCC2)nc(SCc2ccncc2)n1]

The title compound was prepared from N-[(4-methoxyphenyl)methyl]-N-[6-methoxy-2-[[(pyridin-4-yl)methyl]thio]pyrimidin-4-yl]azetidine-1-sulfonamide (the product of step i) (46 mg) by the procedure outlined in Example 121. The crude material was purified by preparative plate chromatography using EtOAc with 0.5% of 7N NH₃/MeOH as eluent to give the title product as a white solid. Yield: 31 mg.
MS: APCI (+ve) 368 [M+H]
¹H NMR: δ (DMSO) 2.09 (bt, 2H), 3.84 (bm, 7H), 4.39 (bs, 2H), 6.11 (bs, 1H), 7.47 (bs, 2H), 8.48 (bs, 2H).

The intermediate for this compound was prepared as follows:

i) N-[(4-Methoxyphenyl)methyl]-N-[6-methoxy-2-[[(pyridin-4-yl)methyl]thio]pyrimidin-4-yl]azetidine-1-sulfonamide 60% NaH (27 mg) was added batchwise to a solution of 4-pyridylethanethiol hydrochloride (60 mg) in anhydrous DMF (2 ml) stirred under nitrogen. After 30 min. the subtitle product of Example 121 step ii) (0.2 g) was added. The reaction mixture was stirred for a further 18 h. KOtBu (40 mg) was added and after 30 min. a further quantity of KOtBu (40 mg) was added. After 10 min, KOtBu (40 mg) followed by 4-pyridylmethyl bromide hydrobromide (96 mg) were added. The reaction mixture was stirred for 5 min., diluted with EtOAc and washed with H₂O and aqueous Na₂CO₃. The separated organic solution was dried (MgSO₄), filtered and the solvent evaporated under reduced pressure. The residue was purified by flash column chromatography on silica gel using EtOAc/iso-hexane (7:3) as eluent to give the product as a yellow gum. Yield: 46 mg.
MS: APCI (+ve) 488 [M+H]

EXAMPLE 123

N-{2-[[(2-Cyanophenyl)methyl]thio]-6-methoxypyrimidin-4-yl}azetidine-1-sulfonamide

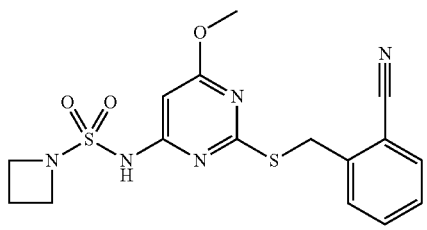 [SMILES: COc1cc(NS(=O)(=O)N2CCC2)nc(SCc2ccccc2C#N)n1]

The title compound was prepared from N-[2-[[(2-cyanophenyl)methyl]thio]-6-methoxy pyrimidin-4-yl]-N-[(4-methoxyphenyl)methyl]-azetidine-1-sulfonamide (60 mg) (the product of step i) by the procedure outlined in Example 121. The crude material was purified by preparative plate chromatography using EtOAc/isohexane (3:7) as eluent to give the title product as a yellow gum. Yield: 31 mg.
MS: APCI (+ve) 392 [M+H]
¹H NMR: δ (DMSO) 2.12 (quintet, 2H), 3.90 (m, 7H), 4.59 (s, 2H), 6.15 (s, 1H), 7.47 (t, 1H), 7.66 (t, 1H), 7.84 (m, 2H), 11.13 (bs, 1H).

The intermediate for this compound was prepared as follows:

i) N-{2-[[(2-Cyanophenyl)methyl]thio]-6-methoxy-pyrimidin-4-yl]-N-[(4-methoxy-phenyl)methyl}azetidine-1-sulfonamide The subtitle compound was prepared from the product of Example 121 step (0.20 g) and (2-cyanophenyl)methyl bromide (78 mg) by the procedure outlined in Example 122 step i). The crude material was purified by flash column chromatography on silica gel using EtOAc/isohexane (3.5:6.5) as eluent to give the product as a gum. Yield: 60 mg
MS: APCI (+ve) 512 [M+H]

EXAMPLE 124

N-{6-Methoxy-2-[(phenylmethyl)thio]pyrimidin-4-yl}azetidine-1-sulfonamide

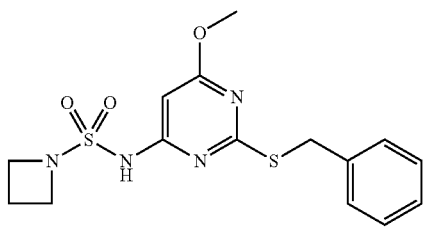 [SMILES: COc1cc(NS(=O)(=O)N2CCC2)nc(SCc2ccccc2)n1]

The title compound was prepared from N-[(4-methoxyphenyl)methyl]-N-[2-[(phenylmethyl) thio]-6-methoxypyrimidin-4-yl]azetidine-1-sulfonamide (the product of step i) (46 mg) by the procedure outlined in Example 121. The crude material was purified by preparative plate chromatography using EtOAc/isohexane (3:7) as eluent to give the title product as a gum.

Yield: 18 mg.
MS: APCI (+ve) 367 [M+H]
$^1$H NMR: δ (DMSO) 2.04 (quintet, 2H), 3.74 (t, 4H), 3.81 (s, 3H), 4.36 (s, 2H), 6.02 (s, 1H), 7.23 (m, 1H), 7.30 (m, 2H), 7.48 (d, 2H).

The intermediate for this compound was prepared as follows:

i) N-[(4-Methoxyphenyl)methyl]-N-[6-methoxy-2-[(phenylmethyl)thio]pyrimidin-4-yl]azetidine-1-sulfonamide KOtBu (46 mg) was added to a mixture of the product of Example 121 step ii) (0.20 g) and phenylmethylthiol (50 mg) in DMF (3 ml) stirred under nitrogen. After 2.5 h, 60% NaH (12 mg) was added. The reaction mixture was stirred for a further 18 h., diluted with EtOAc and washed with H$_2$O. The separated organic solution was dried (MgSO$_4$), filtered and the solvent evaporated under reduced pressure. The residue was purified by flash column chromatography on silica gel using EtOAc/isohexane (2:8) as eluent to give the product as a gum. Yield: 45 mg.
MS: APCI (+ve) 487 [M+H]

EXAMPLE 125

N-{6-Methoxy-2-[[2(-pyrazin-2-yl)ethyl]thio]pyrimidin-4-yl}azetidine-1-sulfonamide

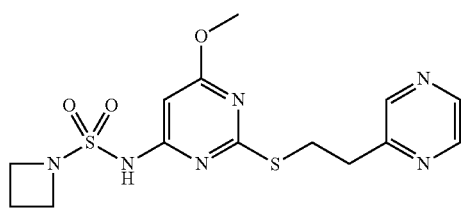 [SMILES: COc1cc(NS(=O)(=O)N2CCC2)nc(SCCc2cnccn2)n1]

The title compound was prepared from N-[(4-methoxyphenyl)methyl]-N-[6-methoxy-2-[2-[(pyrazin-2-yl)ethyl]thio]pyrimidin-4-yl]azetidine-1-sulfonamide (the product of step i) (44 mg) by the procedure outlined in Example 121. The crude material was purified by flash column chromatography on silica gel using EtOAc/isohexane (7:3) as eluent to give the product as a white solid. Yield: 15 mg.
MS: APCI (+ve) 383 [M+H]
$^1$H NMR: δ (DMSO) 2.12 (quintet, 2H), 3.22 (t, 2H), 3.43 (t, 2H), 3.72 (t, 4H), 3.80 (s, 3H), 5.98 (s, 1H), 8.49 (s, 1H), 8.58 (s, 1H), 8.63 (s, 1H).

The intermediate for this compound was prepared as follows:

i) N-[(4-Methoxyphenyl)methyl]-N-[6-methoxy-2-[(pyrazin-2-ylethyl)thio]pyrimidin-4-yl]azetidine-1-sulfonamide The subtitle compound was prepared from the product of Example 121 step ii) (0.20 g) and 2-(pyrazin-2-yl)ethanethiol (57 mg) by the procedure outlined in Example 124 step i). The crude material was purified by flash column chromatography on silica gel using EtOAc/isohexane (1:1) as eluent to give the product as a gum. Yield: 44 mg.
MS: APCI (+ve) 503 [M+H]

EXAMPLE 126

N-{2-[(2,3-Difluorobenzyl)thio]-6-methoxypyrimidin-4-yl}-1,4-diazepane-1-sulfonamide

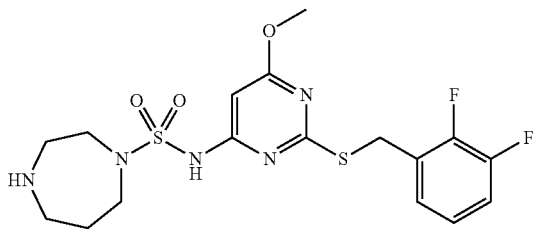 [SMILES: COc1cc(NS(=O)(=O)N2CCCNCC2)nc(SCc2cccc(F)c2F)n1]

A solution of tert-Butyl 4-[({2-[(2,3-difluorobenzyl)thio]-6-methoxypyrimidin-4-yl}amino)sulfonyl]-1,4-diazepane-1-carboxylate (the product of step i, 0.22 g) in 1:1 TFA:methanol (6 ml) was stirred at room temperature for 3 h then the volatiles evaporated and 7M ammonia in methanol (5 ml) added to the residue. The solution was stirred for 30 min then the volatiles evaporated and the resulting solid washed with methanol, DCM, dimethyl sulfoxide and H$_2$O to afford the title compound as a white powder. Yield: 51 mg
MS: APCI (+ve) 446 [M+H$^+$]
$^1$H NMR: δ 4DMSO) 1.90-1.98 (2H, m), 3.17 (4H, t, J=6.0 Hz), 3.36 (2H, t, J=5.9 Hz), 3.49 (2H, t, J=5.8 Hz), 3.77 (3H, s), 4.41 (2H, s), 5.78 (1H, s), 7.11-7.19 (1H, m), 7.28-7.37 (1H, m), 7.42-7.46 (1H, m).

The intermediate for this compound was prepared as follows:

i) tert-Butyl 4-[({2-[(2,3-difluorobenzyl)thio]-6-methoxypyrimidin-4-yl}amino)sulfonyl]-1,4-diazepane-1-carboxylate A mixture of tert-Butyl 4-(aminosulfonyl)-1,4-diazepane-1-carboxylate (the product of example 75, 0.277 g), tris (dibenzylideneacetone)-dipalladium (0) (45 mg), 2-dicyclohexylphosphino-2',4',6'-tri-isopropyl-1,1'-biphenyl (XPHOS) (24 mg), cesium carbonate (0.242 g) and 4-chloro-2-[[(2,3-difluorophenyl)methyl]thio]-6-methoxypyrimidine (the product of example 35 step i, 0.15 g) in anhydrous dioxane (6 ml) was heated at reflux in a microwave at 100° C., 300 W, open vessel with cooling for 15 min. Saturated aqueous ammonium chloride was added and the resulting mixture extracted with EtOAc. The combined organic extracts were washed with saturated aqueous sodium chloride, dried with sodium sulfate, filtered and evaporated. The residue was purified by column chromatography on silica using a 1:19 to 3:7 mixture of EtOAc and iso-hexane as eluent to give the subtitle compound as a yellow oil. Yield: 0.223 g MS: APCI (+ve) 546 [M+H$^+$]

EXAMPLE 127

(3R,5S)—N-{2-[(2,3-Difluorobenzyl)thio]-6-methoxypyrimidin-4-yl}-3,5-dimethylpiperazine-1-sulfonamide

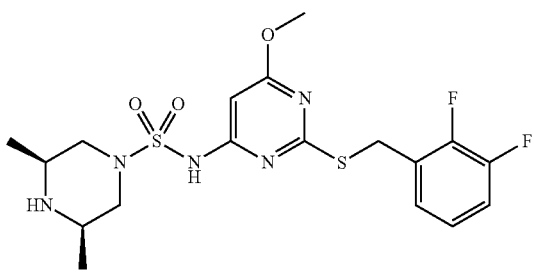 [SMILES: COc1cc(NS(=O)(=O)N2C[C@@H](C)N[C@@H](C)C2)nc(SCc2cccc(F)c2F)n1]

A mixture of (3R,5S)-3,5-dimethylpiperazine-1-sulfonamide (the product of example 72, 0.26 g), tris(dibenzylideneacetone)-dipalladium (0) (61 mg), 2-dicyclohexylphosphino-2',4',6'-tri-isopropyl-1,1'-biphenyl (XPHOS) (32 mg), cesium carbonate (0.32 g) and 4-chloro-2-[[(2,3-difluorophenyl)methyl]thio]-6-methoxypyrimidine (the product of example 35 step i, 0.20 g) in anhydrous dioxane (8 ml) was heated at reflux in a microwave at 100° C., 300 W, open vessel with cooling for 15 min. Saturated aqueous ammonium chloride (5 ml) and EtOAc (5 ml) were added, followed by H$_2$O. The layers were separated and the organic layer extracted with H$_2$O (×3). The organic layer was discarded and the combined aqueous extracts exhaustively extracted with further EtOAc. These extracts were combined, washed with saturated aqueous sodium chloride, dried with sodium sulfate, filtered and evaporated. The resulting solid was washed with H$_2$O to afford the title compound as a white solid. Yield: 0.111 g MS: APCI (+ve) 460 [M+H$^+$]

$^1$H NMR: δ (300 MHz, DMSO) 1.15 (d, 6H), 2.44-2.51 (m, 2H), 3.08-3.23 (m, 2H), 3.57 (dd, 2H), 3.78 (s, 3H), 4.43 (s, 2H), 5.84 (s, 1H), 7.12-7.19 (m, 1H), 7.29-7.38 (m, 1H), 7.45-7.50 (m, 1H).

EXAMPLE 128

3-Amino-N-{2-[(2,3-difluorobenzyl)thio]-6-methoxypyrimidin-4-yl}azetidine-1-sulfonamide

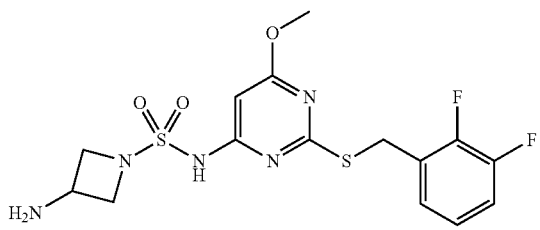 [SMILES: COc1cc(NS(=O)(=O)N2CC(N)C2)nc(SCc2cccc(F)c2F)n1]

A solution of tert-butyl {1-[({2-[(2,3-difluorobenzyl)thio]-6-methoxypyrimidin-4-yl}amino)sulfonyl]azetidin-3-yl}carbamate (the product of step ii, 0.48 g) and TFA (2 ml) in methanol (6 ml) was stirred at room temperature for 1.5 h then the volatiles evaporated and 7M ammonia in methanol (6 ml) added to the residue. The solution was stirred for 2 h then the volatiles evaporated and the residue purified by column chromatography on silica using a 2-8% mixture of methanol in DCM and then further purified by reverse phase HPLC (gradient 5-95% acetonitrile in 0.1% aqueous ammonium acetate) to afford the title compound as a white solid. Yield: 73 mg MS: APCI (+ve) 418 [M+H$^+$]

$^1$H NMR: δ (300 MHz, DMSO) 3.64 (dd, 2H), 3.75-3.83 (m, 1H), 3.79 (s, 3H), 3.90 (t, 2H), 4.43 (s, 2H), 5.93 (s, 1H), 7.12-7.19 (m, 1H), 7.28-7.38 (m, 1H), 7.43-7.48 (m, 1H).

The intermediates for this compound were prepared as follows:

i) tert-Butyl [1-(aminosulfonyl)azetidin-3-yl]carbamate

A solution of tert-butyl azetidin-3-ylcarbamate hydrochloride (prepared according to *J. Antibiot.* 1986, 39, 1243-1256, 0.755 g), Proton-Sponge® (0.85 g) and sulfamide (0.42 g) in dioxane (23 ml) was heated at reflux for 48 h. The residue was partitioned between H$_2$O and EtOAc, and the aqueous layer then extracted with further EtOAc (×4). The combined organic extracts were washed quickly with 2M aqueous hydrochloric acid (×3) then with saturated aqueous sodium bicarbonate, H$_2$O and saturated aqueous sodium chloride, dried with sodium sulfate, filtered and evaporated to afford the subtitle compound as a pale brown powder.

Yield: 0.44 g $^1$H NMR: δ (300 MHz, DMSO) 1.38 (s, 9H), 3.55 (t, 2H), 3.82 (t, 2H), 4.09-4.18 (m, 1H), 6.87 (s, 2H), 7.53 (d, 1H).

ii) tert-Butyl {1-[({2-[(2,3-difluorobenzyl)thio]-6-methoxypyrimidin-4-yl}amino)sulfonyl]azetidin-3-yl}carbamate A mixture of tert-butyl [1-(aminosulfonyl)azetidin-3-yl]carbamate (0.50 g), tris(dibenzylideneacetone)-dipalladium (0) (0.12 g), 2-dicyclohexylphosphino-2',4',6'-tri-isopropyl-1,1'-biphenyl (XPHOS) (63 mg), cesium carbonate (0.65 g) and 4-chloro-2-[[(2,3-difluorophenyl)methyl]thio]-6-methoxypyrimidine (the product of example 35 step i, 0.400 g) in anhydrous dioxane (17 ml) was heated to reflux in a microwave at 100° C., 300 W, open vessel with cooling for 15 min. Saturated aqueous ammonium chloride was added and the resulting mixture extracted with EtOAc. The combined organic extracts were washed with saturated aqueous sodium chloride, dried with sodium sulfate, filtered and evaporated. The residue was purified by column chromatography on silica using a 1:19 to 3:7 mixture of EtOAc and iso-hexane as eluent to give the subtitle compound as a yellow oil. Yield: 0.48 g
MS: APCI (+ve) 518 [M+H⁺]

EXAMPLE 129

N-{2-[(2,3-Difluorobenzyl)thio]-6-methoxypyrimidin-4-yl}-3-hydroxy-3-methylazetidine-1-sulfonamide

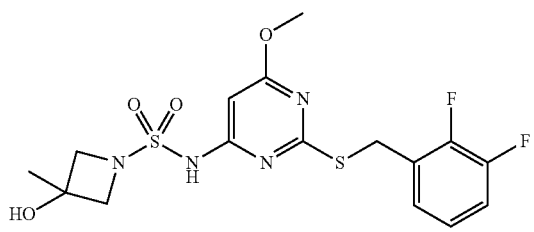 [SMILES: COc1cc(NS(=O)(=O)N2CC(C)(O)C2)nc(SCc2cccc(F)c2F)n1]

A mixture of 3-hydroxy-3-methylazetidine-1-sulfonamide (0.25 g) (prepared according to patent WO 2004/011443), tris(dibenzylideneacetone)-dipalladium (0) (13 mg), 2-dicyclohexylphosphino-2',4',6'-tri-isopropyl-1,1'-biphenyl (XPHOS) (10 mg), cesium carbonate (0.68 g) was treated with a solution of 4-Chloro-2-[[(2,3-difluorophenyl)methyl]thio]-6-methoxypyrimidine (the product of example 35 step i) (0.4 g) in dioxane (10 ml) and the whole then heated at reflux for 30 min. H$_2$O (10 ml) was added followed by 1N hydrochloric acid solution (5 ml) and the resulting mixture extracted with EtOAc. The combined organic extracts were washed with saturated aqueous sodium chloride, dried (MgSO$_4$), filtered and evaporated. The residue was purified by column chromatography on silica gel using EtOAc/DCM (1:4) as eluent to give the subtitle compound as a white solid. Yield: 0.5 g.
MS: APCI (+ve) 433 [M+H⁺], APCI (-ve) 431 [M-H⁻]
¹H NMR δ (DMSO): 1.28 (s, 3H), 3.70 (d, 1H), 3.80 (d, 1H), 3.85 (s, 3H), 4.30 (s, 2H), 5.70 (s, 1H), 6.10 (s, 1H), 7.18 (m, 1H), 7.35 (dd, 1H), 7.43 (t, 1H), 11.20 (bs, 1H)

EXAMPLE 130

3-Amino-N-{2-[(2,3-difluorobenzyl)thio]-6-methoxypyrimidin-4-yl}-3-methylazetidine-1-sulfonamide

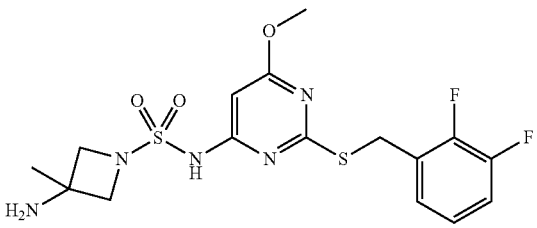 [SMILES: COc1cc(NS(=O)(=O)N2CC(C)(N)C2)nc(SCc2cccc(F)c2F)n1]

A solution of N-{2-[(2,3-difluorobenzyl)thio]-6-methoxypyrimidin-4-yl}-3-hydroxy-3-methylazetidine-1-sulfonamide (the product from example 129, 0.2 g) in THF (5 ml) was treated with diisopropylethylamine (0.45 ml) and methanesulfonylchloride (0.11 ml) under nitrogen.
The whole was stirred at room temperature for 4 h. The solvents were then evaporated in vacuo to dryness and the residue treated with 7N ammonia in methanol (9 ml) and then heated in a sealed vessel at 75° C. for 48 h. The volatiles were then evaporated in vacuo and the residue purified by silica gel chromatography eluting with 10% methanol in DCM to give the subtitle product as a colourless gum. This was triturated with Et$_2$O and iso-hexane mixtures and filtered to give the title product as a white solid. Yield: 50 mg.
MS: APCI (+ve) 432 [M+H⁺], APCI (-ve) 430 [M-H⁻]
¹H NMR δ (CDCl$_3$): 1.45 (s, 3H), 2.90 (bs, 2H), 3.80 (q, 4H), 3.94 (s, 3H), 4.40 (s, 2H), 6.30 (s, 1H), 7.10 (m, 1H), 7.20 (m, 2H)

EXAMPLE 131

N-{2-[(2,3-Difluorobenzyl)thio]-6-methoxypyrimidin-4-yl}-3-methyl-3-(methylamino)azetidine-1-sulfonamide

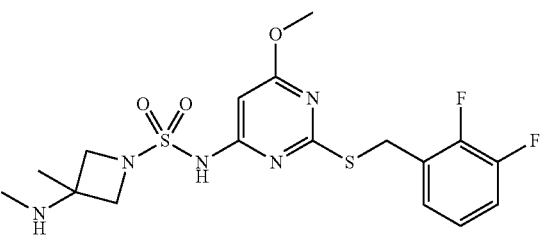 [SMILES: CNC1(C)CN(S(=O)(=O)Nc2cc(OC)nc(SCc3cccc(F)c3F)n2)C1]

A solution of N-(2-[(2,3-difluorobenzyl)thio]-6-methoxy-pyrimidin-4-yl)-3-hydroxy-3-methylazetidine-1-sulfonamide (the product from example 129, 0.16 g) in THF (8 ml) was treated with diisopropylethylamine (0.5 ml) and methanesulfonylchloride (0.113 ml) under nitrogen.
The whole was stirred at room temperature for 16 h. The mixture was then treated with 33% methylamine in ethanol (10 ml) and then heated in a sealed vessel at 70° C. for 24 h. The volatiles were then evaporated in vacuo and the residue purified by silica gel chromatography eluting with 10% methanol in DCM to give the subtitle product as a colourless gum. This was triturated with ethanol and filtered to give the title product as a white solid. Yield: 57 mg.
MS: APCI (+ve) 446 [M+H⁺], APCI (-ve) 444 [M-H⁻]
¹H NMR. (DMSO): 1.33 (s, 3H), 2.35 (s, 3H), 3.60 (d, 2H), 3.80 (s, 3H), 3.85 (d, 2H), 4.40 (s, 2H), 5.92 (s, 1H), 7.10 (m, 1H), 7.30 (m, 1H), 7.40 (m, 1H)

EXAMPLE 132

N-{2-[(2,3-Difluorobenzyl)thio]-6-methoxypyrimidin-4-yl}-4-glycylpiperazine-1-sulfonamide, hydrochloride salt

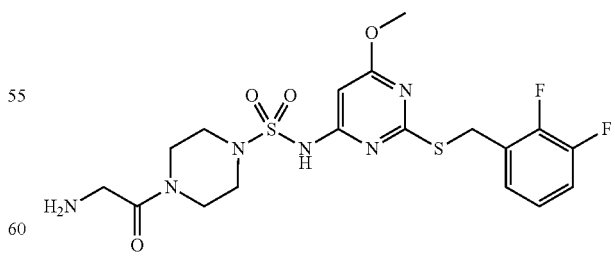

A solution of tert-butyl (2-{4-[({2-[(2,3-difluorobenzyl)thio]-6-methoxypyrimidin-4-yl}amino)sulfonyl]piperazin-1-yl}-2-oxoethyl)carbamate (the product of step ii, 0.19 g) in 10% TFA/DCM (5 mL) was stirred at room temperature for 3 h. The solution was evaporated, and then redissolved in 4N HCl in dioxane (2 mL) and MeOH (8 mL). Evaporation gave a crude residue that was triturated in Et$_2$O, filtered and dried in a vacuum oven at 40° C. overnight to give the title compound as a white solid. Yield: 140 mg.

MS: APCI (−ve) 487 [M−H$^-$]

$^1$H NMR (DMSO) δ 3.20-3.27 (4H, m), 3.41-3.46 (2H, m), 3.53-3.58 (2H, m), 3.86 (2H, s), 3.88 (3H, s), 4.48 (2H, s), 6.09 (1H, s), 7.13-7.21 (1H, m), 7.37-7.44 (2H, m), 8.06 (2H, br s), 11.26 (1H, br s)

the intermediates for this compound were prepared as follows i) N-[2-[[(2,3-Difluorophenyl)methyl]thio]-6-methoxypyrimidin-4-yl]piperazine-1-sulfonamide, hydrochloride salt A solution of N-[2-[[(2,3-Difluorophenyl)methyl]thio]-6-methoxypyrimidin-4-yl]piperazine-1-sulfonamide, trifluoroacetate salt (the product of example 36, 0.6 g) in 4N HCl/dioxane (2 mL) and Et$_2$O (20 mL) was stirred at room temperature for 20 min. The resulting suspension was filtered and the residue dried in a vacuum oven at 40° C. for 2 h to give the subtitle compound as a white solid. Yield: 0.55 g.

MS: APCI (+ve) 432 [M+H$^+$]

ii) tert-Butyl (2-{4-[({2-[(2,3-difluorobenzyl)thio]-6-methoxypyrimidin-4-yl}amino)sulfonyl]piperazin-1-yl}-2-oxoethyl)carbamate To a solution of N-(tert-butoxycarbonyl)glycine (0.11 g) in DMF (10 mL) was added 1,3-Dicyclohexycarbodiimide (0.14 g) and 1-hydroxybenzotriazole hydrate (94 mg). After stirring at room temperature for 1 h, a solution of N-[2-[[(2,3-Difluorophenyl)methyl]thio]-6-methoxypyrimidin-4-yl]piperazine-1-sulfonamide, hydrochloride salt (the product of step i, 0.27 g) and N-methylmorpholine (78 µL) in DMF (5 mL) was added dropwise and stirring continued at room temperature for 24 h. The mixture was filtered, rinsed with DCM and the filtrate evaporated. The crude material was purified by column chromatography on silica gel using EtOAc/isohexane (3:2) as eluent to give the subtitle compound as a foam. Yield: 0.24 g MS: APCI (−ve) 587 [M−H]

EXAMPLE 133

4-β-Alanyl-N-{2-[(2,3-difluorobenzyl)thio]-6-methoxypyrimidin-4-yl}piperazine-1-sulfonamide, hydrochloride salt

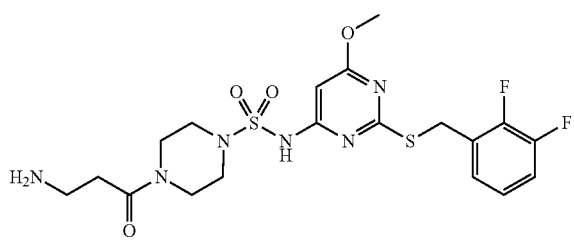 [SMILES: COc1cc(NS(=O)(=O)N2CCN(C(=O)CCN)CC2)nc(SCc2cccc(F)c2F)n1]

The title compound was prepared from tert-butyl (3-{4-[({2-[(2,3-difluorobenzyl)thio]-6-methoxypyrimidin-4-yl}amino)sulfonyl]piperazin-1-yl}-3-oxopropyl)carbamate (the product of step i, 0.22 g) according to the procedure outlined in example 132 to give a white solid.

Yield: 0.15 g.

MS: APCI (+ve) 503 [M+H$^+$]

$^1$H NMR (DMSO) δ 2.66 (2H, t), 2.98 (2H, q), 3.19-3.26 (4H, m), 3.45-3.49 (2H, m), 3.51-3.54 (2H, m), 3.88 (3H, s), 4.48 (2H, s), 6.08 (1H, s), 7.14-7.20 (1H, m), 7.31-7.39 (1H, m), 7.40-7.44 (1H, m), 7.72 (2H, br s), 11.24 (1H, br s)

The intermediate for this compound was prepared as follows:

i) tert-Butyl (3-{4-[({2-[(2,3-difluorobenzyl)thio]-6-methoxypyrimidin-4-yl}amino)sulfonyl]piperazin-1-yl}-3-oxopropyl)carbamate The subtitle compound was prepared from N-(tert-butoxycarbonyl)β-alanine (0.12 g) according to the procedure outline in example 132, step ii). The crude material was purified by column chromatography on silica gel using EtOAc/isohexane (3:2) as eluent to give the subtitle compound as a foam. Yield: 0.22 g MS: APCI (−ve) 601 [M−H]

EXAMPLE 134

N-(2-[(2,3-Difluorobenzyl)thio]-6-methoxypyrimidin-4-yl)-1,2,3,4-tetrahydroisoquinoline-7-sulfonamide

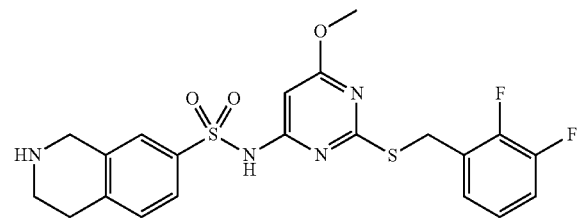 [SMILES: COc1cc(NS(=O)(=O)c2ccc3c(c2)CNCC3)nc(SCc2cccc(F)c2F)n1]

N-(2-[(2,3-difluorobenzyl)thio]-6-methoxypyrimidin-4-yl) 2-(trifluoroacetyl)-1,2,3,4-tetrahydroisoquinoline-7-sulfonamide (0.805 g) was added to a solution of 7N NH$_3$ in MeOH (20 ml), sealed and stirred at room temperature for 2 h. The reaction was reduced in vacuo and the resulting residue purified by prep HPLC to give the title compound as a white solid. Yield: 70 mg MS: APCI (+ve) 479 [M+H$^+$]

$^1$H NMR: (DMSO) δ 3.01-3.08 (m, 2H), 3.35-3.42 (m, 2H), 3.83 (s, 3H), 4.33-4.40 (m, 2H), 4.38 (s, 2H), 6.06 (s, 1H), 7.09-7.20 (m, 1H), 7.31-7.40 (m, 2H), 7.44-7.50 (m, 1H), 7.78-7.87 (m, 2H), 9.00-9.09 (m, 2H)

The intermediate for this compound was prepared as follows:

i) N-(2-[(2,3-Difluorobenzyl)thio]-6-methoxypyrimidin-4-yl)2-(trifluoroacetyl)-1,2,3,4-tetrahydroisoquinoline-7-sulfonamide A mixture of 1,2,3,4-tetrahydroisoquinoline-7-sulfonamide (the product from example 78 step ii, 0.61 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.43 g) and, 4-Chloro-2-[[(2,3-difluorophenyl)methyl]thio]-6-methoxypyrimidine (the product from example step i, 0.4 g) in dioxane (20 ml) was heated at reflux in a microwave at 100° C., 300 W, open vessel with cooling for 3 h. The reaction mixture was then reduced in vacuo and the residue partitioned between DCM (150 ml) and H$_2$O (150 ml). The organics were separated and the aqueous layer was re-extracted with DCM (2×150 ml). Organics were combined, dried (MgSO$_4$) and reduced under to give the subtitle compound as a yellow solid. Yield: 0.81 g MS: APCI (+ve) 575 [M+H$^+$]

EXAMPLE 135

N-(2-[(2,3-Difluorobenzyl)thio]-6-methoxypyrimidin-4-yl)-(2S,5R)-2,5-dimethylpiperazine-1-sulfonamide

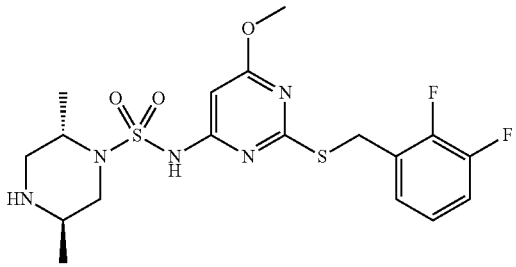 [SMILES: COc1cc(NS(=O)(=O)N2C[C@@H](C)NC[C@@H]2C)nc(SCc2cccc(F)c2F)n1]

To a solution of (2R,5S)-2,5-dimethylpiperazine (2 g) in dioxane (100 ml) was added sulfamide (2.5 g) and the reaction mixture was then heated at reflux in dioxane (100 ml) for 72 h. The reaction mixture was partitioned between EtOAc (150 ml) and H$_2$O (150 ml) and the aqueous re-extracted with EtOAc (2×150 ml). Organics were collected, dried and reduced in vacuo to give (2S,5R)-2,5-dimethylpiperazine-1-sulfonamide as a white solid (1.2 g). A mixture of (2S,5R)-2,5-dimethylpiperazine-1-sulfonamide (0.38 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.43 g) and, 4-Chloro-2-[[(2,3-difluorophenyl)methyl]thio]-6-methoxypyrimidine (the product from example 35 step i), 0.4 g) in dioxane (20 mL) was heated at reflux in a microwave at 100° C., 300 W, open vessel with cooling for 4 h. The reaction mixture was then reduced in vacuo and the residue partitioned between DCM (150 ml) and H$_2$O (150 ml). The organics were separated and the aqueous layer was re-extracted with DCM (2×150 ml). Organics were combined, dried (MgSO$_4$) and reduced in vacuo to give a yellow solid. This residue was then purified by prep HPLC to give the title compound as a white solid. Yield: 9 mg MS: APCI (+ve) 460 [M+H$^+$]

$^1$H NMR: (DMSO) δ 1.05 (d, 3H), 1.23 (d, 3H), 2.58-2.67 (m, 1H), 2.72-2.80 (m, 1H), 3.01-3.54 (m, 4H), 3.77 (s, 3H), 4.40 (s, 2H), 5.83 (s, 1H), 7.07-7.21 (m, 1H), 7.24-7.47 (m, 2H)

EXAMPLE 136

N-(2-[(2,3-Difluorobenzyl)thio]-6-methoxypyrimidin-4-yl)-4-(aminomethyl)benzenesulfonamide

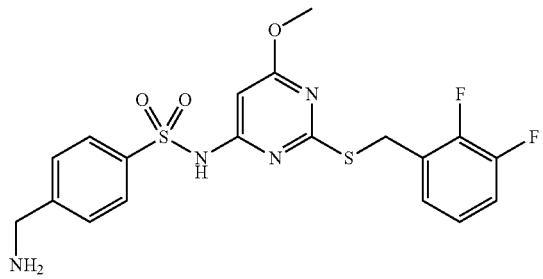 [SMILES: COc1cc(NS(=O)(=O)c2ccc(CN)cc2)nc(SCc2cccc(F)c2F)n1]

A mixture of 4-(aminomethyl)benzenesulfonamide (0.37 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (1.0 g) and, 4-Chloro-2-[[(2,3-difluorophenyl)methyl]thio]-6-methoxypyrimidine (the product from example 35 step i), (0.25 g) in dioxane (20 ml) was heated at reflux in a microwave at 100° C., 300 W, open vessel with cooling for 3 h. The reaction mixture was then reduced in vacuo and the residue partitioned between DCM (150 ml) and H$_2$O (150 ml). The organics were separated and the aqueous layer was re-extracted with DCM (2×150 ml). Organics were combined, dried (MgSO$_4$) and reduced in vacuo to give a yellow solid. This solid was then purified by prep HPLC to give the title compound as a white solid. Yield: 19 mg MS: APCI (+ve) 453 [M+H$^+$]

$^1$H NMR: (DMSO) δ 3.83 (s, 3H), 4.09-4.14 (m, 2H), 4.37 (s, 2H), 6.08 (s, 1H), 7.09-7.22 (m, 1H), 7.31-7.38 (m, 2H), 7.66 (d, 2H), 7.98 (d, 2H), 8.16-8.24 (m, 2H)

EXAMPLE 137

N-{2-[[(3-Fluorophenyl)methyl]thio]-6-methoxypyrimidin-4-yl}azetidine-1-sulfonamide

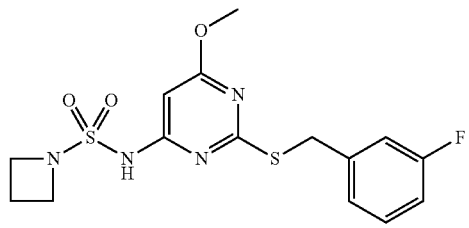 [SMILES: COc1cc(NS(=O)(=O)N2CCC2)nc(SCc2cccc(F)c2)n1]

The title compound was prepared from N-{2-[[(3-fluorophenyl)methyl]thio]-6-methoxypyrimidin-4-yl}-N-[(4-methoxyphenyl)methyl]azetidine-1-sulfonamide (the product of step iv) (42 mg) by the procedure outlined in Example 121. The crude material was purified by preparative plate chromatography using EtOAc/isohexane (4:6) as eluent to give the title product as a gum. Yield: 22 mg.

MS: APCI (+ve) 385 [M+H]

$^1$H NMR: δ (DMSO) 2.10 (quintet, 2H), 3.87 (m, 7H), 4.41 (s, 2H), 6.12 (s, 1H), 7.07 (m, 1H), 7.33 (m, 3H), 11.11 (bs, 1H).

The intermediates for this compound were prepared as follows:

i) N-[(4-Methoxyphenyl)methyl]-N-[6-methoxy-2-[[(2,3,4-trifluorophenyl)methyl]thio]pyrimidin-4-yl]azetidine-1-sulfonamide The subtitle compound was prepared from N-[6-Methoxy-2-[[(2,3,4-trifluorophenyl)methyl]thio]pyrimidin-4-yl]azetidine-1-sulfonamide (the product of Example 146, (5.1 g) by the procedure outlined in Example 121 step i). The crude product was purified by flash column chromatography on silica gel using EtOAc/isohexane (2:8) as eluent to give the product as an oil. Yield: 4.2 g.

MS: APCI (+ve) 541 [M+H]

ii) N-[(4-Methoxyphenyl)methyl]-N-[6-methoxy-2-[[(2,3,4-trifluorophenyl)methyl]sulfonyl]pyrimidin-4-yl]azetidine-1-sulfonamide The subtitle compound was prepared from N-[(4-Methoxyphenyl)methyl]-N-[6-methoxy-2-[[(2,3,4-trifluorophenyl)methyl]thio]pyrimidin-4-yl]azetidine-1-sulfonamide (the subtitle product of step i), (4.2 g) by the procedure outlined in Example 121 step ii). The crude product was purified by flash column chromatography on silica gel using EtOAc/isohexane (1:1) as eluent to give the product as a white foam. Yield: 3.3 g.

MS: APCI (+ve) 573 [M+H]

iii) N-[6-Methoxy-2-thiopyrimdin-4-yl]-N-[(4-methoxyphenyl)methyl]azetidine-1-sulfonamide NaSH (40 mg) was added to a solution of N-[(4-Methoxyphenyl)methyl]-N-[6-methoxy-2-[[(2,3,4-trifluorophenyl)methyl]sulfonyl]pyrimidin-4-yl]azetidine-1-sulfonamide (the subtitle product of step (0.10 g) and stirred in water (1 ml) under nitrogen at 95° C. for 45 min NaSH (40 mg) followed by DMF (1 ml) were added. The reaction mixture was stirred for a further 1.5 h at 95° C., cooled, acidified with dilute HCl and extracted with EtOAc. The separated organic solution was washed with water, dried ($MgSO_4$), filtered and the solvent evaporated under reduced pressure to give the subtitle product as a clear oil.

Yield: 90 mg
MS: APCI (4-ve) 397 [M+H]

iv) N-[2-[[(3-Fluorophenyl)methyl]thio]-6-methoxy pyrimidin-4-yl]-N-[(4-methoxy-phenyl)methyl]-azetidine-1-sulfonamide 60% NaH (8 mg) was added to a solution of N-[6-Methoxy-2-thiopyrimdin-4-yl]-N-[(4-methoxyphenyl)methyl]azetidine-1-sulfonamide (the subtitle product of step iii), (90 mg) in anhydrous DMF (1 ml). After stirring under nitrogen for 5 min (3-fluorophenyl)methyl bromide (42 mg) was added. The reaction mixture was stirred at room temperature for a further 18 h and then diluted with EtOAc. The separated organic solution was washed with water, dried ($MgSO_4$), filtered and the solvent evaporated under reduced pressure. The crude material was purified by flash column chromatography on silica gel using EtOAc/isohexane (3:7) as eluent to give the product as a gum. Yield: 47 mg MS: APCI (+ve) 505 [M+H]

EXAMPLE 138

N-{2-[(2,3-Difluorobenzyl)thio]-6-methoxypyrimidin-4-yl}-4-pyrrolidin-1-ylpiperidine-1-sulfonamide

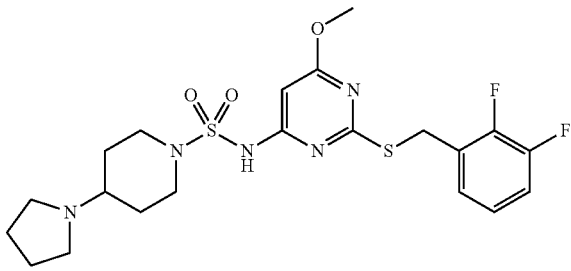 [SMILES: COc1cc(NS(=O)(=O)N2CCC(N3CCCC3)CC2)nc(SCc2cccc(F)c2F)n1]

The title compound was prepared according to the procedure outlined in example 129 using 4-Chloro-2-[[(2,3-difluorophenyl)methyl]thio]-6-methoxypyrimidine (the product of example 35 step i) (0.3 g), tris(dibenzylideneacetone)-dipalladium (0) (20 mg), 2-dicyclohexylphosphino-2',4',6'-tri-isopropyl-1,1'-biphenyl (XPHOS) (15 mg), cesium carbonate (0.70 g) and 4-pyrrolidin-1-ylpiperidine-1-sulfonamide (the product from step i), (0.4 g). The resulting crude material was purified using silica gel chromatography eluting with 5% methanol in DCM and trituration with $Et_2O$ to give the title compound as a white solid.

Yield: 0.27 g

MS: APCI (+ve) 500 [M+H$^+$], APCI (−ve) 498 [M−H$^-$]

$^1$H NMR δ (DMSO) δ 1.60 (m, 2H), 1.90 (bs, 4H), 2.10 (d, 2H), 3.10 (m, 5H), 3.70 (d, 4H), 3.90 (3, 3H), 4.50 (s, 2H), 6.05 (s, 1H), 7.20 (m, 1H), 7.40 (m, 2H)

The intermediates for this compound were prepared as follows:

i) 4-pyrrolidin-1-ylpiperidine-1-sulfonamide

A mixture of 4-pyrrolidin-1-ylpiperidine (0.67 g) and sulfamide (0.46 g) were heated at 115° C. in dry 1,4-dioxane (30 ml) for 16 h. The solvents were evaporated in vacuo and the residue partitioned between EtOAc (containing a little methanol) and $H_2O$. The organic phase was collected and the aqueous layer further extracted with EtOAc (×2). The combined organic phases collected, dried ($MgSO_4$) and the solvent evaporated. The residue was triturated with $Et_2O$ and filtered to give the subtitle product as a beige solid. Yield: 0.43 g $^1$H NMR δ (DMSO) δ 1.50 (m, 2H), 1.70 (m, 4H), 1.90 (m, 2H), 2.05 (m, 1H), 2.50 (m, 2H), 2.60 (m, 2H), 3.40 (m, 4H), 6.70 (s, 2H)

EXAMPLE 139

N-{2-[(2,3-Difluorobenzyl)thio]-6-methoxypyrimidin-4-yl}-3-morpholin-4-ylazetidine-1-sulfonamide

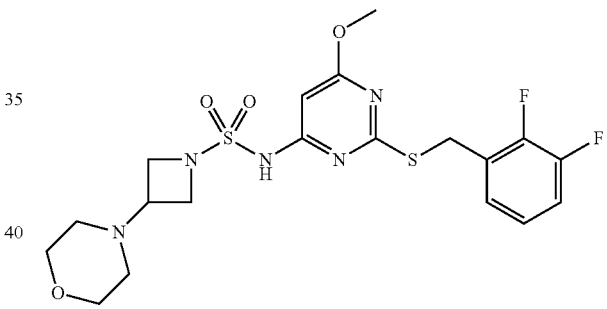

A solution of N-{2-[(2,3-difluorobenzyl)thio]-6-methoxypyrimidin-4-yl}-3-hydroxyazetidine-1-sulfonamide (the product from example 109) (0.28 g) in DCM (10 ml) was treated with triethylamine (0.8 ml) and methanesulfonykhloride (0.9 ml) under nitrogen. After heating the mixture at 50° C. for 16 h the reaction mixture was partitioned between DCM and aqueous $NaHCO_3$. The organic extracts were dried ($MgSO_4$), filtered and the solvent evaporated under reduced pressure. To a solution of the resulting residue in MeOH (10 mL) and morpholine (8 ml) $K_2CO_3$ (0.19 g) was added and heated at 80° C. for 16 h. The reaction mixture was then partitioned between EtOAc and $H_2O$ The organic extracts were washed with brine, dried ($MgSO_4$), filtered and the solvent evaporated under reduced pressure. The residue was purified by reverse phase HPLC (symmetry as the stationary phase and $NH_4OAc$/acetonitrile as the mobile phase) then titurated with $Et_2O$ to give the title compound as a white solid.

Yield: 15 mg

MS: APCI (+ve) 488 [M+H$^+$]

$^1$H NMR δ (DMSO) 2.23 (s, 4H), 3.00-3.08 (m, 1H), 3.51 (t, 4H), 3.76-3.81 (m, 4H), 3.87 (s, 3H), 4.49 (s, 2H), 6.10 (s, 1H), 7.12-7.19 (m, 1H), 7.29-7.38 (m, 1H), 7.44 (t, 1H)

EXAMPLES 140-145

Examples 140-145 were synthesised using the following procedure:—

The title compounds, tabulated below, were prepared from the appropriate 2-thio substituted N-[(4-methoxyphenyl)methyl]-N-[6-methoxy-2-thio]pyrimidin-4-yl]azetidine-1-sulfonamides (the products of step i) by the procedure outlined in Example 121. The crude materials were purified by mass directed purification.

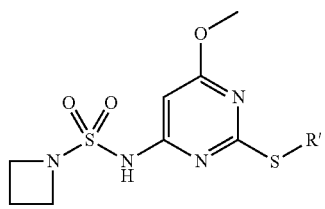

| Example Number | Example | R' | M/Z [M − H] |
|---|---|---|---|
| 140 | N-[2-[[(2-Fluorophenyl)methyl]thio]-6-methoxy pyrimidin-4-yl]azetidine-1-sulfonamide | 2-fluorobenzyl | 383 |
| 141 | N-[6-Methoxy-2-[[(pyridin-3-yl)methyl]thio] pyrimidin-4-yl]azetidine-1-sulfonamide | pyridin-3-ylmethyl | 366 |
| 142 | N-[6-Methoxy-2-[[(pyridin-2-yl)methyl]thio] pyrimidin-4-yl]azetidine-1-sulfonamide | pyridin-2-ylmethyl | 366 |
| 143 | N-[6-Methoxy-2-[[(thiazol-4-yl)methyl]thio] pyrimidin-4-yl]azetidine-1-sulfonamide | thiazol-4-ylmethyl | 372 |
| 144 | N-[2-[[(4-Cyanophenyl)methyl]thio]-6-methoxy pyrimidin-4-yl]azetidine-1-sulfonamide | 4-cyanobenzyl | 390 |
| 145 | N-[2-[[(4-Methanesulfonylphenyl)methyl]-thio]-6-methoxypyrimidin-4-yl]azetidine-1-sulfonamide | 4-methanesulfonylbenzyl | 443 |

The intermediates for compounds 140-145 were prepared as follows:

i) Thio-substituted N-[(4-Methoxyphenyl)methyl]-N-[6-methoxy-2-thio]pyrimidin-4-yl]azetidine-1-sulfonamides Sodium thiolate (30 mg) was added to a solution of N-[(4-Methoxyphenyl)methyl]-N-[6-methoxy-2-[[(2,3,4-trifluorophenyl)methyl]sulfonyl]pyrimidin-4-yl]azetidine-1-sulfonamide (the product of Example 137 step (0.15 g) stirred in anhydrous DMSO under nitrogen. After 30 min, the appropriate bromide or chloride (see R' in the table below) (0.81 mM) was added. The reaction mixture was stirred for a further 30 min, diluted with water and the product extracted with EtOAc. The separated organic solution was washed with water, dried (MgSO$_4$), filtered and the solvent evaporated under reduced pressure. The crude products were purified by flash column chromatography on silica gel using mixtures of EtOAc/isohexane as eluent to give the products, Examples 140 i)-145 i), tabulated below.

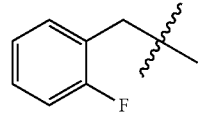 [SMILES: *Cc1ccccc1F]

| Example Number | Example | R' | M/Z [M + H] |
|---|---|---|---|
| 140(i) | N-[2-[[(2-Fluorophenyl)methyl]thio]-6-methoxypyrimidin-4-yl]-N-[(4-methoxyphenyl)methyl]-azetidine-1-sulfonamide | 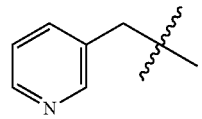 [SMILES: *Cc1cccnc1] | 505 |
| 141(i) | N-[(4-Methoxyphenyl)methyl]-N-[6-methoxy-2-[[(pyridin-3-yl)methyl]thio]pyrimidin-4-yl]-azetidine-1-sulfonamide | 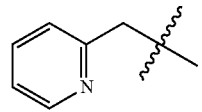 [SMILES: *Cc1ccccn1] | 488 |
| 142(i) | N-[(4-Methoxyphenyl)methyl]-N-[6-methoxy-2-[[(pyridin-2-yl)methyl]thio]pyrimidin-4-yl]-azetidine-1-sulfonamide | 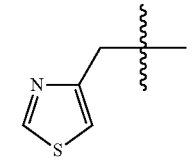 [SMILES: *Cc1cscn1] | 488 |
| 143(i) | N-[(4-Methoxyphenyl)methyl]-N-[6-ethoxy-2-[[(thiazol-4-yl)methyl]thio]pyrimidin-4-yl]-azetidine-1-sulfonamide | 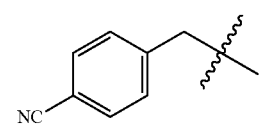 [SMILES: *Cc1ccc(C#N)cc1] | 494 |
| 144(i) | N-[2-[[(4-Cyanophenyl)methyl]thio]-6-methoxypyrimidin-4-yl]-N-[(4-methoxyphenyl)methyl]-azetidine-1-sulfonamide | 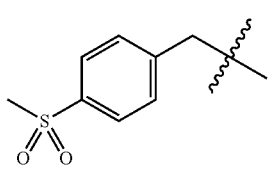 [SMILES: *Cc1ccc(S(C)(=O)=O)cc1] | 512 |
| 145(i) | N-[2-[[(4-Methanesulfonylphenyl)methyl]-thio]-6-methoxypyrimidin-4-yl]N-[(4-methoxyphenyl)methyl]-azetidine-1-sulfonamide | | 565 |

EXAMPLE 146

N-[6-Methoxy-2-[[(2,3,4-trifluorophenyl)methyl]thio]pyrimidin-4-yl]azetidine-1-sulfonamide

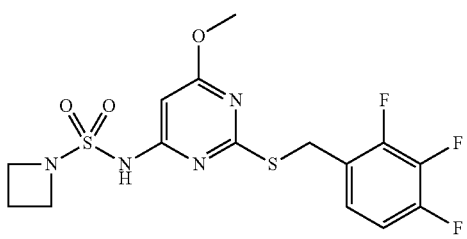 [SMILES: COc1cc(NS(=O)(=O)N2CCC2)nc(SCc2ccc(F)c(F)c2F)n1]

The title compound was prepared from 4-Chloro-6-methoxy-2-[[(2,3,4-trifluorophenyl)methyl]thio]pyrimidine (the subtitle product of step iii) (7.2 g) by the procedure outlined in Example 1 step iv). The crude material was purified by recrystallisation from isohexane/EtOAc to give the product as a yellow solid. Yield: 5.1 g.

MS: APCI (+ve) 421 [M+H]

$^1$H NMR: δ (DMSO) δ 2.13 (quintet, 2H), 3.88 (s, 3H), 3.90 (t, 4H), 4.46 (s, 2H), 6.15 (s, 1H), 7.32-7.24 (m, 1H), 7.53-7.46 (m, 1H), 11.13 (s, 1H)

The intermediates for this compound were prepared as follows:

i) 2-[[(2,3,4-Trifluorophenyl)methyl]thio]pyrimidine-4,6-diol

The subtitle compound was prepared from 2-thiopyrimidine-4,6-diol (80.0 g) and (2,3,4-trifluorophenyl)methyl bromide (125 g) by the procedure outlined in Example 1 step i).

Yield: 150 g.

$^1$H NMR: δ (DMSO) 4.41 (s, 2H), 5.22 (bs, 1H), 7.30 (m, 1H), 7.49 (m, 1H).

ii) 4,6-Dichloro-2-[[(2,3,4-trifluorophenyl)methyl]thio]pyrimidine

The subtitle compound was prepared from the subtitle product of step i) (150 g) by the procedure outlined in Example 1 step ii). The crude material was purified by flash column chromatography on silica gel using EtOAc/isohexane (3:7) as eluent to give the product as a white solid. Yield: 70 g.

$^1$H NMR: δ (CDCl$_3$) 4.37 (s, 2H), 6.91 (m, 1H), 7.06 (s, 1H), 7.26 (m, 1H).

iii) 4-Chloro-6-methoxy-2-[[(2,3,4-trifluorophenyl)methyl]thio]pyrimidine

The subtitle compound was prepared from the subtitle product of step (25.0 g) by the procedure outlined in Example 35 step i). The crude material was purified by recrystallisation from isohexane to give the product as white crystals. Yield: 16.4 g.

MS: APCI (+ve) 321/323 [M+H]

EXAMPLE 147

N'-2{2-[(2,3-Difluorobenzyl)thio]-6-methoxypyrimidin-4-yl}-N-methyl-N-(1-methylpiperidin-4-yl)sulfamide

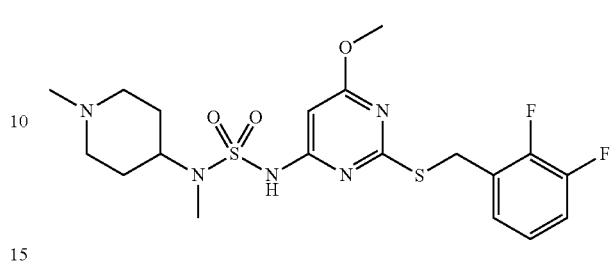

The title compound was prepared from N-methyl-N-(1-methylpiperidin-4-yl)sulfamide (the product of step i) (0.26 g) and 4-chloro-2-[[(2,3-difluorophenyl)methyl]thio]-6-methoxypyrimidine (the product of Example 35, step i) (0.25 g) according to the procedure outlined in Example 1, step iv). The crude material was purified by column chromatography using EtOAc/MeOH (9:1 to 8.5:1.5) as eluent. Yield: 0.17 g MS: APCI (+ve) 474 [M+H]

$^1$H NMR: δ (DMSO) 1.50 (bd, 2H), 1.66 (m, 2H), 2.02 (t, 2H), 2.20 (s, 3H), 2.67 (s, 3H), 2.84 (bd, 2H), 3.63 (m, 1H), 3.82 (s, 3H), 4.44 (s, 2H), 5.90 (s, 1H), 7.14 (q, 1H), 7.33 (q, 1H), 7.41 (t, 1H).

The intermediate for this compound was prepared as follows:

i) N-Methyl-N-(1-methylpiperidin-4-yl)sulfamide

A solution of 1-methyl-4-(methylamino)piperidine (2.6 g) and sulfamide (4.0 g) in 1,4-dioxane (30 ml) was heated at 110° C. for 18 h. The reaction mixture was cooled, the solvent evaporated under reduced pressure and the residue dissolved in water. The aqueous solution was extracted with EtOAc which was washed with a small volume of saturated aqueous brine, dried (MgSO$_4$) and the solvent evaporated under reduced pressure to give the subtitle product as a pale yellow solid. Yield: 1.5 g $^1$H NMR: δ (CDCl$_3$) 1.80 (m, 4H), 2.04 (dt, 2H), 2.27 (s, 3H), 2.79 (s, 3H), 2.91 (bd, 2H), 3.74 (quintet, 1H), 4.44 (bs, 2H).

EXAMPLE 148

N-{2-[(2,3-Difluorobenzyl)thio]-6-methoxypyrimidin-4-yl}-4-morpholin-4-ylpiperidine-1-sulfonamide

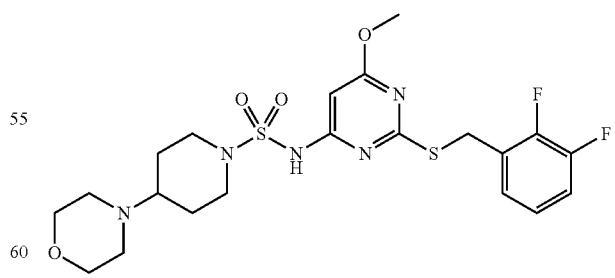

Sodium triacetoxyborohydride (0.48 g) was added to a solution of N-{2-[(2,3-difluorobenzyl)thio]-6-methoxypyrimidin-4-yl}-4-oxopiperidine-1-sulfonamide (the product of step iii) (0.249 g), morpholine (0.2 mL) and 2M aqueous acetic acid (0.5 mL) in DCM (12 mL). The mixture was stirred at room temperature for 18 h then 2M aqueous sodium hydroxide (10 mL) added to the residue. The mixture was shaken vigorously then acidified to pH 8 with 2M aqueous hydrochloric acid and extracted with ethyl acetate. The combined organic extracts were washed with saturated aqueous sodium chloride, dried with sodium sulfate, filtered and evaporated. The residue was purified by column chromatography on silica using a 3:7 to 1:0 mixture of ethyl acetate and iso-hexane as eluent then precipitated slowly from methanol, filtered and washed with further methanol to afford the title compound as a pale yellow solid. Yield: 53 mg MS: APCI (+ve) 516 [M+H$^+$]

$^1$H NMR: δ (300 MHz, DMSO) 1.26-1.41 (m, 2H), 1.76-1.83 (m, 2H), 2.28 (t, 1H), 2.41-2.44 (m, 4H), 2.83 (t, 2H), 3.52-3.58 (m, 4H), 3.68 (d, 2H), 3.88 (s, 3H), 4.49 (s, 2H), 6.07 (s, 1H), 7.14-7.21 (m, 1H), 7.31-7.47 (m, 2H).

The intermediates for this compound were prepared as follows:

i) 1,4-Dioxa-8-azaspiro[4.5]decane-8-sulfonamide

A solution of 1,4-dioxa-8-aza-spiro[4.5]decane (2 mL) and sulfamide (1.65 g) in 1,4-dioxane (28 mL) was heated at reflux for 48 h, then the volatiles were evaporated to afford the title compound as a pale yellow solid. Yield: 3.4 g $^1$H NMR: δ (300 MHz, DMSO) 1.71 (dd, 4H), 3.08 (dd, 4H), 3.91 (s, 4H), 6.77 (s, 2H).

ii) N-{2-[(2,3-Difluorobenzyl)thio]-6-methoxypyrimidin-4-yl}-1,4-dioxa-8-azaspiro[4.5]decane-8-sulfonamide A mixture of 1,4-dioxa-8-azaspiro[4.5]decane-8-sulfonamide (the product of step i), (0.29 g), tris(dibenzylideneacetone)-dipalladium (0) (61 mg), 2-dicyclohexylphosphino-2', 4',6'-tri-isopropyl-1,1'-biphenyl (XPHOS) (32 mg), cesium carbonate (0.32 g) and 4-chloro-2-[[(2,3-difluorophenyl)methyl]thio]-6-methoxypyrimidine (the product of example 35 step i, 0.20 g) in anhydrous dioxane (8 mL) was heated at reflux in a microwave at 100° C., 300 W, open vessel with cooling for 15 min. Saturated aqueous ammonium chloride was added and the resulting mixture extracted with ethyl acetate. The combined organic extracts were washed with saturated aqueous sodium chloride, dried with sodium sulfate, filtered and evaporated. The residue was purified by column chromatography on silica using a 1:19 to 2:3 mixture of ethyl acetate and iso-hexane as eluent to give the subtitle compound as a yellow foam. Yield: 0.27 g MS: APCI (+ve) 489 [M+H$^+$]

iii) N-{2-[(2,3-Difluorobenzyl)thio]-6-methoxypyrimidin-4-yl}-4-oxopiperidine-1-sulfonamide N-{2-[(2,3-Difluorobenzyl)thio]-6-methoxypyrimidin-4-yl}-1,4-dioxa-8-azaspiro[4.5]decane-8-sulfonamide (the product of step ii) (0.85 g) was heated to 50° C. in a mixture of 2M aqueous hydrochloric acid (17 mL) and THF (17 mL). After 24 h, the reaction was allowed to cool to room temperature then diluted with ethyl acetate, the layers separated and the organic material washed with saturated aqueous sodium bicarbonate, water, saturated aqueous sodium chloride, dried with sodium sulfate, filtered and evaporated to afford the subtitle compound as a yellow oil. Yield: 0.83 g MS: APCI (+ve) 445 [M+H$^+$]

EXAMPLE 149

N-{2-[(2,3-Difluorobenzyl)thio]-6-methoxypyrimidin-4-yl}-4-(4-methylpiperazin-1-yl)piperidine-1-sulfonamide

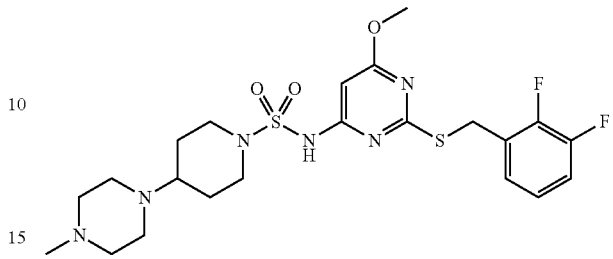

A solution of 1-methyl-piperazine (0.13 mL) in DCM (2 mL) was added to a solution of acetic acid (0.03 mL) and N-{2-[(2,3-difluorobenzyl)thio]-6-methoxypyrimidin-4-yl}-4-oxopiperidine-1-sulfonamide (the product of example 148, step iii) (0.10 g) in DCM (2 mL). The solution was stirred at room temperature for 1 h then sodium triacetoxyborohydride (0.24 g) was added in portions. The mixture was stirred at room temperature overnight then the DCM was evaporated and 3M aqueous sodium hydroxide (6 mL) added to the residue. The mixture was shaken vigorously then acidified to pH 8 with 2M aqueous hydrochloric acid and extracted with ethyl acetate. The combined organic extracts were washed with water, saturated aqueous sodium chloride, dried with sodium sulfate, filtered and evaporated. The residue was purified by reverse phase HPLC (gradient 25-95% acetonitrile in 0.1% aqueous ammonium acetate) to afford the title compound as a white powder. Yield: 22 mg MS: APCI (+ve) 529 [M+H$^+$]

$^1$H NMR: δ (300 MHz, DMSO) 1.26-1.42 (m, 2H), 1.75-1.78 (m, 2H), 2.25-2.77 (m, 11H), 2.27 (s, 3H), 3.63 (d, 2H), 3.84 (s, 3H), 4.46 (s, 2H), 6.01 (s, 1H), 7.13-7.20 (m, 1H), 7.31-7.40 (m, 1H), 7.43-7.48 (m, 1H).

EXAMPLE 150

N-{2-[(2,3-Difluorobenzyl)thio]-6-methoxypyrimidin-4-yl}-4-hydroxypiperidine-1-sulfonamide

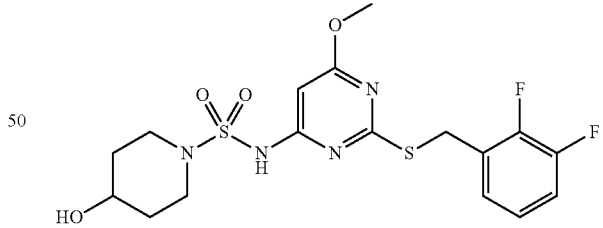

From the crude material obtained after work up to prepare N-{2-[(2,3-difluorobenzyl)thio]-6-methoxypyrimidin-4-yl}-4-morpholin-4-ylpiperidine-1-sulfonamide (Example 148), a second product was also isolated. This was further purified by reverse phase HPLC (gradient 25-95% acetonitrile in 0.1% aqueous ammonium acetate) to afford the title compound as a white powder. Yield: 33 mg MS: APCI (+ve) 447 [M+H$^+$]

$^1$H NMR: δ (300 MHz, DMSO) 1.33-1.44 (m, 2H), 1.70-1.76 (m, 2H), 3.00-3.08 (m, 2H), 3.41-3.49 (m, 2H), 3.57-3.64 (m, 1H), 3.89 (s, 3H), 4.49 (s, 2H), 4.75 (d, 1H), 6.08 (s, 1H), 7.14-7.21 (m, 1H), 7.32-7.47 (m, 2H), 11.07 (s, 1H).

EXAMPLE 151

4-Azetidin-1-yl-N-{2-[(2,3-difluorobenzyl)thio]-6-methoxypyrimidin-4-yl}piperidine-1

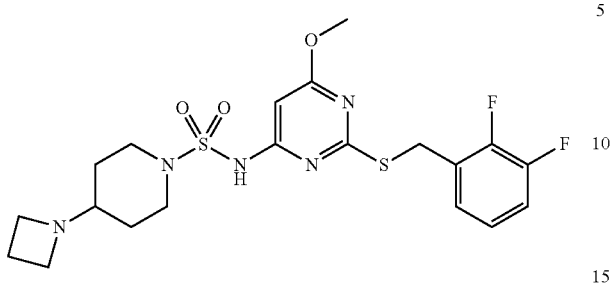

Azetidine hydrochloride (0.11 g) was added to a solution of acetic acid (0.025 mL) and N-{2-[(2,3-difluorobenzyl)thio]-6-methoxypyrimidin-4-yl}-4-oxopiperidine-1-sulfonamide (the product of example 148, step iii) (0.10 g) in DCM (4 mL). The solution was stirred at room temperature for 1 h then sodium triacetoxyborohydride (0.24 g) was added in portions. The mixture was stirred at room temperature overnight then 3M aqueous sodium hydroxide (6 mL) added to the residue. The mixture was shaken vigorously then acidified to pH 8 with 2M aqueous hydrochloric acid and extracted with ethyl acetate. The combined organic extracts were concentrated then methanol (1 mL) was added and the resulting suspension filtered. The solid was washed with water, methanol and ethyl acetate to afford the title compound as a white powder. Yield: 47 mg MS: APCI (+ve) 486 [M+H$^+$]

$^1$H NMR: δ (300 MHz, DMSO) 1.15-1.26 (m, 2H), 1.69-1.78 (m, 2H), 2.01-2.09 (m, 2H), 2.47-3.51 (m, 9H), 3.83 (s, 3H), 4.45 (s, 2H), 5.96 (s, 1H), 7.13-7.20 (m, 1H), 7.30-7.39 (m, 1H), 7.43-7.48 (m, 1H).

EXAMPLE 152

N-{2-[(2,3-Difluorobenzyl)thio]-6-methoxypyrimidin-4-yl}-4-(ethylamino)piperidine-1-sulfonamide

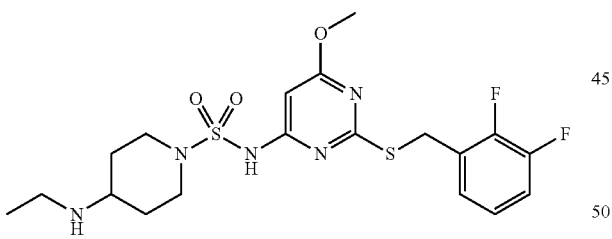

Ethylamine (0.56 mL of 2M solution in methanol) was added to a solution of acetic acid (0.025 mL) and N-{2-[(2,3-difluorobenzyl)thio]-6-methoxypyrimidin-4-yl}-4-oxopiperidine-1-sulfonamide (the product of example 148, step iii) (0.10 g) in DCM (4 mL). The solution was stirred at room temperature for 1 h then sodium triacetoxyborohydride (0.24 g) was added in portions. The mixture was stirred at room temperature overnight then 3M aqueous sodium hydroxide (6 mL) added to the residue. The mixture was shaken vigorously then acidified to pH 8 with 2M aqueous hydrochloric acid and extracted with ethyl acetate. The combined organic extracts were concentrated then methanol (1 mL) was added and the resulting suspension filtered. The solid was washed with water, methanol and ethyl acetate to afford the title compound as a very pale yellow powder. Yield: 52 mg MS: APCI (+ve) 474 [M+H$^+$]

$^1$H NMR: δ (300 MHz, DMSO) 1.17 (t, 3H), 1.41-1.52 (m, 2H), 1.96-2.01 (m, 2H), 2.57-2.61 (m, 2H), 2.94 (q, 2H), 3.00-3.08 (m, 1H), 3.55 (d, 2H), 3.74 (s, 3H), 4.40 (s, 2H), 5.84 (s, 1H), 7.11-7.18 (m, 1H), 7.28-7.36 (m, 1H), 7.44-7.49 (m, 1H).

EXAMPLE 153

4-(Cyclopropylamino)-N-{2-[(2,3-difluorobenzyl)thio]-6-methoxypyrimidin-4-yl}piperidine-1-sulfonamide

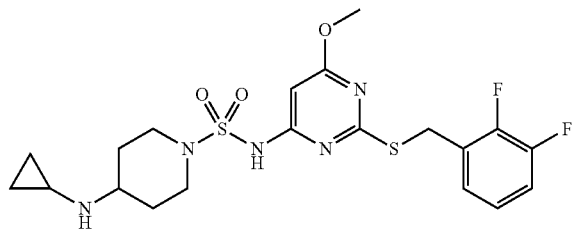 [SMILES: COc1cc(NS(=O)(=O)N2CCC(NC3CC3)CC2)nc(SCc2cccc(F)c2F)n1]

A solution of cyclopropylamine (0.08 mL) in DCM (2 mL) was added to a solution of acetic acid (0.025 mL) and N-{2-[(2,3-difluorobenzyl)thio]-6-methoxypyrimidin-4-yl}-4-oxopiperidine-1-sulfonamide (the product of example 148, step iii) (0.10 g) in DCM (2 mL). The solution was stirred at room temperature for 1 h then sodium triacetoxyborohydride (0.24 g) was added in portions. The mixture was stirred at room temperature overnight then 3M aqueous sodium hydroxide (6 mL) added to the residue. The mixture was shaken vigorously then acidified to pH 8 with 2M aqueous hydrochloric acid and extracted with ethyl acetate. The combined organic extracts were washed with water, saturated aqueous sodium chloride, dried with sodium sulfate, filtered and evaporated. The crude material was purified by reverse phase HPLC (gradient 25-95% acetonitrile in 0.1% aqueous ammonium acetate) to afford the title compound as a white powder. Yield: 21 mg MS: APCI (+ve) 486 [M+H$^+$]

$^1$H NMR: δ (300 MHz, DMSO)-0.02-0.17 (m, 4H), 0.90-1.04 (m, 2H), 1.53-1.58 (m, 2H), 1.85-1.92 (m, 1H), 2.40-2.48 (m, 3H), 3.21 (d, 2H), 3.48 (s, 3H), 4.10 (s, 2H), 5.63 (s, 1H), 6.77-6.84 (m, 1H), 6.95-7.03 (m, 1H), 7.07-7.12 (m, 1H).

EXAMPLE 154

N-[2-[(2,3-Difluorobenzyl)thio]-6-(3-hydroxypropoxy)pyrimidin-4-yl]piperazine-1-sulfonamide

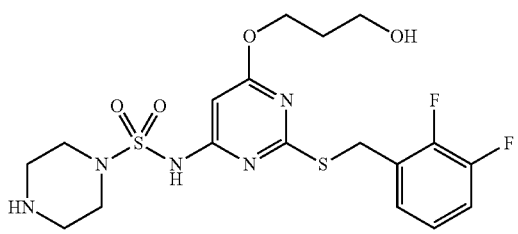 [SMILES: O=S(=O)(Nc1cc(OCCCO)nc(SCc2cccc(F)c2F)n1)N1CCNCC1]

To a solution of tert-butyl 4-({[2-[(2,3-difluorobenzyl)thio]-6-(3-hydroxypropoxy)pyrimidin-4-yl]amino}sulfonyl)piperazine-1-carboxylate (the product from step ii), 0.83 g) in DCM (5 ml) was added TFA (5 ml) slowly. The reaction was then stirred at room temperature for 18 h. The reaction was reduced in vacuo and the residue purified by prep HPLC to give the title compound as a white solid. Yield 160 mg MS: APCI (+ve) 476 [M+H$^+$]

$^1$H NMR: (DMSO) δ 2.52 (q, 2H), 3.19 (t, 4H), 3.44 (t, 4H), 3.52 (t, 2H), 4.38 (t, 2H), 4.49 (s, 2H), 4.59 (s, 1H), 6.07 (s, 1H), 6.99 (s, 1H), 7.14-7.24 (m, 1H), 7.31-7.45 (m, 2H)

The intermediates for this compound was prepared as follows:

(i) 3-({6-Chloro-2-[(2,3-difluorobenzyl)thio]pyrimidin-4-yl}oxy)propan-1-ol

To a solution of 4,6-dichloro-2-[(2,3-difluorobenzyl)thio] pyrimidine (the product of example 1 step ii), 3 g) and propane-1,3-diol (1.1 g) in THF (50 ml) was added NaH (390 mg) slowly and the reaction was then allowed to stir at room temperature for 18 h. The reaction mixture was then partitioned between DCM (150 ml) and H$_2$O (100 ml). The organics were separated and the aqueous layer was re-extracted with DCM (2×150 ml). Organics were combined, dried (MgSO$_4$) and reduced in vacuo to give the subtitle compound as a yellow oil. Yield 2.9 g MS: APCI (+ve) 347/349 [M+H$^+$]

ii) tert-Butyl 4-({[2-[(2,3-difluorobenzyl)thio]-6-(3-hydroxypropoxy)pyrimidin-4-yl]amino}sulfonyl)piperazine-1-carboxylate A mixture of 4-(aminosulfonyl)-1-piperazinecarboxylic acid-1,1-dimethylethyl ester (the product from example 15, step i), 0.4 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.43 g) and 3-({6-chloro-2-[(2,3-difluorobenzyl)thio]pyrimidin-4-yl}oxy)propan-1-ol (the product from step i), 0.4 g) in 1,4-dioxane (40 ml) was heated at reflux in a microwave at 100° C., 300 W, open vessel with cooling for 3 h. The reaction mixture was then reduced in vacuo and the residue separated between DCM (150 ml) and H$_2$O (150 ml). The organics were separated and the aqueous layer was re-extracted with DCM (2×150 ml). Organics were combined, dried (MgSO$_4$) and reduced in vacuo to give the subtitle compound as a yellow solid. Yield 0.83 g MS: APCI (+ve) 576 [M+H$^+$]

EXAMPLE 155

N-{2-[(2,3-Difluorobenzyl)thio]-6-methoxypyrimidin-4-yl}piperidine-4-sulfonamide

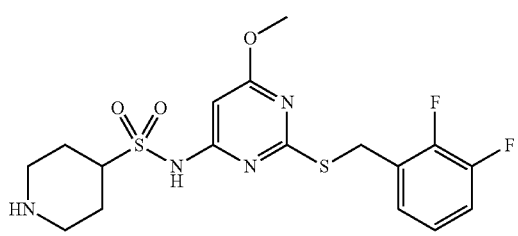

A mixture of piperidine-4-sulfonamide (0.33 g), tris (dibenzylideneacetone)dipalladium (0) (50 mg), 2-dicyclohexylphosphino-2',4',6'-tri-isopropyl-1,1'-biphenyl (XPHOS) (50 mg), cesium carbonate (0.43 g) and, 4-Chloro-2-[[(2,3-difluorophenyl)methyl]thio]-6-methoxypyrimidine (the product from example 35 step i), 0.4 g) in dioxane (20 ml) was heated at reflux in a microwave at 100° C., 300 W, open vessel with cooling for 2 h. The reaction mixture was then reduced in vacuo and the residue partitioned between DCM (100 ml) and H$_2$O (100 ml). The organics were separated and the aqueous layer was re-extracted with DCM (2×100 ml). Organics were combined, dried (MgSO$_4$) and reduced in vacuo and the resulting yellow residue was purified prep HPLC to give the title compound as a white solid. Yield 13 mg MS: APCI (+ve) 431 [M+H$^+$]

$^1$H NMR: (DMSO) δ 1.74-1.86 (m, 2H), 2.00-2.10 (m, 2H), 2.73-2.85 (m, 2H), 3.24-3.60 (m, 3H), 3.73 (s, 3H), 4.40 (s, 2H), 5.71 (s, 1H), 7.09-7.18 (m, 1H), 7.25-7.36 (m, 1H), 7.42-7.50 (m, 1H)

The intermediates for this compound was prepared as follows:

i) Benzyl 4-(aminosulfonyl)piperidine-1-carboxylate

To a solution of 0.88 NH$_3$ (50 ml) was added benzyl 4-(chlorosulfonyl)piperidine-1-carboxylate (4 g) and the reaction stirred for 72 h at RT. The reaction was then extracted with DCM (3×150 ml). Organics were recovered, dried (MgSO$_4$) and reduced in vacuo to give the subtitle compound as a clear oil. Yield 3.3 g $^1$H NMR: (DMSO) δ1.40-1.52 (m, 2H), 1.97-2.03 (m, 2H), 2.81-2.92 (m, 2H), 3.01-3.09 (m, 1H), 4.07-4.12 (m, 2H), 5.07 (s, 2H), 6.77 (s, 2H), 7.28-7.40 (m, 5H)

ii) Piperidine-4-sulfonamide

Benzyl 4-(aminosulfonyl)piperidine-1-carboxylate (the product from step i), 3.3 g) was dissolved in MeOH (20 ml). To this solution was added acetic acid (0.5 ml) and a catalytic amount of Pd/C. The reaction mixture was subjected to a pressure of 5 bar under an atmosphere of hydrogen gas for 18 h at RT. The reaction was filtered through celite and the filtrate was reduced in vacuo to give the subtitle compound as a white solid. Yield 1.7 g $^1$H NMR: (DMSO) δ1.46-1.57 (m, 21-1"), 1.91-1.98 (m, 2H), 2.48-2.57 (m, 2H), 2.85-2.93 (m, 1H), 3.05-3.10 (m, 2H), 5.38 (s, 2H), 6.71 (s, 1H)

EXAMPLE 156

N-(2-[(2,3-Difluorobenzyl)thio]-6-{[(trans)-2-hydroxycyclopentyl]oxy}pyrimidin-4-yl)azetidine-1-sulfonamide

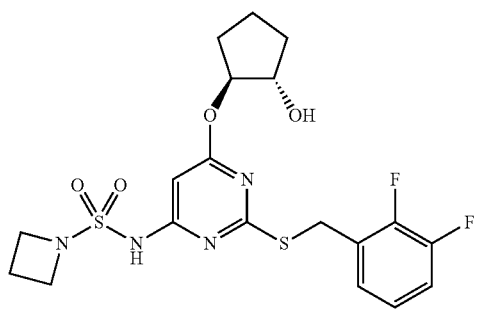 [SMILES: O=S(=O)(Nc1cc(O[C@H]2CCC[C@@H]2O)nc(SCc2cccc(F)c2F)n1)N1CCC1]

A mixture of azetidine-1-sulfonamide (0.27 g), tris(dibenzylideneacetone)dipalladium (0) (50 mg), 2-dicyclohexylphosphino-2',4',6'-tri-isopropyl-1,1'-biphenyl (XPHOS) (50 mg), cesium carbonate (0.43 g) and (trans)-2-(6-chloro-2-[(2,3-difluorobenzyl)thio]pyrimidin-4-yl)cyclopentanol (the product from step i), 0.50 g) in dioxane (20 ml) was heated at reflux in a microwave at 100° C., 300 W, open vessel with cooling for 1 h. The reaction mixture was then reduced in vacuo and the residue partitioned between DCM (150 ml) and H₂O (150 ml). The organics were separated and the aqueous layer was re-extracted with DCM (2×150 ml). Organics were combined, dried (MgSO₄) and reduced under vacuo and the resulting residue purified by prep HPLC to give the title compound as a white solid. Yield 74 mg MS: APCI (+ve) 473 [M+H⁺]

¹H NMR: (DMSO) δ 1.61-1.84 (m, 4H), 2.02-2.18 (m, 2H), 2.26 (q, 2H), 4.01 (t, 4H), 4.11-4.18 (m, 1H), 4.38 (s, 2H), 4.98-5.03 (m, 1H), 6.34 (s, 1H), 6.98-7.11 (m, 2H), 7.17-7.24 (m, 1H)

The intermediate for this compound was prepared as follows:

(i) (trans)-2-{6-Chloro-2-[(2,3-difluorobenzyl)thio]pyrimidin-4-yl}cyclopentanol To a solution of 4,6-dichloro-2-[(2,3-difluorobenzyl)thio]pyrimidine (the product of example 1 step ii), 2.3 g) and (trans)-cyclopentane-1,2-diol (1 g) in THF (50 ml) was added NaH (0.30 g) slowly and the reaction was then allowed to stir for 18 h at RT. The reaction mixture was then partitioned between DCM (150 ml) and H₂O (100 ml). The organics were separated and the aqueous layer was re-extracted with DCM (2×150 ml). Organics were combined, dried (MgSO₄) and reduced in vacuo and the resulting clear oil was purified by column chromatography on silica gel EtOAc/iso-Hexane (2:8) to give the subtitle compound as a clear colourless oil. Yield 0.94 g MS: APCI (+ve) 373/375 [M+H⁺]

The invention claimed is:

1. A method of treating asthma in a patient suffering from, or at risk of, said disease, which comprises administering to the patient a therapeutically-effective amount of a compound of the formula:

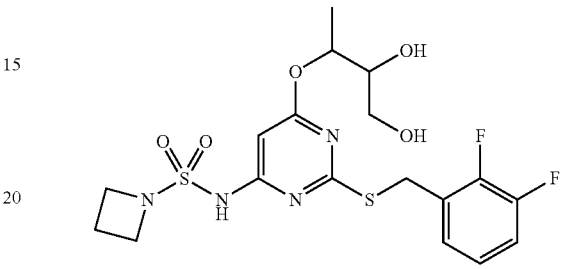

or a pharmaceutically-acceptable salt thereof.

2. A method according to claim 1 in which the compound is N-[2-[[(2,3-difluorophenyl)methyl]thio]-6-{[(1R,2S)-2,3-dihydroxy-1-methylpropyl]oxy}-4-pyrimidinyl]-1-azetidinesulfonamide.

* * * * *